US012680093B2

(12) United States Patent
Sakurai et al.

(10) Patent No.: US 12,680,093 B2
(45) Date of Patent: Jul. 14, 2026

(54) PROTEASE SUBSTRATE, AND POLYPEPTIDE INCLUDING PROTEASE CLEAVAGE SEQUENCE

(71) Applicant: Chugai Seiyaku Kabushiki Kaisha, Tokyo (JP)

(72) Inventors: Mika Sakurai, Shizuoka (JP); Tatsuya Kawa, Shizuoka (JP); Hitoshi Katada, Shizuoka (JP); Naoka Hironiwa, Singapore (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 807 days.

(21) Appl. No.: 17/615,633

(22) PCT Filed: Jun. 5, 2020

(86) PCT No.: PCT/JP2020/022226
§ 371 (c)(1),
(2) Date: Dec. 1, 2021

(87) PCT Pub. No.: WO2020/246567
PCT Pub. Date: Dec. 10, 2020

(65) Prior Publication Data
US 2022/0315909 A1     Oct. 6, 2022

(30) Foreign Application Priority Data
Jun. 5, 2019    (JP) ................................. 2019-105464

(51) Int. Cl.
| | |
|---|---|
| *C07K 7/04* | (2006.01) |
| *C07K 16/28* | (2006.01) |
| *C12N 9/72* | (2006.01) |
| *C12N 15/79* | (2006.01) |
| *A61K 39/00* | (2006.01) |

(52) U.S. Cl.
CPC .............. *C12N 9/6462* (2013.01); *C07K 7/04* (2013.01); *C07K 16/2866* (2013.01); *C12N 15/79* (2013.01); *A61K 2039/505* (2013.01); *C07K 2317/569* (2013.01); *C07K 2319/50* (2013.01); *C12N 2800/107* (2013.01)

(58) Field of Classification Search
CPC .......... C12N 9/6462; C12Y 304/21073; C07K 2319/50
See application file for complete search history.

(56) References Cited

U.S. PATENT DOCUMENTS

| | | | |
|---|---|---|---|
| 7,666,817 | B2 | 2/2010 | Daugherty et al. |
| 7,901,684 | B2 | 3/2011 | Gill et al. |
| 8,518,404 | B2 | 8/2013 | Daugherty et al. |
| 8,809,504 | B2 | 8/2014 | Lauermann |
| 9,737,623 | B2 | 8/2017 | Desnoyers et al. |
| 10,011,858 | B2 | 7/2018 | Igawa et al. |
| 10,357,571 | B2 | 7/2019 | Williams et al. |
| 10,568,977 | B2 | 2/2020 | Desnoyers et al. |
| 10,669,337 | B2 | 6/2020 | Irving et al. |
| 10,696,723 | B2 | 6/2020 | Winston et al. |
| 11,046,759 | B2 | 6/2021 | Moore et al. |
| 11,168,139 | B2 | 11/2021 | Igawa et al. |
| 11,932,697 | B2 | 3/2024 | Igawa et al. |
| 12,030,955 | B2 | 7/2024 | Igawa et al. |
| 12,060,654 | B2 | 8/2024 | Igawa et al. |
| 2004/0259768 | A1 | 12/2004 | Lauermann |
| 2007/0065878 | A1 | 3/2007 | Daugherty et al. |
| 2007/0243589 | A1 | 10/2007 | Gill et al. |
| 2010/0015133 | A1 | 1/2010 | Igawa et al. |
| 2011/0064666 | A1 | 3/2011 | Ogawa et al. |
| 2012/0244154 | A1 | 9/2012 | Daugherty et al. |
| 2015/0064169 | A1 | 3/2015 | Wang et al. |
| 2015/0157748 | A1 | 6/2015 | Desnoyers et al. |
| 2016/0144042 | A1 | 5/2016 | Williams et al. |
| 2016/0194399 | A1 | 7/2016 | Irving et al. |
| 2016/0289324 | A1 | 10/2016 | Moore et al. |
| 2018/0057593 | A1 | 3/2018 | Dennis |
| 2019/0359721 | A1 | 11/2019 | Igawa et al. |
| 2019/0367576 | A1 | 12/2019 | Winston et al. |
| 2020/0207846 | A1 | 7/2020 | Igawa et al. |
| 2020/0369781 | A1 | 11/2020 | Igawa et al. |
| 2021/0155701 | A1 | 5/2021 | Hoshino et al. |
| 2021/0206845 | A1 | 7/2021 | Igawa et al. |
| 2021/0221875 | A1 | 7/2021 | Kitamura et al. |
| 2021/0253672 | A1 | 8/2021 | Ishikawa et al. |

(Continued)

FOREIGN PATENT DOCUMENTS

| | | | |
|---|---|---|---|
| AU | 2016213702 | A1 | 8/2016 |
| CA | 2548338 | A1 | 6/2005 |

(Continued)

OTHER PUBLICATIONS

Thomas, D. A., et al., "A broad-spectrum fluorescence-based peptide library for the rapid identification of protease substrates," Proteomics, 6:2112-2120 (2006).

Abi-Habib, R. J., et al., "A urokinase-activated recombinant diphtheria toxin targeting the granulocyte-macrophage colony-stimulating factor receptor is selectively cytotoxic to human acute myeloid leukemia blasts," Blood, 104:2143-2148 (2004).

Abstract of ACR/ARHP Annual Meeting https://plan.core-apps.com/ tristar_acr17/abstract/7f9a3c05b0ca255af1fc655b034e5eaa. Apr. 23, 2018.

Acchione, M., et al., "Impact of linker and conjugation chemistry on antigen binding, Fc receptor binding and thermal stability of model antibody-drug conjugates," mAbs, 4(3):362-372 (2012).

(Continued)

*Primary Examiner* — Lianko G Garyu
*Assistant Examiner* — Claudia Espinosa
(74) *Attorney, Agent, or Firm* — Nixon & Vanderhye P.C.

(57) ABSTRACT

The present application relates to protease substrates, peptide sequences cleavable by a protease, polypeptides comprising a protease cleavage sequence and methods for production thereof, pharmaceutical compositions comprising a polypeptide comprising a protease cleavage sequence, and methods for releasing an antigen-binding domain or a ligand by the cleavage of a protease cleavage sequence included in a polypeptide.

16 Claims, 20 Drawing Sheets
Specification includes a Sequence Listing.

(56) References Cited

U.S. PATENT DOCUMENTS

| | | |
|---|---|---|
| 2022/0073632 A1 | 3/2022 | Igawa et al. |
| 2022/0324975 A1 | 10/2022 | Sakurai et al. |
| 2023/0069996 A1 | 3/2023 | Igawa et al. |
| 2024/0150476 A1 | 5/2024 | Igawa et al. |

FOREIGN PATENT DOCUMENTS

| | | |
|---|---|---|
| CA | 2591813 A1 | 6/2006 |
| CA | 2607147 A1 | 11/2006 |
| CA | 2666599 A1 | 2/2008 |
| CA | 2678626 A1 | 9/2008 |
| CA | 2548338 C | 6/2015 |
| CA | 3041279 A1 | 5/2018 |
| CA | 2607147 C | 7/2018 |
| CA | 3083346 A1 | 6/2019 |
| CN | 1665932 A | 9/2005 |
| CN | 101821288 A | 9/2010 |
| CN | 1665932 B | 12/2010 |
| CN | 103068847 A | 4/2013 |
| CN | 103842383 A | 6/2014 |
| CN | 103958547 A | 7/2014 |
| CN | 104661676 A | 5/2015 |
| CN | 106459153 A | 2/2017 |
| CN | 107207564 A | 9/2017 |
| CN | 107602706 A | 1/2018 |
| CN | 103958547 B | 8/2018 |
| CN | 103068847 B | 5/2019 |
| CN | 111836828 A | 10/2020 |
| CN | 107602706 B | 12/2020 |
| CN | 106459153 B | 12/2021 |
| CN | 114127277 A | 3/2022 |
| EP | 1505154 A1 | 2/2005 |
| EP | 2957633 A1 | 12/2015 |
| EP | 3296395 A1 | 3/2018 |
| EP | 3546480 A1 | 10/2019 |
| EP | 3546574 A1 | 10/2019 |
| EP | 3556773 A1 | 10/2019 |
| EP | 3719036 A1 | 10/2020 |
| EP | 3981428 A1 | 4/2022 |
| JP | 2005168328 A | 6/2005 |
| JP | 2010536370 A | 12/2010 |
| JP | 2011026298 A | 2/2011 |
| JP | 2012514982 A | 7/2012 |
| JP | 2013538204 A | 10/2013 |
| JP | 2014509605 A | 4/2014 |
| JP | 2015509952 A | 4/2015 |
| JP | 2015517320 A | 6/2015 |
| JP | 5753903 B2 | 7/2015 |
| JP | 5765894 B2 | 8/2015 |
| JP | 5851842 B2 | 2/2016 |
| JP | 6035009 B2 | 11/2016 |
| JP | 6030307 B2 | 5/2017 |
| JP | 6178846 B2 | 8/2017 |
| JP | 2017523176 A | 8/2017 |
| JP | 2017529853 A | 10/2017 |
| JP | 6273215 B2 | 1/2018 |
| JP | 7020909 B2 | 2/2022 |
| RU | 2012110127 A | 9/2013 |
| RU | 2583876 C2 | 5/2016 |
| RU | 2015101803 A | 8/2016 |
| RU | 2636046 C2 | 11/2017 |
| WO | WO2004021861 A2 | 3/2004 |
| WO | WO2005110453 A2 | 11/2005 |
| WO | WO2007027935 A2 | 3/2007 |
| WO | WO2007063308 A2 | 6/2007 |
| WO | WO2007076933 A1 | 7/2007 |
| WO | WO2008045148 A2 | 4/2008 |
| WO | WO2008149149 A2 | 12/2008 |
| WO | WO2008157379 A2 | 12/2008 |
| WO | WO2009021754 A2 | 2/2009 |
| WO | WO2009025846 A2 | 2/2009 |
| WO | WO2010081173 A2 | 7/2010 |
| WO | WO2010115998 A2 | 10/2010 |
| WO | WO2011020783 A3 | 4/2011 |
| WO | WO2011123683 A2 | 10/2011 |
| WO | WO2012025525 A1 | 3/2012 |
| WO | WO2012028697 A1 | 3/2012 |
| WO | WO2012123755 A1 | 9/2012 |
| WO | WO2012158818 A2 | 11/2012 |
| WO | WO2013046704 A2 | 4/2013 |
| WO | WO2013128194 A1 | 9/2013 |
| WO | WO2013148248 A1 | 10/2013 |
| WO | WO2013176730 A1 | 11/2013 |
| WO | WO2013180834 A2 | 12/2013 |
| WO | WO2013192550 A2 | 12/2013 |
| WO | WO2014052462 A2 | 4/2014 |
| WO | WO2014125955 A1 | 8/2014 |
| WO | WO2015066279 A2 | 5/2015 |
| WO | WO2015116933 A2 | 8/2015 |
| WO | WO2015117930 A1 | 8/2015 |
| WO | WO2016014974 A2 | 1/2016 |
| WO | WO2016016269 A1 | 2/2016 |
| WO | WO2016046778 A2 | 3/2016 |
| WO | WO2016077505 A2 | 5/2016 |
| WO | WO2016118629 A1 | 7/2016 |
| WO | WO2016179003 A1 | 11/2016 |
| WO | WO2016182064 A1 | 11/2016 |
| WO | WO2017025698 A1 | 2/2017 |
| WO | WO2017162587 A1 | 9/2017 |
| WO | WO2017205014 A1 | 11/2017 |
| WO | WO2017220990 A1 | 12/2017 |
| WO | WO2018085555 A1 | 5/2018 |
| WO | WO2018097307 A1 | 5/2018 |
| WO | WO2018097308 A1 | 5/2018 |
| WO | WO2018220225 A1 | 12/2018 |
| WO | WO2018220236 A1 | 12/2018 |
| WO | WO2019010219 A1 | 1/2019 |
| WO | WO2019010224 A1 | 1/2019 |
| WO | WO2019032471 A1 | 2/2019 |
| WO | WO2019107380 A1 | 6/2019 |
| WO | WO2019107384 A1 | 6/2019 |
| WO | WO2019132472 A1 | 7/2019 |
| WO | WO2019173832 A2 | 9/2019 |
| WO | WO2019222294 A1 | 11/2019 |
| WO | WO2019222295 A1 | 11/2019 |
| WO | WO2019222296 A1 | 11/2019 |
| WO | WO2019230866 A1 | 12/2019 |
| WO | WO2019230867 A1 | 12/2019 |
| WO | WO2019230868 A1 | 12/2019 |
| WO | WO2020061526 A1 | 3/2020 |
| WO | WO2020069398 A1 | 4/2020 |
| WO | WO2020072821 A2 | 4/2020 |
| WO | WO2020086758 A1 | 4/2020 |
| WO | WO2020246567 A1 | 12/2020 |
| WO | WO2021016640 A1 | 1/2021 |
| WO | WO2021062406 A1 | 4/2021 |
| WO | WO2021149697 A1 | 7/2021 |
| WO | WO2021189139 A1 | 9/2021 |
| WO | WO2021202678 A1 | 10/2021 |
| WO | WO2021212083 A2 | 10/2021 |
| WO | WO2021236676 A1 | 11/2021 |
| WO | WO2022094046 A1 | 5/2022 |
| WO | WO2022155263 A2 | 7/2022 |
| WO | WO2023002952 A1 | 1/2023 |
| WO | WO2023004282 A2 | 1/2023 |
| WO | WO2023043978 A2 | 3/2023 |
| WO | WO2023050006 A1 | 4/2023 |
| WO | WO2023070038 A2 | 4/2023 |
| WO | WO2023242769 A1 | 12/2023 |
| WO | WO2024154744 A1 | 7/2024 |

OTHER PUBLICATIONS

Alberts, B., et al., "Molecular Biology of The Cell," Fifth Edition, Chapter 3 "Proteins," 125, 136 (2008).

Allegra, C. J., et al., "Phase III Trial Assessing Bevacizumab in Stages II and III Carcinoma of the Colon: Results of NSABP Protocol C-08," J Clin Oncol., 29(1):11-16 (2011).

Alley, S.C., et al., "Antibody-Drug Conjugates: Targeted Drug Delivery for Cancer," Current Opinion in Chemical Biology, 14(4):529-537 (2010).-

(56) References Cited

OTHER PUBLICATIONS

Asano, R. and Kumagai, I., "Functionalization of Bispecific Thera-
peutic Antibodies Based on Protein Engineering," Yakugaku Zasshi,
135(7):851-856 (2015), with partial English translation.
Badri, H., et al., "Optimization of radiation dosing schedules for
proneural glioblastoma," J Math Biol., 72:1301-1336 (2016).
Baeuerle, P.A., et al., "BiTE: Teaching Antibodies to Engage T-cells
for Cancer Therapy," Current Opinion in Molecular Therapeutics,
11(1):22-30 (2009).
Baylot, V., et al., "TCTP Has a Crucial Role in the Different Stages
of Prostate Cancer Malignant 4 Progression 5," TCTP/tpt1—
Remodeling Signaling from Stem Cell to Disease. Results and
Problems in Cell Differentiation, 64:255-261 (2017).
Chen, X., et al., "Fusion Protein Linkers: Property, Design and
Functionality," Adv Drug Deliv Rev., 65(10):1357-1369 (2013).
Cohen, S.B., et al., "A Randomized, Double-blind Study of AMG
108 (a Fully Human Monoclonal Antibody to IL-1R1) in Patients
With Osteoarthritis of the Knee," Arthritis Research & Therapy
13(4):R125 (2011).
Colman, P. M., "Effects of amino acid sequence changes on antibody-
antigen interactions," Res Immunol., 145:33-36 (1994).
Dashivets, T., et al., "Oxidation in the complementarity-determining
regions differentially influences the properties of therapeutic anti-
bodies," MAbs, 8(8):1525-1535 (2016).
De Bono, J.S., et al., "ING-1, A Monoclonal Antibody Targeting
Ep-CAM in Patients With Advanced Adenocarcinomas," Clinical
Cancer Research, 10(22):7555-7565 (2004).
Derksen, P. W. B., et al., "Illegitimate WNT signaling promotes
proliferation of multiple myeloma cells," PNAS, 101(16):6122-
6127 (2004).
Desjarlais, J.R., et al., "Optimizing Engagement of the Immune
System by Anti-Tumor Antibodies: An Engineer's Perspective,"
Drug Discovery Today, 12(21-22):898-910 (2007)/.
Desnoyers, L.R., et al., "Tumor-specific Activation of an EGFR-
targeting Probody Enhances Therapeutic Index," Science Transla-
tional Medicine, 5(207):207ra144 (2013)/.
Dirks, P. B., "Brain Tumor Stem Cells: Bringing Order to the Chaos
of Brain Cancer," J Clin Oncol., 26(17):2916-2924 (2008).
Drutskaya, M. S., et al., "Role of IL-6 in Experimental Arthritis
Induced by Transfer of Arthritogenic Antibodies," Medical Immu-
nology (Russia), 18(6):569-574 (2016).
Erster, O., et al., "Site-specific targeting of antibody activity in vivo
mediated by disease-associated proteases," J Control Release, 161:804-
812 (2012).
Final Office Action dated Apr. 5, 2024, in U.S. Appl. No. 16/766,600,
filed May 22, 2020, Igawa et al.
Gerspach, J., et al., "Target-Selective Activation of a TNF Prodrug
by Urokinase-Type Plasminogen Activator (uPA) Mediated Proteolytic
Processing at the Cell Surface," Cancer Immunology, Immunotherapy
55(12):1590-1600 (2006).
Ginaldi, L., et al., "Increased levels of interleukin 31 (IL-31) in
osteoporosis," BMC Immunol., 16:60 (2015).
Gladkov, O., et al., "Cyclophosphamide and Tucotuzumab (huKS-
IL2) Following First-line Chemotherapy in Responding Patients
With Extensive-disease Small-cell Lung Cancer," Anti-Cancer Drugs
26(10):1061-1068 (2015).
Halin, C., et al., "Synergistic Therapeutic Effects of a Tumor
Targeting Antibody Fragment, Fused to Interleukin 12 and to Tumor
Necrosis Factor Alpha," Cancer Research, 63(12):3202-3210 (2003).
Harmsen, M., et al., "Selection and Optimization of Proteolytically
Stable Llama Single-domain Antibody Fragments for Oral
Immunotherapy," Applied Microbiology and Biotechnology, 72(3):544-
551 (2006).
Hussack, G., et al., "Engineered Single-Domain Antibodies with
High Protease Resistance and Thermal Stability," PLoS One,
6(11):e28218 (2011).
Hutt, M., et al., "Plasma Half-life Extension of Small Recombinant
Antibodies by Fusion to Immunoglobulin-binding Domains," J Biol
Chem., 287(7):4462-4469 (2012).
Ishii, A., et al., "A receptor involved in the regulation of the
pharmacokinetics of antibody-based pharmaceuticals: FcRn," Nihon
Yakurigaku Zasshi. Folia Pharmacologica Japonica, 136(5):280-
284 (2010).
Juszczak, A., et al., "Ipilimumab: a novel immunomodulating
therapy causing autoimmune hypophysitis: a case report and review,"
Eur J Endocrinol., 167:1-5 (2012).
Keskin, O., et al., "A new, structurally nonredundant, diverse data
set of protein-protein interfaces and its implications," Protein Sci.,
13:1043-1055 (2004).
Kiani, C., et al., "Structure and Function of Aggrecan," Cell
Research, 12(1):19-32 (2002).
Kim, S. J., et al., "Antibody Engineering for the Development of
Therapeutic Antibodies," Mol Cells, 20(1):17-29 (2005).
Knauf, M. J., et al., "Relationship of Effective Molecular Size to
Systemic Clearance in Rats of Recombinant Interleukin-2 Chemi-
cally Modified with Water-soluble Polymers," J Biol Chem.,
263(29):15064-15070 (1988).
Kromann-Hansen, T., et al., "A Camelid-derived Antibody Frag-
ment Targeting the Active Site of a Serine Protease Balances
Between Inhibitor and Substrate Behavior," The Journal of Biology
Chemistry, 291(29):15156-15168 (2016).
Lewis, G. D., et al., "Differential responses of human tumor cell
lines to anti-p185$^{HER2}$ monoclonal antibodies," Cancer Immunol
Immunother., 37:255-263 (1993).
López-Lázaro, M., "The migration ability of stem cells can explain
the existence of cancer of unknown primary site. Rethinking metas-
tasis." Oncoscience, 2(5):467-475 (2015).
Lutterbuese, R., et al., "T cell-engaging BiTE antibodies specific for
EGFR potently eliminate KRAS- and BRAF-mutated colorectal
cancer cells," PNAS, 107(28):12605-12610 (2010).
Maeda, Y., et al., "Engineering of Functional Chimeric Protein
G-VargulaLuciferase," Anal Biochem., 249(2):147-152 (1997).
Mariuzza, R. A., et al., "The Structural Basis of Antigen-Antibody
Recognition," Ann Rev Biophys Biophys Chem., 16:139-159 (1987).
Martel-Pelletier, J., et al., "Osteoarthritis," Nature Reviews Disease
Primers, 2:16072 (2016).
Muller, S., et al., "Spliceosomal Peptide P140 For Immunotherapy
of Systemic Lupus Erythematosus: Results of an Early Phase II
Clinical Trial," Arthritis and Rheumatism, 58(12):3873-3883 (2008).
Nam, J. L., et al., "Current evidence for the management of
rheumatoid arthritis with biological disease-modifying antirheumatic
drugs: a systematic literature review informing the EULAR recom-
mendations for the management of RA," Ann Rheum Dis., 69:976-
986 (2010).
Neri, D. and Sondel, P. M., "Immunocytokines for cancer treatment:
past, present and future," Curr Opin Immunol., 40:96-102 (2016).
Office Action dated Aug. 8, 2023, in U.S. Appl. No. 16/766,600,
filed May 22, 2020, Igawa et al.
Paoloni, M., et al., "Defining the Pharmacodynamic Profile and
Therapeutic Index of Nhs-IL12 Immunocytokine in Dogs With
Malignant Melanoma," PLoS One 10(6):e0129954 (2015).
Papadia, F., et al., "Isolated Limb Perfusion With the Tumor-
targeting Human Monoclonal Antibody-cytokine Fusion Protein
L19-TNF Plus Melphalan and Mild Hyperthermia in Patients With
Locally Advanced Extremity Melanoma," Journal of Surgical Oncol-
ogy 107(2):173-179 (2013).
Pavlou, A. K. and Belsey, M. J., "The therapeutic antibodies market
to 2008," Eur J Pharmaceut Biopharmaceut 59:389-396 (2005).
Polu, K. R. and Lowman, H. B., "Probody therapeutics for targeting
antibodies to diseased tissue," Expert Opin Biol Ther., 14(8):1049-
1053 (2014).
Puskas, J., et al., "Development of an Attenuated Interleukin-2
Fusion Protein That Can Be Activated by Tumour-Expressed Proteases,"
Immunology 133(2):206-220 (2011).
Qin, Z.-X. and Liu, Z.-M., "The Research Progress in Yapsin
Protease Family," Lett Biotechnol., 19(4):591-596 (2008), with
English abstract.
R&D Systems, "Human Aggrecan G1-IGD-G2 Domains Anti-
body," Monoclonal Mouse IgG2B Clone # 179509, Catalog No.
MAB1220, 1 page (2018).

(56) References Cited

OTHER PUBLICATIONS

Regsiter, A. and William, W., "Short-chain deyhydrogenase/reductase SDR [uncultured *Sphingopyxis* sp.]," GenBank Accession No. SBV32674.1, May 15, 2017.

Reichert, J. M., et al., "Monoclonal antibody successes in the clinic," Nature Biotechnol 23(9):1073-1078 (2005).

Restriction Requirement dated Dec. 15, 2022, in U.S. Appl. No. 16/766,600, filed May 22, 2020, Igawa et al.

Riechelmann, H., et al., "Phase I trial with the CD44v6-targeting immunoconjugate bivatuzumab mertansine in head and neck squamous cell carcinoma," Oral Oncology, 44:823-829 (2008).

Roitt, I., et al., "Immunology," Fifth Edition, Moscow, Mir, 97-113 (2000).

Roitt, I., et al., Immunology, M., Mir, 109-111 (2000) (in Russian, with what is believed to be a published English equivalent of those pages taken from Roitt, et al., Immunology, Fifth Ed., 78-81 (1998).

Rudikoff, S., et al., "Single Amino Acid Substitution Altering Antigen-binding Specificity," Proceedings of the National Academy of Sciences, 79(6):1979-1983 (1982).

Safdari, Y., et al., "Antibody Humanization Methods—A Review and Update," Biotechnology & Genetic Engineering Reviews, 29(2):175-186 (2013).

Sandersjoo, L., et al., "A New Prodrug Form of Affibody Molecules (Pro-affibody) is Selectively Activated by Cancer-associated Proteases," Cellular and Molecular Life Sciences, 72(7):1405-1415 (2015).

Satoh, M., et al., "Non-fucosylated therapeutic antibodies as next-generation therapeutic antibodies," Expert Opin Biol Ther., 6(11):1161-1173 (2006).

Schlapschy, M., et al., "Fusion of a recombinant antibody fragment with a homo-amino-acid polymer: effects on biophysical properties and prolonged plasma half-life," Prot Eng Des Sel., 20(6):273-284 (2007).

Seliverstov, Y.A., et al., "Spinal muscular atrophies: conception, differential diagnostics and prospects for treatment," Nervous Diseases, 3:9-17 (2015).

Severin, Y. S., editor, "Biochemistry, Textbook for Higher Education," Moscow, Geotar-Med, 39-45 (2004).

Singer, M. and Berg, P., "Genes and Genomes," Moscow, Mir, 63 (1998).

Skrombolas, D., et al., "Development of an Interleukin-12 Fusion Protein That is Activated by Cleavage with Matrix Metalloproteinase 9," J Interferon Cytokine Res., 39(4):233-245 (2019).

Takamori, A., et al., "IL-31 is crucial for induction of pruritus, but not inflammation, in contact hypersensitivity," Sci Rep., 8:6639 (2018).

Takeuchi, T. and Kameda, H., "The Japanese experience with biologic therapies for rheumatoid arthritis," Nat Rev Rheumatol., 6:644-652 (2010).

Torres, M. and Casadevall, A., "The Immunoglobulin Constant Region Contributes to Affinity and Specificity," Trends in Immunology, 29(2):91-97 (2008).

Tran, B. and Rosenthal, M. A., "Survival comparison between glioblastoma multiforme and other incurable cancers," J Clin Neurosci., 17:417-421 (2010).

Trinh, V. A. and Hwu, W.-J., "Ipilimumab in the treatment of melanoma," Expert Opin Biol Ther., 12(6):773-782 (2012).

Turk, B. E., et al., "Determination of protease cleavage site motifs using mixture-based oriented peptide libraries," Nat Biotechnol. 19(7):661-667 (2001).

Tzeng, A., et al., "Antigen Specificity Can Be Irrelevant to Immunocytokine Efficacy and Biodistribution," Proceedings of the National Academy of Sciences of the United States of America 112(11):3320-3325 (2015).

Van Roy, M., et al., "The preclinical pharmacology of the high affinity anti-IL-6R Nanobody® ALX-0061 supports its clinical development in rheumatoid arthritis," Arthitis Res Ther., 17:135, 16 pages (2015).

Vignali, D.A.A. and Kuchroo, V.K., "IL-12 Family Cytokines: Immunological Playmakers," Nat Immunol, 13(8):722-728 (2012).

Wei, S., editor, Clinical Tumor Biological Immunotherapy, 186 (2006).

Weiner, L. M., et al., "Monoclonal antibodies: versatile platforms for cancer immunotherapy," Nat Rev Immunol., 10:317-327 (2010).

Wüest, T., et al., "TNF-Selectokine: a novel prodrug generated for tumor targeting and site-specific activation of tumor necrosis factor," Oncogene, 21:4257-4266 (2002).

Xia, B., et al., "Osteoarthritis Pathogenesis: a Review of Molecular Mechanisms," Calcified Tissue International, 95(6):495-505 (2014).

Yamane, B. H., et al., "The development of antibody-IL-2 based immunotherapy with hu14.18-IL2 (EMD-273063) in melanoma and neuroblastoma," Expert Opin Investig Drugs, 18(7):991-1000 (2009).

Yarilin, A. A., Immunology Basics: Manual, Fundamentals of Immunology, Moscow, Medicina, 172-174 (1999).

U.S. Appl. No. 16/766,600, filed May 22, 2020, Igawa et al., related application.

U.S. Appl. No. 10/651,584, Lauermann.

U.S. Appl. No. 12/821,711, Ogawa et al.

U.S. Appl. No. 16/463,218, Igawa et al.

U.S. Appl. No. 16/463,222, Igawa et al.

U.S. Appl. No. 16/767,085, Igawa et al.

U.S. Appl. No. 17/058,889, Hoshino et al.

U.S. Appl. No. 17/058,896, Ishikawa et al.

U.S. Appl. No. 17/058,961, Kitamura et al.

U.S. Appl. No. 17/477,983, Igawa et al.

U.S. Appl. No. 17/615,748, Sakurai et al.

U.S. Appl. No. 17/793,587, Igawa et al.

U.S. Appl. No. 18/393,918, Igawa et al.

U.S. Appl. No. 18/414,813, Chichili et al.

U.S. Appl. No. 18/580,385, Chichili et al.

U.S. Appl. No. 18/656,351, Igawa et al.

U.S. Appl. No. 18/672,417, Igawa et al.

Bannas, P., et al., "Nanobodies and Nanobody-Based Human Heavy Chain Antibodies as Antitumor Therapeutics," Front Immunol., 8:1603, pp. 1-13 (2017).

Chiu, M. L., et al., "Antibody Structure and Function: The Basis for Engineering Therapeutics," Antibodies, 8(4):55, pp. 1-80 (2019).

Office Action dated Nov. 12, 2024, in U.S. Appl. No. 17/058,896, filed Nov. 25, 2020, Ishikawa et al.

Onuoha, S. C., et al., "Rational Design of Antirheumatic Prodrugs Specific for Sites of Inflammation," Arthritis Rheumatol., 67(10):2661-2672 (2015).

Restriction Requirement dated Apr. 1, 2024, in U.S. Appl. No. 17/058,896, filed Nov. 25, 2020, Ishikawa et al.

Robert, R. and Wark, K. L., "Engineered antibody approaches for Alzheimer's disease immunotherapy," Arch Biochem Biophys., 526(2):132-138 (2012).

FIG. 1

(A) Long half-life (B) Short half-life of antigen-binding domain after release

Figure 2:
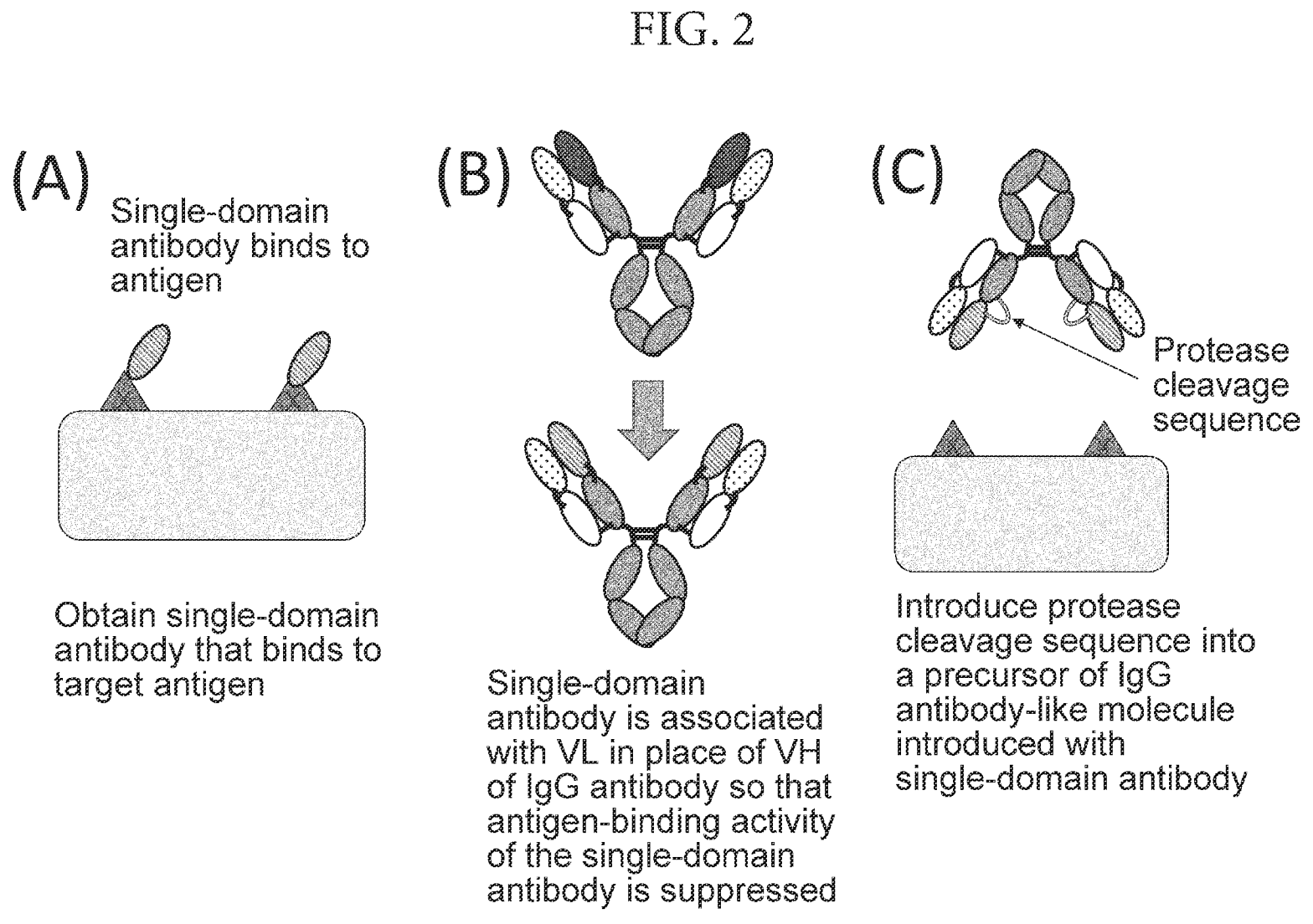

Single-domain
antibody binds to
antigen

Obtain single-domain
antibody that binds to
target antigen (B)

Single-domain
antibody is associated
with VL in place of VH
of IgG antibody so that
antigen-binding activity
of the single-domain
antibody is suppressed (C)

Protease
cleavage
sequence

Introduce protease
cleavage sequence into
a precursor of IgG
antibody-like molecule
introduced with
single-domain antibody

FIG. 4

Second antigen-binding domain
+
Antigen-binding domain (A)

(B)
Carrying moiety (C)
Cancer cell

Ligand

Protease
cleavage
sequence

Single-domain
antibody

Ligand

Single-domain antibody can bind to ligand in a state where protease cleavage sequence is not cleaved cleavage Single-domain antibody is cleaved in a state where protease cleavage sequence is cleaved, it cannot bind to ligand and the ligand is released Single-domain antibody in a fusion polypeptide can bind to ligand in a state where protease cleavage sequence is not cleaved Single-domain antibody in a fusion polypeptide is cleaved in a state where protease cleavage sequence is cleaved, it cannot bind to ligand and a portion of the fusion polypeptide including the ligand is released

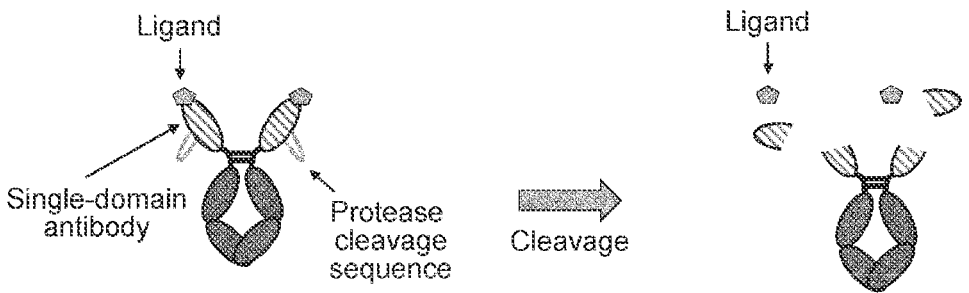

Ligand

Single-domain
antibody

Protease
cleavage
sequence

Cleavage

Ligand

Single-domain antibody contained
in a ligand-binding molecule can
bind to ligand in a state where
protease cleavage sequence is
not cleaved Single-domain antibody contained in
a ligand-binding molecule is cleaved
in a state where protease cleavage
sequence is cleaved, it cannot bind
to ligand and the ligand is released

FIG. 9

Single-domain antibody in a fusion
polypeptide can bind to ligand
in a state where protease cleavage
sequence is not cleaved Single-domain antibody in a fusion
polypeptide is cleaved in a state
where protease cleavage sequence
is cleaved, it cannot bind to ligand
and a portion of the fusion polypeptide
including the ligand is released

| Lane | Sample | Protease |
|---|---|---|
| 1 | Molecular weight marker | Untreated |
| 2 | 6R90H12I001-G1T3dCH1dC | Treated |
| 3 | | Untreated |
| 4 | 6R90H13I001-G1T3dCH1dC | Treated |
| 5 | | Untreated |
| 6 | 6R90H14I001-G1T3dCH1dC | Treated |
| 7 | | Untreated |
| 8 | 6R90H15I001-G1T3dCH1dC | Treated |
| 9 | | Untreated |
| 10 | 6R90H16IG001-G1T3dCH1dC | Treated |
| 11 | | Untreated |
| 12 | IL6R90-G1T3dCH1dC | Treated |
| 13 | | Untreated |
| 14 | | |
| 15 | Molecular weight marker | |

FIG. 13

| Lane | Sample | Protease |
|---|---|---|
| 1 | Molecular weight marker | Untreated |
| 2 | IL6RaG4Sx3.IL6R90-G1T3dCH1dC | Treated |
| 3 | | Untreated |
| 4 | IL6RaG4Sx4.IL6R90-G1T3dCH1dC | Treated |
| 5 | | Untreated |
| 6 | IL6RaG4Sx5.IL6R90-G1T3dCH1dC | Treated |
| 7 | | Untreated |
| 8 | IL6RaG4S.6R90H12t001-G1T3dCH1dC | Treated |
| 9 | | Untreated |
| 10 | IL6RaG4Sx2.6R90H12t001-G1T3dCH1dC | Treated |
| 11 | | Untreated |
| 12 | IL6RaG4Sx3.6R90H12t001-G1T3dCH1dC | Treated |
| 13 | | Untreated |
| 14 | IL6RaG4Sx4.6R90H12t001-G1T3dCH1dC | Treated |
| 15 | | Untreated |

Without cleavage sequence
With cleavage sequence Btw12-13

| Lane | Sample | Protease |
|---|---|---|
| 1 | Molecular weight marker | Untreated |
| 2 | IL6RaG4Sx5.6R90H12t001-G1T3dCH1dC | Treated |
| 3 | | Untreated |
| 4 | IL6RaG4S.6R90H13t001-G1T3dCH1dC | Treated |
| 5 | | Untreated |
| 6 | IL6RaG4Sx2.6R90H13t001-G1T3dCH1dC | Treated |
| 7 | | Untreated |
| 8 | IL6RaG4Sx3.6R90H13t001-G1T3dCH1dC | Treated |
| 9 | | Untreated |
| 10 | IL6RaG4Sx4.6R90H13t001-G1T3dCH1dC | Treated |
| 11 | | Untreated |
| 12 | IL6RaG4Sx5.6R90H13t001-G1T3dCH1dC | Treated |
| 13 | | Untreated |
| 14 | IL6RaG4S.6R90H14iG001-G1T3dCH1dC | Treated |
| 15 | | Untreated |

With cleavage sequence Btw13-14
With cleavage sequence Btw15-16

| Lane | Sample | Protease |
|---|---|---|
| | | With cleavage sequence Btw14-15 |
| 1 | Molecular weight marker | Untreated |
| 2 | IL6RaG4Sx2.6R90H14IG001-G1T3dCH1dC | Treated |
| 3 | | Untreated |
| 4 | IL6RaG4Sx3.6R90H14IG001-G1T3dCH1dC | Treated |
| 5 | | Untreated |
| 6 | IL6RaG4Sx4.6R90H14IG001-G1T3dCH1dC | Treated |
| 7 | | Untreated |
| 8 | IL6RaG4Sx5.6R90H14IG001-G1T3dCH1dC | Treated |
| 9 | | Untreated |

FIG. 15

| Well | Sample | Protease |
|---|---|---|
| 1 | | |
| 2 | Molecular weight marker | Untreated |
| 3 | | Treated |
| 4 | hPD1PD102C3H12-G1T3noCyshinge | Untreated |
| 5 | | Treated |
| 6 | hPD1PD102C3H13-G1T3noCyshinge | Untreated |
| 7 | | Treated |
| 8 | hPD1PD102C12H12-G1T3noCyshinge | Untreated |
| 9 | | Treated |
| 10 | hPD1PD102C12H14-G1T3noCyshinge | Untreated |
| 11 | | Untreated |
| 12 | Molecular weight marker | |
| 13 | | |
| 14 | | |
| 15 | | |

1

PROTEASE SUBSTRATE, AND POLYPEPTIDE INCLUDING PROTEASE CLEAVAGE SEQUENCE

CROSS-REFERENCE TO RELATED APPLICATIONS

This application is a U.S. National Phase of PCT Application No. PCT/JP2020/022226, filed Jun. 5, 2020, which claims the benefit of Japanese Patent Application No. 2019-105464, filed Jun. 5, 2019, each of which is incorporated herein by reference in its entirety.

REFERENCE TO SEQUENCE LISTING SUBMITTED ELECTRONICALLY

The content of the electronically submitted sequence listing (Name: 6663_0191 Sequence_Listing.txt; Size: 4.78 MB; and Date of Creation: Nov. 23, 2021) filed with the application is incorporated herein by reference in its entirety.

TECHNICAL FIELD

The present disclosure provides protease substrates, peptide sequences cleavable by a protease, polypeptides comprising a protease cleavage sequence and methods for production thereof, pharmaceutical compositions comprising a polypeptide comprising a protease cleavage sequence, and methods for releasing an antigen-binding domain or a ligand by the cleavage of a protease cleavage sequence included in a polypeptide.

BACKGROUND ART

Protease is an enzyme that cleaves peptide bonds between amino acid residues. Some proteases are known to break specific peptide bonds based on the presence of a particular amino acid sequence within the protein. Proteases naturally occur in all organisms and are involved in various physiological responses, including simple degradations and highly regulated pathways. However, many pathological conditions are associated with aberrant expression and/or activity of proteases. Thus, inappropriate proteolysis potentially plays a key role in the development and progression of cancer, and cardiovascular diseases, inflammatory diseases, neurodegenerative diseases, eucaryotic diseases, bacterial diseases, viral diseases, and parasitic diseases.

Accordingly, there are needs to identify new substrates for proteases and to use the substrates in a variety of therapeutic, diagnostic, and prophylactic applications.

CITATION LIST

Patent Literature

[PTL 1] WO2018/097307
[PTL 2] WO2018/097308

SUMMARY OF INVENTION

Technical Problem

The present disclosure has been made in view of these circumstances. An objective of the present disclosure is to provide protease substrates, peptide sequences cleavable by a protease, polypeptides comprising a protease cleavage sequence and methods for production thereof, pharmaceutical compositions comprising a polypeptide comprising a protease cleavage sequence, and methods for releasing an antigen-binding domain or a ligand by the cleavage of a protease cleavage sequence included in a polypeptide.

Solution to Problem

As a result of extensive research to achieve the above objective, the inventors of the present disclosure have discovered compounds usable as protease substrates, in particular, peptide sequences usable as protease substrates/cleavable by a protease, and have found that they are useful for disease treatment involving administering a polypeptide comprising a peptide sequence cleavable by a protease (referred to in short as protease cleavage sequence), and that a polypeptide comprising the protease cleavage sequence is useful in the production of pharmaceutical compositions for treating a disease. Also, the inventors of the present disclosure have created polypeptides containing the protease cleavage sequence and a method for producing them, thereby completing the present disclosure.

The present disclosure is based on these findings, and specifically includes the embodiments described below by way of example:

[1] A protease substrate whose cleavage ratio by a protease is higher than that of a protease substrate that comprises any one of the sequences of SEQ ID NOs: 1, 2, and 3.

[2] The protease substrate according to [1], wherein the substrate has a higher cleavage ratio by human uPA than a protease substrate that comprises any one of the sequences of SEQ ID NOs: 1, 2, and 3.

[3] The protease substrate according to any one of [1] to [2], wherein the substrate has a higher cleavage ratio by human MT-SP1 than a protease substrate that comprises any one of the sequences of SEQ ID NOs: 1, 2, and 3

[4] The protease substrate according to any one of [1] to [3], wherein the substrate has a higher cleavage ratio by mouse uPA than a protease substrate that comprises any one of the sequences of SEQ ID NOs: 1, 2, and 3.

[5] The protease substrate according to any one of [1] to [4], wherein the substrate has a higher cleavage ratio by mouse MT-SP1 than a protease substrate that comprises any one of the sequences of SEQ ID NOs: 1, 2, and 3.

[6] The protease substrate according to any one of [1] to [5], wherein the substrate has a higher ratio of the cleavage ratio by human uPA to the cleavage ratio by human serum than a protease substrate that comprises any one of the sequences of SEQ ID NOs: 1, 2, and 3.

[7] The protease substrate according to any one of [1] to [6], wherein the substrate has a higher ratio of the cleavage ratio by human MT-SP1 to the cleavage ratio by human serum than a protease substrate that comprises any one of the sequences of SEQ ID NOs: 1, 2, and 3.

[8] The protease substrate according to any one of [1] to [7], wherein the substrate has a higher ratio of the cleavage ratio by mouse uPA to the cleavage ratio by human serum than a protease substrate that comprises any one of the sequences of SEQ ID NOs: 1, 2, and 3.

[9] The protease substrate according to any one of [1] to [8], wherein the substrate has a higher ratio of the cleavage ratio by mouse MT-SP1 to the cleavage ratio by human serum than a protease substrate that comprises any one of the sequences of SEQ ID NOs: 1, 2, and 3.

[10] The protease substrate according to any one of [1] to [9], wherein the substrate is not cleaved by human serum.

[11] The protease substrate according to [1] to [10], wherein the substrate comprises at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[12] A protease substrate comprising at least one sequence selected from the following: the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[13] The protease substrate according to [12], wherein the protease is matriptase and/or urokinase.

[14] The protease substrate according to any of [12] to [13], wherein the protease is at least one protease selected from human MT-SP1, mouse MT-SP1, human uPA, and mouse uPA.

[15] The protease substrate according to any one of [12] to [14], wherein the substrate has a higher cleavage ratio by said protease than a protease substrate that comprises any one of the sequences of SEQ ID NOs: 1, 2, and 3.

[16] The protease substrate according to any one of [12] to [15], wherein the substrate has a higher cleavage ratio by human uPA than a protease substrate that comprises any one of the sequences of SEQ ID NOs: 1, 2, and 3.

[17] The protease substrate according to any one of [12] to [16], wherein the substrate has a higher cleavage ratio by human MT-SP1 than a protease substrate that comprises any one of the sequences of SEQ ID NOs: 1, 2, and 3.

[18] The protease substrate according to any one of [12] to [17], wherein the substrate has a higher cleavage ratio by mouse uPA than a protease substrate that comprises any one of the sequences of SEQ ID NOs: 1, 2, and 3.

[19] The protease substrate according to any one of [12] to [18], wherein the substrate has a higher cleavage ratio by mouse MT-SP1 than a protease substrate that comprises any one of the sequences of SEQ ID NOs: 1, 2, and 3.

[20] The protease substrate according to any one of [12] to [19], wherein the substrate has a higher ratio of the cleavage ratio by human uPA to the cleavage ratio by human serum than a protease substrate that comprises any one of the sequences of SEQ ID NOs: 1, 2, and 3.

[21] The protease substrate according to any one of [12] to [20], wherein the substrate has a higher ratio of the cleavage ratio by human MT-SP1 to the cleavage ratio by human serum than a protease substrate that comprises any one of the sequences of SEQ ID NOs: 1, 2, and 3.

[22] The protease substrate according to any one of [12] to [21], wherein the substrate has a higher ratio of the cleavage ratio by mouse uPA to the cleavage ratio by human serum than a protease substrate that comprises any one of the sequences of SEQ ID NOs: 1, 2, and 3.

[23] The protease substrate according to any one of [12] to [22], wherein the substrate has a higher ratio of the cleavage ratio by mouse MT-SP1 to the cleavage ratio by human serum than a protease substrate that comprises any one of the sequences of SEQ ID NOs: 1, 2, and 3.

[24] The protease substrate according to any one of [12] to [23], wherein the substrate is not cleaved by human serum.

[25] Use of at least one sequence selected from the following as a protease cleavage sequence:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[26] A polypeptide comprising at least one sequence selected from the following: the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[27] The polypeptide according to [26], wherein said sequence selected from the following is a protease cleavage sequence cleavable by protease:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[28] A method for producing the polypeptide according to [26] or [27].

[29] A polynucleotide encoding the polypeptide according to [26] or [27].

[30] A vector comprising the polynucleotide according to [29].

[31] A host cell comprising the polynucleotide according to [29] or the vector according to [30].

[32] A method for producing the polypeptide according to [26] or [27], wherein the method comprises culturing the host cell according to [31].

[33] The method for producing a polypeptide according to [32], wherein the method comprises isolating the polypeptide from a culture supernatant.

[A-1] The polypeptide according to [27], wherein the polypeptide comprises an antigen-binding domain and a carrying moiety, wherein the carrying moiety has an inhibiting domain for inhibiting the antigen-binding activity of the antigen-binding domain.

[A-2] The polypeptide according to [A-1], wherein the inhibition of the antigen-binding activity of the antigen-binding domain by the inhibiting domain in a state where the protease cleavage sequence is cleaved by protease is weaker than the inhibition of the antigen-binding activity of the antigen-binding domain by the inhibiting domain in a state where the protease cleavage sequence is uncleaved.

[A-3] The polypeptide according to [A-1] or [A-2], wherein the antigen-binding domain has a shorter half-life in blood than the uncleaved polypeptide.

[A-4] The polypeptide according to any one of [A-1] to [A-3], wherein the antigen-binding domain has a shorter half-life in blood than the carrying moiety.

[A-5] The polypeptide according to any one of [A-1] to [A-4], wherein the molecular weight of the antigen-binding domain is smaller than the molecular weight of the carrying moiety.

[A-6] The polypeptide according to any one of [A-1] to [A-5], wherein the molecular weight of the antigen-binding domain is 60 kDa or less.

[A-7] The polypeptide according to any one of [A-1] to [A-6], wherein the carrying moiety has FcRn-binding activity, and the antigen-binding domain does not have FcRn-binding activity or has weaker FcRn-binding activity than the carrying moiety.

[A-8] The polypeptide according to any one of [A-1] to [A-7], wherein the antigen-binding domain can be released from the polypeptide, and wherein the antigen-binding domain has a higher antigen-binding activity in a state where it is released from the polypeptide than the antigen-binding activity in a state where it is not released from the polypeptide.

[A-9] The polypeptide according to any one of [A-1] to [A-8], wherein the antigen-binding activity of the antigen-binding domain is inhibited by the association of the antigen-binding domain with the inhibiting domain of the carrying moiety.

[A-10] The polypeptide according to [A-8], wherein the antigen-binding domain becomes releasable from the polypeptide due to cleavage of the protease cleavage sequence by protease.

[A-11] The polypeptide according to [A-9], wherein the association between the antigen-binding domain and the inhibiting domain of the carrying moiety is abolished by cleavage of the protease cleavage sequence by protease.

[A-12] The polypeptide according to any one of [A-1] to [A-11], wherein the protease is matriptase and/or urokinase.

[A-13] The polypeptide according to any one of [A-1] to [A-11], wherein the protease is at least one protease selected from human MT-SP1, mouse MT-SP1, human uPA, and mouse uPA.

[A-14] The polypeptide according to any one of [A-1] to [A-13], wherein a first flexible linker is further attached to one end of the protease cleavage sequence.

[A-15] The polypeptide according to [A-14], wherein the first flexible linker is a flexible linker consisting of a glycine-serine polymer.

[A-16] The polypeptide according to [A-14] or [A-15], wherein a second flexible linker is further attached to the other end of the protease cleavage sequence.

[A-17] The polypeptide according to [A-16], wherein the second flexible linker is a flexible linker consisting of a glycine-serine polymer.

[A-18] The polypeptide according to any one of [A-1] to [A-17], wherein the antigen-binding domain comprises or is a single-domain antibody, and wherein the inhibiting domain of the carrying moiety inhibits the antigen-binding activity of the single-domain antibody.

[A-19] The polypeptide according to [A-18], wherein the single-domain antibody is VHH, or VH having antigen-binding activity by its single domain, or VL having antigen-binding activity by its single domain.

[A-20] The polypeptide according to any one of [A-1] to [A-19], wherein the antigen-binding domain comprises a single-domain antibody, wherein the inhibiting domain of the carrying moiety is VHH, the antibody VH, or the antibody VL, and wherein the antigen-binding activity of the single-domain antibody is inhibited by the VHH, the antibody VH, or the antibody VL.

[A-21] The polypeptide according to any one of [A-1] to [A-20], wherein the antigen-binding domain comprises a single-domain antibody, wherein the inhibiting domain of the carrying moiety is VHH, antibody VH, or antibody VL, and wherein the antigen-binding activity of the single-domain antibody is inhibited by its association with the VHH, the antibody VH, or the antibody VL.

[A-22] The polypeptide according to any one of [A-18] to [A-21], wherein the single-domain antibody is VHH, or VH having antigen-binding activity by its single domain, wherein the inhibiting domain of the carrying moiety is antibody VL, and wherein the antigen-binding activity of the VHH or the VH having antigen-binding activity by its single domain is inhibited by its association with the antibody VL.

[A-23] The polypeptide according to any one of [A-18] to [A-22], wherein the single-domain antibody is VHH, and wherein the VHH has an amino acid substitution at at least one position selected from amino acid positions 37, 44, 45, and 47 (all according to Kabat numbering).

[A-24] The polypeptide according to any one of [A-18] to [A-22], wherein the single-domain antibody is VHH, and wherein the VHH comprises at least one amino acid selected from the amino acids of 37V, 44G, 45L, and 47W (all according to Kabat numbering).

[A-25] The polypeptide according to any one of [A-18] to [A-22], wherein the single-domain antibody is VHH, and wherein the VHH comprises at least one amino acid substitution selected from the amino acid substitutions F37V, Y37V, E44G, Q44G, R45L, H45L, G47W, F47W, L47W, T47W, and S47W (all according to Kabat numbering).

[A-26] The polypeptide according to any one of [A-18] to [A-22], wherein the single-domain antibody is VHH, and wherein the VHH has an amino acid substitution at at least one set of positions selected from 37/44, 37/45, 37/47, 44/45, 44/47, 45/47, 37/44/45, 37/44/47, 37/45/47, 44/45/47, and 37/44/45/47 (all according to the Kabat numbering).

[A-27] The polypeptide according to any one of [A-18] to [A-22], wherein the single-domain antibody is VHH, and wherein the VHH comprises at least one set of amino acids selected from 37V/44G, 37V/45L, 37V/47W, 44G/45L, 44G/47W, 45L/47W, 37V/44G/45L, 37V/44G/47W, 37V/45L/47W, 44G/45L/47W, and 37V/44G/45L/47W (all according to Kabat numbering).

[A-28] The polypeptide according to any one of [A-18] to [A-22], wherein the single-domain antibody is VHH, and wherein the VHH comprises at least one set of amino acid substitutions selected from F37V/R45L, F37V/G47W, R45L/G47W, and F37V/R45L/G47W (all according to Kabat numbering).

[A-29] The polypeptide according to any one of [A-18] to [A-21], wherein the single-domain antibody is VL having antigen-binding activity by its single domain, wherein the inhibiting domain of the carrying moiety is antibody VH, and wherein the antigen-binding activity of the VL having antigen-binding activity by its single domain is inhibited by its association with the antibody VH.

[A-30] The polypeptide according to any one of [A-1] to [A-29], wherein the carrying moiety has an FcRn-binding region.

[A-31] The polypeptide according to any one of [A-1] to [A-30], wherein the carrying moiety comprises an antibody constant region.

[A-32] The polypeptide according to [A-31], wherein the antibody constant region of the carrying moiety is fused to the antigen-binding domain via or without a linker.

[A-33] The polypeptide according to [A-31], wherein the carrying moiety comprises an antibody heavy-chain constant region, and wherein the antibody heavy-chain constant region is fused to the antigen-binding domain via or without a linker.

[A-34] The polypeptide according to [A-31], wherein the carrying moiety comprises an antibody light-chain constant region, and wherein the antibody light-chain constant region is fused to the antigen-binding domain via or without a linker.

[A-35] The polypeptide according to [A-33], wherein the N-terminus of the antibody heavy-chain constant region of the carrying moiety is fused to the C-terminus of the antigen-binding domain via or without a linker, and wherein the protease cleavage sequence is located within the sequence of the antigen-binding domain or in the antigen-binding domain side than the amino acid at position 122 (according to EU numbering) of the antibody heavy-chain constant region.

[A-36] The polypeptide according to [A-34], wherein the N-terminus of the antibody light-chain constant region of the carrying moiety is fused to the C-terminus of the antigen-binding domain via or without a linker, and wherein the protease cleavage sequence is located within the sequence of the antigen-binding domain or in the antigen-binding domain side than the amino acid at position 113 (according to Kabat numbering) of the antibody light-chain constant region.

[A-37] The polypeptide according to any one of [A-32] to [A-35], wherein the N-terminus of the antibody constant region of the carrying moiety is fused to the C-terminus of the antigen-binding domain via or without a linker, wherein the antigen-binding domain is a single-domain antibody or VHH generated from VH, and wherein the protease cleavage sequence is located within the sequence of the antibody constant region or in the antibody constant region side than the amino acid at position 109 (according to Kabat numbering) of the single-domain antibody of the antigen-binding domain.

[A-38] The polypeptide according to [A-32], wherein the N-terminus of the antibody constant region of the carrying moiety is fused to the C-terminus of the antigen-binding domain via or without a linker, and wherein the protease cleavage sequence is located in the vicinity of the boundary between the antigen-binding domain and the antibody constant region.

[A-39] The polypeptide according to [A-33], wherein the N-terminus of the antibody heavy-chain constant region of the carrying moiety is fused to the C-terminus of the antigen-binding domain via or without a linker, and wherein the protease cleavage sequence is located in the vicinity of the boundary between the antigen-binding domain and the antibody heavy-chain constant region.

[A-40] The polypeptide according to [A-34], wherein the N-terminus of the antibody light-chain constant region of the carrying moiety is fused to the C-terminus of the antigen-binding domain via or without a linker, and wherein the protease cleavage sequence is located in the vicinity of the boundary between the antigen-binding domain and the antibody light-chain constant region.

[A-41] The polypeptide according to [A-39], wherein the antigen-binding domain is a single-domain antibody or VHH generated from VH, and wherein the protease cleavage sequence is located between the amino acid at position 109 (according to Kabat numbering) of the single-domain antibody of the antigen-binding domain and the amino acid at position 122 (according to EU numbering) of the antibody heavy-chain constant region.

[A-42] The polypeptide according to [A-40], wherein the antigen-binding domain is a single-domain antibody or VHH generated from VH, and wherein the protease cleavage sequence is located between the amino acid at position 109 (according to Kabat numbering) of the single-domain antibody of the antigen-binding domain and the amino acid at position 113 (according to Kabat numbering) of the antibody light-chain constant region.

[A-43] The polypeptide according to [A-39], wherein the antigen-binding domain is a single-domain antibody generated from VL, and wherein the protease cleavage sequence is located between the amino acid at position 104 (according to Kabat numbering) of the single-domain antibody of the antigen-binding domain and the amino acid at position 122 (according to EU numbering) of the antibody heavy-chain constant region.

[A-44] The polypeptide according to [A-40], wherein the antigen-binding domain is a single-domain antibody generated from VL, and wherein the protease cleavage sequence is located between the amino acid at position 109 (according to Kabat numbering) of the single-domain antibody of the antigen-binding domain and the amino acid at position 113 (according to Kabat numbering) of the antibody light-chain constant region.

[A-45] The polypeptide according to any one of [A-31] to [A-44], wherein the antibody constant region of the polypeptide is an IgG antibody constant region.

[A-46] The polypeptide according to any one of [A-1] to [A-45], wherein the polypeptide is an IgG antibody-like molecule.

[A-47] The polypeptide according to any one of [A-1] to [A-46], wherein the binding between the antigen-binding domain and the antigen is not observed when assayed using the Bio-Layer Interferometry (BLI) method (Octet) in a state where the antigen-binding domain is not released.

[A-48] The polypeptide according to any one of [A-1] to [A-47], wherein a second antigen-binding domain is further linked to the antigen-binding domain.

[A-49] The polypeptide according to [A-48], wherein the second antigen-binding domain has an antigen-binding specificity different from that of the antigen-binding domain.

[A-50] The polypeptide according to [A-48] or [A-49], wherein the second antigen-binding domain comprises a second single-domain antibody.

[A-51] The polypeptide according to [A-50], wherein the antigen-binding domain is a single-domain antibody, wherein the second antigen-binding domain is a second single-domain antibody, wherein the antigen-binding domain and the second antigen-binding domain can be released from the polypeptide, and wherein the single-domain antibody and the second single-domain antibody form a bispecific antigen-binding molecule in a state where the antigen-binding domain and the second antigen binding domain are released.

[A-52] The polypeptide according to any one of [A-1] to [A-51], wherein the polypeptide further possesses other antigen-binding domain that is different from the antigen-binding domain, and wherein the antigen-binding activity of the other antigen-binding domain is also inhibited by linking with the carrying moiety of the polypeptide.

[A-53] The polypeptide according to [A-52], wherein the other antigen-binding domain and the antigen-binding domain have different antigen-binding specificity.

[A-54] A pharmaceutical composition comprising the polypeptide according to any one of [A-1] to [A-53].

[A-55] A method for producing the polypeptide according to any one of [A-1] to [A-53].

[A-56] A polynucleotide encoding the polypeptide according to any one of [A-1] to [A-53].

[A-57] A vector comprising the polynucleotide according to [A-56].

[A-58] A host cell comprising the polynucleotide according to [A-56] or the vector according to [A-57].

[A-59] A method for producing the polypeptide according to any one of [A-1] to [A-53], wherein the method comprises culturing the host cell according to [A-58].

[A-60] The method for producing a peptide according to [A-59], wherein the method comprises isolating the polypeptide from a culture supernatant.

[A-61] A method for releasing an antigen-binding domain from a polypeptide, wherein the method comprises cleaving with protease a portion that is contained in the polypeptide comprising the antigen-binding domain and that has at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[A-62] The method according to [A-61], wherein the polypeptide further comprises a carrying moiety, wherein the carrying moiety has an inhibiting domain for inhibiting the antigen-binding activity of the antigen-binding domain.

[A-63] The method according to [A-62], wherein the inhibition of the antigen-binding activity of the antigen-binding domain by the inhibiting domain in a state where the protease cleavage sequence is cleaved by protease is weaker than the inhibition of the antigen-binding activity of the antigen-binding domain by the inhibiting domain in a state where the protease cleavage sequence is uncleaved.

[A-64] The method according to [A-62] or [A-63], wherein the antigen-binding domain has a shorter half-life in blood than the uncleaved polypeptide.

[A-65] The method according to any one of [A-62] to [A-64], wherein the antigen-binding domain has a shorter half-life in blood than the carrying moiety.

[A-66] The method according to any one of [A-62] to [A-65], wherein the molecular weight of the antigen-binding domain is smaller than the molecular weight of the carrying moiety.

[A-67] The method according to any one of [A-62] to [A-66], wherein the molecular weight of the antigen-binding domain is 60 kDa or less.

[A-68] The method according to any one of [A-62] to [A-67], wherein the carrying moiety has FcRn-binding activity, and the antigen-binding domain does not have FcRn-binding activity or has weaker FcRn-binding activity than the carrying moiety.

[A-69] The method according to any one of [A-62] to [A-68], wherein the antigen-binding domain has higher antigen-binding activity in a state where the antigen-binding domain is released from the polypeptide than in a state where it is not released from the polypeptide.

[A-70] The method according to any one of [A-62] to [A-69], wherein the antigen-binding activity of the antigen-binding domain is inhibited by association of the antigen-binding domain with the inhibiting domain of the carrying moiety.

[A-71] The method according to [A-70], wherein the association between the antigen-binding domain and the inhibiting domain of the carrying moiety is abolished by cleavage of the protease cleavage sequence by protease.

[A-72] The method according to any one of [A-62] to [A-71], wherein the protease is matriptase and/or urokinase.

[A-73] The method according to any one of [A-62] to [A-71], wherein the protease is at least one protease selected from human MT-SP1, mouse MT-SP1, human uPA, and mouse uPA.

[A-74] The method according to any one of [A-62] to [A-73], wherein a first flexible linker is further attached to one end of the protease cleavage sequence.

[A-75] The method according to [A-74], wherein the first flexible linker is a flexible linker consisting of a glycine-serine polymer.

[A-76] The method according to [A-74] or [A-75], wherein a second flexible linker is further attached to the other end of the protease cleavage sequence.

[A-77] The method according to [A-76], wherein the second flexible linker is a flexible linker consisting of a glycine-serine polymer.

[A-78] The method according to any one of [A-62] to [A-77], wherein the antigen-binding domain comprises or is a single-domain antibody, and wherein the inhibiting domain of the carrying moiety inhibits the antigen-binding activity of the single-domain antibody.

[A-79] The method according to [A-78], wherein the single-domain antibody is VHH, VH having antigen-binding activity by its single domain, or VL having antigen-binding activity by its single domain.

[A-80] The method according to any one of [A-62] to [A-79], wherein the antigen-binding domain comprises a single-domain antibody, wherein the inhibiting domain of the carrying moiety is VHH, antibody VH, or antibody VL, and wherein the antigen-binding activity of the single-domain antibody is inhibited by the VHH, the antibody VH, or the antibody VL.

[A-81] The method according to any one of [A-62] to [A-80], wherein the antigen-binding domain comprises a single-domain antibody, wherein the inhibiting domain of the carrying moiety is VHH, antibody VH, or antibody VL, and wherein the antigen-binding activity of the single-domain antibody is inhibited by association with the VHH, the antibody VH, or the antibody VL.

[A-82] The method according to any one of [A-78] to [A-81], wherein the single-domain antibody is VHH, or VH having antigen-binding activity by its single domain, wherein the inhibiting domain of the carrying moiety is antibody VL, and wherein the antigen-binding activity of the VHH or the VH having antigen-binding activity by its single domain is inhibited by its association with the antibody VL.

[A-83] The method according to any one of [A-78] to [A-82], wherein the single-domain antibody is VHH, and wherein the VHH has an amino acid substitution at at least one position selected from amino acid positions 37, 44, 45, and 47 (all according to Kabat numbering).

[A-84] The method according to any one of [A-78] to [A-82], wherein the single-domain antibody is VHH, and wherein the VHH comprises at least one amino acid selected from the amino acids of 37V, 44G, 45L, and 47W (all according to Kabat numbering).

[A-85] The method according to any one of [A-78] to [A-82], wherein the single-domain antibody is VHH, and wherein the VHH comprises at least one amino acid substitution selected from amino acid substitutions F37V, Y37V, E44G, Q44G, R45L, H45L, G47W, F47W, L47W, T47W, and S47W (all according to Kabat numbering).

[A-86] The method according to any one of [A-78] to [A-82], wherein the single-domain antibody is VHH, and wherein the VHH has an amino acid substitution at at least one set of positions selected from 37/44, 37/45, 37/47, 44/45, 44/47, 45/47, 37/44/45, 37/44/47, 37/45/47, 44/45/47, and 37/44/45/47 (all according to the Kabat numbering).

[A-87] The method according to any one of [A-78] to [A-82], wherein the single-domain antibody is VHH, and wherein the VHH comprises at least one set of amino acids selected from 37V/44G, 37V/45L, 37V/47W, 44G/45L, 44G/47W, 45L/47W, 37V/44G/45L, 37V/44G/47W, 37V/45L/47W, 44G/45L/47W, and 37V/44G/45L/47W (all according to Kabat numbering).

[A-88] The method according to any one of [A-78] to [A-82], wherein the single-domain antibody is VHH, and wherein the VHH comprises at least one set of amino acid substitutions selected from F37V/R45L, F37V/G47W, R45L/G47W, and F37V/R45L/G47W (all according to Kabat numbering).

[A-89] The method according to any one of [A-78] to [A-81], wherein the single-domain antibody is VL having antigen-binding activity by its single domain, wherein the inhibiting domain of the carrying moiety is antibody VH, and wherein the antigen-binding activity of the VL having antigen-binding activity by its single domain is inhibited by its association with the antibody VH.

[A-90] The method according to any one of [A-62] to [A-89], wherein the carrying moiety has an FcRn-binding region.

[A-91] The method according to any one of [A-62] to [A-90], wherein the carrying moiety comprises an antibody constant region.

[A-92] The method according to [A-91], wherein the antibody constant region of the carrying moiety is fused to the antigen-binding domain via or without a linker.

[A-93] The method according to [A-91], wherein the carrying moiety comprises an antibody heavy-chain constant region, and wherein the antibody heavy-chain constant region is fused to the antigen-binding domain via or without a linker.

[A-94] The method according to [A-91], wherein the carrying moiety comprises an antibody light-chain constant region, and wherein the antibody light-chain constant region is fused to the antigen-binding domain via or without a linker.

[A-95] The method according to [A-93], wherein, in the polypeptide, the N-terminus of the antibody heavy-chain constant region of the carrying moiety is fused to the C-terminus of the antigen-binding domain via or without a linker, and wherein the protease cleavage sequence is located within the sequence of the antigen-binding domain or in the antigen-binding domain side than the amino acid at position 122 (according to EU numbering) of the antibody heavy-chain constant region.

[A-96] The method according to [A-94], wherein, in the polypeptide, the N-terminus of the antibody light-chain constant region of the carrying moiety is fused to the C-terminus of the antigen-binding domain via or without a linker, and wherein the protease cleavage sequence is located within the sequence of the antigen-binding domain or in the antigen-binding domain side than the amino acid at position 113 (according to Kabat numbering) of the antibody light-chain constant region.

[A-97] The method according to any one of [A-92] to [A-95], wherein, in the polypeptide, the N-terminus of the antibody constant region of the carrying moiety is fused to the C-terminus of the antigen-binding domain via or without a linker, wherein the antigen-binding domain is a single-domain antibody or VHH generated from VH, and wherein the protease cleavage sequence is located within the sequence of the antibody constant region or in the antibody constant region side than the amino acid at position 109 (according to Kabat numbering) of the single-domain antibody of the antigen-binding domain.

[A-98] The method according to [A-92], wherein, in the polypeptide, the N-terminus of the antibody constant region of the carrying moiety is fused to the C-terminus of the antigen-binding domain via or without a linker, and wherein the protease cleavage sequence is located in the vicinity of the boundary between the antigen-binding domain and the antibody constant region.

[A-99] The polypeptide according to [A-93], wherein, in the polypeptide, the N-terminus of the antibody heavy-chain constant region of the carrying moiety is fused to the C-terminus of the antigen-binding domain via or without a linker, and wherein the protease cleavage sequence is located in the vicinity of the boundary between the antigen-binding domain and the antibody heavy-chain constant region.

[A-100] The method according to [A-34], wherein, in the polypeptide, the N-terminus of the antibody light-chain constant region of the carrying moiety is fused to the C-terminus of the antigen-binding domain via or without a linker, and wherein the protease cleavage sequence is located in the vicinity of the boundary between the antigen-binding domain and the antibody light-chain constant region.

[A-101] The method according to [A-99], wherein the antigen-binding domain is a single-domain antibody or VHH generated from VH, and wherein the protease cleavage sequence is located between the amino acid at position 109 (according to Kabat numbering) of the single-domain antibody of the antigen-binding domain and the amino acid at position 122 (according to EU numbering) of the antibody heavy-chain constant region.

[A-102] The method according to [A-100], wherein the antigen-binding domain is a single-domain antibody or VHH generated from VH, and wherein the protease cleavage sequence is located between the amino acid at position 109 (according to Kabat numbering) of the single-domain antibody of the antigen-binding domain and the amino acid at position 113 (according to Kabat numbering) of the antibody light-chain constant region.

[A-103] The method according to [A-99], wherein the antigen-binding domain is a single-domain antibody generated from VL, and wherein the protease cleavage sequence is located between the amino acid at position 104 (according to Kabat numbering) of the single-domain antibody of the antigen-binding domain and the amino acid at position 122 (according to EU numbering) of the antibody heavy-chain constant region.

[A-104] The method according to [A-100], wherein the antigen-binding domain is a single-domain antibody generated from VL, and wherein the protease cleavage sequence is located between the amino acid at position 109 (according to Kabat numbering) of the single-domain antibody of the antigen-binding domain and the amino acid at position 113 (according to Kabat numbering) of the antibody light-chain constant region.

[A-105] The method according to any one of [A-91] to [A-104], wherein the antibody constant region of the polypeptide is an IgG antibody constant region.

[A-106] The method according to any one of [A-62] to [A-105], wherein the polypeptide is an IgG antibody-like molecule.

[A-107] The method according to any one of [A-62] to [A-106], wherein the binding between the antigen-binding domain and the antigen is not observed when assayed using the Bio-Layer Interferometry (BLI) method (Octet) in a state where the antigen-binding domain is not released.

[A-108] The method according to any one of [A-62] to [A-107], wherein a second antigen-binding domain is further linked to the antigen-binding domain.

[A-109] The method according to [A-108], wherein the second antigen-binding domain has an antigen-binding specificity different from that of the antigen-binding domain.

[A-110] The method according to [A-108] or [A-109], wherein the second antigen-binding domain comprises a second single-domain antibody.

[A-111] The method according to [A-110], wherein the antigen-binding domain is a single-domain antibody, wherein the second antigen-binding domain is a second single-domain antibody, wherein the antigen-binding domain and the second antigen-binding domain can be released from the polypeptide, and wherein the single-domain antibody and the second single-domain antibody form a bispecific antigen-binding molecule in a state where the antigen-binding domain and the second antigen binding domain are released.

[A-112] The method according to any one of [A-62] to [A-111], wherein the polypeptide further possesses other antigen-binding domain that is different from the antigen-binding domain, and wherein the antigen-binding activity of the other antigen-binding domain is also inhibited by linking with the carrying moiety of the polypeptide.

[A-113] The method according to [A-112], wherein the other antigen-binding domain and the antigen-binding domain have different antigen-binding specificity.

[B-1] The polypeptide according to [27], wherein the polypeptide is a ligand-binding molecule capable of binding to a ligand, wherein the binding of the ligand-binding molecule to the ligand in a state where the protease cleavage sequence is cleaved is weaker than the binding of the ligand-binding molecule to the ligand in a state where the protease cleavage sequence is not cleaved.

[B-2] The ligand-binding molecule according to [B-1], wherein the ligand is released from the ligand-binding molecule in a state where the protease cleavage sequence is cleaved.

[B-3] The ligand-binding molecule according to any one of [B-1] to [B-2], wherein the protease is matriptase and/or urokinase.

[B-4] The ligand-binding molecule according to any one of [B-1] to [B-3], wherein the protease is at least one protease selected from human MT-SP1, mouse MT-SP1, human uPA, and mouse uPA.

[B-5] The ligand-binding molecule according to any one of [B-1] to [B-4], wherein a first flexible linker is further attached to one end of the protease cleavage sequence.

[B-6] The ligand-binding molecule according to [B-5], wherein the first flexible linker is a flexible linker consisting of a glycine-serine polymer.

[B-7] The ligand-binding molecule according to [B-5] or [B-6], wherein a second flexible linker is further attached to the other end of the protease cleavage sequence.

[B-8] The ligand-binding molecule according to [B-7], wherein the second flexible linker is a flexible linker consisting of a glycine-serine polymer.

[B-9] The ligand-binding molecule according to any one of [B-1] to [B-8], wherein the ligand binding molecule comprises an antibody VH, an antibody VL, and an antibody constant region.

[B-10] The ligand-binding molecule according to [B-9], wherein the protease cleavage sequence, or the protease cleavage sequence and the first flexible linker, or the protease cleavage sequence, the first flexible linker, and the second flexible linker is located within the antibody constant region.

[B-11] The ligand-binding molecule according to [B-10], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 118 (according to EU numbering) of the antibody heavy-chain constant region to amino acid position 140 (according to EU numbering) of the antibody heavy-chain constant region.

[B-12] The ligand-binding molecule according to [B-10], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 108 (according to Kabat numbering) of the antibody light-chain constant region to amino acid position 131 (according to Kabat numbering) of the antibody light-chain constant region.

[B-13] The ligand-binding molecule according to [B-9], wherein the protease cleavage sequence, or the protease cleavage sequence and the first flexible linker, or the protease cleavage sequence, the first flexible linker, and the second flexible linker is located within the antibody VH or the antibody VL.

[B-14] The ligand-binding molecule according to [B-13], wherein the protease cleavage sequence, or the protease cleavage sequence and the first flexible linker, or the protease cleavage sequence, the first flexible linker, and the second flexible linker is introduced at an arbitrary position in the sequence selected from the group consisting of:

the sequences, in antibody VH, that span:

from amino acid position 7 (according to Kabat numbering) to amino acid position 16 (according to Kabat numbering);

from amino acid position 40 (according to Kabat numbering) to amino acid position 47 (according to Kabat numbering);

from amino acid position 55 (according to Kabat numbering) to amino acid position 69 (according to Kabat numbering);

from amino acid position 73 (according to Kabat numbering) to amino acid position 79 (according to Kabat numbering);

from amino acid position 83 (according to Kabat numbering) to amino acid position 89 (according to Kabat numbering);

from amino acid position 95 (according to Kabat numbering) to amino acid position 99 (according to Kabat numbering); and from amino acid position 101 (according to Kabat numbering) to amino acid position 113 (according to Kabat numbering).

[B-15] The ligand-binding molecule according to [B-13], wherein the protease cleavage sequence, or the protease cleavage sequence and the first flexible linker, or the protease cleavage sequence, the first flexible linker, and the second flexible linker is introduced at an arbitrary position in a sequence selected from the group consisting of: the sequences, in antibody VL, that span:

from amino acid position 7 (according to Kabat numbering) to amino acid position 19 (according to Kabat numbering);

from amino acid position 39 (according to Kabat numbering) to amino acid position 46 (according to Kabat numbering);

from amino acid position 49 (according to Kabat numbering) to amino acid position 62 (according to Kabat numbering); and from amino acid position 96 (according to Kabat numbering) to amino acid position 107 (according to Kabat numbering).

[B-16] The ligand-binding molecule according to [B-9], wherein the protease cleavage sequence, or the protease cleavage sequence and the first flexible linker, or the protease cleavage sequence, the first flexible linker, and the second flexible linker is located in the vicinity of the boundary between the antibody constant region and the antibody VH and/or in the vicinity of the boundary between the antibody constant region and the antibody VL.

[B-17] The ligand-binding molecule according to [B-17], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 109 (according to Kabat numbering) of antibody VH to amino acid position 122 (according to EU numbering) of the antibody heavy-chain constant region.

[B-18] The ligand-binding molecule according to [B-16], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 104 (according to Kabat numbering) of antibody VL to amino acid position 113 (according to Kabat numbering) of the antibody light-chain constant region.

[B-19] The ligand-binding molecule according to any one of [B-9] to [B-18], wherein the antibody VL and the antibody VH in the ligand-binding molecule are associated, and wherein the association is abolished by cleavage of the protease cleavage sequence by protease.

[B-20] The ligand-binding molecule according to any one of [B-1] to [B-19], wherein the ligand is a molecule having biological activity, and wherein the biological activity of the ligand is inhibited by binding of the ligand-binding molecule to the ligand.

[B-21] The ligand-binding molecule according to any one of [B-1] to [B-20], wherein the ligand is a cytokine or chemokine.

[B-22] The ligand-binding molecule according to any one of [B-1] to [B-20], wherein the ligand is a ligand selected from interleukins, interferons, hematopoietic factors, the TNF superfamily, chemokines, cell growth factors, and the TGF-β family.

[B-23] The ligand-binding molecule according to any one of [B-1] to [B-22], wherein the ligand-binding molecule is an IgG antibody.

[B-24] The ligand-binding molecule according to any one of [B-1] to [B-23], which is bound to the ligand.

[B-25] The ligand-binding molecule according to any one of [B-1] to [B-23], which is fused to the ligand.

[B-26] The ligand-binding molecule according to [B-25], which does not further bind to a different ligand in a state where the ligand-binding molecule is fused to the ligand.

[B-27] The ligand-binding molecule according to [B-25] or [B-26], wherein the ligand-binding molecule is fused to the ligand via a linker.

[B-28] The ligand-binding molecule according to [B-27], wherein the linker does not comprise a protease cleavage sequence.

[B-29] A complex formed of the ligand and the ligand-binding molecule according to any one of [B-1] to [B-23] that is bound to the ligand.

[B-30] A fusion protein, wherein the ligand is fused to the ligand-binding molecule according to any one of [B-1] to [B-23].

[B-31] The fusion protein according to [B-30], which does not further bind to a different ligand in a state where the ligand-binding molecule is fused to the ligand.

[B-32] The fusion protein according to [B-30] or [B-31], wherein the ligand-binding molecule is fused to the ligand via a linker.

[B-33] The fusion protein according to [B-32], wherein the linker does not comprise a protease cleavage sequence.

[B-34] The fusion protein according to [B-32] or [B-33], wherein the linker is a linker consisting of a glycine-serine polymer.

[B-35] A pharmaceutical composition comprising the ligand-binding molecule according to any one of [B-1] to [B-28].

[B-36] A pharmaceutical composition comprising the ligand-binding molecule according to any one of [B-1] to [B-24] and a ligand.

[B-37] A pharmaceutical composition comprising the complex according to [B-29].

[B-38] A pharmaceutical composition comprising the fusion protein according to any one of [B-30] to [B-34].

[B-39] A method for producing the ligand-binding molecule according to any one of [B-1] to [B-28].

[B-40] The production method according to [B-39], comprising introducing a protease cleavage sequence into a molecule capable of binding to a ligand.

[B-41] A method for producing the fusion protein according to any one of [B-30] to [B-34], wherein the method comprises fusing a ligand-binding molecule having a protease cleavage sequence to its ligand.

[B-42] A polynucleotide encoding the ligand-binding molecule according to any one of [B-1] to [B-28].

[B-43] A vector comprising the polynucleotide according to [B-42].

[B-44] A host cell comprising the polynucleotide according to [B-42] or the vector according to [B-43].

[B-45] A method for producing the ligand-binding molecule according to any one of [B-1] to [B-28], wherein the method comprises culturing the host cell according to [B-44].

[B-46] A method for producing the ligand-binding molecule according to [B-45], wherein the method comprises isolating a polypeptide from a culture supernatant.

[B-47] A polynucleotide encoding the fusion protein according to any one of [B-30] to [B-34].

[B-48] A vector comprising the polynucleotide according to [B-46].

[B-49] A host cell comprising the polynucleotide according to [B-46] or the vector according to [B-48].

[B-50] A method for producing the fusion protein according to any one of [B-30] to [B-34], wherein the method comprises culturing the host cell according to [B-49].

[B-51] A method for producing the fusion protein according to [B-50], wherein the method comprises isolating a polypeptide from a culture supernatant.

[B-52] A method for releasing a ligand bound to a ligand-binding molecule, wherein the method comprises cleaving, by protease, a portion contained in the ligand-binding molecule capable of binding to the ligand, wherein the portion has at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[B-53] A method for releasing a ligand from a fusion protein of the ligand and a ligand-binding molecule, wherein the method comprises cleaving, by protease, a portion contained in the ligand-binding molecule in the fusion protein, wherein the portion has at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[B-54] The method according to [B-53], wherein the ligand-binding molecule is fused to the ligand via a linker.

[B-55] The method according to [B-54], wherein the linker does not comprise a protease cleavage sequence.

[B-56] The method according to [B-54] or [B-55], wherein the linker is a linker consisting of a glycine-serine polymer.

[B-57] The method according to any one of [B-53] to [B-56], wherein the ligand-binding molecule does not further bind to a different ligand in a state where the ligand-binding molecule is fused to the ligand.

[B-58] The method according to any one of [B-52] to [B-57], wherein the binding of the ligand-binding molecule to the ligand in a state where the protease cleavage sequence is cleaved is weaker than the binding of the ligand-binding molecule to the ligand in a state where the protease cleavage sequence is not cleaved.

[B-59] The method according to any one of [B-52] to [B-58], wherein the protease is matriptase and/or urokinase.

[B-60] The method according to any one of [B-52] to [B-59], wherein the protease is at least one protease selected from human MT-SP1, mouse MT-SP1, human uPA, and mouse uPA.

[B-61] The method according to any one of [B-52] to [B-60], wherein a first flexible linker is further attached to one end of the protease cleavage sequence.

[B-62] The method according to [B-61], wherein the first flexible linker is a flexible linker consisting of a glycine-serine polymer.

[B-63] The method according to [B-61] or [B-62], wherein a second flexible linker is further attached to the other end of the protease cleavage sequence.

[B-64] The method according to [B-63], wherein the second flexible linker is a flexible linker consisting of a glycine-serine polymer.

[B-65] The method according to any one of [B-52] to [B-64], wherein the ligand-binding molecule comprises an antibody VH, an antibody VL, and an antibody constant region.

[B-66] The method according to [B-65], wherein the protease cleavage sequence, or the protease cleavage sequence and the first flexible linker, or the protease cleavage sequence, the first flexible linker, and the second flexible linker is located within the antibody constant region.

[B-67] The method according to [B-66], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 118 (according to EU numbering) of the antibody heavy-chain constant region to amino acid position 140 (according to EU numbering) of the antibody heavy-chain constant region.

[B-68] The method according to [B-66], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 108 (according to Kabat numbering) of the antibody light-chain constant region to amino acid position 131 (according to Kabat numbering) of the antibody light-chain constant region.

[B-69] The method according to [B-65], wherein the protease cleavage sequence, or the protease cleavage sequence and the first flexible linker, or the protease cleavage sequence, the first flexible linker, and the second flexible linker is located within the antibody VH or the antibody VL.

[B-70] The method according to [B-69], wherein the protease cleavage sequence, or the protease cleavage sequence and the first flexible linker, or the protease cleavage sequence, the first flexible linker, and the second flexible linker is introduced at an arbitrary position in a sequence selected from the group consisting of:

the sequences, in antibody VH, that span:

from amino acid position 7 (according to Kabat numbering) to amino acid position 16 (according to Kabat numbering);

from amino acid position 40 (according to Kabat numbering) to amino acid position 47 (according to Kabat numbering);

from amino acid position 55 (according to Kabat numbering) to amino acid position 69 (according to Kabat numbering);

from amino acid position 73 (according to Kabat numbering) to amino acid position 79 (according to Kabat numbering);

from amino acid position 83 (according to Kabat numbering) to amino acid position 89 (according to Kabat numbering);

from amino acid position 95 (according to Kabat numbering) to amino acid position 99 (according to Kabat numbering); and from amino acid position 101 (according to Kabat numbering) to amino acid position 113 (according to Kabat numbering).

[B-71] The method according to [B-69], wherein the protease cleavage sequence, or the protease cleavage sequence and the first flexible linker, or the protease cleavage sequence, the first flexible linker, and the second flexible linker is introduced at an arbitrary position in a sequence selected from the group consisting of:

the sequences, in antibody VL, that span:

from amino acid position 7 (according to Kabat numbering) to amino acid position 19 (according to Kabat numbering);

from amino acid position 39 (according to Kabat numbering) to amino acid position 46 (according to Kabat numbering);

from amino acid position 49 (according to Kabat numbering) to amino acid position 62 (according to Kabat numbering); and from amino acid position 96 (according to Kabat numbering) to amino acid position 107 (according to Kabat numbering).

[B-72] The method according to [B-65], wherein the protease cleavage sequence, or the protease cleavage sequence and the first flexible linker, or the protease cleavage sequence, the first flexible linker, and the second flexible linker is located in the vicinity of the boundary between the antibody constant region and the antibody VH and/or in the vicinity of the boundary between the antibody constant region and the antibody VL.

[B-73] The method according to [B-73], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 109 (according to Kabat numbering) of antibody VH to amino acid position 122 (according to EU numbering) of the antibody heavy-chain constant region.

[B-74] The method according to [B-72], wherein the protease cleavage sequence, or the protease cleavage sequence and the first flexible linker, or the protease cleavage sequence, the first flexible linker, and the second flexible linker is introduced at an arbitrary position in the sequence spanning from amino acid position 104 (according to Kabat numbering) of antibody VL to amino acid position 113 (according to Kabat numbering) of the antibody light-chain constant region.

[B-75] The method according to any one of [B-65] to [B-74], wherein the antibody VL and antibody VH in the ligand-binding molecule are associated, and wherein the association is abolished by cleavage of the protease cleavage sequence by protease.

[B-76] The method according to any one of [B-52] to [B-75], wherein the ligand is a molecule having biological activity, and wherein the biological activity of the ligand is inhibited by binding of the ligand-binding molecule to the ligand.

[B-77] The method according to any one of [B-52] to [B-76], wherein the ligand is a cytokine or chemokine.

[B-78] The method according to any one of [B-52] to [B-76], wherein the ligand is a ligand selected from interleukins, interferons, hematopoietic factors, the TNF superfamily, chemokines, cell growth factors, and the TGF-β family.

[B-79] The method according to any one of [B-52] to [B-78], wherein the ligand-binding molecule is an IgG antibody.

[C-1] The polypeptide according to [27], wherein the polypeptide is a ligand-binding molecule capable of binding to a ligand, wherein the ligand-binding molecule comprises a single-domain antibody, wherein the single-domain antibody is capable of binding to a ligand and is introduced with at least one of the protease cleavage sequences, and wherein the binding of the ligand-binding molecule to the ligand in a state where the protease cleavage sequence is cleaved is attenuated compared to the binding of the ligand-binding molecule to the ligand in a state where the protease cleavage sequence is not cleaved.

[C-2] The ligand-binding molecule according to [C-1], wherein the ligand is released from the ligand-binding molecule in a state where the protease cleavage sequence is cleaved.

[C-3] The ligand-binding molecule according to [C-1] or [C-2], wherein the protease is matriptase and/or urokinase.

[C-4] The ligand-binding molecule according to any one of [C-1] to [C-3], wherein the protease is at least one protease selected from human MT-SP1, mouse MT-SP1, human uPA, and mouse uPA.

[C-5] The ligand-binding molecule according to any one of [C-1] to [C-4], wherein a first flexible linker is further attached to one end of the protease cleavage sequence.

[C-6] The ligand-binding molecule according to [C-5], wherein the first flexible linker is a flexible linker consisting of a glycine-serine polymer.

[C-7] The ligand-binding molecule according to [C-5] or [C-6], wherein a second flexible linker is further attached to the other end of the protease cleavage sequence.

[C-8] The ligand-binding molecule according to [C-7], wherein the second flexible linker is a flexible linker consisting of a glycine-serine polymer.

[C-9] The ligand-binding molecule according to any one of [C-1] to [C-8], wherein the single-domain antibody is VHH, a single-domain VH antibody, or a single-domain VL antibody.

[C-10] The ligand-binding molecule according to [C-9], wherein the single-domain antibody is VHH or a single-domain VH antibody, and wherein the cleavage site, or the protease cleavage sequence, or the protease cleavage sequence and the first flexible linker, or the protease cleavage sequence, the first flexible linker, and the second flexible linker, is introduced at one or a plurality of positions included in one or a plurality of sequences selected from the following sequences of the single-domain antibody:

the sequence spanning from amino acid position 7 (according to Kabat numbering) to amino acid position 17 (according to Kabat numbering) of the single-domain antibody;

the sequence spanning from amino acid position 12 (according to Kabat numbering) to amino acid position 17 (according to Kabat numbering) of the single-domain antibody;

the sequence spanning from amino acid position 31 (according to Kabat numbering) to amino acid position 35b (according to Kabat numbering) of the single-domain antibody;

the sequence spanning from amino acid position 40 (according to Kabat numbering) to amino acid position 47 (according to Kabat numbering) of the single-domain antibody;

the sequence spanning from amino acid position 50 (according to Kabat numbering) to amino acid position 65 (according to Kabat numbering) of the single-domain antibody;

the sequence spanning from amino acid position 55 (according to Kabat numbering) to amino acid position 69 (according to Kabat numbering) of the single-domain antibody;

the sequence spanning from amino acid position 73 (according to Kabat numbering) to amino acid position 79 (according to Kabat numbering) of the single-domain antibody;

the sequence spanning from amino acid position 83 (according to Kabat numbering) to amino acid position 89 (according to Kabat numbering) of the single-domain antibody;

the sequence spanning from amino acid position 95 (according to Kabat numbering) to amino acid position 99 (according to Kabat numbering) of the single-domain antibody;

the sequence spanning from amino acid position 95 (according to Kabat numbering) to amino acid position 102 (according to Kabat numbering) of the single-domain antibody; and the sequence spanning from amino acid position 101 (according to Kabat numbering) to amino acid position 113 (according to Kabat numbering) of the single-domain antibody.

[C-11] The ligand-binding molecule according to [C-9], wherein the single-domain antibody is a single-domain VL antibody, and wherein the cleavage site, or the protease cleavage sequence, or the protease cleavage sequence and the first flexible linker, or the protease cleavage sequence, the first flexible linker, and the second flexible linker is introduced at one or a plurality of positions included in one or a plurality of sequences selected from the following sequences of the single-domain antibody:

the sequence spanning from amino acid position 7 (according to Kabat numbering) to amino acid position 19 (according to Kabat numbering) of the single-domain antibody;

the sequence spanning from amino acid position 24 (according to Kabat numbering) to amino acid position 34 (according to Kabat numbering) of the single-domain antibody;

the sequence spanning from amino acid position 39 (according to Kabat numbering) to amino acid position 46 (according to Kabat numbering) of the single-domain antibody;

the sequence spanning from amino acid position 49 (according to Kabat numbering) to amino acid position 62 (according to Kabat numbering) of the single-domain antibody;

the sequence spanning from amino acid position 50 (according to Kabat numbering) to amino acid position 56 (according to Kabat numbering) of the single-domain antibody;

the sequence spanning from amino acid position 89 (according to Kabat numbering) to amino acid position 97 (according to Kabat numbering) of the single-domain antibody; and the sequence spanning from amino acid position 96 (according to Kabat numbering) to amino acid position 107 (according to Kabat numbering) of the single-domain antibody.

[C-12] The ligand-binding molecule according to any one of [C-1] to [C-11], wherein the ligand is a molecule having biological activity, and wherein the biological activity of the ligand is inhibited by binding of the single-domain antibody to the ligand.

[C-13] The ligand-binding molecule according to any one of [C-1] to [C-12], wherein the ligand is a molecule having biological activity, and wherein the single-domain antibody has neutralizing activity on the ligand.

[C-14] The ligand-binding molecule according to any one of [C-1] to [C-13], wherein the ligand-binding molecule comprises only a single-domain antibody comprising the cleavage site or the protease cleavage sequence.

[C-15] The ligand-binding molecule according to any one of [C-1] to [C-14], wherein the ligand-binding molecule further comprises an antibody Fc region.

[C-16] The ligand-binding molecule according to any one of [C-1] to [C-15], wherein the ligand-binding molecule comprises a series of peptide chains consisting of single-domain antibody-antibody Fc region in the direction from the N-terminus to the C-terminus.

[C-17] The ligand-binding molecule according to [C-1] to [C-15], wherein the ligand-binding molecule is a dimer comprising two series of peptide chains consisting of single-domain antibody-antibody hinge region-antibody Fc region.

[C-18] The ligand-binding molecule according to [C-15] to [C-17], wherein the antibody Fc region is an Fc region comprising one sequence selected from the amino acid sequences shown in SEQ ID NOs: 18004-18007, or an Fc region variant obtained by modifying these Fc regions.

[C-19] The ligand-binding molecule according to any one of [C-1] to [C-18], wherein the ligand is a cytokine or chemokine.

[C-20] The ligand-binding molecule according to any one of [C-1] to [C-19], wherein the ligand is a ligand selected from interleukins, interferons, hematopoietic factors, the TNF superfamily, chemokines, cell growth factors, and the TGF-β family.

[C-21] The ligand-binding molecule according to any one of [C-1] to [C-20], which is bound to the ligand.

[C-22] The ligand-binding molecule according to any one of [C-1] to [C-20], which is fused to the ligand.

[C-23] The ligand-binding molecule according to [C-22], wherein the single-domain antibody contained in the ligand-binding molecule does not further bind to a different ligand in a state where the ligand-binding molecule is fused to the ligand.

[C-24] The ligand-binding molecule according to [C-22] or [C-23], wherein the ligand-binding molecule is fused to the ligand via a linker.

[C-25] The ligand-binding molecule according to [C-24], wherein the linker does not comprise a protease cleavage sequence.

[C-26] A complex formed of the ligand and the ligand-binding molecule according to any one of [C-1] to [C-20].

[C-27] A fusion protein, wherein the ligand is fused to the ligand-binding molecule according to any one of [C-1] to [C-20].

[C-28] The fusion protein according to [C-27], wherein the single-domain antibody does not further bind to a different ligand in a state where the ligand-binding molecule is fused to the ligand.

[C-29] The fusion protein according to [C-27] or [C-28], wherein the ligand-binding molecule is fused to the ligand via a linker.

[C-30] The fusion protein according to [C-29], wherein the linker does not comprise a protease cleavage sequence.

[C-31] The fusion protein according to [C-29] or [C-30], wherein the ligand, the linker, and the ligand-binding molecule are fused in this order in the direction from the N-terminus to the C-terminus.

[C-32] A pharmaceutical composition comprising the ligand-binding molecule according to any one of [C-1] to [C-22].

[C-33] A pharmaceutical composition comprising the ligand-binding molecule according to any one of [C-1] to [C-21] and a ligand.

[C-34] A pharmaceutical composition comprising the complex according to [C-26].

[C-35] A pharmaceutical composition comprising the fusion protein according to any one of [C-27] to [C-31].

[C-36] A method for producing the ligand-binding molecule according to any one of [C-1] to [C-20].

[C-37] The production method according to [C-36], wherein the method comprises introducing a protease cleavage sequence into a single-domain antibody in a ligand-binding molecule comprising the single-domain antibody.

[C-38] A method for producing the fusion protein according to any one of [C-27] to [C-31], wherein the method comprises fusing a ligand-binding molecule containing a single-domain antibody being introduced with a protease cleavage sequence to a ligand capable of binding to the single-domain antibody.

[C-39] A polynucleotide encoding the ligand-binding molecule according to any one of [C-1] to [C-20].

[C-40] A vector comprising the polynucleotide according to [C-39].

[C-41] A host cell comprising the polynucleotide according to [C-39] or the vector according to [C-40].

[C-42] A method for producing the ligand-binding molecule according to any one of [C-1] to [C-20], wherein the method comprises culturing the host cell according to [C-41].

[C-43] The method for producing the ligand-binding molecule according to [C-42], wherein the method comprises isolating a polypeptide from a culture supernatant.

[C-44] A polynucleotide encoding the fusion protein according to any one of [C-27] to [C-31].

[C-45] A vector comprising the polynucleotide according to [C-43].

[C-46] A host cell comprising the polynucleotide according to [C-43] or the vector according to [C-45].

[C-47] A method for producing the fusion protein according to any one of [C-27] to [C-31], wherein the method comprises culturing the host cell according to [C-46].

[C-48] The method for producing the ligand-binding molecule according to [C-47], wherein the method comprises isolating a polypeptide from a culture supernatant.

[C-49] A method for releasing a ligand bound to a ligand-binding molecule, wherein the method comprises cleaving, by protease, a portion contained in a single-domain antibody in the ligand-binding molecule capable of binding to the ligand, wherein the portion has at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[C-50] A method for releasing a ligand from a fusion protein of the ligand and a ligand-binding molecule, wherein the method comprises cleaving, by protease, a portion contained in a single-domain antibody in the ligand-binding molecule capable of binding to the ligand, wherein the portion has at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

[C-51] The method according to [C-50], wherein the ligand-binding molecule is fused to the ligand via a linker.

[C-52] The method according to [C-51], wherein the linker does not comprise a protease cleavage sequence.

[C-53] The method according to [C-51] or [C-52], wherein the linker is a linker consisting of a glycine-serine polymer.

[C-54] The method according to any one of [C-50] to [C-53], wherein the ligand-binding molecule does not further bind to a different ligand in a state where the ligand-binding molecule is fused to the ligand.

[C-55] The method according to any one of [C-49] to [C-54], wherein the binding of the ligand-binding molecule to the ligand in a state where the protease cleavage sequence is cleaved is attenuated compared to the binding of the ligand-binding molecule to the ligand in a state where the protease cleavage sequence is not cleaved.

[C-56] The method according to [C-55], wherein the ligand is released from the ligand-binding molecule in a state where the protease cleavage sequence is cleaved.

[C-57] The method according to [C-55] or [C-56], wherein the protease is matriptase and/or urokinase.

[C-58] The method according to any one of [C-55] to [C-57], wherein the protease is at least one protease selected from human MT-SP1, mouse MT-SP1, human uPA, and mouse uPA.

[C-59] The method according to any one of [C-55] to [C-58], wherein a first flexible linker is further attached to one end of the protease cleavage sequence.

[C-60] The method according to [C-59], wherein the first flexible linker is a flexible linker consisting of a glycine-serine polymer.

[C-61] The method according to [C-59] or [C-60], wherein a second flexible linker is further attached to the other end of the protease cleavage sequence.

[C-62] The method according to [C-61], wherein the second flexible linker is a flexible linker consisting of a glycine-serine polymer.

[C-63] The method according to any one of [C-55] to [C-62], wherein the single-domain antibody is VHH, a single-domain VH antibody, or a single-domain VL antibody.

[C-64] The method according to [C-63], wherein the single-domain antibody is VHH or a single-domain VH antibody, and wherein the cleavage site, or the protease cleavage sequence, or the protease cleavage sequence and the first flexible linker, or the protease cleavage sequence, the first flexible linker, and the second flexible linker is introduced at one or a plurality of positions included in one or a plurality of sequences selected from the following sequences of the single-domain antibody:

the sequence spanning from amino acid position 7 (according to Kabat numbering) to amino acid position 17 (according to Kabat numbering) of the single-domain antibody;

the sequence spanning from amino acid position 12 (according to Kabat numbering) to amino acid position 17 (according to Kabat numbering) of the single-domain antibody;

the sequence spanning from amino acid position 31 (according to Kabat numbering) to amino acid position 35b (according to Kabat numbering) of the single-domain antibody;

the sequence spanning from amino acid position 40 (according to Kabat numbering) to amino acid position 47 (according to Kabat numbering) of the single-domain antibody;

the sequence spanning from amino acid position 50 (according to Kabat numbering) to amino acid position 65 (according to Kabat numbering) of the single-domain antibody;

the sequence spanning from amino acid position 55 (according to Kabat numbering) to amino acid position 69 (according to Kabat numbering) of the single-domain antibody;

the sequence spanning from amino acid position 73 (according to Kabat numbering) to amino acid position 79 (according to Kabat numbering) of the single-domain antibody;

the sequence spanning from amino acid position 83 (according to Kabat numbering) to amino acid position 89 (according to Kabat numbering) of the single-domain antibody;

the sequence spanning from amino acid position 95 (according to Kabat numbering) to amino acid position 99 (according to Kabat numbering) of the single-domain antibody;

the sequence spanning from amino acid position 95 (according to Kabat numbering) to amino acid position 102 (according to Kabat numbering) of the single-domain antibody; and the sequence spanning from amino acid position 101 (according to Kabat numbering) to amino acid position 113 (according to Kabat numbering) of the single-domain antibody.

[C-65] The method according to [C-63], wherein the single-domain antibody is a single-domain VL antibody, and wherein the cleavage site, or the protease cleavage sequence, or the protease cleavage sequence and the first flexible linker, or the protease cleavage sequence, the first flexible linker, and the second flexible linker is introduced at one or a plurality of positions included in one or a plurality of sequences selected from the following sequences of the single-domain antibody:

the sequence spanning from amino acid position 7 (according to Kabat numbering) to amino acid position 19 (according to Kabat numbering) of the single-domain antibody;

the sequence spanning from amino acid position 24 (according to Kabat numbering) to amino acid position 34 (according to Kabat numbering) of the single-domain antibody;

the sequence spanning from amino acid position 39 (according to Kabat numbering) to amino acid position 46 (according to Kabat numbering) of the single-domain antibody;

the sequence spanning from amino acid position 49 (according to Kabat numbering) to amino acid position 62 (according to Kabat numbering) of the single-domain antibody;

the sequence spanning from amino acid position 50 (according to Kabat numbering) to amino acid position 56 (according to Kabat numbering) of the single-domain antibody;

the sequence spanning from amino acid position 89 (according to Kabat numbering) to amino acid position 97 (according to Kabat numbering) of the single-domain antibody; and the sequence spanning from amino acid position 96 (according to Kabat numbering) to amino acid position 107 (according to Kabat numbering) of the single-domain antibody.

[C-66] The method according to any one of [C-55] to [C-65], wherein the ligand is a molecule having biological activity, and wherein the biological activity of the ligand is inhibited by binding of the single-domain antibody to the ligand.

[C-67] The method according to any one of [C-55] to [C-66], wherein the ligand is a molecule having biological activity, and wherein the single-domain antibody has neutralizing activity on the ligand.

[C-68] The method according to any one of [C-55] to [C-67], wherein the ligand-binding molecule comprises only a single-domain antibody comprising the cleavage site or the protease cleavage sequence.

[C-69] The method according to any one of [C-55] to [C-68], wherein the ligand-binding molecule further comprises an antibody Fc region.

[C-70] The method according to any one of [C-55] to [C-69], wherein the ligand-binding molecule comprises a series of peptide chains consisting of single-domain antibody-antibody Fc region in the direction from the N-terminus to the C-terminus.

[C-71] The method according to [C-55] to [C-69], wherein the ligand-binding molecule is a dimer comprising two series of peptide chains consisting of single-domain antibody-antibody hinge region-antibody Fc region.

[C-72] The method according to [C-69] to [C-71], wherein the antibody Fc region is an Fc region comprising one sequence selected from the amino acid sequences shown in SEQ ID NOs: 18004-18007, or an Fc region variant obtained by modifying these Fc regions.

[C-73] The method according to any one of [C-55] to [C-72], wherein the ligand is a cytokine or chemokine.

[C-74] The method according to any one of [C-55] to [C-73], wherein the ligand is a ligand selected from interleukins, interferons, hematopoietic factors, the TNF superfamily, chemokines, cell growth factors, and the TGF-β family.

BRIEF DESCRIPTION OF DRAWINGS

FIG. 1 illustrates an example of a polypeptide comprising a protease cleavage sequence of the present disclosure. In this figure, the polypeptide contains an antigen-binding domain and a carrying moiety. (A) The polypeptide has a long half-life and does not bind to the antigen in a state where the antigen-binding domains and carrying moieties are linked. (B) When the antigen-binding domains are released, for example, by cleavage of the protease cleavage sequences, and bind to the antigen, the released antigen-binding domains have a short half-life.

FIG. 2 illustrates an embodiment of a method for producing the polypeptide shown in FIG. 1. In this embodiment, the polypeptide of interest is an IgG-like molecule. (A) A single-domain antibody that binds to the target antigen is obtained. (B) The single-domain antibody is associated with VL in place of the VH of an IgG antibody, so that the antigen-binding activity of the single-domain antibody is inhibited. (C) Protease cleavage sequence is introduced into a precursor of the IgG antibody-like molecule which is introduced with the single-domain antibody.

FIG. 4 illustrates an example of a polypeptide comprising a protease cleavage sequence of the present disclosure. In this figure, a linked antigen-binding domain and second antigen-binding domain are contained in the polypeptide. In this example, released antigen-binding domain and second antigen-binding domain form a bispecific antigen-binding molecule. (A) The polypeptide in an unreleased state is illustrated. The antigen-binding activity of the antigen-binding domains is inhibited. (B) Release of the bispecific antigen-binding molecule formed of the antigen-binding domain and the second antigen-binding domain is illustrated. (C) A bispecific antigen-binding molecule against, for example, T-cell surface antigen and tumor surface antigen is illustrated as an example of the released bispecific antigen-binding molecule.

FIG. 9 illustrates an example of a polypeptide comprising a protease cleavage sequence of the present disclosure. In this figure, the polypeptide is a dimeric protein comprising a single-domain antibody containing the protease cleavage sequence-antibody hinge region-antibody Fc region.

FIG. 13 shows the results of SDS-PAGE of protease-treated and protease-untreated fusion proteins. While the control molecule containing no protease cleavage sequence shows a band at the same position regardless of whether it is treated or untreated with protease, the respective fusion proteins comprising a ligand-binding molecule containing a single-domain antibody introduced with a protease cleavage sequence show novel bands generated only after protease treatment, thus indicating that the fusion proteins comprising a ligand-binding molecule containing a single-domain antibody introduced with each protease cleavage sequence are cleaved by the protease treatment.

Figure 15:
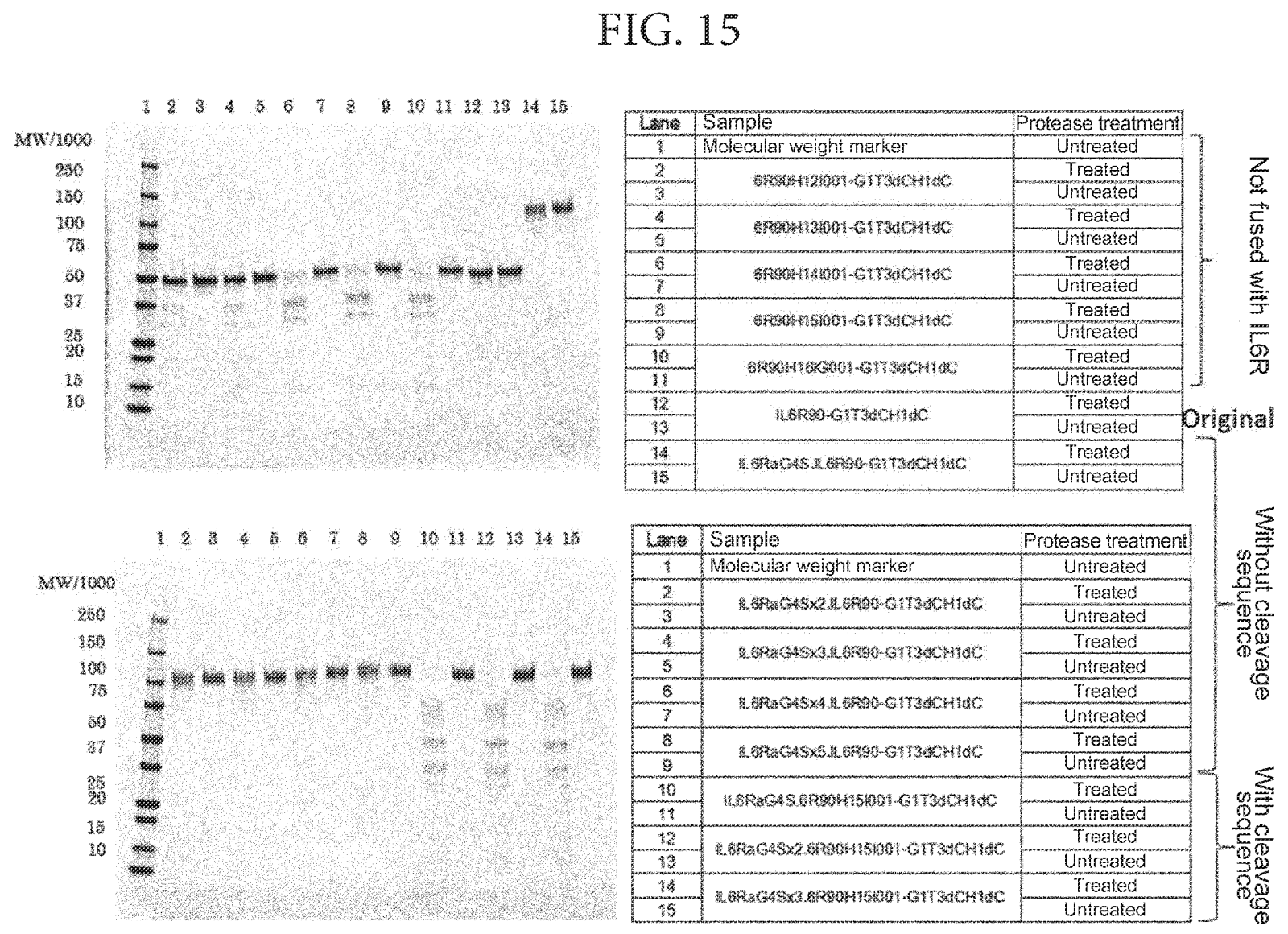

FIG. 15 shows the continuation of FIG. 14.

DESCRIPTION OF EMBODIMENTS

Amino Acids

Figure 3:
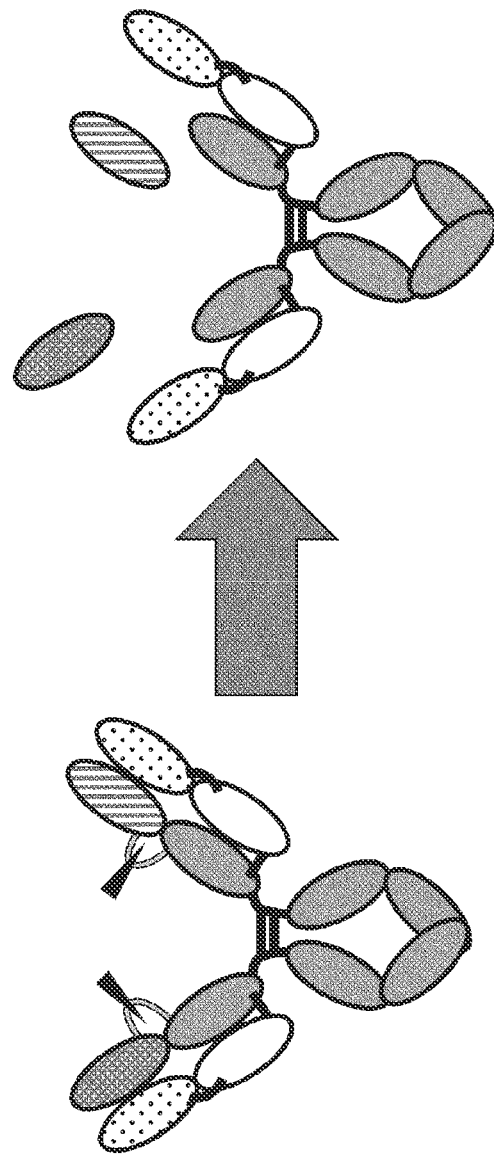
FIG. 3 illustrates an example of a polypeptide comprising the protease cleavage sequence of the present disclosure. In this figure, the polypeptide is an IgG antibody-like molecule, and the portions corresponding to the two variable regions of the IgG antibody are respectively provided with antigen-binding domains. The two antigen-binding domains may have similar or different antigen-binding specificity.

In the present specification, each amino acid is indicated by one-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Native Amino Acids

In the present specification, "native amino acids" refer to 20 types of amino acids contained in a protein. Specifically, the term refers to Gly, Ala, Ser, Thr, Val, Leu, Ile, Phe, Tyr, Trp, His, Glu, Asp, Gln, Asn, Cys, Met, Lys, Arg, and Pro.

Peptides

The term "peptides" as used herein refers to a compound in which two or more amino acid molecules are linked between the amino group of one molecule and the carboxyl group of the other by extracting a water molecule. There is no limit to the number of amino acids contained in a peptide. Thus, both oligopeptides and polypeptides are included in peptides.

Polypeptides

The term polypeptide as used in the present disclosure usually refers to a peptide having a length of about 10 amino acids or more, and a protein. When a chain of amino acids connected by a peptide bond from the N-terminal to the C-terminal is considered as a series of peptide chains, the polypeptide according to the present disclosure may be a complexed protein in which multiple series of peptide chains are formed by interactions such as SS bonds, hydrophobic interactions, and ionic bonds. Furthermore, the polypeptides of the present disclosure are usually polypeptides consisting of artificially designed sequences, but are not particularly limited thereto, and may be, for example, synthetic polypeptides, recombinant polypeptides, or the like. In addition, fragments of the above-mentioned polypeptides are also included in the polypeptides of the present disclosure.

Isolated Polypeptides

The polypeptides of the present disclosure may refer to isolated polypeptides. An "isolated" polypeptide is a polypeptide that is separated from its natural environmental components. In some embodiments, the polypeptides are purified to a purity of over 95% or 99% as determined, for example, by electrophoresis (e.g., SDS-PAGE, isoelectric focusing (IEF), capillary electrophoresis) or chromatography (e.g., ion-exchange chromatography or reverse phase HPLC). When the polypeptides are antibodies, see, for example, Flatman et al., J. Chromatogr. B 848: 79-87 (2007) for a review of a method for evaluating antibody purity.

Proteases

As used herein, the term "protease" refers to an enzyme such as endopeptidase or exopeptidase, which hydrolyzes peptide bonds, and it refers usually to endopeptidase.

Specific examples of the protease include, but are not limited to, cysteine protease (including cathepsin families B, L, S, etc.), aspartyl protease (cathepsins D, E, K, O, etc.), serine protease (including matriptase (including MT-SP1), cathepsins A and G, thrombin, plasmin, urokinase (uPA), tissue plasminogen activator (tPA), elastase, proteinase 3, thrombin, kallikrein, tryptase, and chymase), metalloprotease (metalloprotease (MMP1-28)) including both membrane-bound forms (MMP14-17 and MMP24-25) and secreted forms (MMP1-13, MMP18-23, and MMP26-28), A disintegrin and metalloprotease (ADAM), A disintegrin and metalloprotease with thrombospondin motifs (ADAMTS), meprin (meprin alpha and meprin beta), CD10 (CALLA), prostate-specific antigen (PSA), legumain, TMPRSS3, TMPRSS4, human neutrophil elastase (HNE), beta secretase (BACE), fibroblast activation protein alpha (FAP), granzyme B, guanidinobenzoatase (GB), hepsin, neprilysin, NS3/4A, HCV-NS3/4, calpain, ADAMDEC1, renin, cathepsin C, cathepsin V/L2, cathepsin X/Z/P, cruzipain, otubain 2, kallikrein-related peptidases (KLKs (KLK3, KLK4, KLK5, KLK6, KLK7, KLK8, KLK10, KLK11, KLK13, and KLK14)), bone morphogenetic protein 1 (BMP-1), activated protein C, blood coagulation-related protease (Factor VIIa, Factor IXa, Factor Xa, Factor XIa, and Factor XIIa), HtrA1, lactoferrin, marapsin, PACE4, DESC1, dipeptidyl peptidase 4 (DPP-4), TMPRSS2, cathepsin F, cathepsin H, cathepsin L2, cathepsin O, cathepsin S, granzyme A, Gepsin calpain 2, glutamate carboxypeptidase 2, AMSH-like proteases, AMSH, gamma secretase, antiplasmin-cleaving enzyme (APCE), decysin 1, N-acetylated alpha-linked acidic dipeptidase-like 1 (NAALADL1), and furin.

The protease of the present disclosure may be a protease closely associated with diseased tissue. For example, it may refer to any of the following proteases:

(1) a protease expressed at higher levels in diseased tissue than in normal tissue;

(2) a protease having higher activity in diseased tissue than in normal tissue;

(3) a protease expressed at higher levels in cells in diseased tissue than in normal cells; and (4) a protease having higher activity in target cells in diseased tissue than in normal cells. Examples of diseased tissue include cancer tissue and inflammatory tissue.

The term "cancer tissue" means a tissue containing at least one cancer cell. Thus, considering that, for example, cancer tissue contains cancer cells and vascular vessels, every cell type that contributes to the formation of tumor mass containing cancer cells and endothelial cells is implied. In the present specification, tumor mass refers to a foci of tumor tissue. The term "tumor" is generally used to mean benign neoplasm or malignant neoplasm.

In the present specification, examples of "inflammatory tissue" include the following:

a joint in rheumatoid arthritis or osteoarthritis, a lung (alveolus) in bronchial asthma or COPD, a digestive organ in inflammatory bowel disease, Crohn disease, or ulcerative colitis, a fibrotic tissue in fibrosis in the liver, the kidney, or the lung, a tissue showing rejection reaction in organ transplantation, a vascular vessel or heart (cardiac muscle) in arteriosclerosis or heart failure, a visceral fat in metabolic syndrome, a skin tissue in atopic dermatitis and other dermatitides, and a spinal nerve in disk herniation or chronic lumbago.

Urokinase (uPA)

Urokinase (uPA), also referred to as urokinase-type plasminogen activator, is one type of an extracellular serine protease. The terms "urokinase," "urokinase-type plasminogen activator," and "uPA" are interchangeably used herein, and include any uPA that may be derived from any preferred organism, that is naturally occurring, that is produced endogenously, and/or that is in a recombinant form, as long as it has serine protease activity. For example, in one embodiment of the present disclosure, uPA is in a two-chain active form (tc-uPA). Urokinase further includes human uPA and uPA derived from different species, such as mammalian uPA, including uPA from primates (e.g., chimpanzees, cynomolgus monkeys, or rhesus monkeys); rodents (e.g., mice or rats); rabbits (e.g., rabbits); and artiodactyls (e.g., cattle, sheep, pigs, or camels). The terms "urokinase-type plasminogen activator" and "uPA" further include uPA generated by recombination, which includes any uPA "generated by a genetic recombination technique", including, but not limited to, proteins expressed in mammalian cell systems, or bacteria, or yeast.

Urokinase (uPA) is considered to be highly associated with cancer tissue, and the peptide sequences cleavable by urokinase (uPA) are cleaved more frequently in cancer tissue than in normal tissue.

Matriptase

Matriptase is one type of a serine protease. The matriptase of the present disclosure includes any matriptase that may be derived from any preferred organism, that is naturally occurring, that is produced endogenously, and/or that is in a recombinant form, as long as it has serine protease activity. The matriptase further includes human matriptase and matriptase derived from different species, such as mammalian matriptase including matriptase from primates (e.g., chimpanzees, cynomolgus monkeys, or rhesus monkeys); rodents (e.g., mice or rats); rabbits (e.g., rabbits); or artiodactyls (e.g., cattle, sheep, pigs, or camels). The matriptase further includes matriptase generated by recombination, which includes any matriptase "generated by a genetic recombination technique", including, but not limited to, proteins expressed in mammalian cell systems, or bacteria, or yeast.

Matriptase includes MT-SP1, and MT-SP1 includes any MT-SP1 that may be derived from any preferred organism, that is naturally occurring, that is produced endogenously, and/or that is in a recombinant form, as long as it has serine protease activity. MT-SP1 includes human MT-SP1 and MT-SP1 derived from different species, such as mammalian MT-SP1 including MT-SP1 from primates (e.g., chimpanzees, cynomolgus monkeys, or rhesus monkeys); rodents (e.g., mice or rats); rabbits (e.g., rabbits); or artiodactyls (e.g., cattle, sheep, pigs, or camels). MT-SP1 further includes MT-SP1 generated by recombination, which includes any MT-SP1 "generated by a genetic recombination technique", including, but not limited to, proteins expressed in mammalian cell systems, or bacteria, or yeast.

Matriptase (including MT-SP1) is considered to be highly associated with cancer tissue, and the peptide sequences cleavable by matriptase (including MT-SP1) are cleaved more frequently in cancer tissue than in normal tissue.

Since the sequences of human MT-SP1 and mouse MT-SP1 are considerably similar, their enzymatic activity to the same substrate is considered to be similar.

Method for Confirming the Cleavage by Protease

The method described in Mol Cell Proteomics. 2014 June; 13(6):1585-97. doi: 10.1074/mcp.M113.033308. Epub 2014 Apr. 4 is exemplified as a method for evaluating the cleavage by protease of the protease substrate or protease cleavage sequence described in the specification of the present application.

The protease substrate or protease cleavage sequence to be evaluated is immobilized on a peptide array, the peptide array is treated with a solution containing the protease to be evaluated, and the cleavage ratio can be calculated as described below, using the fluorescence value measured from the chip:

Cleavage ratio (proteolytic activity ratio: PAR) by protease=Fluorescence upon treatment with PBS only (RFU)/Fluorescence upon treatment with a protease-containing solution (RFU)

The type and concentration of protease, the treatment temperature, and the treatment time used for the evaluation may be appropriately selected. By way of example, PBS containing 1000 nM human uPA, PBS containing 1000 nM mouse uPA, PBS containing 500 nM human MT-SP1, or PBS containing 500 nM mouse MT-SP1 may be used, and treatment can be carried out at 37° C. for one hour.

Also, serum (including human serum, mouse serum) can be used instead of a protease-containing solution, to treat the peptide array, and the cleavage rate can be calculated as described below, using the fluorescence value measured from the chip:

Cleavage ratio (proteolytic activity ratio: PAR) by serum=Fluorescence upon treatment with PBS only (RFU)/Fluorescence upon treatment with serum (RFU)

The type and concentration of serum, the treatment temperature, and the treatment time used for the evaluation may be appropriately selected. By way of example, human serum diluted to a concentration of 80% can be used as a treatment solution, and the treatment can be carried out at 37° C. overnight. As used herein, the phrase "not cleaved by serum" may refer to a cleavage ratio by serum of 1.5 or less as measured and calculated according to the above method, or a cleavage ratio by serum that is lower than that of the peptide shown in SEQ ID NO: 4, as measured and calculated according to the above method.

As the method for qualitatively confirming whether the protease cleavage sequence included in a polypeptide is cleaved by protease or not, SDS-PAGE (polyacrylamide gel electrophoresis) can be performed on a solution containing the polypeptide including the protease cleavage sequence to determine the molecular weight of fragments, thereby allowing for the confirmation. The cleavage can also be confirmed by comparing the molecular weight between the protease-treated and protease-untreated polypeptides.

In the present specification, the term "cleaved" refers to a state where the polypeptides are disrupted after alteration of the protease cleavage sequence by protease and/or reduction of a cysteine-cysteine disulfide bond at the protease cleavage sequence. In the present specification, the term "uncleaved" refers to a state where moieties at both sides of the protease cleavage sequence in a polypeptide are linked in the absence of the protease cleavage of the protease cleavage sequence and/or in the absence of the reduction of a cysteine-cysteine disulfide bond at the protease cleavage sequence.

Further, cleavage fragments after protease treatment can be separated by electrophoresis such as SDS-PAGE and quantified to evaluate the protease cleavage sequence and the cleavage ratio of a molecule into which the protease cleavage sequence has been introduced. A non-limiting embodiment of the method of evaluating the cleavage ratio of a molecule into which a protease cleavage sequence has been introduced includes the following method. For example, when the cleavage ratio of an antibody variant into which a protease cleavage sequence has been introduced is evaluated using recombinant human u-Plasminogen Activator/Urokinase (human uPA, huPA) (R&D Systems; 1310-SE-010) or recombinant human Matriptase/ST14 Catalytic Domain (human MT-SP1, hMT-SP1) (R&D Systems; 3946-SE-010), 100 μg/mL of the antibody variant is reacted with 40 nM huPA or 3 nM hMT-SP1 in PBS at 37° C. for one hour, and then subjected to capillary electrophoresis immunoassay. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. Before and after cleavage, the light chain can be detected using anti-human lambda chain HRP-labeled antibody (abcam; ab9007), but any antibody that can detect cleavage fragments may be used. The area of each peak obtained after protease treatment is output using software for Wes (Compass for SW; Protein Simple), and the cleavage ratio (%) of the antibody variant can be determined with the following formula:

$$\text{(Peak area of cleaved light chain)} \times 100 / \text{(Peak area of cleaved light chain} + \text{Peak area of uncleaved light chain)}$$

Cleavage ratios can be determined if protein fragments are detectable before and after protease treatment. Cleavage ratios can be determined not only for antibody variants but also for various protein molecules into which a protease cleavage sequence has been introduced.

The in vivo cleavage ratio of a molecule into which a protease cleavage sequence has been introduced can be determined by administering the molecule into animals and detecting the administered molecule in blood samples. For example, an antibody variant into which a protease cleavage sequence has been introduced is administered to mice, and plasma is collected from their blood samples. The antibody is purified from the plasma by a method known to those skilled in the art using Dynabeads Protein A (Thermo; 10001D), and then subjected to capillary electrophoresis immunoassay to evaluate the protease cleavage ratio of the antibody variant. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. The light chain of the antibody variant collected from mice can be detected using anti-human lambda chain HRP-labeled antibody (abcam; ab9007), but any antibody that can detect cleavage fragments may be used. Once the area of each peak obtained by capillary electrophoresis immunoassay is output using software for Wes (Compass for SW; Protein Simple), the ratio of the remaining light chain can be calculated as [Peak area of light chain]/[Peak area of heavy chain] to determine the ratio of the full-length light chain that remain uncleaved in the mouse body. In vivo cleavage efficiencies can be determined if protein fragments collected from a living organism are detectable. Cleavage ratios can be determined not only for antibody variants but also for various protein molecules into which a protease cleavage sequence has been introduced. Calculation of cleavage ratios by the above-mentioned methods enables, for example, comparison of the in vivo cleavage ratios of antibody variants into which different cleavage sequences have been introduced, and comparison of the cleavage ratio of a single antibody variant between different animal models such as a normal mouse model and a tumor-transplanted mouse model.

Protease Substrate

One aspect of the present disclosure relates to a protease substrate. In one embodiment, the protease substrate refers to a peptide or polypeptide having an amino acid sequence that is hydrolyzed by the action of protease. In another embodiment, the protease substrate is a peptide with a length of about 5-15 amino acids.

The protease substrate of the present disclosure may be modified (cleaved) specifically by protease at a rate of about 0.001 to $1500 \times 10^4$ $M^{-1}S^{-1}$, or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500 \times 10^4$ $M^{-1}S^{-1}$.

In certain embodiments, the protease substrate of the present disclosure has a higher cleavage ratio by protease than the protease substrates comprising any one of the sequences of SEQ ID NOs: 1, 2, and 3.

In certain embodiments, the protease substrate of the present disclosure has a higher cleavage ratio by human uPA than the protease substrates comprising any one of the sequences of SEQ ID NOs: 1, 2, and 3. In certain embodiments, the cleavage ratio of the protease substrate of the present disclosure by human uPA is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more.

In certain embodiments, the protease substrate of the present disclosure has a higher cleavage ratio by human MT-SP1 than the protease substrates comprising any one of the sequences of SEQ ID NOs: 1, 2, and 3. In certain embodiments, the cleavage ratio of the protease substrate of the present disclosure by human MT-SP1 is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more.

In certain embodiments, the protease substrate of the present disclosure has a higher cleavage ratio by mouse uPA than the protease substrates comprising any one of the sequences of SEQ ID NOs: 1, 2, and 3. In certain embodiments, the cleavage ratio of the protease substrate of the present disclosure by mouse uPA is 1 or more, 1.1 or more, 1.2 or more, 1.3 or more, 1.4 or more, 1.5 or more, 1.6 or more, 1.7 or more, 1.8 or more, 1.9 or more, 2 or more, 2.5 or more, 3 or more, 3.5 or more, or 4 or more.

In certain embodiments, the protease substrate of the present disclosure has a higher cleavage ratio by mouse MT-SP1 than the protease substrates comprising any one of the sequences of SEQ ID NOs: 1, 2, and 3. In certain embodiments, the cleavage ratio of the protease substrate of the present disclosure by mouse MT-SP1 is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more.

In certain embodiments, the protease substrate of the present disclosure has a higher ratio of the cleavage ratio by human uPA to the cleavage ratio by human serum than the protease substrates comprising any one of the sequences of SEQ ID NOs: 1, 2, and 3. In certain embodiments, the ratio of the cleavage ratio of the protease substrate of the present disclosure by human uPA to the cleavage ratio by human serum is 0.9 or more, 0.95 or more, 1 or more, 1.2 or more, 1.4 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, or 4 or more. In these embodiments, when the cleavage ratio by human serum is 1 or less, after converting it to 1, it can be used to calculate the ratio of the cleavage ratio by human uPA to the cleavage ratio by human serum.

In certain embodiments, the protease substrate of the present disclosure has a higher ratio of the cleavage ratio by human MT-SP1 to the cleavage ratio by human serum than the protease substrates comprising any one of the sequences of SEQ ID NOs: 1, 2, and 3. In certain embodiments, the ratio of the cleavage ratio of the protease substrate of the present disclosure by human MT-SP1 to the cleavage ratio by human serum is 0.7 or more, 0.8 or more, 0.9 or more, 0.95 or more, 1 or more, 1.2 or more, 1.4 or more, 1.6 or more, 1.8 or more, 2 or more, 2.2 or more, 2.4 or more, 2.5 or more, or 2.6 or more. In these embodiments, when the cleavage ratio by human serum is 1 or less, after converting it to 1, it can be used to calculate the ratio of the cleavage ratio by human MT-SP1 to the cleavage ratio by human serum.

In certain embodiments, the protease substrate of the present disclosure has a higher ratio of the cleavage ratio by mouse uPA to the cleavage ratio by human serum than the protease substrates comprising any one of the sequences of SEQ ID NOs: 1, 2, and 3. In certain embodiments, the ratio of the cleavage ratio of the protease substrate of the present disclosure by mouse uPA to the cleavage ratio by human serum is 0.6 or more, 0.7 or more, 0.8 or more, 0.9 or more, 0.95 or more, 1 or more, 1.1 or more, 1.2 or more, 1.3 or more, 1.4 or more, 1.5 or more, 1.6 or more, 1.7 or more, 1.8 or more, 1.9 or more, or 2 or more. In these embodiments, when the cleavage ratio by human serum is 1 or less, after converting it to 1, it can be used to calculate the ratio of the cleavage ratio by mouse uPA to the cleavage ratio by human serum.

In certain embodiments, the protease substrate of the present disclosure has a higher ratio of the cleavage ratio by mouse MT-SP1 to the cleavage ratio by human serum than the protease substrates comprising any one of the sequences of SEQ ID NOs: 1, 2, and 3. In certain embodiments, the ratio of the cleavage ratio of the protease substrate of the present disclosure by mouse MT-SP1 to the cleavage ratio by human serum is 0.7 or more, 0.8 or more, 0.9 or more, 0.95 or more, 1 or more, 1.2 or more, 1.4 or more, 1.6 or more, 1.8 or more, 2 or more, 2.2 or more, 2.4 or more, 2.5 or more, or 2.6 or more. In these embodiments, when the cleavage ratio by human serum is 1 or less, after converting it to 1, it can be used to calculate the ratio of the cleavage ratio by mouse MT-SP1 to the cleavage ratio by human serum.

In certain embodiments, the protease substrate of the present disclosure is not cleaved by human serum. By way of specific example, the cleavage ratio of the protease substrate of the present disclosure by human serum is 1.5 or less. By way of another specific example, the cleavage ratio of the protease substrate of the present disclosure by human serum is lower than the cleavage ratio of the peptide shown in SEQ ID NO: 4 by human serum.

By way of further specific example, a peptide shown, for example, in any of the following sequences is useful as a protease substrate hydrolyzed by the action of protease:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

By way of another specific example, a peptide shown with the sequence composed of "a sequence selected from Group A listed below-a sequence selected from Group B listed below" in this order from the N-terminus is also useful as a protease substrate hydrolyzed by the action of protease:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

The protease substrates of the present disclosure can be utilized as, for example, a library from which one with properties that suit the purpose can be selected to incorporate into a polypeptide. Specifically, in order to cleave the polypeptide selectively by a protease localized in the lesion, the substrates can be evaluated for sensitivity to that protease. When a polypeptide is administered in vivo, the molecule may come in contact with various proteases before reaching the lesion. Therefore, the molecule should preferably have sensitivity to the protease localized to the lesion and also as high resistance as possible to the other proteases. In order to select a desired protease substrate depending on the purpose, each protease substrate can be analyzed in advance for sensitivity to various proteases comprehensively to find its protease resistance. Based on the obtained protease resistance spectra, it is possible to find a protease substrate with necessary sensitivity and resistance.

Alternatively, a polypeptide into which a protease substrate has been incorporated undergoes not only enzymatic actions by proteases but also various environmental stresses such as pH changes, temperature, and oxidative/reductive stress, before reaching the lesion. Based on the comparative information about resistance to these external factors among the protease substrates, protease substrate with desired properties can be selected.

Protease Cleavage Sequence

In one aspect, the present disclosure relates to a protease cleavage sequence. The protease cleavage sequence is a particular amino acid sequence that is specifically recognized by a protease when a polypeptide is hydrolyzed by the protease in an aqueous solution. In the present disclosure, a protease cleavage sequence may be referred to as a peptide sequence that is cleavable by a protease.

The protease cleavage sequence of the present disclosure may be modified (cleaved) specifically by protease at a rate of about 0.001 to $1500 \times 10^4$ $M^{-1}S^{-1}$, or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500 \times 10^4$ $M^{-1}S^{-1}$.

For example, the following sequences are all useful as the protease cleavage sequence:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequences shown in SEQ ID NOs: 5-18003.

The present disclosure also relates to the use of these sequences as the protease cleavage sequence.

For example, the sequences composed of "a sequence selected from Group A listed below-a sequence selected from Group B listed below" in this order from the N-terminus are all useful as the protease cleavage sequence. The present disclosure also relates to the use of these sequences as the protease cleavage sequence:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

In certain embodiments, the protease cleavage sequence is linked to an antibody or attached thereto by other means. For example, the protease cleavage sequence is used to link one or a plurality of agents to an antibody that binds to a predetermined target such that when the protease cleavage sequence is exposed to protease, i.e., matriptase and/or uPA, it is cleaved and the agent(s) is released from the antibody.

In certain embodiments, the protease cleavage sequence of the present disclosure has a higher cleavage ratio by protease than the protease substrates comprising any one of the sequences of SEQ ID NOs: 1, 2, and 3.

In certain embodiments, the protease cleavage sequence of the present disclosure has a higher cleavage ratio by human uPA than the protease substrates comprising any one of the sequences of SEQ ID NOs: 1, 2, and 3. In certain embodiments, the cleavage ratio of the protease cleavage sequence of the present disclosure by human uPA is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more.

In certain embodiments, the protease cleavage sequence of the present disclosure has a higher cleavage ratio by human MT-SP1 than the protease substrates comprising any one of the sequences of SEQ ID NOs: 1, 2, and 3. In certain embodiments, the cleavage ratio of the protease cleavage sequence of the present disclosure by human MT-SP1 is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more.

In certain embodiments, the protease cleavage sequence of the present disclosure has a higher cleavage ratio by mouse uPA than the protease substrates comprising any one of the sequences of SEQ ID NOs: 1, 2, and 3. In certain embodiments, the cleavage ratio of the protease cleavage sequence of the present disclosure by mouse uPA is, in certain embodiments, the cleavage ratio of the protease substrate of the present disclosure by mouse uPA is 1 or more, 1.1 or more, 1.2 or more, 1.3 or more, 1.4 or more, 1.5 or more, 1.6 or more, 1.7 or more, 1.8 or more, 1.9 or more, 2 or more, 2.5 or more, 3 or more, 3.5 or more, or 4 or more.

In certain embodiments, the protease cleavage sequence of the present disclosure has a higher cleavage ratio by mouse MT-SP1 than the protease substrates comprising any one of the sequences of SEQ ID NOs: 1, 2, and 3. In certain embodiments, the cleavage ratio of the protease cleavage sequence of the present disclosure by mouse MT-SP1 is 1.5 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, 3.9 or more, or 4 or more. In certain embodiments, the protease cleavage sequence of the present disclosure has a higher ratio of the cleavage ratio by human uPA to the cleavage ratio by human serum than the protease substrates comprising any one of the sequences of SEQ ID NOs: 1, 2, and 3. In certain embodiments, the ratio of the cleavage ratio of the protease cleavage sequence of the present disclosure by human uPA to the cleavage ratio by human serum is 0.9 or more, 0.95 or more, 1 or more, 1.2 or more, 1.4 or more, 1.6 or more, 1.8 or more, 2 or more, 2.2 or more, 2.4 or more, 2.6 or more, 2.8 or more, 3 or more, 3.2 or more, 3.4 or more, 3.6 or more, 3.8 or more, or 4 or more. In these embodiments, when the cleavage ratio by human serum is 1 or less, after converting it to 1, it can be used to calculate the ratio of the cleavage ratio by human uPA to the cleavage ratio by human serum.

In certain embodiments, the protease cleavage sequence of the present disclosure has a higher ratio of the cleavage ratio by human MT-SP1 to the cleavage ratio by human serum than the protease substrates comprising any one of the sequences of SEQ ID NOs: 1, 2, and 3. In certain embodiments, the ratio of the cleavage ratio of the protease cleavage sequence of the present disclosure by human MT-SP1 to the cleavage ratio by human serum is 0.7 or more, 0.8 or more, 0.9 or more, 0.95 or more, 1 or more, 1.2 or more, 1.4 or more, 1.6 or more, 1.8 or more, 2 or more, 2.2 or more, 2.4 or more, 2.5 or more, or 2.6 or more. In these embodiments, when the cleavage ratio by human serum is 1 or less, after converting it to 1, it can be used to calculate the ratio of the cleavage ratio by human MT-SP1 to the cleavage ratio by human serum.

In certain embodiments, the protease cleavage sequence of the present disclosure has a higher ratio of the cleavage ratio by mouse uPA to the cleavage ratio by human serum than the protease substrates comprising any one of the sequences of SEQ ID NOs: 1, 2, and 3. In certain embodiments, the ratio of the cleavage ratio of the protease cleavage sequence of the present disclosure by mouse uPA to the cleavage ratio by human serum is 0.6 or more, 0.7 or more, 0.8 or more, 0.9 or more, 0.95 or more, 1 or more, 1.1 or more, 1.2 or more, 1.3 or more, 1.4 or more, 1.5 or more, 1.6 or more, 1.7 or more, 1.8 or more, 1.9 or more, or 2 or more. In these embodiments, when the cleavage ratio by human serum is 1 or less, after converting it to 1, it can be used to calculate the ratio of the cleavage ratio by mouse uPA to the cleavage ratio by human serum.

In certain embodiments, the protease cleavage sequence of the present disclosure has a higher ratio of the cleavage ratio by mouse MT-SP1 to the cleavage ratio by human serum than the protease substrates comprising any one of the sequences of SEQ ID NOs: 1, 2, and 3. In certain embodiments, the ratio of the cleavage ratio of the protease cleavage sequence of the present disclosure by mouse MT-SP1 to the cleavage ratio by human serum is 0.7 or more, 0.8 or more, 0.9 or more, 0.95 or more, 1 or more, 1.2 or more, 1.4 or more, 1.6 or more, 1.8 or more, 2 or more, 2.2 or more, 2.4 or more, 2.5 or more, or 2.6 or more. In these embodiments, when the cleavage ratio by human serum is 1 or less, after converting it to 1, it can be used to calculate the ratio of the cleavage ratio by mouse MT-SP1 to the cleavage ratio by human serum.

In certain embodiments, the protease cleavage sequence of the present disclosure is not cleaved by human serum. By way of specific example, the cleavage ratio of the protease cleavage sequence of the present disclosure by human serum is 1.5 or less. By way of another specific example, the cleavage ratio of the protease substrate of the present disclosure by human serum is lower than the cleavage ratio of the peptide shown in SEQ ID NO: 4 by human serum.

The protease cleavage sequences of the present disclosure may be utilized, for example, upon incorporation into a polypeptide, as a library for selecting a sequence with properties suitable for a purpose. Specifically, in order to selectively cleave a polypeptide by a protease localized in a focus of a disease, its susceptibility to the protease can be evaluated. After being administered to a living body, a polypeptide may reach the focus after contacting various proteases. Thus, it is desirable that the polypeptide is susceptible to the protease localized in the focus of a disease while it is resistant as much as possible to other proteases. In order to select a desired protease cleavage sequence according to the intended purpose, a preliminary exhaustive analysis of the susceptibility of each protease cleavage sequence to a variety of protease may be performed, which allows for understanding of the protease resistance of the sequence. Based on the protease resistance spectrum thus obtained, a protease cleavage sequence having a required susceptibility and resistance may be identified.

Alternatively, a polypeptide introduced with a protease cleavage sequence reaches the focus of a disease not only after experiencing enzymatic action by protease, but also after experiencing a variety of environmental stresses, such as pH shifts, temperature, and oxidative and reductive stresses. For external factors like these also, a protease cleavage sequence having desired properties according to the intended purpose may be selected, based on the information concerning the comparison of resistance of each protease cleavage sequence.

In some embodiments, the protease cleavage sequence can be cleaved by at least matriptase. In some embodiments, the protease cleavage sequence can be cleaved by at least MT-SP1. In some embodiments, the protease cleavage sequence can be cleaved by at least uPA. In some embodiments, the protease cleavage sequence can be cleaved by at least matriptase and uPA. In some embodiments, the protease cleavage sequence can be cleaved by at least MT-SP1 and uPA.

In some embodiments, the protease cleavage sequence is a substrate for matriptase and/or uPA, and the substrate is resistant to cleavage by at least other proteases. In some embodiments, the protease cleavage sequence is a substrate for matriptase and/or uPA, and the substrate is resistant to cleavage by at least plasmin. In some embodiments, the protease cleavage sequence is a substrate for matriptase and/or uPA, and the substrate is resistant to cleavage by at least tissue plasminogen activator (tPA). In some embodiments, the protease cleavage sequence is a substrate for matriptase and/or uPA, and the substrate is resistant to cleavage by at least human serum.

Amino Acid Alteration

For the alteration of an amino acid in the amino acid sequence of a polypeptide, a method known in the art such as site-directed mutagenesis (Kunkel et al. (Proc. Natl. Acad. Sci. USA (1985) 82, 488-492)) or overlap extension PCR can be appropriately adopted. A plurality of methods known in the art can also be adopted as alteration methods for substituting an amino acid by an amino acid other than a natural amino acid (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express)) in which a non-natural amino acid is bound to an amber suppressor tRNA complementary to UAG codon (amber codon), which is a stop codon, is also preferably used.

In the present specification, the term "and/or" used to represent amino acid alteration sites is meant to include every combination in which "and" and "or" are appropriately combined. Specifically, for example, the phrase "amino acids at positions 37, 45, and/or 47 are substituted" includes the following variations of amino acid alteration:

(a) position 37, (b) position 45, (c) position 47, (d) positions 37 and 45, (e) positions 37 and 47, (f) positions 45 and 47, and (g) positions 37, 45, and 47.

In the present specification, expression in which the one-letter codes or three-letter-codes of amino acids before and after alteration are written prior to and subsequent to a number representing a particular position can be appropriately used for representing amino acid alteration. For example, the alteration F37V or Phe37Val used for substituting an amino acid contained in an antibody variable region represents the substitution of Phe at position 37 defined by the Kabat numbering with Val. Specifically, the number represents an amino acid position defined by the Kabat numbering; the one-letter code or three-letter code of the amino acid written prior to the number represents the amino acid before the substitution; and the one-letter code or three-letter code of the amino acid subsequent to the number represents the amino acid after the substitution. Likewise, the alteration P238A or Pro238Ala used for substituting an amino acid in an Fc region contained in an antibody constant region represents the substitution of Pro at position 238 defined by the EU numbering with Ala. Specifically, the number represents an amino acid position defined by the EU numbering; the one-letter code or three-letter code of the amino acid written prior to the number represents the amino acid before the substitution; and the one-letter code or three-letter code of the amino acid subsequent to the number represents the amino acid after the substitution.

To "insert" amino acid sequence A into amino acid sequence B refers to splitting amino acid sequence B into two parts without deletion, and linking the two parts with amino acid sequence A (that is, producing such an amino acid sequence as "first half of amino acid sequence B-amino acid sequence A-second half of amino acid sequence B"). To "introduce" amino acid sequence A into amino acid sequence B refers to splitting amino acid sequence B into two parts and linking the two parts with amino acid sequence

US 12,680,093 B2

49

A. This encompasses not only "inserting" amino acid sequence A into amino acid sequence B as mentioned above, but also linking the two parts with amino acid sequence A after deleting one or a plurality of amino acid residues of amino acid sequence B including those adjacent to amino acid sequence A (that is, replacing a portion of amino acid sequence B with amino acid sequence A).

Further, in the present specification, the term "near the boundary between sites A and B" refers to sites that are before and after the linkage site of sites A and B in a polypeptide and which do not largely affect the secondary structure of site A and/or site B.

Antibody and Antibody Fragment

In the present specification, the term "antibody" is used in the broadest sense and encompasses various antibody structures including, but are not limited to, a monoclonal antibody, a polyclonal antibody, a multispecific antibody (e.g., a bispecific antibody), and an antibody fragment as long as the antibody exhibits the desired antigen binding activity.

"Antibody fragment" refers to a molecule, other than a complete antibody, including a portion of a complete antibody and binding to an antigen to which the complete antibody binds. Examples of the antibody fragment include, but are not limited to, Fv, Fab, Fab', Fab'-SH, F(ab')$_2$, diabodies, linear antibodies, single-chain antibody molecules (e.g., scFv), and multispecific antibodies formed from antibody fragments.

The terms "full-length antibody", "complete antibody", and "whole antibody" are used interchangeably with each other in the present specification and refer to an antibody having a structure substantially similar to a natural antibody structure, or having a heavy chain containing an Fc region defined in the present specification.

The present specification includes an embodiment wherein an antibody comprises a protease cleavage sequence, and regardless of whether a protease cleavage sequence is contained or not, it can be expressed as an "antibody".

Variable Region

The term "variable region" or "variable domain" refers to a domain of an antibody heavy chain or light chain involved in the binding of the antibody to its antigen. Usually, antibody heavy chain and light chain variable domains (VH and VL, respectively) have a similar structure and each domain contains 4 conserved framework regions (FRs) and 3 complementarity determining regions (CDRs) (see, e.g., Kindt et al., Kuby Immunology, 6th ed., W.H. Freeman and Co., page 91 (2007)). One VH or VL domain should be sufficient for conferring antigen binding specificity.

CDR

The term "complementarity determining region" or "CDR" used in the present specification is hypervariable in the sequence, and/or forms a structurally determined loop ("hypervariable loop"), and/or refers to antigen contact residues ("antigen contacts") or each region of an antibody variable domain or a single-domain antibody.

Usually, an antibody contains 6 CDRs: three in VH (H1, H2, and H3), and three in VL (L1, L2, and L3). In the present specification, exemplary antibody CDRs include the following:

(a) hypervariable loops occurring at amino acid residues 26 to 32 (L1), 50 to 52 (L2), 91 to 96 (L3), 26 to 32 (H1), 53 to 55 (H2), and 96 to 101 (H3) (Chothia and Lesk, J. Mol. Biol. 196: 901-917 (1987));

(b) CDRs occurring at amino acid residues 24 to 34 (L1), 50 to 56 (L2), 89 to 97 (L3), 31 to 35b (H1), 50 to 65 (H2), and 95 to 102 (H3) (Kabat et al., Sequences of

50

Proteins of Immunological Interest, 5th Ed. Public Health Service, National Institutes of Health, Bethesda, MD (1991));

(c) antigen contacts occurring at amino acid residues 27c to 36 (L1), 46 to 55 (L2), 89 to 96 (L3), 30 to 35b (H1), 47 to 58 (H2), and 93 to 101 (H3) (MacCallum et al., J. Mol. Biol. 262: 732-745 (1996)); and (d) a combination of (a), (b), and/or (c) containing CDR amino acid residues 46 to 56 (L2), 47 to 56 (L2), 48 to 56 (L2), 49 to 56 (L2), 26 to 35 (H1), 26 to 35b (H1), 49 to 65 (H2), 93 to 102 (H3), or 94 to 102 (H3).

Generally, a single-domain antibody comprises three CDRs: CDR1, CDR2, and CDR3. When a single-domain antibody is a VHH or a single-domain VH antibody, the single-domain antibody CDRs exemplarily include the following:

(a) hypervariable loops occurring at amino acid residues 26 to 32 (CDR1), 53 to 55 (CDR2), and 96 to 101 (CDR3) (Chothia and Lesk, J. Mol. Biol. 196: 901-917 (1987));

(b) CDRs occurring at amino acid residues 31 to 35b (CDR1), 50 to 65 (CDR2), and 95 to 102 (CDR3) (Kabat et al., Sequences of Proteins of Immunological Interest, 5th Ed. Public Health Service, National Institutes of Health, Bethesda, MD (1991));

(c) antigen contacts occurring at amino acid residues 30 to 35b (CDR1), 47 to 58 (CDR2), and 93 to 101 (CDR3) (MacCallum et al., J. Mol. Biol. 262: 732-745 (1996)); and (d) a combination of (a), (b), and/or (c), including CDR amino acid residues 26 to 35 (CDR1), 26 to 35b (CDR1), 49 to 65 (CDR2), 93 to 102 (CDR3), or 94 to 102 (CDR3).

When the single-domain antibody is a single-domain VL antibody, the single-domain antibody CDRs exemplarily include the following:

(a) hypervariable loops occurring at amino acid residues 26 to 32 (CDR1), 50 to 52 (CDR2), and 91 to 96 (CDR3) (Chothia and Lesk, J. Mol. Biol. 196: 901-917 (1987));

(b) CDRs occurring at amino acid residues 24 to 34 (CDR1), 50 to 56 (CDR2), and 89 to 97 (CDR3) (Kabat et al., Sequences of Proteins of Immunological Interest, 5th Ed. Public Health Service, National Institutes of Health, Bethesda, MD (1991));

(c) antigen contacts occurring at amino acid residues 27c to 36 (CDR1), 46 to 55 (CDR2), and 89 to 96 (CDR3) (MacCallum et al., J. Mol. Biol. 262: 732-745 (1996)); and (d) a combination of (a), (b), and/or (c), including CDR amino acid residues 46 to 56 (CDR2), 47 to 56 (CDR2), 48 to 56 (CDR2), or 49 to 56 (CDR2).

In the present specification, CDR residues and other residues (e.g., FR residues) in a variable domain are numbered according to Kabat et al. (supra), unless otherwise specified.

FR

The term "framework" or "FR" refers to variable domain residues or single-domain antibody residues other than complementarity determining region (CDR) residues. FRs in a variable domain or a single-domain antibody generally consist of 4 FR domains: FR1, FR2, FR3, and FR4. Accordingly, the sequences of CDRs and FRs usually appear in VH (or VL) in the following order: FR1-H1 (L1)-FR2-H2 (L2)-FR3-H3 (L3)-FR4. In a single-domain antibody, the sequences of CDRs and FRs generally appear in the following order: FR1-CDR1-FR2-CDR2-FR3-CDR3-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

Constant Region

In the present specification, the term "constant region" or "constant domain" refers to a part other than variable regions in an antibody. For example, an IgG antibody is a heterotetrameric glycoprotein of approximately 150,000 Da constituted by two identical light chains and two identical heavy chains connected through disulfide bonds. Each heavy chain has a variable region (VH) also called variable heavy chain domain or heavy chain variable domain, followed by a heavy chain constant region (CH) containing a CH1 domain, a hinge region, a CH2 domain, and a CH3 domain, from the N terminus to the C terminus. Likewise, each light chain has a variable region (VL) also called variable light chain domain or light chain variable domain, followed by a constant light chain (CL) domain, from the N terminus to the C terminus. The light chains of natural antibodies may be attributed to one of two types called kappa ($\kappa$) and lambda ($\lambda$) on the basis of the amino acid sequences of their constant domains. The term "comprising/comprises a constant region" may include the entire constant region or may include a part of a constant region.

Unless otherwise specified particularly herein, the numbering of amino acid residues in the antibody variable regions and antibody light-chain and heavy-chain constant regions is according to the Kabat numbering system described in Kabat et al., Sequences of Proteins of Immunological Interest, 5th Ed. Public Health Service, National Institutes of Health, Bethesda, MD 1991.

The "class" of an antibody refers to the type of a constant domain or a constant region carried by the heavy chain of the antibody. Antibodies have 5 major classes: IgA, IgD, IgE, IgG, and IgM. Some of these classes may be further divided into subclasses (isotypes), for example, IgG1, IgG2, IgG3, IgG4, IgA1, and IgA2. Heavy chain constant domains corresponding to immunoglobulins of different classes are called $\alpha$, $\delta$, $\epsilon$, $\gamma$, and $\mu$, respectively.

Fc Region

In the present specification, the term "Fc region" is used for defining the C-terminal region of immunoglobulin heavy chains, including at least a portion of constant regions. This term includes an Fc region having a natural sequence and a mutant Fc region. In one embodiment, the heavy chain Fc region of human IgG1 spans from Cys226 or from Pro230 to the carboxyl terminus of the heavy chain. However, the C-terminal lysine (Lys447) or glycine-lysine (Gly446-Lys447) of the Fc region may be present or absent. In the present specification, amino acid residues in an Fc region or an antibody heavy chain constant region are numbered according to the EU numbering system (also called EU index) described in Kabat et al., Sequences of Proteins of Immunological Interest, 5th Ed. Public Health Service, National Institutes of Health, Bethesda, MD 1991, unless otherwise specified.

Hinge Region

The term "hinge region" or "antibody hinge region" can refer to the region composed of the $216^{th}$ to $230^{th}$ amino acids according to EU numbering in the antibody heavy chain, or a part thereof.

Single-Domain Antibody

In the present specification, the "single-domain antibody" is an antibody capable of exhibiting an antigen-binding activity by that domain alone. The structure of a single-domain antibody is not limited as long as it can exert an antigen-binding activity by that domain alone. Ordinary antibodies, exemplified by IgG antibodies and such, show antigen binding activity in a state where a variable region is formed by VH and VL pairing, whereas a single-domain antibody does not pair with other domains, and it is known that the domain structure of the single-domain antibody itself can exert antigen-binding activity. Single-domain antibodies usually have a relatively low molecular weight and exist in the form of monomers. In several embodiments, the form of the single-domain antibody is similar to those of an antibody heavy chain variable region or an antibody light chain variable region.

Examples of single-domain antibodies include, but are not limited to, the variable region of the heavy chain antibody from animals of the family Camelidae (VHH), an antigen-binding molecule congenitally lacking a light chain such as shark $V_{NAR}$, or antibody fragments that include all or part of an antibody VH domain or all or part of an antibody VL domain. Examples of single-domain antibodies that are antibody fragments that include all or part of an antibody VH/VL domain include, but are not limited to, an artificially-produced single-domain antibody starting from the human antibody VH or human antibody VL (hereinafter, single-domain VH antibody, single-domain VL antibody) as described in U.S. Pat. No. 6,248,516 B1, and such.

The single-domain antibody can be obtained from an animal capable of producing the single-domain antibody or by the immunization of the animal capable of producing the single-domain antibody. Examples of the animal capable of producing the single-domain antibody include, but are not limited to, animals of the family Camelidae, and transgenic animals harboring a gene capable of raising the single-domain antibody. The animals of the family Camelidae include camels, lamas, alpacas, one-hump camels and guanacos, etc. Examples of the transgenic animals harboring a gene capable of raising the single-domain antibody include, but are not limited to, transgenic animals described in WO2015/143414 and U.S. Patent Publication No. US2011/0123527 A1. The framework sequences of the single-domain antibody obtained from the animal may be converted to human germline sequences or sequences similar thereto to obtain a humanized single-domain antibody. The humanized single-domain antibody (e.g., humanized VHH) is also one embodiment of the single-domain antibody of the present specification.

Alternatively, the single-domain antibody can be obtained by ELISA, panning, or the like from a polypeptide library containing single-domain antibodies. Examples of the polypeptide library containing single-domain antibodies include, but are not limited to, naive antibody libraries obtained from various animals or humans (e.g., Methods in Molecular Biology 2012 911 (65-78); and Biochimica et Biophysica Acta—Proteins and Proteomics 2006 1764: 8 (1307-1319)), antibody libraries obtained by the immunization of various animals (e.g., Journal of Applied Microbiology 2014 117: 2 (528-536)), and synthetic antibody libraries prepared from antibody genes of various animals or humans (e.g., Journal of Biomolecular Screening 2016 21: 1 (35-43); Journal of Biological Chemistry 2016 291:24 (12641-12657); and AIDS 2016 30: 11 (1691-1701)).

In the present disclosure, there is an embodiment in which a protease cleavage sequence is included in a single-domain antibody, but the expression "single-domain antibody" can be used regardless of whether or not a protease cleavage sequence is included.

In several embodiments, the single-domain antibody of the present specification can generally be defined as a polypeptide comprising:

a) an amino acid sequence consisting of four framework regions/sequences having three complementarity determining regions/sequences inserted therebetween (the amino acid residue at position 11 according to Kabat numbering is selected from the group consisting of L, M, S, V, and W, and is preferably L), and/or b) an amino acid sequence consisting of four framework regions/sequences having three complementarity determining regions/sequences inserted therebetween (the amino acid residue at position 37 according to Kabat numbering is selected from the group consisting of F, Y, H, I, L, and V, and is preferably F or Y), and/or c) an amino acid sequence consisting of four framework regions/sequences having three complementarity determining regions/sequences inserted therebetween (the amino acid residue at position 44 according to Kabat numbering is selected from the group consisting of G, E, A, D, Q, R, S, and L, and is preferably G, E or Q, and is more preferably G or E), and/or d) an amino acid sequence consisting of four framework regions/sequences having three complementarity determining regions/sequences inserted therebetween (the amino acid residue at position 45 according to Kabat numbering is selected from the group consisting of L, R, C, I, L, P, Q, and V, and is preferably L or R), and/or e) an amino acid sequence consisting of four framework regions/sequences having three complementarity determining regions/sequences inserted therebetween (the amino acid residue at position 47 according to Kabat numbering is selected from the group consisting of W, L, F, A, G, I, M, R, S, V, and Y, and is preferably W, L, F or R), and/or f) an amino acid sequence consisting of four framework regions/sequences having three complementarity determining regions/sequences inserted therebetween (the amino acid residue at position 83 according to Kabat numbering is selected from the group consisting of R, K, N, E, G, I, M, Q, and T, and is preferably K or R, and is more preferably K), and/or g) an amino acid sequence consisting of four framework regions/sequences having three complementarity determining regions/sequences inserted therebetween (the amino acid residue at position 84 according to Kabat numbering is selected from the group consisting of P, A, L, R, S, T, D, and V, and is preferably P), and/or h) an amino acid sequence consisting of four framework regions/sequences having three complementarity determining regions/sequences inserted therebetween (the amino acid residue at position 103 according to Kabat numbering is selected from the group consisting of W, P, R and S, and is preferably W), and/or i) an amino acid sequence consisting of four framework regions/sequences having three complementarity determining regions/sequences inserted therebetween (the amino acid residue at position 104 according to Kabat numbering is G or D, and is preferably G), and/or j) an amino acid sequence consisting of four framework regions/sequences having three complementarity determining regions/sequences inserted therebetween (the amino acid residue at position 108 according to Kabat numbering is selected from the group consisting of Q, L and R, and is preferably Q or L).

More specifically, but not exclusively, a single-domain antibody can be defined as a polypeptide comprising any one of the amino acid sequences consisting of four framework regions/sequences having the following three complementarity determining regions/sequences inserted therebetween:

k) an amino acid sequence in which the amino acid residues at positions 43 to 46 according to Kabat numbering are KERE or KQRE;

l) an amino acid sequence in which the amino acid residues at positions 44 to 47 according to Kabat numbering are GLEW; and, m) an amino acid sequence in which the amino acid residues at positions 83 to 84 according to Kabat numbering are KP or EP.

Chimeric Antibody

The term "chimeric" antibody refers to an antibody in which a portion of the heavy and/or light chain is derived from a particular source or species, while the remainder of the heavy and/or light chain is derived from a different source or species. The term "chimeric single-domain antibody" refers to a single-domain antibody in which a portion of the single-domain antibody is derived from a particular source or species, while the remainder of the single-domain antibody is derived from a different source or species.

Humanized Antibody

"Humanized" antibody refers to chimeric antibodies that contain amino acid residues from non-human CDRs and amino acid residues from human FRs. In some embodiments, the humanized antibody includes substantially all of, at least one, and typically two variable domains, in which all or substantially all CDRs correspond to those of a nonhuman antibody, and all or substantially all FRs correspond to those of a human antibody. "Humanized single-domain antibody" refers to a chimeric single-domain antibody that contains amino acid residues from non-human CDRs and amino acid residues from human FRs. In some embodiments, in the humanized single-domain antibody, all or substantially all CDRs correspond to those of a non-human antibody, and all or substantially all FRs correspond to those of a human antibody. In a humanized antibody, even if some of the residues in the FRs do not correspond to those of a human antibody, it is considered as an example where substantially all FRs correspond to those of a human antibody. For example, when humanizing VHH, which is one embodiment of a single-domain antibody, it is necessary to make some of the residues in FRs into residues that do not correspond to those of a human antibody (C Vincke et al., The Journal of Biological Chemistry 284, 3273-3284.).

A humanized antibody may optionally include at least a portion of an antibody constant region derived from a human antibody. The "humanized form" of an antibody (e.g., a non-human antibody) is an antibody that has undergone humanization.

Association

In the present specification, "association" can refer to, for example, a state where two or more polypeptide regions interact with each other. In general, a hydrophobic bond, a hydrogen bond, an ionic bond, or the like is formed between the intended polypeptide regions to form an associate. As one example of common association, an antibody represented by a natural antibody is known to retain a paired structure of a heavy chain variable region (VH) and a light chain variable region (VL) through a noncovalent bond or the like therebetween.

Cancelation of association can refer to, for example, cancelation of a whole or part of the state where two or more polypeptide regions are interacting with each other. Cancelation of the association between VH and VL can include cancelation of the interaction between VH and VL as a whole, or cancelation of a part of the interaction between VH and VL.

FcRn-Binding Region

The "FcRn-binding region" in the present specification refers to a region having binding activity against FcRn and may have any structure as long as the region used has binding activity against FcRn.

The molecule containing a FcRn-binding region is capable of being taken up into cells and then brought back into plasma through the salvage pathway of FcRn. For example, an IgG molecule has a relatively long circulation time in plasma (slow disappearance) because FcRn known as a salvage receptor of the IgG molecule functions. An IgG molecule taken up into the endosome through pinocytosis binds to FcRn expressed in the endosome under intraendosomal acidic conditions. An IgG molecule that has failed to bind to FcRn is moved to the lysosome and degraded therein, whereas the IgG molecule bound with FcRn is transferred to cell surface, then dissociated from the FcRn under neutral conditions in plasma, and thereby brought back into plasma.

The FcRn-binding region is preferably a region binding directly to FcRn. Preferred examples of the FcRn-binding region can include antibody Fc regions. However, a region capable of binding to a polypeptide, such as albumin or IgG, which has FcRn-binding ability is capable of binding indirectly to FcRn via albumin, IgG, or the like. Therefore, the FcRn-binding region according to the present disclosure may be a region binding to such a polypeptide having FcRn-binding ability.

The binding activity of the FcRn-binding region according to the present disclosure against FcRn, particularly, human FcRn may be measured by a method known to those skilled in the art, as mentioned in the above section about binding activity. The conditions therefor may be appropriately determined by those skilled in the art. The binding activity against human FcRn can be evaluated as KD (dissociation constant), apparent KD (apparent dissociation constant), kd (dissociation rate), or apparent kd (apparent dissociation rate), etc. These values can be measured by methods known to those skilled in the art. For example, Biacore (GE Healthcare Japan Corp.), Scatchard plot, flow cytometers, and the like can be used.

The conditions for measuring the binding activity of the FcRn-binding region against FcRn are not particularly limited and may be appropriately selected by those skilled in the art. The binding activity can be measured under conditions involving, for example, a MES buffer and at 37° C., as described in WO2009/125825. Also, the binding activity of the FcRn-binding region of the present disclosure against FcRn may be measured by a method known to those skilled in the art and can be measured using, for example, Biacore (GE Healthcare Japan Corp.). In the measurement of the binding activity of the FcRn-binding region against FcRn, FcRn and the FcRn-binding region or the carrying moiety containing the FcRn-binding region can be injected as analytes to chips onto which the FcRn-binding region or the molecule containing the FcRn-binding region and FcRn, respectively, are immobilized, followed by evaluation.

As for pH for use in the measurement conditions, the binding affinity of the FcRn-binding region for FcRn may be evaluated at any pH of 4.0 to 6.5. Preferably, a pH of 5.8 to 6.0, which is close to pH in the early endosome in vivo, is used for determining the binding affinity of the FcRn-binding region for human FcRn. As for temperature for use in the measurement conditions, the binding affinity of the FcRn-binding region for FcRn may be evaluated at any temperature of 10° C. to 50° C. Preferably, a temperature of 15° C. to 40° C. is used for determining the binding affinity of the FcRn-binding region for human FcRn. More preferably, any temperature from 20° C. to 35° C., for example, any one of 20, 21, 22, 23, 24, 25, 26, 27, 28, 29, 30, 31, 32, 33, 34, and 35° C., is also used for determining the binding affinity of the FcRn-binding region for FcRn. The temperature of 25° C. is one non-limiting example of the embodiments of the present disclosure.

One example of the FcRn-binding region includes, but is not limited to, an IgG antibody Fc region. In the case of using an IgG antibody Fc region, its type is not limited, and for example, IgG1, IgG2, IgG3, or IgG4 Fc region may be used. For example, an Fc region containing one sequence selected from the amino acid sequences represented by SEQ ID NOs: 18004, 18005, 18006, and 18007 may be used.

A native IgG antibody Fc region as well as an Fc region variant having one or more amino acid substitutions may be used as long as the Fc region has FcRn-binding activity.

For example, an Fc region variant containing an amino acid sequence derived from an IgG antibody Fc region by the substitution of at least one amino acid selected from EU numbering positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434 and 436 with another amino acid may be used.

More specifically, an Fc region variant containing at least one amino acid substitution selected from an amino acid substitution to substitute Gly at position 237 with Met, an amino acid substitution to substitute Pro at position 238 with Ala, an amino acid substitution to substitute Ser at position 239 with Lys, an amino acid substitution to substitute Lys at position 248 with Ile, an amino acid substitution to substitute Thr at position 250 with Ala, Phe, Ile, Met, Gln, Ser, Val, Trp, or Tyr, an amino acid substitution to substitute Met at position 252 with Phe, Trp, or Tyr, an amino acid substitution to substitute Ser at position 254 with Thr, an amino acid substitution to substitute Arg at position 255 with Glu, an amino acid substitution to substitute Thr at position 256 with Asp, Glu, or Gln, an amino acid substitution to substitute Pro at position 257 with Ala, Gly, Ile, Leu, Met, Asn, Ser, Thr, or Val, an amino acid substitution to substitute Glu at position 258 with His, an amino acid substitution to substitute Asp at position 265 with Ala, an amino acid substitution to substitute Asp at position 270 with Phe, an amino acid substitution to substitute Asn at position 286 with Ala or Glu, an amino acid substitution to substitute Thr at position 289 with His, an amino acid substitution to substitute Asn at position 297 with Ala, an amino acid substitution to substitute Ser at position 298 with Gly, an amino acid substitution to substitute Val at position 303 with Ala, an amino acid substitution to substitute Val at position 305 with Ala, an amino acid substitution to substitute Thr at position 307 with Ala, Asp, Phe, Gly, His, Ile, Lys, Leu, Met, Asn, Pro, Gln, Arg, Ser, Val, Trp, or Tyr, an amino acid substitution to substitute Val at position 308 with Ala, Phe, Ile, Leu, Met, Pro, Gln, or Thr, an amino acid substitution to substitute Leu or Val at position 309 with Ala, Asp, Glu, Pro, or Arg, an amino acid substitution to substitute Gln at position 311 with Ala, His, or Ile, an amino acid substitution to substitute Asp at position 312 with Ala or His, an amino acid substitution to substitute Leu at position 314 with Lys or Arg, an amino acid substitution to substitute Asn at position 315 with Ala or His, an amino acid substitution to substitute Lys at position 317 with Ala, an amino acid substitution to substitute Asn at position 325 with Gly, an amino acid substitution to substitute Ile at position 332 with Val, an amino acid substitution to substitute Lys at position 334 with Leu, an amino acid substitution to substitute Lys at position 360 with His, an amino acid substitution to substitute Asp at position 376 with Ala, an amino acid substitution to substitute Glu at position 380 with Ala, an amino acid substitution to substitute Glu at position 382 with Ala, an amino acid substitution to substitute Asn or Ser at position 384 with Ala, an amino acid substitution to substitute Gly at position 385 with Asp or His, an amino acid substitution to substitute Gln at position 386 with Pro, an amino acid substitution to substitute Pro at position 387 with Glu, an amino acid substitution to substitute Asn at position 389 with Ala or Ser, an amino acid substitution to substitute Ser at position 424 with Ala, an amino acid substitution to substitute Met at position 428 with Ala, Asp, Phe, Gly, His, Ile, Lys, Leu, Asn, Pro, Gln, Ser, Thr, Val, Trp, or Tyr, an amino acid substitution to substitute His at position 433 with Lys, an amino acid substitution to substitute Asn at position 434 with Ala, Phe, His, Ser, Trp, or Tyr, and an amino acid substitution to substitute Tyr or Phe at position 436 with His (all according to the EU numbering) in an IgG antibody Fc region may be used as an FcRn-binding region.

From another viewpoint, an Fc region containing at least one amino acid selected from Met as the amino acid at position 237, Ala as the amino acid at position 238, Lys as the amino acid at position 239, Ile as the amino acid at position 248, Ala, Phe, Ile, Met, Gln, Ser, Val, Trp, or Tyr as the amino acid at position 250, Phe, Trp, or Tyr as the amino acid at position 252, Thr as the amino acid at position 254, Glu as the amino acid at position 255, Asp, Glu, or Gln as the amino acid at position 256, Ala, Gly, Ile, Leu, Met, Asn, Ser, Thr, or Val as the amino acid at position 257, His as the amino acid at position 258, Ala as the amino acid at position 265, Phe as the amino acid at position 270, Ala or Glu as the amino acid at position 286, His as the amino acid at position 289, Ala as the amino acid at position 297, Gly as the amino acid at position 298, Ala as the amino acid at position 303, Ala as the amino acid at position 305, Ala, Asp, Phe, Gly, His, Ile, Lys, Leu, Met, Asn, Pro, Gln, Arg, Ser, Val, Trp, or Tyr as the amino acid at position 307, Ala, Phe, Ile, Leu, Met, Pro, Gln, or Thr as the amino acid at position 308, Ala, Asp, Glu, Pro, or Arg as the amino acid at position 309, Ala, His, or Ile as the amino acid at position 311, Ala or His as the amino acid at position 312, Lys or Arg as the amino acid at position 314, Ala or His as the amino acid at position 315, Ala as the amino acid at position 317, Gly as the amino acid at position 325, Val as the amino acid at position 332, Leu as the amino acid at position 334, His as the amino acid at position 360, Ala as the amino acid at position 376, Ala as the amino acid at position 380, Ala as the amino acid at position 382, Ala as the amino acid at position 384, Asp or His as the amino acid at position 385, Pro as the amino acid at position 386, Glu as the amino acid at position 387, Ala or Ser as the amino acid at position 389, Ala as the amino acid at position 424, Ala, Asp, Phe, Gly, His, Ile, Lys, Leu, Asn, Pro, Gln, Ser, Thr, Val, Trp, or Tyr as the amino acid at position 428, Lys as the amino acid at position 433, Ala, Phe, His, Ser, Trp, or Tyr as the amino acid at position 434, and His as the amino acid at position 436

(all according to the EU numbering)

in an IgG antibody Fc region may be used as an FcRn-binding region.

Affinity

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

Monoclonal Antibody

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

Antibody Production Method

Methods for producing an antibody having a desired binding activity are known to those skilled in the art. A method for producing an antibody that binds to IL-6R (anti-IL-6R antibody) is exemplified below. Antibodies that bind to antigens other than IL-6R can also be appropriately produced according to the following examples. When producing a single-domain antibody, although there are differences in immunized animals and such, the single-domain antibody can be appropriately produced according to the following examples.

The anti-IL-6R antibody can be obtained as a polyclonal or monoclonal antibody by use of an approach known in the art. A mammal-derived monoclonal antibody can be preferably prepared as the anti-IL-6R antibody. The mammal-derived monoclonal antibody includes, for example, those produced by hybridomas and those produced by host cells transformed by a genetic engineering approach with an expression vector containing an antibody gene. The antibody described in the present application includes a "humanized antibody" and a "chimeric antibody".

The monoclonal antibody-producing hybridomas can be prepared by use of a technique known in the art, for example, as discussed below. Mammals are immunized with IL-6R protein used as a sensitizing antigen according to a usual immunization method. Immunocytes thus obtained are fused with known parental cells by a usual cell fusion method. Next, cells producing a monoclonal antibody are screened for selecting hybridomas producing the anti-IL-6R antibody by a usual screening method.

Specifically, the monoclonal antibody is prepared, for example, as discussed below. First, the IL-6R gene can be expressed to obtain the IL-6R protein which is used as a sensitizing antigen for antibody obtainment. Specifically, a gene sequence encoding IL-6R is inserted into a known expression vector with which appropriate host cells are then transformed. The desired human IL-6R protein is purified from the host cells or from a culture supernatant thereof by a method known in the art. In order to obtain soluble IL-6R from the culture supernatant, for example, soluble IL-6R as described by Mullberg et al. (J. Immunol. (1994) 152 (10), 4958-4968) is expressed. Alternatively, purified natural IL-6R protein can also be used as a sensitizing antigen.

The purified IL-6R protein can be used as the sensitizing antigen for use in the immunization of mammals. A partial peptide of IL-6R can also be used as the sensitizing antigen. The partial peptide may be obtained by chemical synthesis from the amino acid sequence of human IL-6R. Alternatively, the partial peptide may be obtained by incorporating a portion of the IL-6R gene to an expression vector followed by its expression. Furthermore, the partial peptide can also be obtained by degrading the IL-6R protein with a proteolytic enzyme. The region and size of the IL-6R peptide for use as a partial peptide are not particularly limited by specific embodiments. The number of amino acids constituting a peptide to be used as the sensitizing antigen is preferably at least 5 or more, for example, 6 or more, or 7 or more. More specifically, a peptide of 8 to 50, preferably 10 to 30 residues can be used as the sensitizing antigen.

Also, a fusion protein comprising a desired partial polypeptide or peptide of the IL-6R protein fused with a different polypeptide can be used as the sensitizing antigen. For example, an antibody Fc fragment or a peptide tag can be preferably used for producing the fusion protein for use as the sensitizing antigen. A vector for the expression of the fusion protein can be prepared by fusing in frame genes encoding two or more types of the desired polypeptide fragments, and inserting the fusion gene into an expression vector as described above. The method for preparing the fusion protein is described in Molecular Cloning 2nd ed. (Sambrook, J. et al., Molecular Cloning 2nd ed., 9.47-9.58 (1989), Cold Spring Harbor Lab. Press). The method for obtaining IL-6R for use as the sensitizing antigen and the immunization method using it are also specifically described in WO2003/000883, WO2004/022754, WO2006/006693, etc.

The mammals to be immunized with the sensitizing antigen are not limited to particular animals and are preferably selected in consideration of compatibility with the parental cells for use in cell fusion. In general, rodents (e.g., mice, rats, and hamsters), rabbits, monkeys, or the like are preferably used. When obtaining a single-domain antibody, animals of the family Camelidae, or transgenic animals harboring a gene capable of raising the single-domain antibody are preferably used.

The above animals are immunized with the sensitizing antigen according to a method known in the art. For example, as a general method, immunization is carried out by administering the sensitizing antigen to the mammals by intraperitoneal or subcutaneous administration. Specifically, the sensitizing antigen diluted with PBS (phosphate-buffered saline), physiological saline, or the like at an appropriate dilution ratio is mixed, if desired, with a usual adjuvant, for example, a Freund's complete adjuvant and emulsified. Then, the resulting sensitizing antigen is administered to the mammals several times at 4- to 21-day intervals. Also, an appropriate carrier can be used in the immunization with the sensitizing antigen. Particularly, in the case of using a partial peptide having a small molecular weight as the sensitizing antigen, immunization with the sensitizing antigen peptide bound with a carrier protein such as albumin or keyhole limpet hemocyanin may be desirable in some cases.

Alternatively, hybridomas producing the desired antibody can also be prepared as described below by use of DNA immunization. DNA immunization is an immunization method which involves immunostimulating immunized animals by expressing in vivo the sensitizing antigen in the immunized animals administered with a vector DNA that has been constructed in a form capable of expressing the gene encoding the antigenic protein in the immunized animals. DNA immunization can be expected to be superior to the general immunization method in which a protein antigen is administered to animals to be immunized as follows:

DNA immunization can provide immunostimulation while maintaining the structure of a membrane protein (e.g., TL-6R); and DNA immunization does not require purification of the immunizing antigen.

In order to obtain a monoclonal antibody of the present disclosure by DNA immunization, first, DNA for IL-6R protein expression is administered to the animals to be immunized. The DNA encoding IL-6R can be synthesized by a method known in the art such as PCR. The obtained DNA is inserted into an appropriate expression vector, which is then administered to the animals to be immunized. For example, a commercially available expression vector such as pcDNA3.1 can be preferably used as the expression vector. A generally used method can be used as a method for administering the vector to a living body. For example, gold particles with the expression vector adsorbed thereon are transfected into the cells of animal individuals to be immunized using a gene gun to thereby perform DNA immunization. Furthermore, an antibody recognizing IL-6R can also be prepared by use of a method described in WO 2003/104453.

A rise in the titer of the antibody binding to IL-6R is confirmed in the serum of the mammals thus immunized. Then, immunocytes are collected from the mammals and subjected to cell fusion. Particularly, spleen cells can be used as preferred immunocytes.

Mammalian myeloma cells are used as cells to be fused with the immunocytes. The myeloma cells preferably have an appropriate selection marker for screening. The selection marker refers to a trait that can survive (or cannot survive) under particular culture conditions. For example, hypoxanthine guanine phosphoribosyltransferase deficiency (hereinafter, abbreviated as HGPRT deficiency) or thymidine kinase deficiency (hereinafter, abbreviated as TK deficiency) is known as the selection marker. Cells having the HGPRT or TK deficiency are sensitive to hypoxanthine aminopterin thymidine (hereinafter, abbreviated as HAT-sensitive). HAT-sensitive cells are killed in a HAT selective medium because the cells fail to synthesize DNA. By contrast, these cells, when fused with normal cells, become able to grow even in the HAT selective medium because the fused cells can continue DNA synthesis through the use of the salvage pathway of the normal cells.

Cells having HGPRT or TK deficiency can be selected in a medium containing 6-thioguanine or 8-azaguanine (hereinafter, abbreviated as 8AG) or 5'-bromodeoxyuridine, respectively. The normal cells are killed by incorporating these pyrimidine analogs into their DNAs. By contrast, the cells deficient in these enzymes can survive in the selective medium because the cells cannot incorporate the pyrimidine analogs. In addition, a selection marker called G418 resistance confers resistance to a 2-deoxystreptamine antibiotic (gentamicin analog) through a neomycin resistance gene. Various myeloma cells suitable for cell fusion are known in the art.

For example, P3 (P3x63Ag8.653) (J. Immunol. (1979) 123 (4), 1548-1550), P3x63Ag8U.1 (Current Topics in Microbiology and Immunology (1978) 81, 1-7), NS-1 (C. Eur. J. Immunol. (1976) 6 (7), 511-519), MPC-11 (Cell (1976) 8 (3), 405-415), SP2/0 (Nature (1978) 276 (5685), 269-270), FO (J. Immunol. Methods (1980) 35 (1-2), 1-21), 5194/5.XX0.BU.1 (J. Exp. Med. (1978) 148 (1), 313-323), and R210 (Nature (1979) 277 (5692), 131-133) can be preferably used as such myeloma cells.

Basically, cell fusion of the immunocytes with the myeloma cells is performed according to a method known in the art, for example, the method of Kohler and Milstein et al. (Methods Enzymol. (1981) 73, 3-46).

More specifically, cell fusion can be carried out, for example, in a usual nutrient medium in the presence of a cell fusion promoter. For example, polyethylene glycol (PEG) or hemagglutinating virus of Japan (HVJ) is used as the fusion promoter. In addition, an auxiliary such as dimethyl sulfoxide is added thereto, if desired, for enhancing fusion efficiency and then used.

The ratio between the immunocytes and the myeloma cells used can be arbitrarily set. For example, the amount of the immunocytes is preferably set to 1 to 10 times the amount of the myeloma cells. For example, an RPMI1640 medium or a MEM medium suitable for the growth of the myeloma cell line as well as a usual medium for use in this kind of cell culture is used as the medium in the cell fusion. Preferably, a solution supplemented with serum (e.g., fetal calf serum (FCS)) can be further added to the medium.

For cell fusion, predetermined amounts of the immunocytes and the myeloma cells are mixed well in the medium, and a PEG solution (e.g., average molecular weight of PEG of about 1000 to 6000) preheated to approximately 37° C. is added thereto usually at a concentration of 30 to 60% (w/v). The mixed solution is gently mixed and the desired fusion cells (hybridomas) are thus formed. Subsequently, appropriate medium listed above is sequentially added, and the supernatant is removed by centrifugation. This operation can be repeated to remove cell fusion agents or the like unfavorable for hybridoma growth.

The hybridomas thus obtained can be cultured in a usual selective medium, for example, a HAT medium (medium containing hypoxanthine, aminopterin, and thymidine), for selection. The culture using the HAT medium can be continued for a time sufficient (usually, sufficient time is several days to several weeks) to kill cells other than the desired hybridomas (non-fused cells). Subsequently, hybridomas producing the desired antibody are screened for and single-cell-cloned by a usual limiting dilution method.

The hybridomas thus obtained can be selected through the use of a selective medium according to the selection marker possessed by the myeloma cells used in the cell fusion. For example, cells having HGPRT or TK deficiency can be selected by culturing in a HAT medium (medium containing hypoxanthine, aminopterin, and thymidine). Specifically, in the case of using HAT-sensitive myeloma cells in cell fusion, cells successfully fused with normal cells can grow selectively in the HAT medium. The culture using the HAT medium is continued for a time long enough to kill cells other than the desired hybridomas (non-fused cells). Specifically, the culture can generally be performed for several days to several weeks to select the desired hybridomas. Subsequently, hybridomas producing the desired antibody can be screened for and single-cell-cloned by a usual limiting dilution method.

Screening and single-cell-cloning of the desired antibody can be preferably carried out by a screening method based on known antigen-antibody reactions. For example, a monoclonal antibody that binds to IL-6R can bind to IL-6R expressed on the cell surface. Such a monoclonal antibody can be screened, for example, by FACS (fluorescence activated cell sorting). FACS is a system capable of measuring the binding of an antibody to the cell surface by analyzing cells contacted with a fluorescent antibody using laser beam, and measuring the fluorescence emitted from the individual cells.

In order to screen for hybridomas that produce the monoclonal antibody of the present disclosure by FACS, first, IL-6R-expressing cells are prepared. Cells preferred for screening are mammalian cells forced to express IL-6R. Untransformed mammalian cells used as host cells can be used as a control to selectively detect the binding activity of an antibody against IL-6R on the cell surface. Specifically, hybridomas producing the IL-6R monoclonal antibody can be obtained by selecting hybridomas producing an antibody that binds to cells forced to express IL-6R but that does not bind to the host cells.

Alternatively, the antibody can be evaluated for its binding activity against immobilized IL-6R-expressing cells on the basis of the principle of ELISA. The IL-6R-expressing cells are immobilized onto each well of, for example, an ELISA plate. The hybridoma culture supernatant is contacted with the immobilized cells in the well to detect an antibody that binds to the immobilized cells. When the monoclonal antibody is derived from a mouse, the antibody bound with the cell can be detected using an anti-mouse immunoglobulin antibody. Hybridomas producing the desired antibody having antigen binding capacity thus selected by screening can be cloned by a limiting dilution method or the like.

The monoclonal antibody-producing hybridomas thus prepared can be passage cultured in a usual medium. Further, the hybridomas can be preserved over a long period in liquid nitrogen.

The hybridomas are cultured according to a usual method, and the desired monoclonal antibody can be obtained from the culture supernatant thereof. Alternatively, the hybridomas may be administered to mammals compatible therewith and grown, and the monoclonal antibody can be obtained from the ascitic fluids of the mammals. The former method is suitable for obtaining highly pure antibodies.

An antibody encoded by an antibody gene cloned from antibody-producing cells such as hybridomas can also be preferably used. The cloned antibody gene is integrated to an appropriate vector, which is then transfected into hosts so that the antibody encoded by the gene is expressed. Methods for isolating an antibody gene, integrating the gene to a vector, and transforming a host cell are already established by, for example, Vandamme et al. (Eur. J. Biochem. (1990) 192 (3), 767-775). A method for producing a recombinant antibody is also known, as mentioned below.

For example, cDNA encoding the variable region (V region) of the anti-IL-6R antibody is obtained from hybridoma cells producing the anti-IL-6R antibody. For this purpose, usually, total RNA is first extracted from the hybridomas. For example, the following methods can be used as a method for extracting mRNA from cells:

a guanidine ultracentrifugation method (Biochemistry (1979) 18 (24), 5294-5299), and an AGPC method (Anal. Biochem. (1987) 162 (1), 156-159).

The extracted mRNA can be purified using mRNA Purification Kit (manufactured by GE Healthcare Bio-Sciences Corp.) or the like. Alternatively, a kit for directly extracting total mRNA from cells is also commercially available, such as QuickPrep mRNA Purification Kit (manufactured by GE Healthcare Bio-Sciences Corp.). The mRNA can be obtained from hybridomas using such a kit. From the obtained mRNA, cDNA encoding the antibody V region can be synthesized using reverse transcriptase. The cDNA can be synthesized using, for example, AMV Reverse Transcriptase First-strand cDNA Synthesis Kit (manufactured by Seikagaku Corp.). Alternatively, a 5'-RACE method (Proc. Natl. Acad. Sci. USA (1988) 85 (23), 8998-9002; and Nucleic Acids Res. (1989) 17 (8), 2919-2932) using SMART RACE cDNA amplification kit (manufactured by Clontech Laboratories, Inc.) and PCR can be appropriately used for cDNA synthesis and amplification. In the course of such cDNA synthesis, appropriate restriction enzyme sites mentioned later can be further introduced to both ends of the cDNA.

The cDNA fragment of interest is purified from the obtained PCR product and subsequently ligated with vector DNA. The recombinant vector thus prepared is transfected into E. coli or the like. After colony selection, the desired recombinant vector can be prepared from the E. coli that has formed the colony. Then, whether or not the recombinant vector has the nucleotide sequence of the cDNA of interest is confirmed by a method known in the art, for example, a dideoxynucleotide chain termination method.

The 5'-RACE method using primers for amplifying a variable region gene is conveniently used for obtaining a gene encoding the variable region. First, a 5'-RACE cDNA library is obtained by cDNA synthesis using RNAs extracted from hybridoma cells as templates. A commercially available kit such as SMART RACE cDNA amplification kit is appropriately used in the synthesis of the 5'-RACE cDNA library.

The antibody gene is amplified by PCR using the obtained 5'-RACE cDNA library as a template. Primers for amplifying mouse antibody genes can be designed on the basis of a known antibody gene sequence. These primers have nucleotide sequences differing depending on immunoglobulin subclasses. Thus, the subclass is desirably determined in advance using a commercially available kit such as Iso Strip mouse monoclonal antibody isotyping kit (Roche Diagnostics K.K.).

Specifically, primers capable of amplifying genes encoding $\gamma 1$, $\gamma 2a$, $\gamma 2b$, and $\gamma 3$ heavy chains and $\kappa$ and $\lambda$ light chains can be used, for example, for the purpose of obtaining a gene encoding mouse IgG. In order to amplify an IgG variable region gene, a primer that anneals to a moiety corresponding to a constant region close to the variable region is generally used as a 3' primer. On the other hand, a primer attached to the 5' RACE cDNA library preparation kit is used as a 5' primer.

The PCR products thus obtained by amplification can be used to reshape immunoglobulins composed of combinations of heavy and light chains. The desired antibody can be screened for using the binding activity of the reshaped immunoglobulin against IL-6R as an index. More preferably, the binding of the antibody to IL-6R is specific, for example, for the purpose of obtaining an antibody against IL-6R. An antibody that binds to IL-6R can be screened for, for example, by the following steps:

(1) contacting IL-6R-expressing cells with an antibody containing the V region encoded by the cDNA obtained from the hybridomas;

(2) detecting the binding of the antibody to the IL-6R-expressing cells; and (3) selecting the antibody binding to the IL-6R-expressing cells.

A method for detecting the binding of an antibody (including single-domain antibody) to IL-6R-expressing cells is known in the art. Specifically, the binding of an antibody to IL-6R-expressing cells can be detected by an approach such as FACS mentioned above. A fixed preparation of IL-6R-expressing cells can be appropriately used for evaluating the binding activity of the antibody.

A panning method using phage vectors is also preferably used as a method of screening for an antibody using binding activity as an index. Also in the case of screening for a single-domain antibody, screening can be suitably carried out according to the following examples.

When antibody genes are obtained as libraries of heavy chain and light chain subclasses from a polyclonal antibody-expressing cell population, a screening method using phage vectors is advantageous. Genes encoding heavy chain and light chain variable regions can be linked via an appropriate linker sequence to form a single-chain Fv (scFv). The gene encoding scFv can be inserted into phage vectors to obtain phages expressing scFv on their surface. After contacting the phages with the desired antigen, phages bound with the antigen can be recovered to recover DNA encoding scFv having the binding activity of interest. This operation can be repeated as necessary to enrich scFvs having the desired binding activity.

After obtaining the cDNA encoding the V region of the anti-IL-6R antibody of interest, this cDNA is digested with restriction enzymes that recognize the restriction sites inserted at both ends of the cDNA. The restriction enzymes preferably recognize and digest a nucleotide sequence that appears at low frequency in the nucleotide sequence constituting the antibody gene. Preferably, sites for restriction enzymes that provide cohesive ends are inserted for inserting one copy of the digested fragment in the correct orientation into a vector. The thus-digested cDNA encoding the V region of the anti-IL-6R antibody can be inserted into an appropriate expression vector to obtain an antibody expression vector. In this case, a gene encoding an antibody constant region (C region) and the gene encoding the V region are fused in frame to obtain a chimeric antibody. In this context, a "chimeric antibody" implies that the origin of the constant and variable regions is different. Thus, heterogeneous (e.g., mouse-human) chimeric antibodies as well as human-human homogeneous chimeric antibodies are also included in the chimeric antibody according to the present disclosure. The V region gene can be inserted into an expression vector preliminarily having a constant region gene to construct a chimeric antibody expression vector. Specifically, for example, a recognition sequence for a restriction enzyme that digests the V region gene can be appropriately placed on the 5' side of an expression vector carrying the DNA encoding the desired antibody constant region (C region). Both are digested with the same combination of restriction enzymes and are fused in frame to construct a chimeric antibody expression vector.

In order to produce the anti-IL-6R monoclonal antibody, the antibody gene is integrated to an expression vector such that the antibody gene is expressed under the control of expression control regions. The expression control regions for antibody expression include, for example, an enhancer and a promoter. Also, an appropriate signal sequence can be added to the amino terminus such that the expressed antibody is extracellularly secreted. For example, a peptide having an amino acid sequence MGWSCIILFL-VATATGVHS (SEQ ID NO: 18008) can be used as the signal sequence, and other suitable signal sequences may be added. The expressed polypeptide is cleaved at the carboxyl-terminal moiety of the above sequence. The cleaved polypeptide can be extracellularly secreted as a mature polypeptide. Subsequently, appropriate host cells can be transformed with this expression vector to obtain recombinant cells expressing DNA encoding the anti-IL-6R antibody.

Polynucleotide (Nucleic Acid)

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Vector

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Host Cells and Such

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Polypeptide Comprising a Protease Cleavage Sequence

One aspect of the present disclosure relates to a polypeptide comprising a protease cleavage sequence.

Another aspect of the present disclosure relates to a polypeptide comprising at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

Another aspect of the present disclosure relates to a polypeptide comprising any of a sequence composed of "a sequence selected from Group A listed below-a sequence selected from Group B listed below" in this order from the N-terminus:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

In certain embodiments of the polypeptide of the present disclosure, at least one sequence selected from the sequences listed below is contained in the polypeptide and said sequence in the polypeptide can be cleaved by protease, i.e., said sequence functions as a protease cleavage sequence in the polypeptide:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

Also, in certain embodiments of the polypeptide of the present disclosure, any of the sequences composed of "a sequence selected from Group A listed below-a sequence selected from Group B listed below" in this order from the N-terminus is contained in the polypeptide and said sequence in the polypeptide can be cleaved by protease, i.e., said sequence functions as a protease cleavage sequence in the polypeptide:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

In one embodiment of the polypeptide of the present disclosure, a flexible linker is further attached to one end or both ends of the protease cleavage sequence. The flexible linker at one end of the protease cleavage sequence can be referred to as "first flexible linker", and the flexible linker at the other end can be referred to as "second flexible linker". In a particular embodiment, the protease cleavage sequence and the flexible linker have any of the following formulas:

(protease cleavage sequence), (first flexible linker)-(protease cleavage sequence), (protease cleavage sequence)-(second flexible linker), and (first flexible linker)-(protease cleavage sequence)-(second flexible linker).

The flexible linker according to the present embodiment is preferably a peptide linker. The first flexible linker and the second flexible linker each exist independently and arbitrarily and are identical or different flexible linkers containing at least one flexible amino acid (Gly, etc.). The flexible linker contains, for example, number of residues (amino acids arbitrarily selected from Arg, Ile, Gln, Glu, Cys, Tyr, Trp, Thr, Val, His, Phe, Pro, Met, Lys, Gly, Ser, Asp, Asn, Ala, etc., particularly Gly, Ser, Asp, Asn, and Ala, more particularly, Gly and Ser, especially Gly, etc.) sufficient for the protease cleavage sequence to obtain the desired protease accessibility.

The flexible linker suitable for use at both ends of the protease cleavage sequence is usually a flexible linker that improves the access of protease to the protease cleavage sequence and elevates the cleavage efficiency of the protease. A suitable flexible linker may be readily selected and can be preferably selected from among different lengths such as 1 amino acid (Gly, etc.) to 20 amino acids, 2 amino acids to 15 amino acids, or 3 amino acids to 12 amino acids including 4 amino acids to 10 amino acids, 5 amino acids to 9 amino acids, 6 amino acids to 8 amino acids, or 7 amino acids to 8 amino acids. In some embodiments of the present disclosure, the flexible linker is a peptide linker of 1 to 7 amino acids.

Examples of the flexible linker include, but are not limited to, glycine polymers (G)n, glycine-serine polymers (including e.g., (GS)n, (GSGGS: SEQ ID NO: 18018)n, and (GGGS: SEQ ID NO: 18009)n, wherein n is an integer of at least 1), glycine-alanine polymers, alanine-serine polymers, and other flexible linkers well known in conventional techniques.

Among them, glycine and glycine-serine polymers are receiving attention because these amino acids are relatively unstructured and can easily function as neutral tethers between components.

Examples of the flexible linker consisting of the glycine-serine polymer can include, but are not limited to,

```
Ser

Gly-Ser (GS)

Ser-Gly (SG)

Gly-Gly-Ser (GGS)

Gly-Ser-Gly (GSG)

Ser-Gly-Gly (SGG)

Gly-Ser-Ser (GSS)

Ser-Ser-Gly (SSG)
```

```
-continued
Ser-Gly-Ser (SGS)

Gly-Gly-Gly-Ser (GGGS, SEQ ID NO: 18009)

Gly-Gly-Ser-Gly (GGSG, SEQ ID NO: 18010)

Gly-Ser-Gly-Gly (GSGG, SEQ ID NO: 18011)

Ser-Gly-Gly-Gly (SGGG, SEQ ID NO: 18012)

Gly-Ser-Ser-Gly (GSSG, SEQ ID NO: 18013)

Gly-Gly-Gly-Gly-Ser (GGGGS, SEQ ID NO: 18014)

Gly-Gly-Gly-Ser-Gly (GGGSG, SEQ ID NO: 18015)

Gly-Gly-Ser-Gly-Gly (GGSGG, SEQ ID NO: 18016)

Gly-Ser-Gly-Gly-Gly (GSGGG, SEQ ID NO: 18017)

Gly-Ser-Gly-Gly-Ser (GSGGS, SEQ ID NO: 18018)

Ser-Gly-Gly-Gly-Gly (SGGGG, SEQ ID NO: 18019)

Gly-Ser-Ser-Gly-Gly (GSSGG, SEQ ID NO: 18020)

Gly-Ser-Gly-Ser-Gly (GSGSG, SEQ ID NO: 18021)

Ser-Gly-Gly-Ser-Gly (SGGSG, SEQ ID NO: 18022)

Gly-Ser-Ser-Ser-Gly (GSSSG, SEQ ID NO: 18023)

Gly-Gly-Gly-Gly-Gly-Ser (GGGGGS, SEQ ID NO: 18024)

Ser-Gly-Gly-Gly-Gly-Gly (SGGGGG, SEQ ID NO: 18025)

Gly-Gly-Gly-Gly-Gly-Gly-Ser (GGGGGGS, SEQ ID NO:
18026)

Ser-Gly-Gly-Gly-Gly-Gly-Gly (SGGGGGG, SEQ ID NO:
18027)

(Gly-Gly-Gly-Gly-Ser (GGGGS, SEQ ID NO: 18014))n (Ser-Gly-Gly-Gly-Gly (SGGGG, SEQ ID NO: 18019))n
``` wherein n is an integer of 1 or larger.

However, the length and sequence of the peptide linker can be appropriately selected by those skilled in the art according to the purpose.

A polypeptide comprising a protease cleavage sequence of the present disclosure may have any composition as long as it contains at least one sequence selected from the following:

the sequence spanning from the N-terminal fourth to fifteenth amino acids of a sequence selected from SEQ ID NOs: 5-17201;

the sequence spanning from the N-terminal fourth to thirteenth amino acids of a sequence selected from SEQ ID NOs: 5-17201;

the sequence spanning from the N-terminal sixth to thirteenth amino acids of a sequence selected from SEQ ID NOs: 5-17201;

the sequence spanning from the N-terminal first to twelfth amino acids of a sequence selected from SEQ ID NOs: 17202-17993;

the sequence spanning from the N-terminal third to twelfth amino acids of a sequence selected from SEQ ID NOs: 17202-17993;

the sequence spanning from the N-terminal third to eleventh amino acids of a sequence selected from SEQ ID NOs: 17202-17993;

the sequence spanning from the N-terminal third to tenth amino acids of a sequence selected from SEQ ID NOs: 17202-17993;

the sequence spanning from the N-terminal third to fourteenth amino acids of a sequence selected from SEQ ID NOs: 17994-18003;

the sequence spanning from the N-terminal fifth to twelfth amino acids of a sequence selected from SEQ ID NOs: 17994-18003;

the sequence spanning from the N-terminal fifth to tenth amino acids of a sequence selected from SEQ ID NOs: 17994-18003; and the sequence shown in any of SEQ ID NOs: 5-18003.

Also, a polypeptide comprising a protease cleavage sequence of the present disclosure may have any composition as long as it contains any of the sequences composed of "a sequence selected from Group A listed below-a sequence selected from Group B listed below" in this order from the N-terminus:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

A polypeptide comprising a protease cleavage sequence of the present disclosure may be an activatable antibody. For example, an activatable antibody includes the following:

(i) an antibody that specifically binds to a target;

(ii) a masking moiety that inhibits the binding of the antibody to the target when the protease cleavage sequence is present in an uncleaved state; and (iii) a cleavable moiety to be coupled to the antibody, wherein the cleavable moiety is at least one sequence selected from the protease cleavage sequences of the present disclosure.

Polypeptide Comprising an Antigen-Binding Domain and a Carrying Moiety

In one embodiment of the polypeptide of the present disclosure, the polypeptide comprises an antigen-binding domain and a carrying moiety, and the carrying moiety has an inhibiting domain for inhibiting the antigen-binding activity of the antigen-binding domain. The present disclosure also relates to a method for releasing an antigen-binding domain from a polypeptide, comprising cleaving by protease a protease cleavage sequence in the polypeptide comprising the antigen-binding domain and the carrying moiety described herein.

In the present specification, the "antigen-binding domain" is limited only by binding to the antigen of interest. The antigen-binding domain can be a domain having any structure as long as the domain used binds to the antigen of interest. Examples of such a domain include, but are not limited to, an antibody heavy chain variable region (VH), an antibody light chain variable region (VL), a single-domain antibody (sdAb), a module called A domain of approximately 35 amino acids contained in an in vivo cell membrane protein avimer (WO2004/044011 and WO2005/040229), adnectin containing a 10Fn3 domain serving as a protein binding domain derived from a glycoprotein fibronectin expressed on cell membranes (WO2002/032925), Affibody containing an IgG binding domain scaffold constituting a three-helix bundle composed of 58 amino acids of protein A (WO1995/001937), DARPins (designed ankyrin repeat proteins) which are molecular surface-exposed regions of ankyrin repeats (AR) each having a 33-amino acid residue structure folded into a subunit of a turn, two antiparallel helices, and a loop (WO2002/020565), anticalin having four loop regions connecting eight antiparallel strands bent toward the central axis in one end of a barrel structure highly conserved in lipocalin molecules such as neutrophil gelatinase-associated lipocalin (NGAL) (WO2003/029462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (WO2008/016854).

Preferred examples of the antigen-binding domain of the present disclosure include an antigen-binding domain that can exert an antigen binding function by a molecule constituted only by the antigen-binding domain, and an antigen-binding domain that can exert an antigen binding function by itself after being released from an additional peptide linked thereto. Examples of such an antigen-binding domain include, but are not limited to, single-domain antibodies, scFv, Fv, Fab, Fab', and F(ab')$_2$.

One preferred example of the antigen-binding domain of the present disclosure includes an antigen-binding domain having a molecular weight of 60 kDa or smaller. Examples of such an antigen-binding domain include, but are not limited to, single-domain antibodies, scFv, Fab, and Fab'. The antigen-binding domain having a molecular weight of 60 kDa or smaller is usually likely to be subjected to clearance by the kidney when existing as a monomer in blood (see J Biol Chem. 1988 Oct. 15; 263 (29): 15064-70). From another viewpoint, one preferred example of the antigen-binding domain of the present disclosure includes an antigen-binding domain having a half-life in blood of 12 hours or shorter. Examples of such an antigen-binding domain include, but are not limited to, single-domain antibodies, scFv, Fab, and Fab'.

One preferred example of the antigen-binding domain of the present disclosure includes a single-domain antibody (sdAb).

In the present specification, the "antigen" is limited only by containing an epitope to which the antigen-binding domain binds. Preferred examples of the antigen include, but are not limited to, animal- or human-derived peptides, polypeptides, and proteins. Preferred examples of the antigen include, but are not limited to, molecules expressed on the surface of target cells (e.g., cancer cells and inflammatory cells), molecules expressed on the surface of other cells in tissues containing target cells, molecules expressed on the surface of cells having an immunological role against target cells and tissues containing target cells, and macromolecules present in the stromata of tissues containing target cells.

Examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Axl, b2M, B7-1, B7-2, B7-H, B-lymphocyte stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer-associated antigens, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, PD-1, PD-L1, LAG3, TIM3, galectin-9, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigens, DAN, DCC, DcR3, DC-SIGN, decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, ePO, ERCC, E-selectin, ET-1, factor IIa, factor VII, factor VIIIc, factor IX, fibroblast-activating protein (FAP), Fas, FcRI, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, gITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM, HRG, Hrk, human heart myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-21, IL-23, IL-27, interferon (INF)-alpha, INF-beta, INF-gamma, inhibin, iNOS, insulin chain A, insulin chain B, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bpI, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, metalloproteinases, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mudl), MUC18, mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha/beta, TNF-beta 2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGMI, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TLR (toll-like receptor) 1, TLR2, TLR3, TLR4, TLR5, TLR6, TLR7, TLR8, TLR9, TLR10, TSG, TSLP, tumor-associated antigen CA125, tumor-associated antigen-expressing Lewis-Y-related carbohydrate, TWEAK, TXB2, Ung, uPAR, uPAR-1, urokinase, VCAM, VCAM-1, VECAD, VE-cadherin, VE-cadherin-2, VEFGR-1 (flt-1), VEGF, VEGFR, VEGFR-3 (flt-4), VEGI, VIM, viral antigens, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, A$, CD81, CD97, CD98, DDR1, DKK1, EREG, Hsp90, IL-17/IL-17R, IL-20/IL-20R, oxidized LDL, PCSK9, prekallikrein, RON, TMEMi6F, SOD1, chromogranin A, chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, Cir, Cis, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIiI, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, syndecan-1, syndecan-2, syndecan-3, syndecan-4, LPA, SIP, and receptors for hormones or growth factors.

Although the examples of the antigen listed above also include receptors, these receptors even existing in a soluble form in a body fluid can be used as the antigen to which the antigen-binding domain of the present disclosure binds.

The examples of the antigen listed above include membrane molecules expressed on cell membranes, and soluble molecules secreted from cells to the outside of the cells. When the antigen-binding domain of the present disclosure binds to a soluble molecule secreted from cells, the antigen-binding domain preferably has neutralizing activity.

The solution containing the soluble molecule is not limited, and this soluble molecule may exist in a body fluid, i.e., every vascular liquid or every liquid filling between tissues or cells in living bodies. In a non-limiting aspect, the soluble molecule to which the antigen-binding domain of the present disclosure binds can exist in an extracellular fluid. The extracellular fluid refers to a generic name for plasma, intercellular fluid, lymph, tight connective tissues, cerebrospinal fluid, spinal fluid, aspirates, synovial fluid, or such components in the bone and cartilage, alveolar fluid (bronchoalveolar lavage fluid), ascitic fluid, pleural effusion, cardiac effusion, cyst fluid, aqueous humor (hydatoid), or such transcellular fluids (various fluids in glandular cavities resulting from the active transport or secretory activity of cells, and fluids in the lumen of the gut and other body cavities) in vertebrates.

In the present specification, the term "carrying moiety" refers to a moiety other than an antigen-binding domain in a polypeptide. The carrying moiety of the present disclosure is usually a peptide or a polypeptide constituted by amino acids. In a specific embodiment, the carrying moiety in the polypeptide is linked to the antigen-binding domain via a protease cleavage sequence. The carrying moiety of the present disclosure may be a series of peptides or polypeptides connected through an amide bond(s), or may be a complex formed from a plurality of peptides or polypeptides through a covalent bond(s) such as a disulfide bond or a noncovalent bond such as a hydrogen bond or hydrophobic interaction.

The carrying moiety of the present disclosure has an inhibiting domain that inhibits the antigen-binding activity of the antigen-binding domain. In the present specification, the term "inhibiting domain" is limited only by the inhibition the antigen-binding activity of the antigen-binding domain. The inhibiting domain can be a domain having any structure as long as the domain used can inhibit the antigen-binding activity of the antigen-binding domain. Examples of such an inhibiting domain include, but are not limited to, antibody heavy chain variable regions (VH), antibody light chain variable regions (VL), pre-B cell receptors, and single-domain antibodies. The inhibiting domain may constitute the whole of the carrying moiety or may constitute a portion of the carrying moiety.

In certain embodiments, when the polypeptide of the present disclosure comprises an antigen-binding domain and a carrying moiety, the inhibition of the antigen-binding activity of the antigen-binding domain by the inhibiting domain in a state where the protease cleavage sequence is cleaved by protease is weaker than the inhibition of the antigen-binding activity of the antigen-binding domain by the inhibiting domain in a state where the protease cleavage sequence is uncleaved.

In certain embodiments, when the polypeptide of the present disclosure comprises an antigen-binding domain and a carrying moiety, the antigen-binding domain has a shorter blood half-life than the uncleaved polypeptide. In certain embodiments, when the polypeptide of the present disclosure comprises an antigen-binding domain and a carrying moiety, the antigen-binding domain has a shorter blood half-life than the carrying moiety.

In certain embodiments, when the polypeptide of the present disclosure comprises an antigen-binding domain and a carrying moiety, the antigen-binding domain has a lower molecular weight than the carrying moiety. In certain embodiments, the antigen-binding domain may have a molecular weight of 60 kDa or less.

In certain embodiments, when the polypeptide of the present disclosure comprises an antigen-binding domain and a carrying moiety, the carrying moiety has FcRn-binding activity, and the antigen-binding domain does not have FcRn-binding activity or has weaker FcRn-binding activity than the carrying moiety.

In certain embodiments, when the polypeptide of the present disclosure comprises an antigen-binding domain and a carrying moiety, the polypeptide comprising an antigen-binding domain and a carrying moiety has a longer half-life in blood than the antigen-binding domain existing alone. In certain embodiments, when the polypeptide of the present disclosure comprises an antigen-binding domain and a carrying moiety, the carrying moiety is designed so as to have a longer half-life in blood, for the longer half-life of the polypeptide. In such embodiments, examples of the approach of extending the half-life in blood of the carrying moiety include, but are not limited to, a large molecular weight of the carrying moiety, FcRn-binding activity possessed by the carrying moiety, albumin-binding activity possessed by the carrying moiety, and the PEGylation of the carrying moiety. In certain embodiments, when the polypeptide of the present disclosure comprises an antigen-binding domain and a carrying moiety, the carrying moiety has a longer half-life in blood than the antigen-binding domain (in other words, the antigen-binding domain has a shorter half-life in blood than the carrying moiety).

In the present disclosure, the half-lives of the antigen-binding domain alone and the polypeptide, or the half-lives in blood of the antigen-binding domain and the carrying moiety are preferably compared in terms of their half-lives in blood in humans. If the half-lives in blood are difficult to measure in humans, the half-lives in blood in humans can be predicted on the basis of their half-lives in blood in mice (e.g., normal mice, transgenic mice expressing a human antigen, and transgenic mice expressing human FcRn) or monkeys (e.g., cynomolgus monkeys).

In one embodiment, the approach of extending the half-life in blood of the carrying moiety includes a large molecular weight of the carrying moiety. In one embodiment, the approach of rendering the half-life in blood of the carrying moiety longer than that of the antigen-binding domain includes making the molecular weight of the carrying moiety be higher than that of the antigen-binding domain.

In one embodiment, the approach of extending the half-life in blood of the carrying moiety includes conferring FcRn-binding activity to the carrying moiety. The carrying moiety can usually possess FcRn-binding activity by a method of establishing a FcRn-binding region in the carrying moiety.

The FcRn-binding activity possessed by the carrying moiety does not mean that the antigen-binding domain has no FcRn-binding activity. In the embodiments in which the carrying moiety has a longer half-life in blood than that of the antigen-binding domain, the antigen-binding domain may have no FcRn-binding activity, as a matter of course, or the antigen-binding domain may have FcRn-binding activity as long as the FcRn-binding activity is weaker than that of the carrying moiety.

In one embodiment, the method for extending the half-life in blood of the carrying moiety involves binding the carrying moiety to albumin. Since albumin does not undergo renal excretion and has FcRn-binding ability, its half-life in blood is as long as 17 days to 19 days (J Clin Invest. 1953 August; 32 (8): 746-768). Hence, it has been reported that a protein bound to albumin becomes bulky and capable of binding indirectly to FcRn and therefore has an increased half-life in blood (Antibodies 2015, 4 (3), 141-156).

In one embodiment, the alternative method for extending the half-life in blood of the carrying moiety involves PEGylating the carrying moiety. The PEGylation of a protein is considered to render the protein bulky and also suppress its degradation by protease in blood, thereby extending the half-life in blood of the protein (J Pharm Sci. 2008 October; 97 (10): 4167-83).

In certain embodiments, when the polypeptide of the present disclosure comprises an antigen-binding domain and a carrying moiety, the carrying moiety contains an antibody Fc region. In a specific embodiment, the carrying moiety contains a CH2 domain and a CH3 domain of a human IgG antibody. In a specific embodiment, the carrying moiety contains a moiety extending from human IgG1 antibody heavy chain Cys226 or Pro230 to the carboxyl-terminus of the heavy chain. However, the C-terminal lysine (Lys447) or glycine-lysine (Gly446-Lys447) of the Fc region may or may not be present.

In certain embodiments, when the polypeptide of the present disclosure comprises an antigen-binding domain and a carrying moiety, the carrying moiety contains an antibody constant region. In a more preferred embodiment, the carrying moiety contains an IgG antibody constant region. In a further preferred embodiment, the carrying moiety contains a human IgG antibody constant region.

In certain embodiments, when the polypeptide of the present disclosure comprises an antigen-binding domain and a carrying moiety, the carrying moiety contains: a region substantially similar in structure to an antibody heavy chain constant region; and a region substantially similar in structure to an antibody light chain, connected to the region via a covalent bond such as a disulfide bond or a noncovalent bond such as a hydrogen bond or hydrophobic interaction.

In certain embodiments, when the polypeptide of the present disclosure comprises an antigen-binding domain and a carrying moiety, the antigen-binding domain can be released from the polypeptide and has higher antigen-binding activity in a state where the antigen-binding domain is released from the polypeptide than the antigen-binding domain in a state where it is not released from the polypeptide.

In certain embodiments, when the polypeptide of the present disclosure comprises an antigen-binding domain and a carrying moiety, the antigen-binding domain becomes releasable from the polypeptide due to cleavage of the protease cleavage sequence by protease.

In certain embodiments, when the polypeptide of the present disclosure comprises an antigen-binding domain and a carrying moiety, the antigen-binding domain released from the polypeptide has higher antigen-binding activity than that before the release. In other words, the antigen-binding activity of the antigen-binding domain is inhibited by the inhibiting domain in a state where the antigen-binding domain is unreleased from the polypeptide. Whether the antigen-binding activity of the antigen-binding domain is inhibited by the inhibiting domain is confirmed by a method such as FACS (fluorescence activated cell sorting), ELISA (enzyme-linked immunosorbent assay), ECL (electrogenerated chemiluminescence), a SPR (surface plasmon resonance) method (Biacore), BLI (biolayer interferometry) (Octet). In certain embodiments, when the polypeptide of the present disclosure comprises an antigen-binding domain and a carrying moiety, the antigen-binding activity of the antigen-binding domain released from the polypeptide is a value equal to or greater than twice, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, 2000 times, or 3000 times the binding activity of the antigen-binding domain unreleased from the polypeptide. In certain embodiments, when the polypeptide of the present disclosure comprises an antigen-binding domain and a carrying moiety, the binding of the antigen-binding domain before the release to the antigen is not seen when the antigen-binding activity of the antigen-binding domain is measured by one method selected from among the methods described above.

In certain embodiments, when the polypeptide of the present disclosure comprises an antigen-binding domain and a carrying moiety, the protease cleavage sequence is cleaved so that the antigen-binding domain becomes capable of being released from the polypeptide. In such aspects, therefore, the antigen-binding activity can be compared between before and after the cleavage of the polypeptide. Specifically, the antigen-binding activity measured using the cleaved polypeptide is a value equal to or greater than twice, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, 2000 times, or 3000 times the antigen-binding activity measured using the uncleaved polypeptide. In some more specific embodiments, the binding of the antigen-binding domain of the uncleaved polypeptide to the antigen is not seen when the antigen-binding activity is measured by one method selected from among the methods described above.

In certain embodiments, when the polypeptide of the present disclosure comprises an antigen-binding domain and a carrying moiety, the protease cleavage sequence is cleaved by protease. In such aspects, therefore, the antigen-binding activity can be compared between before and after the protease treatment of the polypeptide. Specifically, the antigen-binding activity measured using the polypeptide after the protease treatment is a value equal to or greater than twice, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, 2000 times, or 3000 times the antigen-binding activity measured using the polypeptide without the protease treatment. In some more specific embodiments, the binding of the antigen-binding domain of the protease-untreated polypeptide to the antigen is not seen when the antigen-binding activity is measured by one method selected from among the methods described above.

In certain embodiments, when the polypeptide of the present disclosure comprises an antigen-binding domain and a carrying moiety, the antigen-binding activity of the antigen-binding domain is inhibited by association of the antigen-binding domain with the inhibiting domain of the carrying moiety.

In certain embodiments, when the polypeptide of the present disclosure comprises an antigen-binding domain and a carrying moiety, the association between the antigen-binding domain and the inhibiting domain of the carrying moiety is abolished by cleavage of the protease cleavage sequence by protease.

In certain embodiments, when the polypeptide of the present disclosure comprises an antigen-binding domain and a carrying moiety, the antigen-binding domain comprises or is a single-domain antibody, and the inhibiting domain of the carrying moiety inhibits the antigen-binding activity of the single-domain antibody. The single-domain antibody may be VHH, or VH having antigen-binding activity by its single domain, or VL having antigen-binding activity by its single domain.

In certain embodiments, when the polypeptide of the present disclosure comprises an antigen-binding domain and a carrying moiety, the inhibiting domain of the carrying moiety is associated with the antigen-binding domain. The inhibiting domain may constitute a portion of the carrying moiety or may constitute the whole of the carrying moiety. From another viewpoint, the inhibiting domain can also be defined as a moiety being associated with the antigen-binding domain, in the carrying moiety.

In a more specific embodiment, the antigen-binding domain which is a single-domain antibody and the inhibiting domain which is VL, VH or VHH form association as found between antibody VH and antibody VL. In a further specific embodiment, the antigen-binding domain which is a single-domain antibody and the inhibiting domain which is VL, VH or VHH form association as found between antibody VH and antibody VL, and in a state of the association thus formed, the inhibiting domain conformationally inhibits the binding of the antigen-binding domain to the antigen or conformationally changes the antigen-binding site of the antigen-binding domain so that the antigen-binding activity of the single-domain antibody is inhibited by the VL, the VH or the VHH. In an embodiment using VHH as the single-domain antibody, it is considered that the binding of the VHH to the antigen is conformationally inhibited by the inhibiting domain when CDR3, a main antigen-binding site of the VHH, or its neighboring site exists at the interface of association with the inhibiting domain.

The association of the antigen-binding domain with the inhibiting domain may be canceled, for example, by cleaving the cleavage site. The cancelation of the association can be used interchangeably with, for example, the cancelation of the state where two or more polypeptide regions interact with each other. The interaction between the two or more polypeptide regions may be wholly canceled, or the interaction between the two or more polypeptide regions may be partially canceled.

In the present specification, the "interface" usually refers to a face at which two regions associate or interact with each other. Amino acid residues forming the interface are usually one or a plurality of amino acid residues contained in each polypeptide region subjected to the association and more preferably refer to amino acid residues that approach each other upon association and participate in interaction. Specifically, the interaction includes noncovalent bonds such as a hydrogen bond, electrostatic interaction, or salt bridge formation between the amino acid residues approaching each other upon association.

In the present specification, the "amino acid residues forming the interface" specifically refers to amino acid residues contained in polypeptide regions constituting the interface. As one example, the polypeptide regions constituting the interface refer to polypeptide regions responsible for intramolecular or intermolecular selective binding in antibodies, ligands, receptors, substrates, etc. Specific examples of such polypeptide regions in antibodies can include heavy chain variable regions and light chain variable regions. In certain embodiments, when the polypeptide of the present disclosure comprises an antigen-binding domain and a carrying moiety, examples include antigen-binding domains and inhibiting domains.

Examples of the amino acid residues forming the interface include, but are not limited to, amino acid residues approaching each other upon association. The amino acid residues approaching each other upon association can be found, for example, by analyzing the conformations of polypeptides and examining the amino acid sequences of polypeptide regions forming the interface upon association of the polypeptides.

In certain embodiments, when the polypeptide of the present disclosure comprises an antigen-binding domain and a carrying moiety, an amino acid residue(s) involved in association in the antigen-binding domain, or an amino acid residue(s) involved in association in the inhibiting domain can be altered/modified in order to promote the association of the antigen-binding domain with the inhibiting domain. In a further specific embodiment, an amino acid residue(s) forming the interface with the inhibiting domain, in the antigen-binding domain, or an amino acid residue(s) forming the interface with the antigen-binding domain, in the inhibiting domain can be altered. In a preferred embodiment, the amino acid residue(s) forming the interface can be altered by a method of introducing a mutation(s) to the interface amino acid residue(s) such that two or more amino acid residues forming the interface have different charges. The alteration of the amino acid residue(s) to result in different charges includes the alteration of a positively charged amino acid residue(s) to a negatively charged amino acid residue(s) or an uncharged amino acid residue, the alteration of a negatively charged amino acid residue to a positively charged amino acid residue(s) or an uncharged amino acid residue(s), and the alteration of an uncharged amino acid residue(s) to a positively or negatively charged amino acid residue(s). Such an amino acid alteration is performed for the purpose of promoting the association and is not limited by the position of the amino acid alteration or the type of the amino acid as long as the purpose of promoting the association can be achieved. Examples of the alteration include, but are not limited to, substitution.

In certain embodiments, when the polypeptide of the present disclosure comprises an antigen-binding domain and a carrying moiety, VHH serving as the antigen-binding domain is associated with VL serving as the inhibiting domain. The amino acid residue involved in association with VL, in VHH can refer to, for example, an amino acid residue forming the interface between the VHH and the VL. Examples of the amino acid residue involved in association with VL, in VHH include, but are not limited to, amino acid residues at positions 37, 44, 45, and 47 (J. Mol. Biol. (2005) 350, 112-125). The activity of the VHH is inhibited by promoting the association between the VHH and the VL. Likewise, the amino acid residue involved in association with VHH, in VL can refer to, for example, an amino acid residue forming the interface between the VHH and the VL.

An amino acid residue involved in the association with VL, in VHH can be altered in order to promote the association between the VHH and the VL. Examples of such an amino acid substitution include, but are not limited to, F37V, Y37V, E44G, Q44G, R45L, H45L, G47W, F47W, L47W, T47W, or/and S47W. Instead of altering each residue in VHH, VHH originally having an amino acid residue 37V, 44G, 45L, or/and 47W may also be used. Instead of the VHH amino acid, an amino acid residue involved in association with VHH, in VL may be altered, and amino acid alterations may also be introduced to both VHH and VL, as long as the purpose of promoting the association between the VHH and the VL can be achieved.

In certain embodiments, when the polypeptide of the present disclosure comprises an antigen-binding domain and a carrying moiety, the antigen-binding domain and the inhibiting domain can be associated with each other by using VHH as the antigen-binding domain and using VH or VHH as the inhibiting domain. An amino acid residue involved in association with VH or VHH serving as the inhibiting domain, in VHH serving as the antigen-binding domain can be identified and altered in order to promote the association of the antigen-binding domain VHH with the inhibiting domain VH or VHH. Also, amino acid residues involved in association with VHH serving as the antigen-binding domain, in VH or VHH serving as the inhibiting domain, can be identified and altered.

In the case of using a single-domain antibody other than VHH as the antigen-binding domain, amino acid residues involved in association, in the antigen-binding domain or the inhibiting domain can also be identified and altered similarly to above.

In certain embodiments, when the polypeptide of the present disclosure comprises an antigen-binding domain and a carrying moiety, the carrying moiety and the antigen-binding domain are fused via a linker. In a more specific embodiment, the carrying moiety and the antigen-binding domain are fused via a linker containing a protease cleavage sequence. In an alternative specific embodiment, the carrying moiety and the antigen-binding domain are fused via a linker, and the fusion protein thus formed contains a protease cleavage sequence.

In certain embodiments, when the polypeptide of the present disclosure comprises an antigen-binding domain and a carrying moiety, the carrying moiety and the antigen-binding domain are fused without a linker. In a more specific embodiment, an amino bond is formed between the N-terminal amino acid of the carrying moiety and the C-terminal amino acid of the antigen-binding domain to form a fusion protein. The formed fusion protein contains a protease cleavage sequence. In a particular embodiment, one to several N-terminal amino acids of the carrying moiety or/and one to several C-terminal amino acids of the antigen-binding domain are altered, and the N terminus of the carrying moiety and the C terminus of the antigen-binding domain are fused to form a protease cleavage sequence near the fusion position. More specifically, when using LSGRSDNH (SEQ ID NO: 18031) as the protease cleavage sequence, the protease cleavage sequence can be formed, for example, by converting four C-terminal amino acids of the antigen-binding domain to an LSGR sequence and converting four N-terminal amino acids of the carrying moiety to an SDNH sequence.

When the polypeptide of the present disclosure comprises an antigen-binding domain and a carrying moiety, the protease cleavage sequence may be placed at any position in the polypeptide as long as the antigen-binding domain is released by protease cleavage and does not lose its antigen-binding activity after the release.

In certain embodiments, when the polypeptide of the present disclosure comprises an antigen-binding domain and a carrying moiety, the carrying moiety comprises an antibody constant region, and the N terminus of the antibody constant region and the C terminus of the antigen-binding domain are fused via a linker or without a linker.

In a particular embodiment, the protease cleavage sequence is located within the antibody constant region contained in the carrying moiety. In this case, the protease cleavage sequence can be located within the antibody constant region such that the antigen-binding domain is released by protease cleavage. In a specific embodiment, the protease cleavage sequence is located within an antibody heavy chain constant region contained in the carrying moiety, and more specifically located in the antibody heavy chain constant region on the side closer to the antigen-binding domain beyond the amino acid of position 140 (EU numbering), or in the antibody heavy chain constant region on the side closer to the antigen-binding domain beyond the amino acid of position 122 (EU numbering). In an alternative specific embodiment, the protease cleavage sequence is located within an antibody light chain constant region contained in the carrying moiety, and more specifically located in the antibody light chain constant region on the side closer to the antigen-binding domain beyond the amino acid of position 130 (Kabat numbering), or in the antibody light chain constant region on the side closer to the antigen-binding domain beyond the amino acid of position 113 (Kabat numbering).

In certain embodiments, when the polypeptide of the present disclosure comprises an antigen-binding domain and a carrying moiety, the antigen-binding domain is a single-domain antibody, and the C terminus of the single-domain antibody and the N terminus of the carrying moiety are fused via a linker or without a linker.

In a particular embodiment, the protease cleavage sequence is located within the single-domain antibody. In a more specific embodiment, the single-domain antibody is a single-domain antibody prepared from VH, or from VHH, and the protease cleavage sequence is located in the single-domain antibody on the side closer to the carrying moiety beyond the amino acid of position 35b (Kabat numbering), or in the single-domain antibody on the side closer to the carrying moiety beyond the amino acid of position 95 (Kabat numbering), or in the single-domain antibody on the side closer to the carrying moiety beyond the amino acid of position 109 (Kabat numbering). In an alternative specific embodiment, the single-domain antibody is a single-domain antibody prepared from VL, and the protease cleavage sequence is located in the single-domain antibody on the side closer to the carrying moiety beyond the amino acid of position 32 (Kabat numbering), or in the single-domain antibody on the side closer to the carrying moiety beyond the amino acid of position 91 (Kabat numbering), or in the single-domain antibody on the side closer to the carrying moiety beyond the amino acid of position 104 (Kabat numbering).

In certain embodiments, when the polypeptide of the present disclosure comprises an antigen-binding domain and a carrying moiety, the carrying moiety comprises an antibody constant region, the antigen-binding domain is a single-domain antibody, and the antibody constant region and the single-domain antibody are fused via a linker or without a linker. In a more specific embodiment, the N terminus of the antibody constant region and the C terminus of the single-domain antibody are fused via a linker or without a linker. In an alternative specific embodiment, the C terminus of the antibody constant region and the N terminus of the single-domain antibody are fused via a linker or without a linker.

In a particular embodiment, the protease cleavage sequence is located within the antibody constant region contained in the carrying moiety. In a more specific embodiment, the protease cleavage sequence is located in an antibody heavy chain constant region on the side closer to the single-domain antibody beyond the amino acid of position 140 (EU numbering), or in an antibody heavy chain constant region on the side closer to the single-domain antibody beyond the amino acid of position 122 (EU numbering). In an alternative specific embodiment, the protease cleavage sequence is located in an antibody light chain constant region on the side closer to the antigen-binding domain beyond the amino acid of position 130 (Kabat numbering), or in an antibody light chain constant region on the side closer to the antigen-binding domain beyond the amino acid of position 113 (Kabat numbering).

In a particular embodiment, the protease cleavage sequence is located within the single-domain antibody. In a more specific embodiment, the single-domain antibody is a single-domain antibody prepared from VH, or from VHH, and the protease cleavage sequence is located in the single-domain antibody on the side closer to the antibody constant region beyond the amino acid of position 35b (Kabat numbering), or in the single-domain antibody on the side closer to the antibody constant region beyond the amino acid of position 95 (Kabat numbering), or in the single-domain antibody on the side closer to the antibody constant region beyond the amino acid of position 109 (Kabat numbering). In an alternative specific embodiment, the single-domain antibody is a single-domain antibody prepared from VL, and the protease cleavage sequence is located in the single-domain antibody on the side closer to the antibody constant region beyond the amino acid of position 32 (Kabat numbering), or in the single-domain antibody on the side closer to the antibody constant region beyond the amino acid of position 91 (Kabat numbering), or in the single-domain antibody on the side closer to the antibody constant region beyond the amino acid of position 104 (Kabat numbering).

In a particular embodiment, the protease cleavage sequence is located near the boundary between the antigen-binding domain and the carrying moiety. The phrase "near the boundary between the antigen-binding domain and the carrying moiety" refers to a moiety that resides upstream or downstream of the linking site between the antigen-binding domain and the carrying moiety and does not largely influence the secondary structure of the antigen-binding domain.

In a more specific embodiment, the antigen-binding domain is linked to the antibody constant region contained in the carrying moiety, and the protease cleavage sequence is located near the boundary between the antigen-binding domain and the antibody constant region. The phrase "near the boundary between the antigen-binding domain and the antibody constant region" can refer to near the boundary between the antigen-binding domain and an antibody heavy chain constant region, or near the boundary between the antigen-binding domain and an antibody light chain constant region. When the antigen-binding domain is a single-domain antibody prepared from VH, or from VHH and is connected to an antibody heavy chain constant region, the phrase "near the boundary between the antigen-binding domain and the antibody constant region" can refer to between the amino acid of position 101 (Kabat numbering) of the single-domain antibody and the amino acid of position 140 (EU numbering) of the antibody heavy chain constant region or can refer to between the amino acid of position 109 (Kabat numbering) of the single-domain antibody and the amino acid of position 122 (EU numbering) of the antibody heavy chain constant region. When the antigen-binding domain is a single-domain antibody prepared from VH, or from VHH and is connected to an antibody light chain constant region, the phrase "near the boundary between the antigen-binding domain and the antibody light chain constant region" can refer to between the amino acid of position 101 (Kabat numbering) of the single-domain antibody and the amino acid of position 130 (Kabat numbering) of the antibody light chain constant region or can refer to between the amino acid of position 109 (Kabat numbering) of the single-domain antibody and the amino acid of position 113 (Kabat numbering) of the antibody light chain constant region. When the antigen-binding domain is a single-domain antibody prepared from VL, the phrase "near the boundary between the antigen-binding domain and the antibody constant region" refers to between the amino acid of position 96 (Kabat numbering) of the single-domain antibody and the prescribed position of the antibody constant region, or between the amino acid of position 104 (Kabat numbering) of the single-domain antibody and the prescribed position of the antibody constant region.

In certain embodiments, when the polypeptide of the present disclosure comprises an antigen-binding domain and a carrying moiety, the polypeptide is an IgG antibody-like molecule. Examples of such embodiments include, but are not limited to: an embodiment in which the carrying moiety comprises an IgG antibody constant region, a single-domain antibody serving as the antigen-binding domain takes the place of VH of an IgG antibody, and the antigen-binding activity is inhibited by VL; an embodiment in which the carrying moiety comprises an IgG antibody constant region, a single-domain antibody serving as the antigen-binding domain takes the place of VL of an IgG antibody, and the antigen-binding activity is inhibited by VH; and an embodiment in which the carrying moiety comprises an IgG antibody constant region, a single-domain antibody serving as the antigen-binding domain takes the place of one of VH and VL of an IgG antibody, and an additional single-domain antibody inhibits the antigen-binding activity of the antigen-binding domain takes the place of the other domain of the IgG antibody.

The term "IgG antibody-like molecule" used in the present specification is used to define a molecule having moieties substantially similar in structure to constant domains or constant regions as in an IgG antibody, and moieties substantially similar in structure to variable domains or variable regions as in the IgG antibody, and having conformation substantially similar to that of the IgG antibody. In the IgG antibody-like molecule, the domain similar to antibody CH1 and the domain similar to CL may be used interchangeably; that is, as long as interaction similar to the interaction between CH1 and CL of an IgG antibody is present between the domains, the domains linked to the portion similar to the antibody hinge region may be an antibody CH1 domain or an antibody CL domain. However, in the present specification, the "IgG antibody-like molecule" may or may not exert antigen-binding activity while retaining the structures similar to those of the IgG antibody.

When the polypeptide of the present disclosure comprises an antigen-binding domain and a carrying moiety, the polypeptide may comprise one or a plurality of antigen-binding domains. One or a plurality of inhibiting domains may inhibit the antigen-binding activity of a plurality of antigen-binding domains. A plurality of antigen-binding domains may each be associated with the inhibiting domain. A plurality of antigen-binding domains may each be fused with the carrying moiety. A plurality of antigen-binding domains may each be capable of being released from the polypeptide. The protease cleavage sequence(s) for release of a plurality of antigen-binding domains may be a plurality of protease cleavage sequences corresponding to the number of antigen-binding domains.

When the polypeptide is an IgG antibody-like molecule, antigen-binding domains may be respectively established at moieties corresponding to two variable regions of the IgG antibody, as shown in FIG. 3. Such an embodiment should be understandable by those skilled in the art with reference to the present disclosure. The antigen-binding domains incorporated in both arms may have the same antigen-binding specificity or may differ in antigen-binding specificities. Such an embodiment should be understandable by those skilled in the art with reference to the present disclosure. It is obvious that these embodiments are included in the scope of the present disclosure.

In certain embodiments, when the polypeptide of the present disclosure comprises an antigen-binding domain and a carrying moiety, the antigen-binding domain is further linked to a second antigen-binding domain. Examples of the second antigen-binding domain include, but are not limited to, single-domain antibodies, antibody fragments, a module called A domain of approximately 35 amino acids contained in an in vivo cell membrane protein avimer (WO2004/044011 and WO2005/040229), adnectin containing a 10Fn3 domain serving as a protein binding domain derived from a glycoprotein fibronectin expressed on cell membranes (WO2002/032925), Affibody containing an IgG binding domain scaffold constituting a three-helix bundle composed of 58 amino acids of protein A (WO1995/001937), DARPins (designed ankyrin repeat proteins) which are molecular surface-exposed regions of ankyrin repeats (AR) each having a 33-amino acid residue structure folded into a subunit of a turn, two antiparallel helices, and a loop (WO2002/020565), anticalin having four loop regions connecting eight antiparallel strands bent toward the central axis in one end of a barrel structure highly conserved in lipocalin molecules such as neutrophil gelatinase-associated lipocalin (NGAL) (WO2003/029462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (WO2008/016854). In a preferred embodiment, the second antigen-binding domain has antigen-binding specificity different from that of the antigen-binding domain. In a preferred embodiment, the molecular weight of the antigen-binding domain and the second antigen-binding domain linked is 60 kDa or smaller.

In some more specific embodiments, the antigen-binding domain and the second antigen-binding domain are single-domain antibodies differing in antigen-binding specificities, the antigen-binding domain and the second antigen-binding domain linked are capable of being released from the polypeptide, and the antigen-binding domain and the second antigen-binding domain form a bispecific antigen-binding molecule after release. Examples of such a bispecific antigen-binding molecule include, but are not limited to, a bispecific antigen-binding molecule having an antigen-binding domain specifically binding to the target cell surface antigen and a second antigen-binding domain specifically binding to an immunocyte surface antigen, a bispecific antigen-binding molecule having an antigen-binding domain and a second antigen-binding domain binding to different subunits of the same antigen, and a bispecific antigen-binding molecule having an antigen-binding domain and a second antigen-binding domain binding to different epitopes in the same antigen. Such a bispecific antigen-binding molecule can recruit immunocytes to the vicinity of target cells and is thus considered useful in the treatment of a disease caused by the target cells.

The antigen-binding activity of the second antigen-binding domain may or may not be inhibited by the carrying moiety. The second antigen-binding domain may or may not be associated with a partial structure of the carrying moiety. Particularly, when the antigen-binding domain and the second antigen-binding domain differ in antigen-binding specificities, the antigen-binding domain in an unreleased state cannot exert antigen-binding activity, as shown in, for example, FIG. 4, even if the antigen-binding activity of the second antigen-binding domain is not inhibited and even if the second antigen-binding domain is not associated with a partial structure of the carrying moiety. This bispecific antigen-binding molecule comprising the antigen-binding domain linked to the second antigen-binding domain cannot exert a function of bispecifically binding to two types of antigens.

Figure 4:
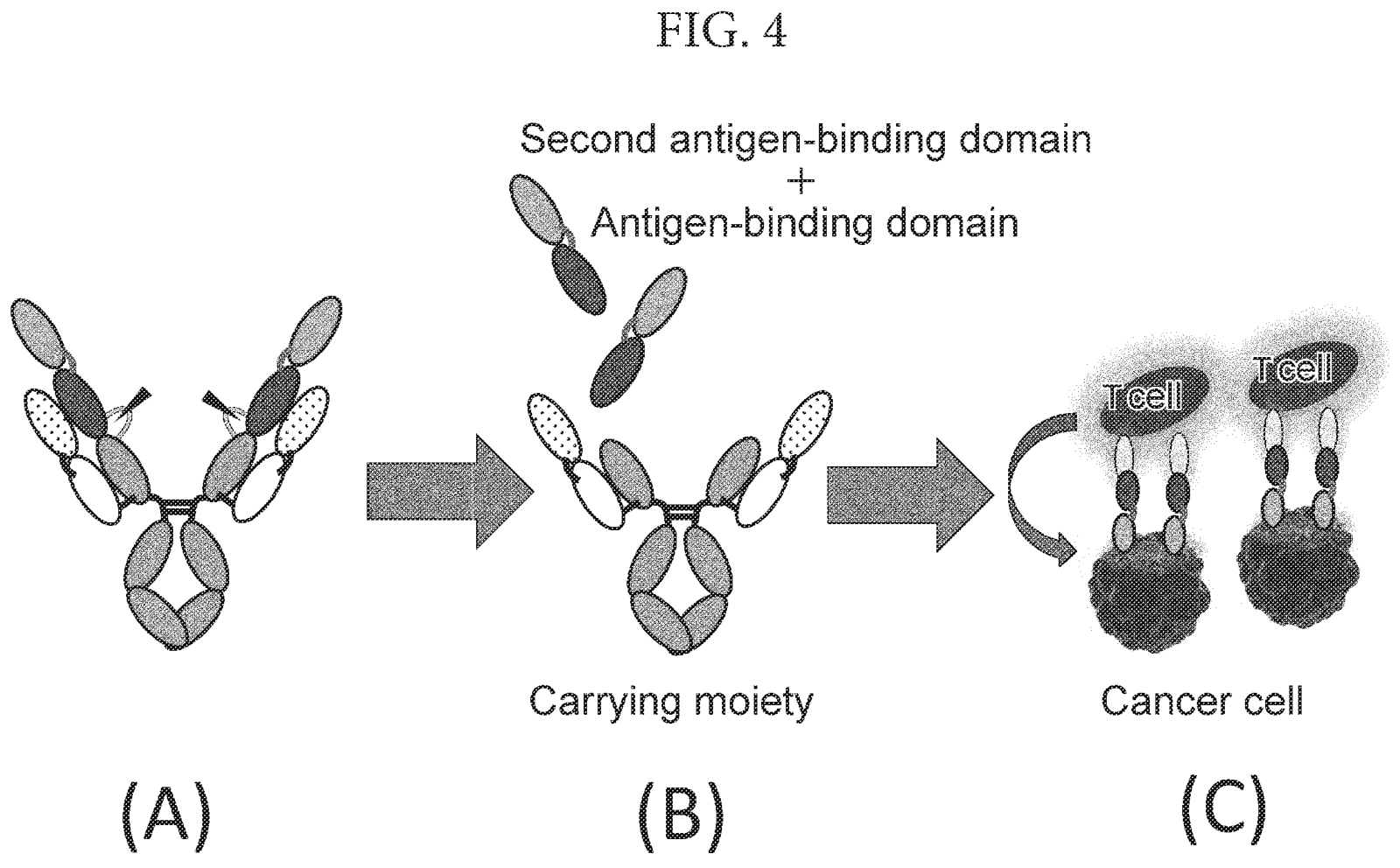

FIG. 4 shows one exemplary form in which the antigen-binding domain is further linked to the second antigen-binding domain.

In the present specification, the term "specificity" refers to a property by which one of specifically binding molecules does not substantially bind to a molecule other than its one or more binding partner molecules. This term is also used when the antigen-binding domain has specificity for an epitope contained in a particular antigen. The term is also used when the antigen-binding domain has specificity for a particular epitope among a plurality of epitopes contained in an antigen. In this context, the term "not substantially bind" is determined according to the method described in the section about binding activity and means that the binding activity of a specific binding molecule for a molecule other than the binding partner(s) is 80% or less, usually 50% or less, preferably 30% or less, particularly preferably 15% or less, of its binding activity for the binding partner molecule(s).

Figure 1:
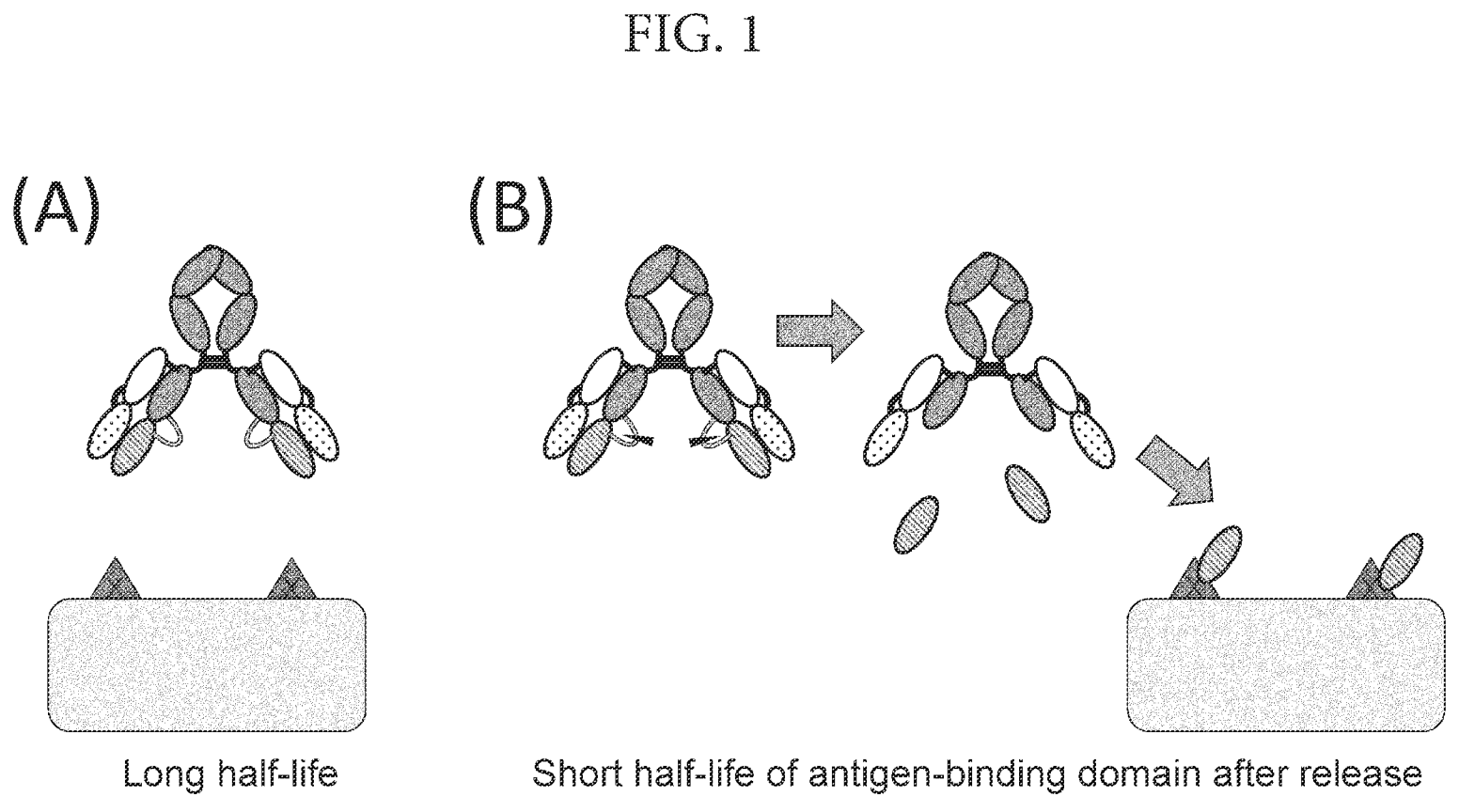

The sequence shown in any of SEQ ID NOs: 5-18003, or a partial sequence comprised in those sequences that is useable as a protease cleavage sequence (the sequence spanning from the N-terminal fourth to fifteenth amino acids of a sequence selected from SEQ ID NOs: 5-17201; the sequence spanning from the N-terminal fourth to thirteenth amino acids of a sequence selected from SEQ ID NOs: 5-17201; the sequence spanning from the N-terminal sixth to thirteenth amino acids of a sequence selected from SEQ ID NOs: 5-17201; the sequence spanning from the N-terminal first to twelfth amino acids of a sequence selected from SEQ ID NOs: 17202-17993; the sequence spanning from the N-terminal third to twelfth amino acids of a sequence selected from SEQ ID NOs: 17202-17993; the sequence spanning from the N-terminal third to eleventh amino acids of a sequence selected from SEQ ID NOs: 17202-17993; the sequence spanning from the N-terminal third to tenth amino acids of a sequence selected from SEQ ID NOs: 17202-17993; the sequence spanning from the N-terminal third to fourteenth amino acids of a sequence selected from SEQ ID NOs: 17994-18003; the sequence spanning from the N-terminal fifth to twelfth amino acids of a sequence selected from SEQ ID NOs: 17994-18003; and the sequence spanning from the N-terminal fifth to tenth amino acids of a sequence selected from SEQ ID NOs: 17994-18003) can be used as the protease cleavage site in the polypeptide illustrated in FIG. 1.

Also, a sequence composed of "a sequence selected from Group A listed below-a sequence selected from Group B listed below" in this order from the N-terminus can be used as the protease cleavage site in the polypeptide illustrated in FIG. 1:

(Group A)

the sequence spanning from the N-terminal first to nineth amino acids of a sequence selected from SEQ ID NOs: 5-17201, the sequence spanning from the N-terminal second to nineth amino acids of a sequence selected from SEQ ID NOs: 5-17201, the sequence spanning from the N-terminal third to nineth amino acids of a sequence selected from SEQ ID NOs: 5-17201, the sequence spanning from the N-terminal fourth to nineth amino acids of a sequence selected from SEQ ID NOs: 5-17201, the sequence spanning from the N-terminal fifth to nineth amino acids of a sequence selected from SEQ ID NOs: 5-17201, the sequence spanning from the N-terminal sixth to nineth amino acids of a sequence selected from SEQ ID NOs: 5-17201, the sequence spanning from the N-terminal seventh to nineth amino acids of a sequence selected from SEQ ID NOs: 5-17201, the sequence spanning from the N-terminal eighth to nineth amino acids of a sequence selected from SEQ ID NOs: 5-17201, the sequence spanning from the N-terminal first to sixth amino acids of a sequence selected from SEQ ID NOs: 17202-17993, the sequence spanning from the N-terminal second to sixth amino acids of a sequence selected from SEQ ID NOs: 17202-17993, the sequence spanning from the N-terminal third to sixth amino acids of a sequence selected from SEQ ID NOs: 17202-17993, the sequence spanning from the N-terminal fourth to sixth amino acids of a sequence selected from SEQ ID NOs: 17202-17993, the sequence spanning from the N-terminal fifth to sixth amino acids of a sequence selected from SEQ ID NOs: 17202-17993, the sequence spanning from the N-terminal first to eighth amino acids of a sequence selected from SEQ ID NOs: 17994-18003, the sequence spanning from the N-terminal second to eighth amino acids of a sequence selected from SEQ ID NOs: 17994-18003, the sequence spanning from the N-terminal third to eighth amino acids of a sequence selected from SEQ ID NOs: 17994-18003, the sequence spanning from the N-terminal fourth to eighth amino acids of a sequence selected from SEQ ID NOs: 17994-18003, the sequence spanning from the N-terminal fifth to eighth amino acids of a sequence selected from SEQ ID NOs: 17994-18003, the sequence spanning from the N-terminal sixth to eighth amino acids of a sequence selected from SEQ ID NOs: 17994-18003, and the sequence spanning from the N-terminal seventh to eighth amino acids of a sequence selected from SEQ ID NOs: 17994-18003;

(Group B)

the sequence spanning from the N-terminal tenth to fifteenth amino acids of a sequence selected from SEQ ID NOs: 5-17201, the sequence spanning from the N-terminal tenth to fourteenth amino acids of a sequence selected from SEQ ID NOs: 5-17201, the sequence spanning from the N-terminal tenth to thirteenth amino acids of a sequence selected from SEQ ID NOs: 5-17201, the sequence spanning from the N-terminal tenth to twelfth amino acids of a sequence selected from SEQ ID NOs: 5-17201, the sequence spanning from the N-terminal tenth to eleventh amino acids of a sequence selected from SEQ ID NOs: 5-17201, the sequence spanning from the N-terminal seventh to fifteenth amino acids of a sequence selected from SEQ ID NOs: 17202-17993, the sequence spanning from the N-terminal seventh to fourteenth amino acids of a sequence selected from SEQ ID NOs: 17202-17993, the sequence spanning from the N-terminal seventh to thirteenth amino acids of a sequence selected from SEQ ID NOs: 17202-17993, the sequence spanning from the N-terminal seventh to twelfth amino acids of a sequence selected from SEQ ID NOs: 17202-17993, the sequence spanning from the N-terminal seventh to eleventh amino acids of a sequence selected from SEQ ID NOs: 17202-17993, the sequence spanning from the N-terminal seventh to tenth amino acids of a sequence selected from SEQ ID NOs: 17202-17993, the sequence spanning from the N-terminal seventh to nineth amino acids of a sequence selected from SEQ ID NOs: 17202-17993, the sequence spanning from the N-terminal seventh to eighth amino acids of a sequence selected from SEQ ID NOs: 17202-17993, the sequence spanning from the N-terminal nineth to fifteenth amino acids of a sequence selected from SEQ ID NOs: 17994-18003, the sequence spanning from the N-terminal nineth to fourteenth amino acids of a sequence selected from SEQ ID NOs: 17994-18003, the sequence spanning from the N-terminal nineth to thirteenth amino acids of a sequence selected from SEQ ID NOs: 17994-18003, the sequence spanning from the N-terminal nineth to twelfth amino acids of a sequence selected from SEQ ID NOs: 17994-18003, the sequence spanning from the N-terminal nineth to eleventh amino acids of a sequence selected from SEQ ID NOs: 17994-18003, and the sequence spanning from the N-terminal nineth to tenth amino acids of a sequence selected from SEQ ID NOs: 17994-18003.

The molecule shown in FIG. 1 has a long half-life when it is a polypeptide that is in a state where the antigen-binding domain and carrying moiety are connected. In this state, the antigen-binding activity of the antigen-binding domain is inhibited, and the molecule does not bind to the antigen (A). After release of the antigen-binding domain, the antigen-binding activity is restored and the half-life becomes short (B).

Although the polypeptide shown in FIG. 1 has many variations, it can be produced according to the production method illustrated in FIG. 2 when an IgG antibody-like molecule is used. Initially, a single-domain antibody (e. g., VH or VHH) that binds to a target antigen is obtained (A). Either one of the VH and VL of an IgG antibody having a germline sequence is replaced with the single-domain antibody obtained, which is then associated with the other one of VH and VL to form an IgG antibody-like molecule (B). A protease cleavage sequence is introduced into the IgG antibody-like molecule (C). The position of introduction may be, for example, in the vicinity of the boundary between the introduced single-domain antibody (VH or VHH) and the constant region (CH1 or CL).

A single-domain antibody has antigen-binding activity when existing as a single domain; however, it loses antigen-binding activity when it forms a variable region with, for example, VL/VH/VHH. Considering that VL/VH is a natural human antibody sequence having a germline sequence, the immunogenicity risk is low and the possibility of an anti-drug antibody that recognizes the VL/VH being induced is extremely low. Also, humanization of VHH may reduce the immunogenicity risk and may reduce the possibility of inducing anti-drug antibodies that recognize the humanized VHH, when VHH is used to form a variable region together with a single-domain antibody. The single-domain antibody is released by cleavage by protease of the protease cleavage sequence inserted into the IgG antibody-like molecule. The single-domain antibody thus released has antigen-binding activity. While the IgG antibody-like molecule has a structure similar to that of general IgG molecules before the cleavage by protease and thus has long retentivity in blood, the single-domain antibody released by cleavage by protease does not have any Fc region and its molecular weight is about 13 kDa, and thus it is rapidly eliminated by renal excretion. In fact, while full-length IgGs have a half-life of about 2-3 weeks (Blood., Mar. 31, 2016, 127(13): 1633-41), the half-life of single domain antibodies is about 2 hours (Antibodies, 2015, 4(3): 141-156). Thus, antigen-binding molecules activated by protease have a short half-life in blood, and they are less likely to bind to antigens in normal tissue.

When the single-domain antibody is VL, the same concept can be attained, for example, by introducing a protease cleavage sequence near the boundary between VL and CL.

The present disclosure also relates to methods for producing a polypeptide when the polypeptide comprises a carrying moiety having an inhibiting domain, and an antigen-binding domain.

One method for producing the polypeptide of the present disclosure comprising a carrying moiety having an inhibiting domain, and an antigen-binding domain is a method comprising: obtaining an antigen-binding domain having antigen-binding activity; linking the antigen-binding domain to a carrying moiety such that the antigen-binding activity of the antigen-binding domain is inhibited by an inhibiting domain, to form a polypeptide precursor; and further inserting a protease cleavage sequence into the polypeptide precursor or altering a portion of the polypeptide precursor to a protease cleavage sequence. The method for introducing the protease cleavage sequence can be any of the insertion of the protease cleavage sequence and the alteration of a portion of the polypeptide precursor as long as the protease cleavage sequence can be introduced into the polypeptide precursor. Alternatively, a protease cleavage sequence may be introduced into the polypeptide precursor by the combination of both the approaches. Such an embodiment should be obvious to those skilled in the art with reference to the present specification and is included in the scope of the present disclosure.

Another method for producing the polypeptide of the present disclosure comprising a carrying moiety having an inhibiting domain, and an antigen-binding domain is a method comprising: obtaining an antigen-binding domain having antigen-binding activity; and linking the antigen-binding domain to a carrying moiety via a protease cleavage sequence such that the antigen-binding activity of the antigen-binding domain is inhibited by an inhibiting domain, to form a polypeptide. When the antigen-binding domain is linked to the carrying moiety via a protease cleavage sequence, the protease cleavage sequence may be sandwiched between the antigen-binding domain and the carrying moiety, or a portion of the antigen-binding domain or/and a portion of the carrying moiety may be altered and used as a portion of the protease cleavage sequence.

In an embodiment using a single-domain antibody as the antigen-binding domain, the methods for producing the polypeptide comprising a carrying moiety having an inhibiting domain, and an antigen-binding domain will be described below.

In one embodiment of the present disclosure, the method for producing a polypeptide comprising a carrying moiety having an inhibiting domain, and an antigen-binding domain is a production method comprising the following steps:
  (a) obtaining a single-domain antibody binding to a target antigen;
  (b) linking the single-domain antibody obtained in the step (a) to a carrying moiety such that the antigen-binding activity of the single-domain antibody is inhibited by an inhibiting domain of the carrying moiety, to form a polypeptide precursor; and (c) introducing a protease cleavage sequence into the polypeptide precursor.

In one embodiment of the present disclosure, the method for producing a polypeptide comprising a carrying moiety having an inhibiting domain, and an antigen-binding domain is a production method comprising the following steps:
  (a) obtaining a single-domain antibody binding to a target antigen;
  (b) linking the single-domain antibody obtained in the step (a) to a carrying moiety such that the antigen-binding activity of the single-domain antibody is inhibited by an inhibiting domain of the carrying moiety, to form a polypeptide precursor; and
  (c) introducing a protease cleavage sequence to near the boundary between the single-domain antibody and the carrying moiety.

In one embodiment of the present disclosure, the method for producing a polypeptide comprising a carrying moiety having an inhibiting domain, and an antigen-binding domain is a production method comprising the following steps:
  (a) obtaining a single-domain antibody binding to a target antigen; and
  (b) linking the single-domain antibody obtained in the step (a) to the carrying moiety via a protease cleavage sequence such that the antigen-binding activity of the single-domain antibody is inhibited by an inhibiting domain of the carrying moiety, to form a polypeptide.

In a particular embodiment, the method for producing a polypeptide comprising a carrying moiety having an inhibiting domain, and an antigen-binding domain is the production method further comprising the following step:
  (d) confirming that the binding activity of the single-domain antibody incorporated into the polypeptide or into the polypeptide precursor against the target antigen is weakened or lost.

In the present disclosure, the phrase "binding activity is weakened" means that the binding activity against the target antigen is decreased as compared with that before the linking, and the degree of this decrease is not limited.

In a particular embodiment, the method for producing a polypeptide comprising a carrying moiety having an inhibiting domain, and an antigen-binding domain is the production method further comprising the following step:
  (e) releasing the single-domain antibody by the protease cleavage of the protease cleavage sequence and confirming that the released single-domain antibody binds to the antigen.

In one embodiment of the present disclosure, the method for producing a polypeptide which is an IgG antibody-like molecule comprising a carrying moiety having an inhibiting domain, and an antigen-binding domain is a production method comprising the following steps:
  (a) obtaining a single-domain antibody binding to a target antigen;
  (b) allowing the single-domain antibody obtained in the step (a) to be associated with a VL as a substitute for VH of an IgG antibody, or allowing the single-domain antibody to be associated with a VH as a substitute for VL of an IgG antibody such that the antigen-binding activity of the single-domain antibody is inhibited, to form an IgG antibody-like molecule precursor harboring the single-domain antibody; and
  (c) introducing a protease cleavage sequence into the IgG antibody-like molecule precursor harboring the single-domain antibody.

In one embodiment of the present disclosure, the method for producing a polypeptide which is an IgG antibody-like molecule comprising a carrying moiety having an inhibiting domain, and an antigen-binding domain is a production method comprising the following steps:
  (a) obtaining a single-domain antibody binding to a target antigen;
  (b) allowing the single-domain antibody obtained in the step (a) to be associated with a VL as a substitute for VH of an IgG antibody, or allowing the single-domain antibody to be associated with a VH as a substitute for VL of an IgG antibody such that the antigen-binding activity of the single-domain antibody is inhibited, to form an IgG antibody-like molecule precursor harboring the single-domain antibody; and (c) introducing a protease cleavage sequence to near the boundary between the single-domain antibody and an antibody constant region in the IgG antibody-like molecule precursor.

In one embodiment of the present disclosure, the method for producing a polypeptide which is an IgG antibody-like molecule comprising a carrying moiety having an inhibiting domain, and an antigen-binding domain is a production method comprising the following steps:

(a) obtaining a single-domain antibody binding to a target antigen; and (b) linking the single-domain antibody obtained in the step (a) as a substitute for IgG antibody VH or VL to an IgG antibody heavy chain constant region or light chain constant region via a protease cleavage sequence such that the antigen-binding activity of the single-domain antibody is inhibited, to form an IgG antibody-like molecule harboring the single-domain antibody.

In a particular embodiment, the method for producing a polypeptide which is an IgG antibody-like molecule comprising a carrying moiety having an inhibiting domain, and an antigen-binding domain is the production method further comprising the following step:

(d) confirming that the binding activity of the single-domain antibody introduced into the IgG antibody-like molecule or into the IgG antibody-like molecule precursor against the target antigen is weakened or lost.

In the present disclosure, the phrase "binding activity is weakened" means that the binding activity against the target antigen is decreased as compared with that before the association or the linking, and the degree of this decrease is not limited.

In a particular embodiment, the method for producing a polypeptide which is an IgG antibody-like molecule comprising a carrying moiety having an inhibiting domain, and an antigen-binding domain is the production method further comprising the following step:

(e) releasing the single-domain antibody by the protease cleavage of the protease cleavage sequence and confirming that the released single-domain antibody binds to the target antigen.

In the case of using VH, VL or VHH as the inhibiting domain, the method for inhibiting the antigen-binding activity of the single-domain antibody by the inhibiting domain of the carrying moiety includes a method of allowing the single-domain antibody to be associated with VH, VL or VHH. The VH, the VL or the VHH that inhibits the antigen-binding activity of the provided single-domain antibody can be screened for by allowing known VH, VL or VHH to be associated with the single-domain antibody and comparing the antigen-binding activity of the single-domain antibody between before and after the association.

In another method for inhibiting the antigen-binding activity of the single-domain antibody by particular VH, VL or VHH, an amino acid residue involved in association with VH, VL or VHH, in the single-domain antibody can be substituted to promote the association, or a single-domain antibody/inhibiting domain pair having the desired level of difference in antigen-binding activity between before and after the association can also be provided by using a single-domain antibody originally having, as such an amino acid residue, an amino acid that can promote the association.

In one embodiment of the present disclosure, the method for producing a polypeptide which is an IgG antibody-like molecule comprising a carrying moiety having an inhibiting domain, and an antigen-binding domain is a production method comprising the following steps:

(a) substituting an amino acid residue in a single-domain antibody that is involved in association with antibody VH, or substituting an amino acid residue in a single-domain antibody that is involved in association with antibody VL to prepare a variant single-domain antibody retaining the binding activity of the single-domain antibody against the target antigen;

(b) allowing the variant single-domain antibody prepared in the step (a) to be associated with antibody VH, or allowing the variant single-domain antibody to be associated with antibody VL such that the antigen-binding activity of the variant single-domain antibody is inhibited, to form an IgG antibody-like molecule precursor harboring the variant single-domain antibody; and (c) introducing a protease cleavage sequence into the IgG antibody-like molecule precursor harboring the variant single-domain antibody.

In one embodiment of the present disclosure, the method for producing a polypeptide which is an IgG antibody-like molecule comprising a carrying moiety having an inhibiting domain, and an antigen-binding domain is a production method comprising the following steps:

(a) substituting an amino acid residue in a single-domain antibody that is involved in association with antibody VH, or substituting an amino acid residue in a single-domain antibody that is involved in association with antibody VL, to prepare a variant single-domain antibody retaining the binding activity of the single-domain antibody against the target antigen;

(b) allowing the variant single-domain antibody prepared in the step (a) to be associated with antibody VH, or allowing the variant single-domain antibody to be associated with antibody VL such that the antigen-binding activity of the variant single-domain antibody is inhibited, to form an IgG antibody-like molecule precursor harboring the variant single-domain antibody; and (c) introducing a protease cleavage sequence to near the boundary between the variant single-domain antibody and a constant region in the IgG antibody-like molecule precursor.

In one embodiment of the present disclosure, the method for producing a polypeptide which is an IgG antibody-like molecule comprising a carrying moiety having an inhibiting domain, and an antigen-binding domain is a production method comprising the following steps:

(a) substituting an amino acid residue in a single-domain antibody that is involved in association with antibody VH, or substituting an amino acid residue in a single-domain antibody that is involved in association with antibody VL, to prepare a variant single-domain antibody retaining the binding activity of the single-domain antibody against the target antigen; and (b) linking the variant single-domain antibody prepared in the step (a) to an IgG antibody heavy chain constant region via a protease cleavage sequence, or linking the variant single-domain antibody to an IgG antibody light chain constant region via a protease cleavage sequence such that the antigen-binding activity of the variant single-domain antibody is inhibited, to form an IgG antibody-like molecule harboring the variant single-domain antibody.

In a particular embodiment, the method for producing a polypeptide which is an IgG antibody-like molecule comprising a carrying moiety having an inhibiting domain, and an antigen-binding domain is the production method further comprising the following step:

(d) confirming that the binding activity of the variant single-domain antibody harbored in the IgG antibody-like molecule or the IgG antibody-like molecule precursor against the target antigen is weakened or lost.

In the present disclosure, the phrase "binding activity is weakened" means that the binding activity against the target antigen is decreased as compared with that before the association or the linking, and the degree of this decrease is not limited.

In a particular embodiment, the method for producing a polypeptide which is an IgG antibody-like molecule comprising a carrying moiety having an inhibiting domain, and an antigen-binding domain is the production method further comprising the following step:

(e) releasing the variant single-domain antibody by the protease cleavage of the protease cleavage sequence and confirming that the released variant single-domain antibody binds to the target antigen.

Ligand-Binding Molecules

In one embodiment of the polypeptide of the present disclosure, the polypeptide is a ligand-binding molecule capable of binding to a ligand, in which the binding of the ligand-binding molecule to the ligand in a state where the protease cleavage sequence is cleaved is weaker than the binding of the ligand-binding molecule to the ligand in a state where the protease cleavage sequence is not cleaved.

The present disclosure also relates to a method for releasing a ligand bound to a ligand-binding molecule, the method comprising cleaving, by protease, a protease cleavage sequence contained in the ligand-binding molecule described herein.

The present disclosure also relates to a method for releasing a ligand from a fusion protein of the ligand and a ligand-binding molecule described herein, the method comprising cleaving, by protease, a protease cleavage sequence contained in the ligand-binding molecule.

The term "ligand-binding molecule" in the present specification refers to a molecule capable of binding to a ligand, particularly, a molecule capable of binding to a ligand in an uncleaved state. In this context, the "binding" usually refers to binding through interaction based mainly on a noncovalent bond such as electrostatic force, van der Waals' force, or a hydrogen bond. Preferred examples of the ligand binding form of the ligand-binding molecule of the present disclosure include, but are not limited to, antigen-antibody reaction through which an antigen binding region, an antigen binding molecule, an antibody, an antibody fragment, or the like binds to the antigen.

The phrase "capable of binding to a ligand" means that the ligand-binding molecule is capable of binding to the ligand even if the ligand-binding molecule and the ligand are separate molecules, and does not mean that the ligand-binding molecule and the ligand are connected through a covalent bond. For example, the fact that the ligand and the ligand-binding molecule are covalently bound via a linker is not referred to as "capable of binding to a ligand". Also, the phrase "ligand binding is attenuated" means that the capability of binding (binding capacity) described above is attenuated. For example, when the ligand and the ligand-binding molecule are covalently bound via a linker, cleavage of the linker does not mean attenuation of the ligand binding. In the present disclosure, the ligand-binding molecule may be connected with the ligand via a linker or the like as long as the ligand-binding molecule is capable of binding to the ligand.

The ligand-binding molecule of the present disclosure is limited only by its binding to the ligand in an uncleaved state, and can be a molecule having any structure as long as it can bind to the ligand of interest in an uncleaved state. Examples of the ligand-binding molecule include, but are not limited to, an antibody heavy chain variable region (VH), an antibody light chain variable region (VL), a single-domain antibody (sdAb), a module called A domain of approximately 35 amino acids contained in a cell membrane protein avimer which is present in vivo (WO2004/044011 and WO2005/040229), adnectin containing a 10Fn3 domain which is a domain that binds to a protein in a glycoprotein fibronectin expressed on cell membranes (WO2002/032925), Affibody containing an IgG binding domain scaffold constituting a three-helix bundle composed of 58 amino acids of protein A (WO1995/001937), DARPins (designed ankyrin repeat proteins) which are molecular surface-exposed regions of ankyrin repeats (AR) having a structure in which a subunit comprising 33-amino acid residues and a turn, two antiparallel helices, and a loop is repeatedly stacked (WO2002/020565), anticalin having four loop regions that support one side of a barrel structure formed by eight antiparallel strands bent toward the central axis which is highly conserved in lipocalin molecules such as neutrophil gelatinase-associated lipocalin (NGAL) (WO2003/029462), and a depressed region in the internal parallel sheet structure of a horseshoe-shaped structure composed of repeated stacks of leucine-rich-repeat (LRR) modules of an immunoglobulin structure-free variable lymphocyte receptor (VLR) as seen in the acquired immune systems of jawless vertebrates such as lamprey and hagfish (WO2008/016854).

When the polypeptide of the present disclosure is a ligand-binding molecule, the protease cleavage sequence may be placed at any position in the polypeptide as long as the binding of the ligand-binding molecule to the ligand is attenuated by cleavage of the sequence. The number of the protease cleavage sequence contained in the polypeptide may be one or more.

In certain embodiments, when the polypeptide of the present disclosure is a ligand-binding molecule, the ligand-binding molecule binds to the ligand more weakly (i.e., ligand binding is attenuated) in a cleaved state compared with an uncleaved state. In an embodiment in which the ligand binding of the ligand-binding molecule is based on antigen-antibody reaction, attenuation of the ligand binding can be evaluated on the basis of the ligand binding activity of the ligand-binding molecule.

The binding activity of the ligand-binding molecule to a ligand can be assessed by a well-known method such as FACS, an ELISA format, a BIACORE method using amplified luminescent proximity homogeneous assay (ALPHA) screening or surface plasmon resonance (SPR) phenomena, or bio-layer interferometry (BLI) (Octet) (Proc. Natl. Acad. Sci. USA (2006) 103 (11), 4005-4010).

ALPHA screening is carried out based on the following principle according to ALPHA technology that uses two beads, a donor and an acceptor. Luminescence signals are detected only when molecules bound with the donor beads interact with molecules bound with the acceptor beads and when the two beads are close to one another. Laser-excited photosensitizers in the donor beads convert ambient oxygen into singlet oxygen in an excited state. The singlet oxygen molecules spread around the donor beads and when they reach the nearby acceptor beads, they induce chemiluminescent reaction in the beads to result in light emission. When the molecule bound with the donor bead and the molecule bound with the acceptor bead do not interact, chemiluminescent reaction does not occur because singlet oxygen produced by the donor bead does not reach the acceptor bead.

For example, a biotin-labeled ligand-binding molecule is bound to the donor bead, and a glutathione S transferase (GST)-tagged ligand is bound to the acceptor bead. In the absence of a competing untagged ligand-binding molecule, the ligand-binding molecule interacts with the ligand to generate signals of 520 to 620 nm. The untagged ligand-binding molecule competes with the tagged ligand-binding molecule for interaction with the ligand. Decrease in fluorescence resulting from the competition can be quantified to determine relative binding affinity. Biotinylation of a ligand-binding molecule, such as an antibody, using sulfo-NHS-biotin or the like is known in the art. A method which involves, for example, fusing a polynucleotide encoding the ligand in-frame with a polynucleotide encoding GST to form a fused gene, expressing the GST-fused ligand in cells or the like carrying a vector that permits expression of the fused gene, and purifying the GST-fused ligand using a glutathione column, can be appropriately adopted as a method for tagging a ligand with GST. The obtained signals are preferably analyzed using, for example, the software GRAPH-PAD PRISM (GraphPad Software, Inc., San Diego) adapted to a one-site competition model based on non-linear regression analysis.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other one (analyte) of the substances between which the interaction is to be observed is poured onto the surface of the sensor chip, and when the analyte binds with the ligand the mass of the immobilized ligand molecule increases and results in the change of refractive index of the solvent on the sensor chip surface. This change in refractive index shifts the position of the SPR signal (in contrast, the position of the signal returns when dissociation occurs). The Biacore system plots on the ordinate the amount of the above-mentioned shift, i.e., change in mass on the sensor chip surface, and displays time-dependent change in mass as assay data (sensorgram). Kinetics (association rate constant (ka) and dissociation rate constant (kd)) is determined from the curve of the sensorgram, and dissociation constant (KD) is determined from the ratio between the two constants. Inhibition assay or equilibrium analysis is also preferably used in the BIACORE method. Examples of inhibition assay are described in Proc. Natl. Acad. Sci. USA (2006) 103 (11), 4005-4010, and examples of equilibrium analysis are described in Methods Enzymol. 2000; 323: 325-40.

The phrase "the function of a ligand-binding molecule to bind with a ligand is attenuated" means that the amount of ligand bound per a test ligand-binding molecule is, for example, 50% or less, preferably 45% or less, 40% or less, 35% or less, 30% or less, 20% or less, or 15% or less, particularly preferably 10% or less, 9% or less, 8% or less, 7% or less, 6% or less, 5% or less, 4% or less, 3% or less, 2% or less, or 1% or less, of the amount of ligand bound to a control ligand-binding molecule, on the basis of the measurement method described above. Desired index may be appropriately used as a binding activity index, and a dissociation constant (KD) may be used. In the case of using a dissociation constant (KD) as an index for evaluating binding activity, a larger dissociation constant (KD) of the test ligand-binding molecule for the ligand than the dissociation constant (KD) of a control ligand-binding molecule for the ligand means that the test ligand-binding molecule has weaker binding activity against the ligand than the control ligand-binding molecule. The phrase "the function of binding to a ligand is attenuated" means that the dissociation constant (KD) of the test ligand-binding molecule for the ligand is, for example, 2 times or more, preferably 5 times or more, or 10 times or more, and particularly preferably 100 times or more compared to the dissociation constant (KD) of the control ligand-binding molecule for the ligand.

Examples of the control ligand-binding molecule include an uncleaved form of a ligand-binding molecule.

In the present specification, the term "ligand" is a molecule having biological activity. The molecule having biological activity usually functions by interacting with a receptor on cell surface and thereby performing biological stimulation, inhibition, or modulation in other modes. These functions are usually thought to participate in the intracellular signaling pathways of cells carrying the receptor.

In the present specification, the ligand encompasses a desired molecule that exerts biological activity through interaction with a biomolecule. For example, the ligand not only means a molecule that interacts with a receptor but also includes a molecule that exerts biological activity through interaction with the molecule, such as a receptor that interacts with the molecule, or a binding fragment thereof. For example, a ligand binding site of a protein known as a receptor, and a protein containing a site of the receptor which interacts with another molecule are included in the ligand according to the present disclosure. Specifically, a soluble receptor, a soluble fragment of a receptor, an extracellular domain of a transmembrane receptor, and polypeptides containing them and such are included in the ligand according to the present disclosure.

The ligand of the present disclosure can usually exert desirable biological activity by binding to one or more binding partners. The binding partner of the ligand can be an extracellular, intracellular, or transmembrane protein. In one embodiment, the binding partner of the ligand is an extracellular protein, for example, a soluble receptor. In another embodiment, the binding partner of the ligand is a membrane-bound receptor.

The ligand of the present disclosure can specifically bind to the binding partner with a dissociation constant (KD) of 10 µM, 1 µM, 100 nM, 50 nM, 10 nM, 5 nM, 1 nM, 500 pM, 400 pM, 350 pM, 300 pM, 250 pM, 200 pM, 150 pM, 100 pM, 50 pM, 25 pM, 10 pM, 5 pM, 1 pM, 0.5 pM, or 0.1 pM or less.

Examples of the molecule having biological activity include, but are not limited to, cytokines, chemokines, polypeptide hormones, growth factors, apoptosis inducing factors, PAMPs, DAMPs, nucleic acids, and fragments thereof. In a specific embodiment, an interleukin, an interferon, a hematopoietic factor, a member of the TNF superfamily, a chemokine, a cell growth factor, a member of the TGF-β family, a myokine, an adipokine, or a neurotrophic factor can be used as the ligand. In a more specific embodiment, CXCL10, IL-2, IL-7, IL-12, IL-15, IL-18, IL-21, IFN-α, IFN-β, IFN-g, MIG, I-TAC, RANTES, MIP-1a, MIP-1b, IL-1R1 (Interleukin-1 receptor, type I), IL-1R2 (Interleukin-1 receptor, type II), IL-1RAcP (Interleukin-1 receptor accessory protein), or IL-1Ra (Protein Accession No. NP_776214, mRNA Accession No. NM_173842.2) can be used as the ligand.

Chemokines are a family of homogeneous serum proteins of 7 to 16 kDa originally characterized by their ability to induce leukocyte migration. Most of chemokines have four characteristic cysteines (Cys) and are classified into CXC or alpha, CC or beta, C or gamma and CX3C or delta chemokine classes, according to motifs displayed by the first two cysteines. Two disulfide bonds are formed between the first and third cysteines and between the second and fourth cysteines. In general, the disulfide bridges are considered necessary. Clark-Lewis and collaborators have reported that the disulfide bonds are crucial for the chemokine activity of at least CXCL10 (Clark-Lewis et al., J. Biol. Chem. 269: 16075-16081, 1994). The only one exception to having four cysteines is lymphotactin, which has only two cysteine residues. Thus, lymphotactin narrowly maintains its functional structure by only one disulfide bond.

Subfamilies of CXC or alpha are further classified, according to the presence of an ELR motif (Glu-Leu-Arg) preceding the first cysteine, into two groups: ELR-CXC chemokines and non-ELR-CXC chemokines (see e.g., Clark-Lewis, supra; and Belperio et al., "CXC Chemokines in Angiogenesis", J. Leukoc. Biol. 68: 1-8, 2000).

In certain embodiments, when the polypeptide of the present disclosure is a ligand-binding molecule, the ligand is a cytokine.

Cytokines are a secretory cell signaling protein family involved in immunomodulatory and inflammatory processes. These cytokines are secreted by glial cells of the nervous system and by many cells of the immune system. The cytokines can be classified into proteins, peptides and glycoproteins, and encompass large and diverse family of regulatory factors. The cytokines can induce intracellular signal transduction through binding to their cell surface receptors, thereby causing the regulation of enzyme activity, upregulation or downregulation of some genes and transcriptional factors thereof, or feedback inhibition, etc.

In certain embodiments, when the polypeptide of the present disclosure is a ligand-binding molecule, the cytokine of the present disclosure includes immunomodulatory factors such as interleukins (IL) and interferons (IFN). A suitable cytokine can contain a protein derived from one or more of the following types: four a-helix bundle families (which include the IL-2 subfamily, the IFN subfamily and IL-10 subfamily); the IL-1 family (which includes IL-1 and IL-8); and the IL-17 family. The cytokine can also include those classified into type 1 cytokines (e.g., IFN-γ and TGF-β) which enhance cellular immune response, or type 2 cytokines (e.g., IL-4, IL-10, and IL-13) which work advantageously for antibody reaction.

In certain embodiments, when the polypeptide of the present disclosure is a ligand-binding molecule, the ligand is a chemokine. Chemokines generally act as chemoattractants that mobilize immune effector cells to chemokine expression sites. This is considered beneficial for expressing a particular chemokine gene together with, for example, a cytokine gene, for the purpose of mobilizing other immune system components to a treatment site. Such chemokines include CXCL10, RANTES, MCAF, MIP1-α, and MIP1-β. Those skilled in the art should know that certain cytokines also have a chemoattractive effect and acknowledge that such cytokines can be classified by the term "chemokine".

In certain embodiments, when the polypeptide of the present disclosure is a ligand-binding molecule, a cytokine variant, a chemokine variant, or the like (e.g., Annu Rev Immunol. 2015; 33: 139-67) or a fusion protein containing them (e.g., Stem Cells Transl Med. 2015 January; 4 (1): 66-73) can be used as the ligand.

In certain embodiments, when the polypeptide of the present disclosure is a ligand-binding molecule, the ligand is selected from CXCL10, PD-1, IL-12, IL-6R, IL-1R1, IL-1R2, IL-1RAcP, and IL-1Ra. The CXCL10, PD-1, IL-12, IL-6R, IL-1R1, IL-1R2, IL-1RAcP, and IL-1Ra may have the same sequences as those of naturally occurring CXCL10, PD-1, IL-12, IL-6R, IL-1R1, IL-1R2, IL-1RAcP, and IL-1Ra, respectively, or may be a ligand variant that differs in sequence from naturally occurring CXCL10, PD-1, IL-12, IL-6R, IL-1R1, IL-1R2, IL-1RAcP, and IL-1Ra, but retains the physiological activity of the corresponding natural ligand. In order to obtain the ligand variant, an alteration may be artificially added to the ligand sequence for various purposes. Preferably, an alteration to resist protease cleavage (protease resistance alteration) is added thereto to obtain a ligand variant.

In certain embodiments, when the polypeptide of the present disclosure is a ligand-binding molecule, in the ligand-binding molecule, the ligand is released from the ligand-binding molecule by the cleavage of the cleavage site. In this context, when the ligand is bound with a portion of the ligand-binding molecule via a linker and the linker does not have a protease cleavage sequence, the ligand is released while connected with the portion of the ligand-binding molecule via the linker (see e.g., FIG. 5). Even when the ligand is released together with a portion of the ligand-binding molecule as mentioned above, it can be concluded that the ligand is released from the ligand-binding molecule as long as the ligand is released from the majority of the ligand-binding molecule.

A method for detecting the release of the ligand from the ligand-binding molecule by the cleavage of the cleavage site includes a method of detecting the ligand using, for example, an antibody for ligand detection that recognizes the ligand. When the ligand-binding molecule is an antibody fragment, the antibody for ligand detection preferably binds to the same epitope as that for the ligand-binding molecule. The ligand detected using the antibody for ligand detection can be confirmed by a well-known method such as FACS, an ELISA format, a BIACORE method using amplified luminescent proximity homogeneous assay (ALPHA) screening or surface plasmon resonance (SPR) phenomena, or biolayer interferometry (BLI) (Octet) (Proc. Natl. Acad. Sci. USA (2006) 103 (11), 4005-4010).

In the case of detecting the release of the ligand using, for example, Octet, the antibody for ligand detection that recognizes the ligand is biotinylated and contacted with a biosensor. Then, binding to the ligand in a sample can be measured to detect the release of the ligand. Specifically, the amount of the ligand is measured in a sample containing the ligand and the ligand-binding molecule before protease treatment or after protease treatment, using the antibody for ligand detection. The amount of the ligand detected in the sample can be compared between before and after protease treatment to detect the release of the ligand. Alternatively, the amount of the ligand is measured using the antibody for ligand detection in a sample containing protease, ligand-binding molecule, and ligand and a sample containing ligand-binding molecule and ligand without containing protease. The amount of the ligand detected in the sample with or without protease can be compared to detect the release of the ligand. More specifically, release of the ligand can be detected by a method described in the Examples of the present application. When the ligand-binding molecule is fused with the ligand to form a fusion protein, the amount of the ligand is measured using the antibody for ligand detection in a sample containing the fusion protein before protease treatment or after protease treatment. The amount of the ligand detected in the sample can be compared between before and after protease treatment to detect the release of the ligand. Alternatively, the amount of the ligand is measured using the antibody for ligand detection in a sample containing protease and the fusion protein and a sample containing the fusion protein without containing protease. The amount of the ligand detected in the sample with or without protease can be compared to detect the release of the ligand. More specifically, release of the ligand can be detected by a method described in the Examples of the present application.

In an embodiment in which the physiological activity of the ligand is inhibited upon binding to the ligand-binding molecule, a method for detecting the release of the ligand from the ligand-binding molecule includes measuring the physiological activity of the ligand in a sample for detecting ligand release. Specifically, the physiological activity of the ligand can be measured in a sample containing the ligand and the ligand-binding molecule before protease treatment or after protease treatment and then compared to detect the release of the ligand. Alternatively, the physiological activity of the ligand can be measured and compared in a sample containing protease, ligand-binding molecule, and ligand and a sample containing ligand-binding molecule and ligand without containing protease to detect the release of the ligand. When the ligand-binding molecule is fused with the ligand to form a fusion protein, the physiological activity of the ligand can be measured and compared in a sample containing the fusion protein before protease treatment or after protease treatment to detect the release of the ligand. Alternatively, the physiological activity of the ligand can be measured and compared in a sample containing protease and fusion protein and a sample containing fusion protein without containing protease to detect the release of the ligand.

In certain embodiments, when the polypeptide of the present disclosure is a ligand-binding molecule, the ligand-binding molecule comprises an Fc region. In the case of using an IgG antibody Fc region, its type is not limited, and for example, Fc region of IgG1, IgG2, IgG3, or IgG4 may be used. For example, an Fc region comprising one sequence selected from the amino acid sequences represented by SEQ ID NOs: 18004, 18005, 18006, and 18007, or an Fc region mutant prepared by adding an alteration to the Fc regions may be used. In some embodiments of the present disclosure, the ligand-binding molecule comprises an antibody constant region.

In certain embodiments, when the polypeptide of the present disclosure is a ligand-binding molecule, the ligand-binding molecule is an antibody. In the case of using an antibody as the ligand-binding molecule, the binding to the ligand is achieved by a variable region. In some further specific embodiments, the ligand-binding molecule is an IgG antibody. In the case of using an IgG antibody as the ligand-binding molecule, its type is not limited, and IgG1, IgG2, IgG3, IgG4, or the like can be used. In the case of using an IgG antibody as the ligand-binding molecule, the binding to the ligand is also achieved by a variable region. One or both of the two variable regions of the IgG antibody can achieve the binding to the ligand.

In certain embodiments, when the polypeptide of the present disclosure is a ligand-binding molecule, a domain having ligand binding activity in the ligand-binding molecule is divided by the cleavage of the protease cleavage sequence in the ligand-binding molecule, and the binding to the ligand is attenuated. In the case of using an IgG antibody as the ligand-binding molecule, an exemplary embodiment includes placing the protease cleavage sequence in an antibody variable region and attenuating the binding to the ligand in a cleaved state by lack of ability to form a complete antibody variable region.

In certain embodiments, when the polypeptide of the present disclosure is a ligand-binding molecule, the biological activity of the ligand is inhibited by binding to the uncleaved ligand-binding molecule. Examples of the embodiments in which the biological activity of the ligand is inhibited include, but are not limited to, embodiments in which the binding of the ligand to the uncleaved ligand-binding molecule substantially or significantly interferes or competes with the binding of the ligand to its binding partner. In the case of using an antibody or a fragment thereof having ligand neutralizing activity as the ligand-binding molecule, the ligand-binding molecule bound with the ligand is capable of inhibiting the biological activity of the ligand by exerting its neutralizing activity.

In certain embodiments, when the polypeptide of the present disclosure is a ligand-binding molecule, preferably, the uncleaved ligand-binding molecule can sufficiently neutralize the biological activity of the ligand by binding to the ligand. That is, the biological activity of the ligand bound with the uncleaved ligand-binding molecule is preferably lower than that of the ligand unbound with the uncleaved ligand-binding molecule. The biological activity of the ligand bound with the uncleaved ligand-binding molecule can be, for example, 90% or less, preferably 80% or less, 70% or less, 60% or less, 50% or less, 40% or less, or 30% or less, particularly preferably 20% or less, 10% or less, 9% or less, 8% or less, 7% or less, 6% or less, 5% or less, 4% or less, 3% or less, 2% or less, or 1% or less, of the biological activity of the ligand unbound with the uncleaved ligand-binding molecule, though not limited thereto. The administration of the ligand-binding molecule can be expected to prevent the ligand from exerting its biological activity before arriving at a diseased tissue, by sufficiently neutralizing the biological activity of the ligand.

Alternatively, the present disclosure provides methods for neutralizing the biological activity of a ligand. The methods of the present disclosure comprise the steps of contacting a ligand-binding molecule of the present disclosure with a ligand whose biological activity should be neutralized, and collecting the product of binding of the two molecules. Cleavage of the ligand-binding molecule in the collected binding product can restore the neutralized biological activity of the ligand. Thus, the methods for neutralizing the biological activity of a ligand according to the present disclosure may further comprise the step of restoring the biological activity of the ligand by cleaving the ligand-binding molecule in the binding product which consists of the ligand and the ligand-binding molecule (in other words, cancelling the neutralizing activity of the ligand-binding molecule).

In certain embodiments, when the polypeptide of the present disclosure is a ligand-binding molecule, the binding activity of the cleaved ligand-binding molecule against the ligand is preferably lower than that of an in vivo natural ligand binding partner (e.g., natural receptor for the ligand) against the ligand. The binding activity of the cleaved ligand-binding molecule against the ligand exhibits, for example, 90% or less, preferably 80% or less, 70% or less, 60% or less, 50% or less, 40% or less, or 30% or less, particularly preferably 20% or less, 10% or less, 9% or less, 8% or less, 7% or less, 6% or less, 5% or less, 4% or less, 3% or less, 2% or less, or 1% or less, of the amount of the ligand bound with the in vivo natural binding partner (per unit binding partner), though not limited thereto. The desired index may be appropriately used as an index for binding activity. For example, a dissociation constant (KD) may be used. In the case of using a dissociation constant (KD) as an index for evaluating binding activity, a larger dissociation constant (KD) of the cleaved ligand-binding molecule for the ligand than that of the in vivo natural binding partner for the ligand means that the cleaved ligand-binding molecule has weaker binding activity against the ligand than that of the in vivo natural binding partner. The dissociation constant (KD) of the cleaved ligand-binding molecule for the ligand is, for example, 1.1 times or more, preferably 1.5 times or more, 2 times or more, 5 times or more, or 10 times or more, particularly preferably 100 times or more of the dissociation constant (KD) of the in vivo natural binding partner for the ligand. The ligand-binding molecule having only low binding activity against the ligand or hardly having binding activity against the ligand after cleavage guarantees that the ligand is released by the cleavage of the ligand-binding molecule, and can be expected to be prevented from binding to another ligand molecule again.

The ligand desirably restores the suppressed biological activity after cleavage of the ligand-binding molecule. Attenuation of the binding of the cleaved ligand-binding molecule to the ligand desirably results in attenuation of the function of the ligand-binding molecule to inhibit the biological activity of the ligand. Those skilled in the art can confirm the biological activity of the ligand by a known method, for example, a method of detecting the binding of the ligand to its binding partner.

In certain embodiments, when the polypeptide of the present disclosure is a ligand-binding molecule, the uncleaved ligand-binding molecule forms a complex with the ligand through antigen-antibody binding. In a more specific embodiment, the complex of the ligand-binding molecule and the ligand is formed through a noncovalent bond, for example, antigen-antibody binding, between the ligand-binding molecule and the ligand.

In certain embodiments, when the polypeptide of the present disclosure is a ligand-binding molecule, the uncleaved ligand-binding molecule is fused with the ligand to form a fusion protein. The ligand-binding molecule moiety and the ligand moiety in the fusion protein further interact with each other through antigen-antibody binding. The ligand-binding molecule and the ligand can be fused via a linker or without a linker. Even when the ligand-binding molecule and the ligand in the fusion protein are fused via or without a linker, the noncovalent bond still exists between the ligand-binding molecule moiety and the ligand moiety. In other words, even in the embodiments in which the ligand-binding molecule is fused with the ligand, the noncovalent bond between the ligand-binding molecule moiety and the ligand moiety is similar to that in embodiments in which the ligand-binding molecule is not fused with the ligand. The noncovalent bond is attenuated by the cleavage of the ligand-binding molecule. In short, the ligand binding of the ligand-binding molecule is attenuated.

In certain embodiments, when the polypeptide of the present disclosure is a ligand-binding molecule, the ligand-binding molecule and the ligand are fused via a linker. For example, an arbitrary peptide linker that can be introduced by genetic engineering, or a linker disclosed as a synthetic compound linker (see e.g., Protein Engineering, 9 (3), 299-305, 1996) can be used as the linker in the fusion of the ligand-binding molecule with the ligand. In the present embodiment, a peptide linker is preferred. The length of the peptide linker is not particularly limited and may be appropriately selected by those skilled in the art according to the purpose. Examples of the peptide linker can include, but are not limited to, linkers of the glycine-serine polymers.

However, the length and sequence of the peptide linker can be appropriately selected by those skilled in the art according to the purpose.

The synthetic compound linker (chemical cross-linking agent) is a cross-linking agent usually used in peptide cross-linking, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), or bis[2-(sulfosuccinimidoxycarbonyloxy)ethyl]sulfone (sulfo-BSOCOES). These cross-linking agents are commercially available.

In some embodiments of the present disclosure, the fusion protein of the ligand-binding molecule and the ligand is a fusion protein in which the N-terminus of the ligand-binding molecule and the C-terminus of the ligand are fused with or without a linker.

When the ligand-binding molecule of the present disclosure is a multimer, the ligand may be a fusion protein in which the ligand is fused at either the N- or C-terminus of an arbitrary peptide chain in the ligand-binding molecule via or without a linker. By way of example, when the ligand-binding molecule is an IgG antibody, the ligand may be fused at the N-terminus of VH or N-terminus of VL via or without a linker.

Listed below are several embodiments of the structure of fusion proteins of the ligand-binding molecule and the ligand when the ligand-binding molecule of the present disclosure comprises a single-domain antibody. The following embodiments are shown in the order from the N- to C-terminus. It would be apparent to one skilled in the art having the benefit of the present disclosure that the fusion proteins may be either monomers or multimers (including dimers).

Ligand-single-domain antibody

Ligand-linker-single-domain antibody

Ligand-single-domain antibody-antibody constant region (or a fragment thereof)

Ligand-linker-single-domain antibody-antibody constant region (or a fragment thereof)

Ligand-single-domain antibody-antibody hinge region-antibody CH2-antibody CH3

Ligand-linker-single-domain antibody-antibody hinge region-antibody CH2-antibody CH3

Ligand-Binding Molecule Comprising VH and VL

In certain embodiments, when the polypeptide of the present disclosure is a ligand-binding molecule, the ligand-binding molecule comprises antibody VH and antibody VL. Examples of the ligand-binding molecule comprising VH and VL include, but are not limited to, Fv, scFv, Fab, Fab', Fab'-SH, F(ab')$_2$, and complete antibodies.

In certain embodiments, when the polypeptide of the present disclosure is a ligand-binding molecule, VH and VL contained in the ligand-binding molecule associate with each other. The association between antibody VH and antibody VL may be canceled, for example, by the cleavage of the protease cleavage sequence.

The ligand-binding molecule of the present disclosure encompasses a ligand-binding molecule in which the association between antibody VL or a portion thereof and antibody VH or a portion thereof in the ligand-binding molecule is canceled by the cleavage of the protease cleavage sequence by the protease.

In certain embodiments, when the polypeptide of the present disclosure is a ligand-binding molecule, the ligand-binding molecule comprises antibody VH and antibody VL, and the antibody VH and the antibody VL in the ligand-binding molecule are associated with each other in a state where the protease cleavage sequence of the ligand-binding molecule is uncleaved, whereas the association between the antibody VH and the antibody VL in the ligand-binding molecule is canceled by the cleavage of the protease cleavage sequence. The protease cleavage sequence in the ligand-binding molecule may be placed at any position in the ligand-binding molecule as long as the binding of the ligand-binding molecule to the ligand can be attenuated by the cleavage of the protease cleavage sequence.

In certain embodiments, when the polypeptide of the present disclosure is a ligand-binding molecule, the ligand-binding molecule comprises antibody VH, antibody VL, and an antibody constant region.

As mentioned by Rothlisberger et al. (J Mol Biol. 2005 Apr. 8; 347 (4): 773-89), it is known that the VH and VL domains or the CH and CL domains of an antibody interact with each other via many amino acid side chains. VH-CH1 and VL-CL are known to be capable of forming a stable structure as a Fab domain. As reported, amino acid side chains between VH and VL generally interact with a dissociation constant in the range of $10^{-5}$ M to $10^{-8}$ M. When only VH and VL domains exist, only a small proportion may form an associated state.

In certain embodiments, when the polypeptide of the present disclosure is a ligand-binding molecule, the ligand-binding molecule is designed such that the protease cleavage sequence is provided in the ligand-binding molecule comprising antibody VH and antibody VL, and the entire heavy chain-light chain interaction is present between two peptides in the Fab structure before cleavage, whereas the interaction between the peptide containing the VH (or a portion of the VH) and the peptide containing the VL (or a portion of the VL) is attenuated by the cleavage of the protease cleavage sequence so that the association between the VH and the VL is canceled.

In certain embodiments, when the polypeptide of the present disclosure is a ligand-binding molecule, the protease cleavage sequence is located within the antibody constant region. In a more specific embodiment, the protease cleavage sequence is located on the variable region side with respect to amino acid position 140 (EU numbering) in an antibody heavy chain constant region, or on the variable region side with respect to amino acid position 122 (EU numbering) in an antibody heavy chain constant region. In some specific embodiments, the protease cleavage sequence is inserted into any position within the sequence from amino acid 118 in the antibody heavy chain constant region (EU numbering) to amino acid 140 in the antibody heavy chain constant region (EU numbering). In another more specific embodiment, the protease cleavage sequence is located on the variable region side with respect to amino acid position 130 (Kabat numbering) in an antibody light chain constant region, or on the variable region side with respect to amino acid position 113 (Kabat numbering) in an antibody light chain constant region or on the variable region side with respect to amino acid position 112 (Kabat numbering) in an antibody light chain constant region. In some specific embodiments, the protease cleavage sequence is inserted into any position within the sequence from amino acid 108 in the antibody light chain constant region (Kabat numbering) to amino acid 131 in the antibody light chain constant region (Kabat numbering).

In certain embodiments, when the polypeptide of the present disclosure is a ligand-binding molecule, the protease cleavage sequence is located within the antibody VH or within the antibody VL. In a more specific embodiment, the protease cleavage sequence is located on the antibody constant region side with respect to amino acid position 7 (Kabat numbering) of the antibody VH, or on the antibody constant region side with respect to amino acid position 40 (Kabat numbering) of the antibody VH, or on the antibody constant region side with respect to amino acid position 101 (Kabat numbering) of the antibody VH, or on the antibody constant region side with respect to amino acid position 109 (Kabat numbering) of the antibody VH or on the antibody constant region side with respect to amino acid position 111 (Kabat numbering) of the antibody VH. In a more specific embodiment, the cleavage site or the protease cleavage sequence is located on the antibody constant region side with respect to amino acid position 7 (Kabat numbering) of the antibody VL, or on the antibody constant region side with respect to amino acid position 39 (Kabat numbering) of the antibody VL, or on the antibody constant region side with respect to amino acid position 96 (Kabat numbering) of the antibody VL, or on the antibody constant region side with respect to amino acid position 104 (Kabat numbering) of the antibody VL or on the antibody constant region side with respect to amino acid position 105 (Kabat numbering) of the antibody VL.

In certain embodiments, when the polypeptide of the present disclosure is a ligand-binding molecule, the protease cleavage sequence is inserted at a position of residues forming a loop structure in the antibody VH or the antibody VL, and residues close to the loop structure. The loop structure in the antibody VH or the antibody VL refers to a portion that does not form a secondary structure such as α-helix or β-sheet, in the antibody VH or the antibody VL. Specifically, the position of the residues forming the loop structure and the residues close to the loop structure can refer to the range of amino acid position 7 (Kabat numbering) to amino acid position 16 (Kabat numbering), amino acid position 40 (Kabat numbering) to amino acid position 47 (Kabat numbering), amino acid position 55 (Kabat numbering) to amino acid position 69 (Kabat numbering), amino acid position 73 (Kabat numbering) to amino acid position 79 (Kabat numbering), amino acid position 83 (Kabat numbering) to amino acid position 89 (Kabat numbering), amino acid position 95 (Kabat numbering) to amino acid position 99 (Kabat numbering), or amino acid position 101 (Kabat numbering) to amino acid position 113 (Kabat numbering) of the antibody VH, or amino acid position 7 (Kabat numbering) to amino acid position 19 (Kabat numbering), amino acid position 39 (Kabat numbering) to amino acid position 46 (Kabat numbering), amino acid position 49 (Kabat numbering) to amino acid position 62 (Kabat numbering), or amino acid position 96 (Kabat numbering) to amino acid position 107 (Kabat numbering) of the antibody VL.

In certain embodiments, when the polypeptide of the present disclosure is a ligand-binding molecule, the protease cleavage sequence is inserted at any position in a sequence from amino acid position 7 (Kabat numbering) to amino acid position 16 (Kabat numbering), from amino acid position 40

(Kabat numbering) to amino acid position 47 (Kabat numbering), from amino acid position 55 (Kabat numbering) to amino acid position 69 (Kabat numbering), from amino acid position 73 (Kabat numbering) to amino acid position 79 (Kabat numbering), from amino acid position 83 (Kabat numbering) to amino acid position 89 (Kabat numbering), from amino acid position 95 (Kabat numbering) to amino acid position 99 (Kabat numbering), or from amino acid position 101 (Kabat numbering) to amino acid position 113 (Kabat numbering) of the antibody VH.

In certain embodiments, when the polypeptide of the present disclosure is a ligand-binding molecule, the protease cleavage sequence is inserted at any position in a sequence from amino acid position 7 (Kabat numbering) to amino acid position 19 (Kabat numbering), from amino acid position 39 (Kabat numbering) to amino acid position 46 (Kabat numbering), from amino acid position 49 (Kabat numbering) to amino acid position 62 (Kabat numbering), or from amino acid position 96 (Kabat numbering) to amino acid position 107 (Kabat numbering) of the antibody VL.

In certain embodiments, when the polypeptide of the present disclosure is a ligand-binding molecule, the protease cleavage sequence is located near the boundary between the antibody VH and the antibody constant region. The phrase "near the boundary between the antibody VH and the antibody heavy chain constant region" can refer to between amino acid position 101 (Kabat numbering) of the antibody VH and amino acid position 140 (EU numbering) of the antibody heavy chain constant region or can refer to between amino acid position 109 (Kabat numbering) of the antibody VH and amino acid position 122 (EU numbering) of the antibody heavy chain constant region, or between amino acid position 111 (Kabat numbering) of the antibody VH and amino acid position 122 (EU numbering) of the antibody heavy chain constant region. When antibody VH is linked to an antibody light chain constant region, the phrase "near the boundary between the antibody VH and the antibody light chain constant region" can refer to between amino acid position 101 (Kabat numbering) of the antibody VH and amino acid position 130 (Kabat numbering) of the antibody light chain constant region or can refer to between amino acid position 109 (Kabat numbering) of the antibody VH and amino acid position 113 (Kabat numbering) of the antibody light chain constant region, or between amino acid position 111 (Kabat numbering) of the antibody VH and amino acid position 112 (Kabat numbering) of the antibody light chain constant region.

In certain embodiments, when the polypeptide of the present disclosure is a ligand-binding molecule, the protease cleavage sequence is located near the boundary between the antibody VL and the antibody constant region. The phrase "near the boundary between the antibody VL and the antibody light chain constant region" can refer to between amino acid position 96 (Kabat numbering) of the antibody VL and amino acid position 130 (Kabat numbering) of the antibody light chain constant region or can refer to between amino acid position 104 (Kabat numbering) of the antibody VL and amino acid position 113 (Kabat numbering) of the antibody light chain constant region, or between amino acid position 105 (Kabat numbering) of the antibody VL and amino acid position 112 (Kabat numbering) of the antibody light chain constant region. When antibody VL is linked to an antibody heavy chain constant region, the phrase "near the boundary between the antibody VL and the antibody heavy chain constant region" can refer to between amino acid position 96 (Kabat numbering) of the antibody VL and amino acid position 140 (EU numbering) of the antibody heavy chain constant region or can refer to between amino acid position 104 (Kabat numbering) of the antibody VL and amino acid position 122 (EU numbering) of the antibody heavy chain constant region, or between amino acid position 105 (Kabat numbering) of the antibody VL and amino acid position 122 (EU numbering) of the antibody heavy chain constant region.

The protease cleavage sequence can be provided at a plurality of positions in the ligand-binding molecule, for example, at a plurality of positions selected from: within the antibody constant region, within the antibody VH, within the antibody VL, near the boundary between the antibody VH and the antibody constant region, and near the boundary between antibody VL and the antibody constant region. Those skilled in the art who referred to the present disclosure can change the form of a molecule comprising antibody VH, antibody VL, and an antibody constant region, for example, by swapping the antibody VH with the antibody VL. Such a molecular form does not depart from the scope of the present disclosure.

Ligand-Binding Molecule Comprising a Single-Domain Antibody

In certain embodiments, when the polypeptide of the present disclosure is a ligand-binding molecule, the ligand-binding molecule comprises a single-domain antibody. The protease cleavage sequence in the ligand-binding molecule may be placed at any position in the ligand-binding molecule as long as the binding of the ligand-binding molecule to the ligand is attenuated by cleavage of the sequence.

In certain embodiments, when the polypeptide of the present disclosure is a ligand-binding molecule comprising a single-domain antibody, the protease cleavage sequence is introduced into the single-domain antibody within the ligand-binding molecule. In some more specific embodiments, the protease cleavage sequence is introduced at the position of residues forming a loop structure, and at the position of residues close to a loop structure, within the single-domain antibody. The loop structure within a single-domain antibody refers to a part that does not form a secondary structure such as an u-helix and R-sheet within the single-domain antibody.

When the polypeptide of the present disclosure is a ligand-binding molecule comprising a single-domain antibody, in an embodiment in which the single-domain antibody is VHH or a single-domain VH antibody, the position of residues forming a loop structure and residues close to a loop structure may specifically refer to the range of: amino acid 7 (Kabat numbering) to amino acid 17 (Kabat numbering); amino acid 12 (Kabat numbering) to amino acid 17 (Kabat numbering); amino acid 31 (Kabat numbering) to amino acid 35b (Kabat numbering); amino acid 40 (Kabat numbering) to amino acid 47 (Kabat numbering); amino acid 50 (Kabat numbering) to amino acid 65 (Kabat numbering); amino acid 55 (Kabat numbering) to amino acid 69 (Kabat numbering); amino acid 73 (Kabat numbering) to amino acid 79 (Kabat numbering); amino acid 83 (Kabat numbering) to amino acid 89 (Kabat numbering); amino acid 95 (Kabat numbering) to amino acid 99 (Kabat numbering); amino acid 95 (Kabat numbering) to amino acid 102 (Kabat numbering); and amino acid 101 (Kabat numbering) to amino acid 113 (Kabat numbering) of the single-domain antibody.

When the polypeptide of the present disclosure is a ligand-binding molecule comprising a single-domain antibody, in an embodiment where the single-domain antibody is VHH or a single-domain VH antibody, the protease cleavage sequence is introduced into one or more positions contained in one or more sequences selected from the following sequences of the single-domain antibody:

the sequence from amino acid 7 (Kabat numbering) to amino acid 17 (Kabat numbering) of the single-domain antibody; the sequence from amino acid 12 (Kabat numbering) to amino acid 17 (Kabat numbering) of the single-domain antibody; the sequence from amino acid 31 (Kabat numbering) to amino acid 35b (Kabat numbering) of the single-domain antibody; the sequence from amino acid 40 (Kabat numbering) to amino acid 47 (Kabat numbering) of the single-domain antibody; the sequence from amino acid 50 (Kabat numbering) to amino acid 65 (Kabat numbering) of the single-domain antibody; the sequence from amino acid 55 (Kabat numbering) to amino acid 69 (Kabat numbering) of the single-domain antibody; the sequence from amino acid 73 (Kabat numbering) to amino acid 79 (Kabat numbering) of the single-domain antibody; the sequence from amino acid 83 (Kabat numbering) to amino acid 89 (Kabat numbering) of the single-domain antibody; the sequence from amino acid 95 (Kabat numbering) to amino acid 99 (Kabat numbering) of the single-domain antibody; the sequence from amino acid 95 (Kabat numbering) to amino acid 102 (Kabat numbering) of the single-domain antibody; and the sequence from amino acid 101 (Kabat numbering) to amino acid 113 (Kabat numbering) of the single-domain antibody.

When the polypeptide of the present disclosure is a ligand-binding molecule comprising a single-domain antibody, in an embodiment where the single-domain antibody is a single-domain VL antibody, the position of residues forming a loop structure and residues close to a loop structure may specifically refer to the range of: amino acid 7 (Kabat numbering) to amino acid 19 (Kabat numbering); amino acid 24 (Kabat numbering) to amino acid 34 (Kabat numbering); amino acid 39 (Kabat numbering) to amino acid 46 (Kabat numbering); amino acid 49 (Kabat numbering) to amino acid 62 (Kabat numbering); amino acid 50 (Kabat numbering) to amino acid 56 (Kabat numbering); amino acid 89 (Kabat numbering) to amino acid 97 (Kabat numbering); and amino acid 96 (Kabat numbering) to amino acid 107 (Kabat numbering) of the single-domain antibody.

When the polypeptide of the present disclosure is a ligand-binding molecule comprising a single-domain antibody, in an embodiment where the single-domain antibody is a single-domain VL antibody, the protease cleavage sequence is introduced into one or more positions contained in one or more sequences selected from the following sequences of the single-domain antibody:

the sequence from amino acid 7 (Kabat numbering) to amino acid 19 (Kabat numbering) of the single-domain antibody; the sequence from amino acid 24 (Kabat numbering) to amino acid 34 (Kabat numbering) of the single-domain antibody; the sequence from amino acid 39 (Kabat numbering) to amino acid 46 (Kabat numbering) of the single-domain antibody; the sequence from amino acid 49 (Kabat numbering) to amino acid 62 (Kabat numbering) of the single-domain antibody; the sequence from amino acid 50 (Kabat numbering) to amino acid 56 (Kabat numbering) of the single-domain antibody; the sequence from amino acid 89 (Kabat numbering) to amino acid 97 (Kabat numbering) of the single-domain antibody; and the sequence from amino acid 96 (Kabat numbering) to amino acid 107 (Kabat numbering) of the single-domain antibody.

Multiple protease cleavage sequences can be provided within a ligand-binding molecule, for example, in multiple positions within the single-domain antibody in the ligand-binding molecule.

In certain embodiments, when the polypeptide of the present disclosure is a ligand-binding molecule comprising a single-domain antibody, an uncleaved ligand-binding molecule has a longer half-life than the single-domain antibody alone. An example of an embodiment for making the blood half-life of a ligand-binding molecule longer than the blood half-life of a single-domain antibody alone include, but are not limited to, increasing the molecular weight of the ligand-binding molecule, or fusing a portion having an FcRn binding ability with the single-domain antibody, or fusing a portion having albumin binding ability with the single-domain antibody, or fusing a PEGylated portion with the single-domain antibody.

When the polypeptide of the present disclosure is a ligand-binding molecule comprising a single-domain antibody, it is preferable to use the blood half-life in humans when comparing the half-life of the single-domain antibody alone and the half-life of the ligand-binding molecule. When it is difficult to measure the blood half-life in humans, it is possible to predict the blood half-life in humans based on the blood half-life in mice (e.g., normal mice, transgenic mice expressing a human antigen, transgenic mice with human FcRn expression, etc.), or in monkeys (for example, cynomolgus monkeys).

When the polypeptide of the present disclosure is a ligand-binding molecule comprising a single-domain antibody, one embodiment of increasing the blood half-life of the ligand-binding molecule over the blood half-life of the single-domain antibody alone includes increasing the molecular weight of the ligand-binding molecule. In a preferred embodiment, the molecular weight of the ligand-binding molecule is 60 kDa or more. Molecules with a molecular weight of 60 kDa or more are usually unlikely to undergo clearance by the kidney when it is present in blood, and is likely to have a long blood half-life (see J Biol Chem. 1988 Oct. 15; 263(29):15064-70).

When the polypeptide of the present disclosure is a ligand-binding molecule comprising a single-domain antibody, one embodiment of increasing the blood half-life of the ligand-binding molecule compared to the blood half-life of the single-domain antibody alone includes fusing the single-domain antibody with an FcRn-binding region.

When the polypeptide of the present disclosure is a ligand-binding molecule comprising a single-domain antibody, as one embodiment for increasing the blood half-life of the ligand-binding molecule compared to the blood half-life of the single-domain antibody alone, there is the method of fusing the single-domain antibody with a portion having an albumin-binding property. Albumin does not undergo renal excretion and also has FcRn binding ability, it has a long half-life in blood of 17 to 19 days (J Clin Invest. 1953 August; 32(8): 746-768). Therefore, a protein bound to albumin becomes bulky and can also indirectly bind to FcRn, and it is reported that the half-life in blood is increased (Antibodies 2015, 4(3), 141-156).

Moreover, as one embodiment for increasing the blood half-life of the ligand-binding molecule compared to the blood half-life of the single-domain antibody alone, there is the method of fusing the single-domain antibody with a PEGylated portion. It is thought that PEGylating a protein makes the protein bulky, and at the same time suppresses the decomposition by blood proteases, thus prolongs the blood half-life of the protein (J Pharm Sci. 2008 October; 97(10): 4167-83).

Examples of the method for introducing a protease cleavage sequence into a molecule capable of binding to a ligand include a method of inserting the protease cleavage sequence into the amino acid sequence of a polypeptide capable of binding to the ligand, and a method of replacing a portion of the amino acid sequence of a polypeptide capable of binding to the ligand with the protease cleavage sequence.

Examples of the method for obtaining the molecule capable of binding to a ligand include a method of obtaining a ligand binding region having the ability to bind to the ligand. The ligand binding region is obtained by a method using, for example, an antibody preparation method known in the art.

The antibody obtained by the preparation method may be used directly for the ligand binding region, or only a Fv region in the obtained antibody may be used. When the Fv region in a single-chain (also referred to as "sc") form is capable of recognizing the antigen, only the single chain may be used. Alternatively, a Fab region containing the Fv region may be used.

The molecule with a protease cleavage sequence introduced in the molecule capable of binding to a ligand serves as the ligand-binding molecule of the disclosure. Whether the ligand-binding molecule is cleaved by treatment with protease appropriate for the protease cleavage sequence can be optionally confirmed. The presence or absence of the cleavage of the protease cleavage sequence can be confirmed, for example, by contacting the protease with the molecule with a protease cleavage sequence introduced in the molecule capable of binding to a ligand, and determining the molecular weight of the protease-treated product by an electrophoresis method such as SDS-PAGE.

In certain embodiments, when the polypeptide of the present disclosure is a ligand-binding molecule, a method for producing a ligand-ligand-binding molecule is provided. For example, provided is a method for producing a complex of a ligand and a ligand-binding molecule, the method comprising contacting the ligand-binding molecule with the ligand, and recovering the complex consisting of the ligand-binding molecule and the ligand. This complex may be formulated with a pharmaceutically acceptable carrier to provide a pharmaceutical composition.

The present disclosure also relates to a method for producing a ligand-binding molecule whose binding to a ligand is attenuated when it is cleaved, or a fusion protein of the ligand-binding molecule fused with a ligand. When the polypeptide of the present disclosure is a ligand-binding molecule, in one embodiment, the present disclosure provides a method for producing the ligand-binding molecule or the fusion protein, comprising introducing a protease cleavage sequence into a molecule capable of binding to a ligand.

Method of Producing a Polypeptide

The present disclosure also relates to a polynucleotide encoding a polypeptide comprising a protease substrate or a protease cleavage sequence.

The polynucleotide according to the present disclosure is usually carried by (or inserted in) an appropriate vector and transfected into host cells. The vector is not particularly limited as long as the vector can stably retain an inserted nucleic acid. For example, when E. coli is used as the host, a pBluescript vector (manufactured by Stratagene Corp.) or the like is preferred as a vector for cloning, although various commercially available vectors can be used. In the case of using a vector for the purpose of producing the polypeptide of the present disclosure, an expression vector is particularly useful. The expression vector is not particularly limited as long as the vector permits expression of the polypeptide in vitro, in E. coli, in cultured cells, or in individual organisms. The expression vector is preferably, for example, a pBEST vector (manufactured by Promega Corp.) for in vitro expression, a pET vector (manufactured by Invitrogen Corp.) for expression in E. coli, a pME18S-FL3 vector (GenBank Accession No. AB009864) for expression in cultured cells, and a pME18S vector (Mol Cell Biol. 8: 466-472 (1988)) for expression in individual organisms. The insertion of the DNA of the present disclosure into the vector can be performed by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for expressing the polypeptide may include bacterial cells (e.g., Streptococcus, Staphylococcus, E. coli, Streptomyces, and Bacillus subtilis), fungal cells (e.g., yeasts and Aspergillus), insect cells (e.g., Drosophila S2 and Spodoptera SF9), animal cells (e.g., CHO, COS, HeLa, C127, 3T3, BHK, HEK293, and Bowes melanoma cells) and plant cells. The transfection of the vector to the host cells may be performed by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL/Thermo Fisher Scientific Inc.), or a microinjection method.

An appropriate secretory signal can be incorporated into the polypeptide of interest, in order to secrete the polypeptide expressed in the host cells to the endoplasmic reticulum lumen, periplasmic space, or an extracellular environment. The signal may be endogenous to the polypeptide of interest, or may be a foreign signal.

When the polypeptide of the present disclosure is secreted into a medium, the recovery of the polypeptide in the above production method includes recovery of the medium. When the polypeptide of the present disclosure is produced in cells, the cells are first lysed, followed by the recovery of the polypeptide.

A method known in the art including ammonium sulfate or ethanol precipitation, acid extraction, anion- or cation-exchange chromatography, phosphocellulose chromatography, hydrophobic interaction chromatography, affinity chromatography, hydroxylapatite chromatography, and lectin chromatography can be used for recovering and purifying the polypeptide of the present disclosure from the recombinant cell cultures.

Treatment

The "treatment" (and its grammatically derived words, for example, "treat" and "treating") used in the present specification means clinical intervention that intends to alter the natural course of an individual to be treated, and it can be carried out both for prevention and during the course of a clinical pathological condition. The desirable effects of the treatment include, but not limited to, the prevention of the development or recurrence of a disease, the alleviation of symptoms, the attenuation of any direct or indirect pathological influence of the disease, the prevention of metastasis, reduction in the rate of progression of the disease, recovery from or alleviation of a disease condition, and ameliorated or improved prognosis. In some embodiments, the polypeptide of the present disclosure comprising a protease cleavage sequence can be used for delaying the onset of a disease or delaying the progression of the disease.

Pharmaceutical Composition

The present disclosure also relates to a pharmaceutical composition (agent) comprising a polypeptide comprising a protease cleavage sequence and a pharmaceutically acceptable carrier; a pharmaceutical composition (agent) comprising a polypeptide comprising a protease cleavage sequence, a ligand, and a pharmaceutically acceptable carrier; and a pharmaceutical composition (agent) comprising a fusion protein in which a polypeptide comprising a protease cleavage sequence is fused to a ligand, and a pharmaceutically acceptable carrier.

In the present disclosure, the pharmaceutical composition generally refers to an agent used for the treatment or prevention of disease, or an agent for examination or diagnosis.

In the present disclosure, the term "pharmaceutical composition comprising a polypeptide comprising a protease cleavage sequence" may be rephrased as "method for the treatment of a disease, comprising administering a polypeptide comprising a protease cleavage sequence to a subject to be treated", or rephrased as "use of a polypeptide comprising a protease cleavage sequence for the treatment of a disease", or as "use of a polypeptide comprising a protease cleavage sequence in the production of a medicament for the treatment of a disease".

In the present disclosure, the term "pharmaceutical composition comprising a ligand and a polypeptide comprising a protease cleavage sequence" may be rephrased as "method for the treatment of a disease, comprising administering a ligand and a polypeptide comprising a protease cleavage sequence to a subject to be treated", or rephrased as "use of a ligand and a polypeptide comprising a protease cleavage sequence for the treatment of a disease", or rephrased as "use of a ligand and a polypeptide comprising a protease cleavage sequence in the production of a medicament for the treatment of a disease".

In the present disclosure, the term "pharmaceutical composition comprising a fusion protein" may be rephrased as "method for the treatment of a disease, comprising administering a fusion protein to a subject to be treated", or rephrased as "use of a fusion protein for the treatment of a disease", or rephrased as "use of a fusion protein in the production of a medicament for the treatment of a disease".

The pharmaceutical composition of the present disclosure can be formulated by use of a method known to those skilled in the art. For example, the pharmaceutical composition can be parenterally used in a form of an injection of a sterile solution or suspension with water or any other pharmaceutically acceptable liquids. The pharmaceutical composition can be formulated, for example, by appropriately combining with a pharmacologically acceptable carrier or medium, specifically, sterile water or physiological saline, a vegetable oil, an emulsifier, a suspending agent, a surfactant, a stabilizer, a flavoring agent, an excipient, a vehicle, an antiseptic, a binder, etc. and mixing them into a unit dosage form required for generally accepted pharmaceutical practice. The amount of the active ingredient in these formulations is set so as to give an appropriate volume in a prescribed range.

A sterile composition for injection can be formulated according to usual pharmaceutical practice using a vehicle such as injectable distilled water. Examples of the injectable aqueous solution include isotonic solutions containing physiological saline, glucose, or other adjuvants (e.g., D-sorbitol, D-mannose, D-mannitol, and sodium chloride).

The aqueous solution can be used in combination with an appropriate solubilizer, for example, an alcohol (ethanol, etc.), a polyalcohol (propylene glycol, polyethylene glycol, etc.), or a nonionic surfactant (Polysorbate 80™, HCO-50, etc.).

Examples of the oily liquid include sesame oil and soybean oil, and benzyl benzoate and/or benzyl alcohol can be used in combination as a solubilizer. The oily liquid can be combined with a buffer (e.g., a phosphate buffer solution and a sodium acetate buffer solution), a soothing agent (e.g., procaine hydrochloride), a stabilizer (e.g., benzyl alcohol and phenol), or an antioxidant. The prepared injection solution is usually filled into an appropriate ampule.

The pharmaceutical composition of the present disclosure is preferably administered through a parenteral route. For example, a composition for injection, transnasal administration, transpulmonary administration, or percutaneous administration is administered. The pharmaceutical composition can be administered systemically or locally by, for example, intravenous injection, intramuscular injection, intraperitoneal injection, or subcutaneous injection.

The administration method can be appropriately selected according to the age and symptoms of a patient. The dose of the pharmaceutical composition of the present disclosure can be determined to the range of, for example, 0.0001 mg to 1000 mg per kg body weight per dose. Alternatively, the dose can be determined to, for example, 0.001 to 100000 mg per patient. However, the present disclosure is not necessarily limited by these numerical values. The dose and the administration method vary depending on the body weight, age, symptoms, and such of a patient, and those skilled in the art can determine an appropriate dose and administration method in consideration of these conditions.

When the polypeptide of the present disclosure is a ligand-binding molecule, in some embodiments, a composition containing the ligand-binding molecule can be administered to an individual. The ligand-binding molecule administered to an individual binds to a ligand originally present in the individual, for example, in blood or in a tissue, and the ligand-binding molecule in a state bound with the ligand is further transported in vivo. The ligand-binding molecule transported to a diseased tissue can be cleaved in the diseased tissue so that its binding to the ligand can be attenuated to release the bound ligand in the diseased tissue. The released ligand can exert biological activity in the diseased tissue and treat a disease originated in the diseased tissue. In the embodiments in which the ligand-binding molecule suppresses the biological activity of the ligand when bound with the ligand, and is cleaved specifically in a diseased tissue, the ligand does not exert biological activity during transport and exerts biological activity only when the ligand-binding molecule is cleaved in the diseased tissue. As a result, the disease can be treated with reduced systemic adverse reactions.

When the polypeptide of the present disclosure is a ligand-binding molecule, in some embodiments, a composition containing the ligand-binding molecule and a composition containing the ligand can be administered separately or concurrently to an individual. Alternatively, a composition containing both the ligand-binding molecule and the ligand may be administered to an individual. In the case of administering a composition containing both the ligand-binding molecule and the ligand to an individual, the ligand-binding molecule and the ligand in the composition may form a complex. In the case of administering both the ligand-binding molecule and the ligand to an individual, the ligand-binding molecule binds to the ligand administered to the individual, and the ligand-binding molecule in a state bound with the ligand is transported in vivo. The ligand-binding molecule transported to a diseased tissue can be cleaved in the diseased tissue so that its binding to the ligand is attenuated to release the bound ligand in the diseased tissue. The released ligand can exert biological activity in the diseased tissue and treat a disease originated in the diseased tissue. In the embodiments in which the ligand-binding molecule suppresses the biological activity of the ligand when bound with the ligand, and is cleaved specifically in a diseased tissue, the ligand does not exert biological activity during transport and exerts biological activity only when the ligand-binding molecule is cleaved in the diseased tissue. As a result, the disease can be treated with systemic adverse reactions reduced. The ligand-binding molecule administered to the individual is also capable of binding to a ligand originally present in the individual, in addition to the ligand administered to the individual. The ligand-binding molecule in a state bound with the ligand originally present in the individual or the ligand administered to the individual can be transported in vivo.

When the polypeptide of the present disclosure is a ligand-binding molecule, in some embodiments, the fusion protein of the ligand-binding molecule fused with a ligand can be administered to an individual. In these embodiments, the ligand-binding molecule and the ligand in the fusion protein are fused via or without a linker. The noncovalent bond still exists between the ligand-binding molecule moiety and the ligand moiety. In the case of administering the fusion protein of the ligand-binding molecule fused with a ligand to an individual, the fusion protein is transported in vivo, and then the ligand-binding molecule moiety in the fusion protein is cleaved in a diseased tissue so that the noncovalent bond of the ligand-binding molecule moiety to the ligand is attenuated to release the ligand and a portion of the ligand-binding molecule from the fusion protein. The released ligand and the released portion of the ligand-binding molecule can exert the biological activity of the ligand in the diseased tissue, and treat a disease originated in the diseased tissue. In the embodiments in which the ligand-binding molecule suppresses the biological activity of the ligand when bound with the ligand, and is cleaved specifically in a diseased tissue, the ligand in the fusion protein does not exert biological activity during transport and exerts biological activity only when the fusion protein is cleaved in the diseased tissue. As a result, the disease can be treated with reduced systemic adverse reactions.

Since the protease cleavage sequence contained in the polypeptide of the present disclosure is cleaved by matriptase and/or urokinase, it is expected to be cleaved in cancer tissue, which allows for the treatment of cancer while reducing systemic side effects.

It should be understood by those skilled in the art that any combination of one or more of the embodiments described in the present specification are also included in the present disclosure as long as there is no technical contradiction based on the common technical knowledge in the art. Also, the invention(s) excluded from the present disclosure, which is/are any combination of one or more of the embodiments described in the present specification, should be regarded as the invention(s) intended or described in the present specification, as long as there is no technical contradiction on the basis of the common technical knowledge in the art.

EXAMPLES

The following are examples of the methods and compositions of the present disclosure. It will be understood that various other embodiments can be carried out in light of the general description described above.

Example 1

Exploration of Protease Cleavage Sequence Using Peptide Array 1-1. Designing and Construction of Peptide Library Peptide libraries of 15 amino acids were designed based on the sequence TSTSGRSANPRG (SEQ ID NO: 1), which can be cleaved by uPA and MP-SP1. To either or both of the N- and C-termini of the sequence shown as SEQ ID NO: 1, Gly or Ser, or both, were added, and part of the amino acids of the sequence shown as SEQ ID NO: 1 were further altered so that it has any naturally occurring amino acids other than C, R, and K, thereby designing Library 1: GGSXXXXXXR-SANPRG (SEQ ID NO: 18079), Library 2: TSTS-GRXXXXXXGGGS (SEQ ID NO: 18080), and Library 3: GGGSXXXRXXGGGSG (SEQ ID NO: 18081) (X denotes any one of the 17 naturally occurring amino acids except for C, R, and K). The peptide libraries Library 1, Library 2, and Library 3 were synthesized according to the method described in Mol Cell Proteomics, 2014 Jun. 13(6): 1585-97; doi: 10.1074/mcp.M113.033308; Epub 2014 Apr. 4, and peptide arrays on which these peptide libraries were immobilized were prepared.

1-2. Cleavage of Peptides and Data Analysis

Evaluation of cleavage of the peptides on the arrays by protease was performed according to the method described in Mol Cell Proteomics, 2014 Jun. 13(6): 1585-97; doi: 10.1074/mcp.M113.033308; Epub 2014 Apr. 4.

To evaluate the cleavage by protease, each peptide array was treated with each of Recombinant Human u-Plasminogen Activator/Urokinase (human uPA, huPA) (R&D Systems; 1310-SE-010), Recombinant Human Matriptase/ST14 Catalytic Domain (human MT-SP1, hMT-SP1) (R&D Systems; 3946-SE-010), and Recombinant Mouse u-Plasminogen Activator/Urokinase (mouse uPA, muPA) (abcam; ab92641). To evaluate the cleavage of the peptides in serum, each peptide array was treated with human serum (hserum) (Valley Biomedical; HS1004C). The treatment conditions are shown in Tables 1 and 2. As a control (positive control) for the protease cleavage, GGSTSTSGRSANPRG (SEQ ID NO: 2) was used in Library 1 and TSTSGRSANPRGGS (SEQ ID NO: 3) in Libraries 2 and 3. As a control (negative control) for non-specific cleavage, GGGSGGGSGGGSGGG (SEQ ID NO: 4) was used.

Cleavage ratio (Proteolytic Activity Ratio, abbreviated as PAR) was calculated according to: Fluorescence (RFU) upon treatment with PBS only/Fluorescence (RFU) upon treatment with protease.

TABLE 1

| Treatment conditions for cleavage with protease | | | | |
|---|---|---|---|---|
| Protease | Protease concentration | Buffer | Reaction time | Reaction temperature |
| Human uPA | 1000 nM | PBS | 1 hour | 37° C. |
| Human MT-SP1 | 500 nM | PBS | 1 hour | 37° C. |
| Mouse uPA | 1000 nM | PBS | 1 hour | 37° C. |

121

122

TABLE 2

Treatment conditions for cleavage with serum

| Protease | Reaction solution | Reaction time | Reaction temperature |
|---|---|---|---|
| Human serum | Human serum diluted to 80% | Over night | 37° C. |

In Library 1, 17, 197 sequences showed higher cleavage ratios than the sequence shown as SEQ ID NO: 2 for both the cleavages by human uPA and human MT-SP1 (SEQ ID NOs: 5-17201), and 3,200 sequences showed higher cleavage ratios than the sequence shown as SEQ ID NO: 2 for all the cleavages by human uPA, human MT-SP1, and mouse uPA (SEQ ID NOs: 5-3204). Among them, 452 sequences showed lower cleavage ratios than the sequence shown as SEQ ID NO: 4 in human serum (SEQ ID NOs: 5-456). Among the 17,197 sequences that showed higher cleavage ratios than the sequence shown as SEQ ID NO: 2 for both the cleavages by human uPA and human MT-SP1, there were 7,567 sequences that scored higher regarding all of the values obtained by dividing the cleavage ratios for human uPA, human MT-SP1, and mouse uPA by the cleavage ratio for human serum (when the cleavage ratio for human serum was less than 1, after converting it to 1) than that of the sequence shown as SEQ ID NO: 2, and also showed higher cleavage ratios than the sequence shown as SEQ ID NO: 2 for both human uPA and human MT-SP1 (SEQ ID NOs: 5-1811 and 3205-8964).

In Library 2, 792 sequences showed higher cleavage ratios than the sequence shown as SEQ ID NO: 3 for both the cleavages by human uPA and human MT-SP1 (SEQ ID NOs: 17202-17993). Among them, two sequences also showed higher cleavage ratios for mouse uPA than the sequence shown as SEQ ID NO: 3 (SEQ ID NOs: 17202 and 17203). Among the 792 sequences that showed higher cleavage ratios than the sequence shown as SEQ ID NO: 3 for human uPA and human MT-SP1, 175 sequences showed lower cleavage ratios in human serum than the sequence shown as SEQ ID NO: 4 (SEQ ID NOs: 17204-17378).

In Library 3, 10 sequences showed higher cleavage ratios than the sequence shown as SEQ ID NO: 3 for both the cleavages by human uPA and human MT-SP1 (SEQ ID NOs: 17994-18003). Among them, six sequences also showed higher cleavage ratios for mouse uPA than the sequence shown as SEQ ID NO: 3 (SEQ ID NOs: 17994-17999). Among the 10 sequences that showed higher cleavage ratios than the sequence shown as SEQ ID NO: 3 for human uPA and human MT-SP1, seven sequences showed lower cleavage ratios in human serum than the sequence shown as SEQ ID NO: 4 (SEQ ID NOs: 17994-17996 and 18000-18003).

Example 2

Example of Ligand-Binding Molecule Introduced with Protease Cleavage Sequence

Figure 5:
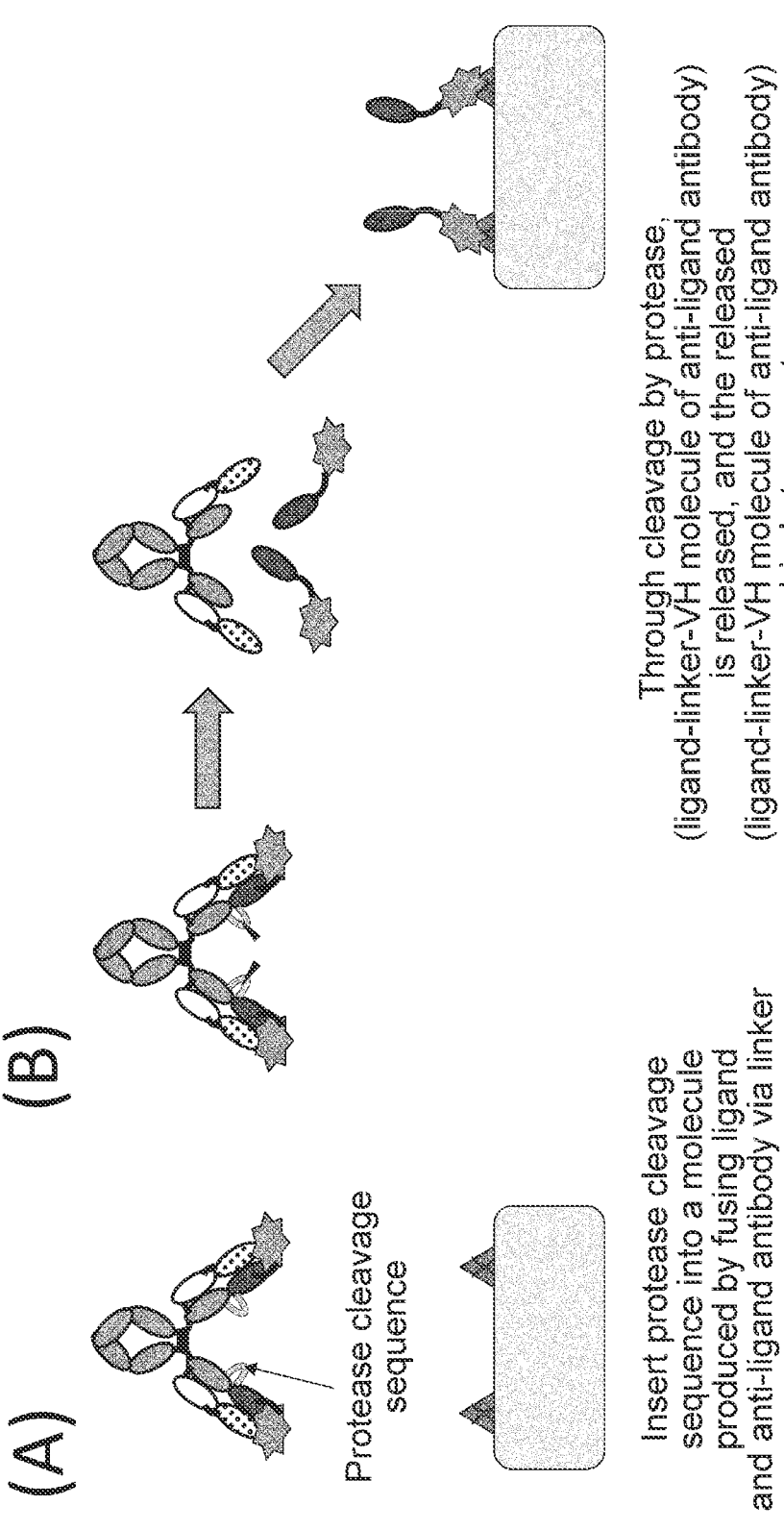
FIG. 5 illustrates an example of a polypeptide comprising a protease cleavage sequence of the present disclosure. In this figure, the polypeptide is a fusion protein of a ligand and an anti-ligand antibody. (A) The protease cleavage sequence is included within the anti-ligand antibody, and the ligand is bound to the anti-ligand antibody in a state where the protease cleavage sequence is not cleaved. (B) The ligand and a portion of the anti-ligand antibody are released from the polypeptide in a state where the protease cleavage sequence is cleaved, and the ligand becomes capable of binding to the receptor.
Figure 6:
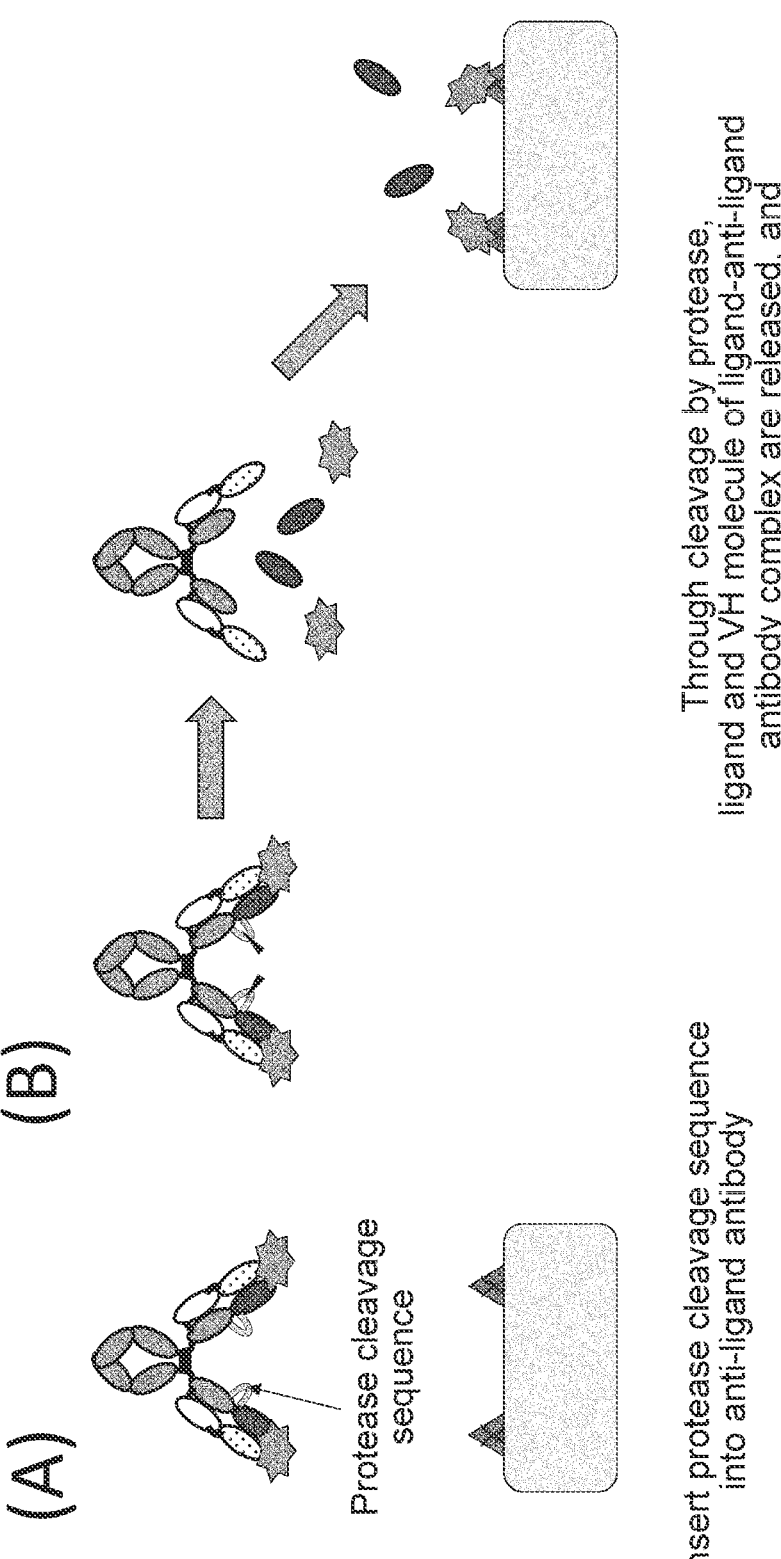
FIG. 6 illustrates an example of a polypeptide comprising a protease cleavage sequence of the present disclosure. In this figure, the polypeptide is an anti-ligand antibody. (A) The protease cleavage sequence is included within the anti-ligand antibody, and the anti-ligand antibody is capable of binding to the ligand in a state where the protease cleavage sequence is not cleaved. (B) The ligand-binding activity of the anti-ligand antibody is weakened in a state where the protease cleavage sequence is cleaved, and the ligand dissociates from the anti-ligand antibody and becomes capable of binding to the receptor.

FIGS. 5 and 6 illustrate examples of molecules in which when the polypeptide is a ligand-binding molecule, an antibody is used as the ligand-binding molecule. In these examples, a neutralizing antibody against the ligand is initially obtained. Subsequently, a protease cleavage sequence is introduced into the anti-ligand neutralizing antibody in the vicinity of the boundary between its variable region (VH or VL) and constant region (CH1 or CL). The retention of ligand-binding activity of the anti-ligand antibody after the introduction of the protease cleavage sequence is confirmed. Dissociation of the ligand by the protease cleavage is confirmed in a state where the ligand is bound to the anti-ligand neutralizing antibody. Exertion of biological activity of the ligand thus dissociated is confirmed.

In FIG. 5, the C-terminus of the ligand and the N-terminus of VH of the anti-ligand antibody are connected via a linker, and a protease cleavage sequence is introduced in the vicinity of the boundary between the VH and CH1. When the anti-ligand antibody has sufficiently strong affinity for the ligand, the biological activity of the ligand is sufficiently inhibited. This ligand-anti-ligand antibody fusion does not exert its biological activity when it is administered systemically, because the ligand is neutralized. The ligand-anti-ligand antibody fusion has an Fc region; therefore, it has a long half-life. From the systemically administered ligand-anti-ligand antibody fusion, the VH molecules of the ligand-linker-anti-ligand antibody are released when the protease cleavage sequence placed in the vicinity of the boundary between VH and CH1 is cleaved by a protease highly expressed in tumor tissue. Since VH or VL alone is unable to bind to the ligand (both VH and VL are necessary for binding to the ligand), the neutralization of the ligand is abolished, and the ligand is able to exert its biological activity in tumor tissue. Also, the released VH molecule of the ligand-linker-anti-ligand antibody lacks the Fc region and has a small molecular weight; therefore, it has a very short half-life and is rapidly eliminated systemically. As a result, it is possible to minimize the systemic adverse effects caused by the ligand.

In FIG. 6, unlike in FIG. 5, the ligand and the anti-ligand antibody are not connected via a linker, and the anti-ligand antibody introduced with a protease cleavage sequence at a position in the vicinity of the boundary between VH and CH1 is admixed with the ligand and then administered. When the anti-ligand antibody has sufficiently strong affinity for the ligand and when there is sufficient anti-ligand antibody relative to the ligand concentration, the biological activity of the ligand is sufficiently inhibited. This ligand-anti-ligand antibody complex does not exert its biological activity when it is administered systemically, because the ligand is neutralized. The ligand-anti-ligand antibody complex has an Fc region; therefore, it has a long half-life. From the systemically administered ligand-anti-ligand antibody complex, the VH molecules of the anti-ligand antibody are released when the protease cleavage sequence placed in the vicinity of the boundary between VH and CH1 is cleaved by a protease highly expressed in tumor tissue. Since VH or VL alone is unable to bind to the ligand (both VH and VL are necessary for binding to the ligand), the neutralization of the ligand is abolished, and the ligand is able to exert its biological activity in tumor tissue. Also, the released ligand molecule lacks the Fc region and has a small molecular weight; therefore, it has a very short half-life and is rapidly eliminated systemically. As a result, it is possible to minimize the systemic side effects caused by the ligand.

Thus, use of an anti-ligand antibody into which a protease cleavage sequence is introduced in the vicinity of the boundary between VH and CH1 may allow for selective release of the ligand in protease-expressing tissue, thereby allowing the ligand to exert its biological activity. When the ligand is a cytokine, the cytokine may be allowed to selectively exert its effect in protease-expressing tissue. When the ligand is a chemokine, the chemokine may make chemokine receptor-expressing cells to migrate into protease-expressing tissue, because the chemokine is present at a high concentration in the protease-expressing tissue and the chemokine concentration is reduced in peripheral blood.

Example 3

Example of Ligand-Binding Molecule Containing Single-Domain Antibody Introduced with Protease Cleavage Sequence FIGS. 7-10 illustrate examples of a ligand-binding molecule containing a single-domain antibody introduced with a protease cleavage sequence, when the polypeptide is a ligand-binding molecule comprising a single-domain antibody.

Figure 7:
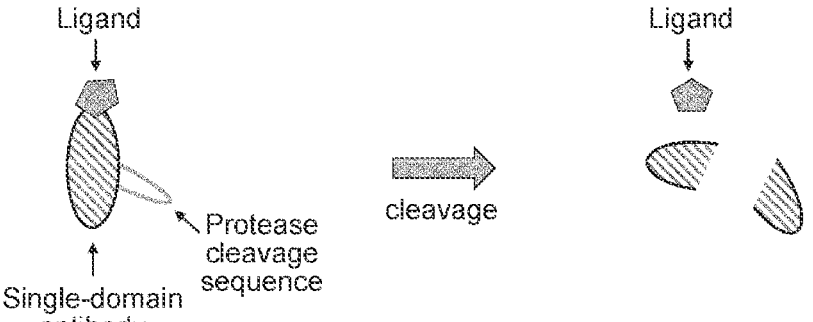
FIG. 7 illustrates an example of a polypeptide comprising a protease cleavage sequence of the present disclosure. In this figure, the polypeptide is a single-domain antibody comprising the protease cleavage sequence. The single-domain antibody is capable of binding to the ligand in a state where the protease cleavage sequence contained in the single-domain antibody is uncleaved, while, in a state where the protease cleavage sequence is cleaved, the single-domain antibody is cleaved and is incapable of binding to the ligand, and the ligand is released.

FIG. 7 illustrates an example of a ligand-binding molecule that contains only a single-domain antibody into which a protease cleavage sequence is introduced. In a state where the protease cleavage sequence is not cleaved, the single-domain antibody is capable of binding to the ligand, and, when the single-domain antibody has sufficiently strong affinity for the ligand, the biological activity of the ligand is sufficiently inhibited. Even if this ligand-binding molecule and ligand are administered systemically, the ligand does not exert its biological activity because the ligand in the ligand-ligand-binding molecule complex is neutralized. The ligand-ligand-binding molecule complex has a longer half-life than the ligand alone. In the systemically administered complex formed of a ligand and a ligand-binding molecule, when the protease cleavage sequence placed in the single-domain antibody is cleaved by a protease highly expressed in tumor tissue, the single-domain antibody is no longer able to bind to the ligand, the neutralization of the ligand is abolished, and the ligand is able to exert its biological activity in tumor tissue.

Figure 8:
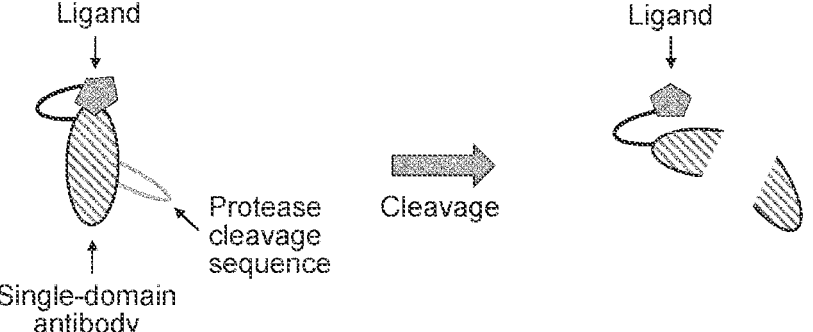
FIG. 8 illustrates an example of a polypeptide comprising a protease cleavage sequence of the present disclosure. In this figure, the polypeptide is a fusion protein formed of a ligand and a single-domain antibody comprising the protease cleavage sequence. The single-domain antibody in the fusion protein is capable of binding to the ligand in the fusion protein in a state where the protease cleavage sequence contained in the single-domain antibody is uncleaved, while, in a state where the protease cleavage sequence is cleaved, the single-domain antibody is cleaved and is incapable of binding to the ligand, and a portion of the fusion protein that includes the ligand is released.

FIG. 8 illustrates an example of a fusion polypeptide in which a ligand is fused with a ligand-binding molecule containing only a single-domain antibody into which a protease cleavage sequence is introduced. In a state where the protease cleavage sequence is not cleaved, the single-domain antibody in the fusion polypeptide is able to bind to the ligand, and when the affinity of the single-domain antibody for the ligand is sufficiently strong, the biological activity of the ligand is sufficiently inhibited. Even when this fusion polypeptide is administered systemically, the ligand in the fusion polypeptide does not exert its biological activity because it is neutralized, and the fusion polypeptide has a longer half-life than the ligand alone. In the systemically administered fusion polypeptide, when the protease cleavage sequence placed in the single-domain antibody is cleaved by a protease highly expressed in tumor tissue, the single-domain antibody in the fusion polypeptide is no longer able to bind to the ligand, the neutralization of the ligand is abolished, part of the fusion polypeptide that contains the ligand is released, and the ligand is able to exert its biological activity in tumor tissue.

Figure 10:
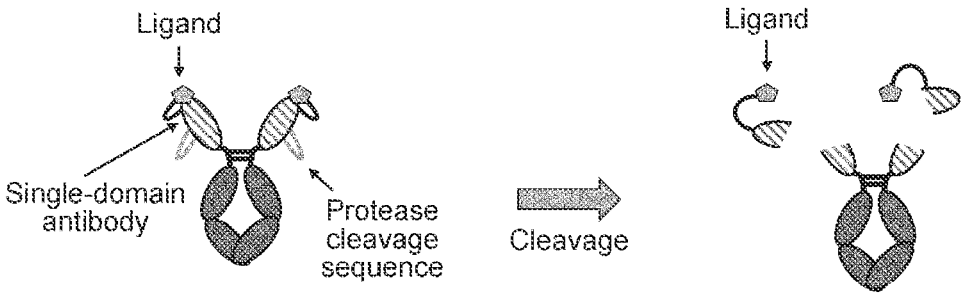
FIG. 10 illustrates an example of a polypeptide comprising a protease cleavage sequence of the present disclosure. In this figure, the polypeptide is a fusion protein of a ligand and a dimeric protein comprising a single-domain antibody containing the protease cleavage sequence-antibody hinge region-antibody Fc region.

FIGS. 9 and 10 illustrate examples of a ligand-binding molecule comprising a single-domain antibody into which a protease cleavage sequence is introduced, an antibody hinge region, and an antibody Fc region, and a fusion polypeptide of the ligand-binding molecule and the ligand. As in the embodiments illustrated in FIGS. 7 and 8, the ligand can be neutralized by a single-domain antibody in an uncleaved state, and it can be released in a cleaved state to exert its biological activity. In the examples illustrated in FIGS. 9 and 10, the half-life of the fusion polypeptides is expected to be further longer in an uncleaved state than in the examples illustrated in FIGS. 7 and 8, considering that the antibody Fc region is contained the complexes or fusion polypeptides in an uncleaved state.

Example 4

Anti-Human IL-6R Single-Domain Antibody-Containing Ligand-Binding Molecule Introduced with a Protease Cleavage Sequence 4-1. Preparation of Ligand-Binding Molecules by Introducing a Protease Cleavage Sequence into a Polypeptide Containing Anti-Human IL-6R Single-Domain Antibody A single-domain antibody-containing ligand-binding molecule introduced with a protease cleavage sequence was prepared by inserting a protease cleavage sequence into the single-domain antibody included in the polypeptide IL6R90-G1T3dCHdC (SEQ ID NO: 18030), prepared by fusing the C-terminus of a single-domain antibody against human IL-6R (SEQ ID NO: 18028) and the N-terminus of an antibody hinge region and Fc region sequences shown in SEQ ID NO: 18029. Initially, a sequence containing the peptide sequence (LSGRSDNH, SEQ ID NO: 18031) that is reportedly cleaved by cancer-specifically expressed MT-SP1 is inserted into the polypeptide IL6R90-G1T3dCHdC, and ligand-binding molecules shown in Table 3 were prepared. These molecules were expressed by transient expression using Expi293 (Life Technologies) and purified by the protein A-based method known to those skilled in the art. As a control molecule not containing protease cleavage sequence, IL6R90-G1T3dCHdC was expressed and purified. The ligand-binding molecules and control molecule thus prepared are dimeric proteins as illustrated in FIG. 9.

TABLE 3

| Ligand-binding molecules | | |
| --- | --- | --- |
| Ligand-binding molecules | | Position of insertion of the protease cleavage sequence in a single-domain antibody comprised in a ligand-binding |
| Name | SEQ ID NO: | molecule (Kabat numbering) |
| 6R90H12I001-G1T3dCH1dC | 18032 | Between 12 and 13 |
| 6R90H13I001-G1T3dCH1dC | 18033 | Between 13 and 14 |
| 6R90H14I001-G1T3dCH1dC | 18034 | Between 14 and 15 |
| 6R90H15I001-G1T3dCH1dC | 18035 | Between 15 and 16 |
| 6R90H16IG001-G1T3dCH1dC | 18036 | Between 16 and 17 |

4-2. Evaluation of Binding to Human IL-6R of Ligand-Binding Molecules Containing Anti-Human IL-6R Single-Domain Antibody Introduced with a Protease Cleavage Sequence 4-2-1. Protease Treatment To 0.1 mg/mL of the ligand-binding molecules prepared in Example 4-1, Recombinant Human Matriptase/ST14 Catalytic Domain (hMT-SP1, R&D systemsm 3946-SE-010) was added at a final concentration of 25 nM and incubated overnight at 37° C., thereby preparing a solution containing a protease-treated ligand-binding molecule. The conditions for preparing a solution containing a protease-untreated ligand-binding molecule were that the same volume of PBS was added in place of protease and stored under the same conditions.

4-2-2. Confirmation of Protease Cleavage of Ligand Binding Molecules (SDS-PAGE)

Figure 11:
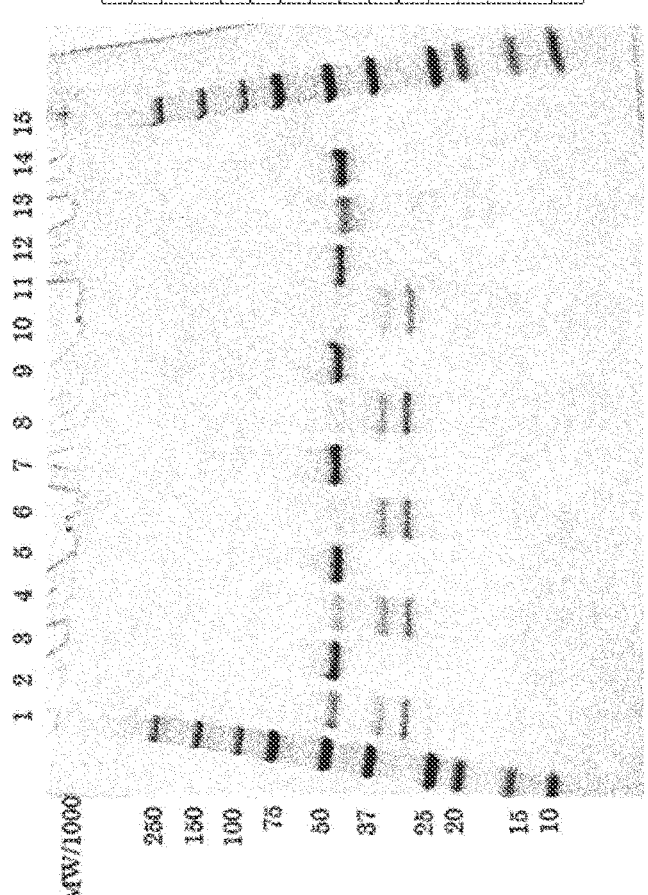
FIG. 11 shows the results of SDS-PAGE of protease-treated and protease-untreated ligand-binding molecules. While the control molecule containing no protease cleavage sequence shows a band at the same position regardless of whether it is treated or untreated with protease (Lanes 12 and 13), the ligand-binding molecules introduced with the respective protease cleavage sequences show novel bands generated only after protease treatment, indicating that the ligand-binding molecules containing single-domain antibodies introduced with the respective protease cleavage sequences were cleaved by the protease treatment.

SDS-PAGE was performed to confirm whether the ligand-binding molecules were cleaved by the protease treatment performed in Example 4-2-1. Nine μL of a solution containing the protease-treated ligand-binding molecule/protease-untreated ligand-binding molecule prepared in Example 4-2-1 was mixed with 3 μL of sample buffer and incubated at 95° C. for 1 minute. Subsequently, electrophoresis was performed using Mini-PROTEAN TGX gel (4-20% 15 well) (Bio-Rad #456-1096), and the protein was stained with Sample Blue Safe Stain (novex, LC6065). The results are shown in FIG. 11. As shown in FIG. 11, while the control molecule containing no protease cleavage sequence shows a band at the same position regardless of whether it is treated or untreated with protease (Lanes 12 and 13), the ligand-binding molecules introduced with the respective protease cleavage sequences show new bands only when they are treated with protease, indicating that the ligand-binding molecules containing single-domain antibodies introduced with the respective protease cleavage sequences are cleaved by the protease treatment.

Figure 12:
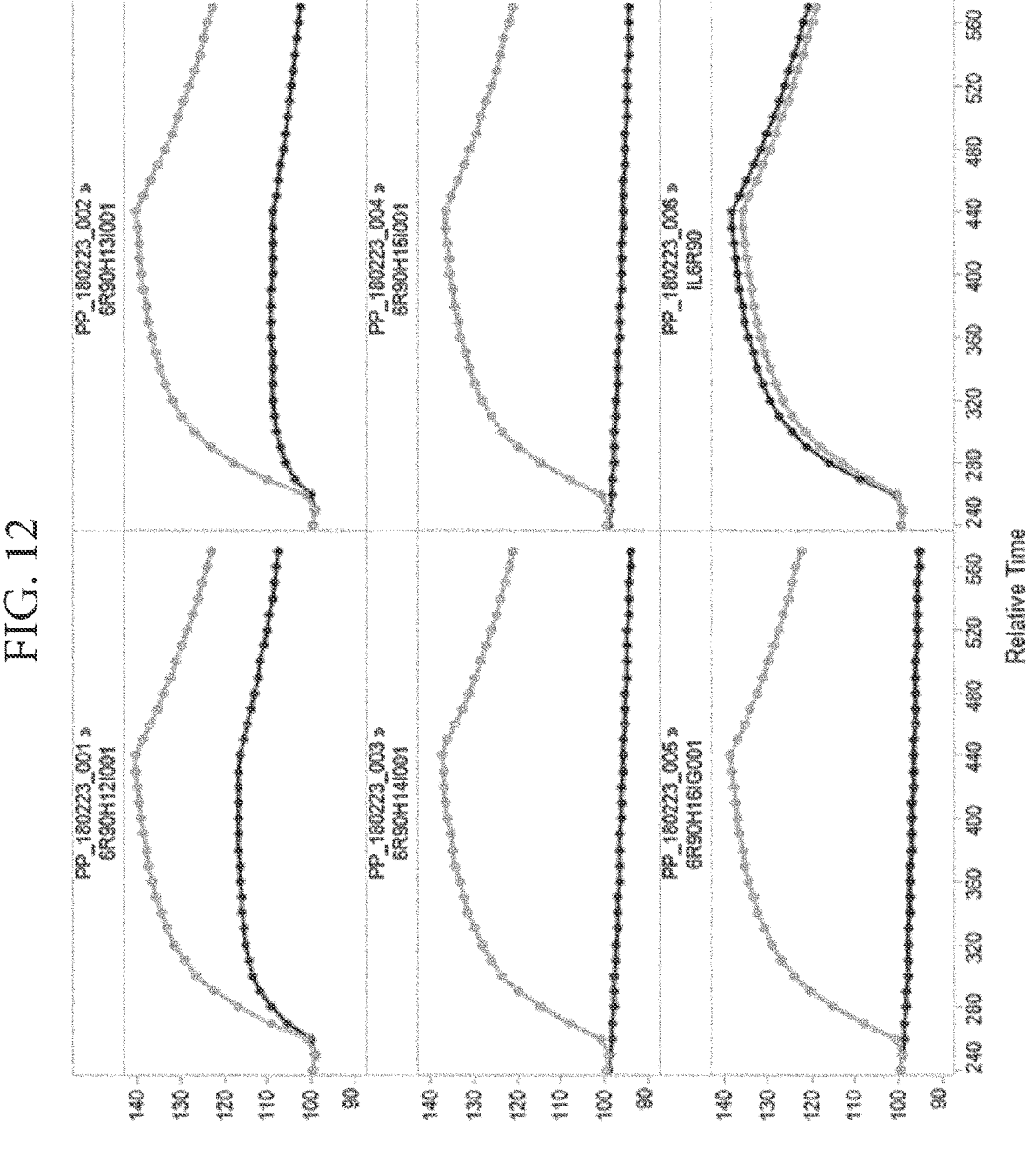
FIG. 12 shows graphs of the real-time binding that evaluate the binding of protease-treated and protease-untreated ligand-binding molecules to IL-6R. The title of each graph is the name of the measured sample. The vertical axis indicates the relative binding of the ligand-binding molecule and IL-6R, and the horizontal axis shows the time (s). The gray line shows the data from the protease-untreated samples, and the black line shows the data from the protease-treated samples.
Figure 14:
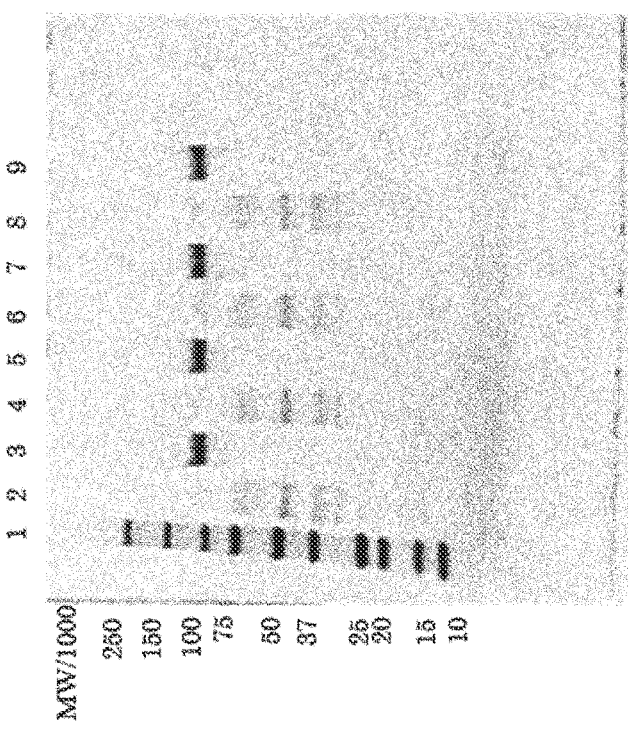
FIG. 14 shows the continuation of FIG. 13.
Figure 16:
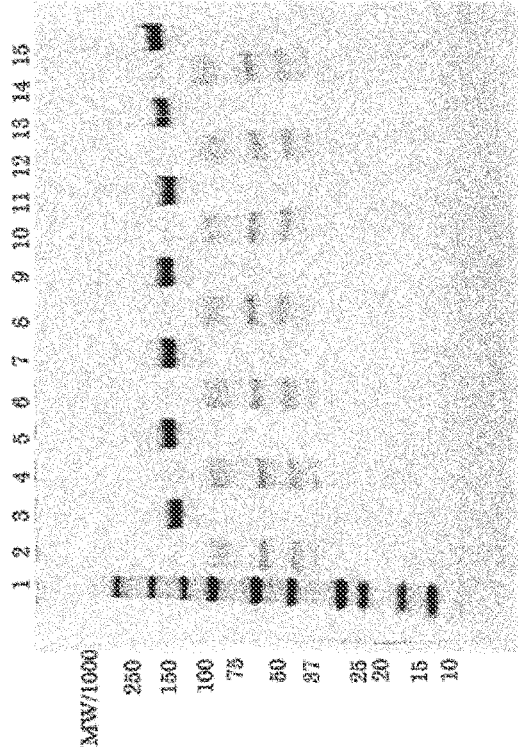
FIG. 16 shows the continuation of FIG. 15.

4-2-3. Evaluation of Binding of Protease-Treated Ligand-Binding Molecule/Protease-Untreated Ligand-Binding Molecule to Human IL-6R To 20 μL of a solution containing the protease-treated ligand-binding molecules/protease-untreated ligand-binding molecules prepared in Example 4-2-1, 60 μL of PBS was added to prepare a sample for evaluating the IL-6R binding. The evaluation of the sample for IL-6R binding was carried out using biolayer interferometry (BLI method). The IL-6R binding evaluation sample and IL-6R were dispensed into a Tilted bottom (TW384) Microplate (Forte bio, 18-5076). A Protein G sensor (ForteBio, 18-0022) was hydrated with PBS and the measurement was performed using Octet RED 384 at a setting of 25 degrees. Baseline measurements were performed in the wells containing PBS for 30 seconds, after which the antibody was allowed to bind to the Protein G sensor for 200 seconds. Again, the baseline measurements were performed in the wells containing PBS for 30 seconds, then the binding was measured for 180 seconds in the wells containing 500 nM human IL-6R, and dissociation was measured for 180 seconds in the wells containing PBS. FIG. 12 shows real-time binding graphs showing the binding. As shown in FIG. 12, the amount of binding of human IL-6R decreased when the ligand-binding molecules each of which is introduced with a protease cleavage sequence were used, as compared to when the protease-untreated ligand-binding molecules were used.

Example 5

Preparation and Evaluation of a Fusion Protein of Human IL-6R and a Ligand-Binding Molecule Containing an Anti- Human IL-6R Single-Domain Antibody Introduced with a Protease Cleavage Sequence (Ligand-Binding Molecule-IL-6R Fusion Protein)

5-1. Preparation of a Fusion Protein of Human IL-6R and a Ligand-Binding Molecule Containing an Anti-Human IL-6R Single-Domain Antibody Introduced with a Protease Cleavage Sequence Ligand-binding molecule-IL-6R fusion proteins were prepared by fusing the N-terminus of the ligand-binding molecules prepared in Example 4-1 with the C-terminus of human IL-6R (SEQ ID NO: 18037) via various linkers consisting of glycine and serine (Table 4). These fusion proteins were expressed by transient expression using Expi293 (Life Technologies) by a method known to those skilled in the art, and purification was performed using a protein A-based method known to those skilled in the art. The fusion proteins thus prepared are dimeric proteins each of which has two peptide chains having the sequences shown in Table 4.

TABLE 4

| Ligand-binding molecule-IL6R fusion proteins | |
| --- | --- |
| Name | SEQ ID NO: |
| IL6RaG4S.6R90H12I001-G1T3dCH1dC | 18038 |
| IL6RaG4Sx2.6R90H12I001-G1T3dCH1dC | 18039 |
| IL6RaG4Sx3.6R90H12I001-G1T3dCH1dC | 18040 |
| IL6RaG4Sx4.6R90H12I001-G1T3dCH1dC | 18041 |
| IL6RaG4Sx5.6R90H12I001-G1T3dCH1dC | 18042 |
| IL6RaG4S.6R90H13I001-G1T3dCH1dC | 18043 |
| IL6RaG4Sx2.6R90H13I001-G1T3dCH1dC | 18044 |
| IL6RaG4Sx3.6R90H13I001-G1T3dCH1dC | 18045 |
| IL6RaG4Sx4.6R90H13I001-G1T3dCH1dC | 18046 |
| IL6RaG4Sx5.6R90H13I001-G1T3dCH1dC | 18047 |
| IL6RaG4S.6R90H14IG001-G1T3dCH1dC | 18048 |
| IL6RaG4Sx2.6R90H14IG001-G1T3dCH1dC | 18049 |
| IL6RaG4Sx3.6R90H14IG001-G1T3dCH1dC | 18050 |
| IL6RaG4Sx4.6R90H14IG001-G1T3dCH1dC | 18051 |
| IL6RaG4Sx5.6R90H14IG001-G1T3dCH1dC | 18052 |
| IL6RaG4S.6R90H15I001-G1T3dCH1dC | 18053 |
| IL6RaG4Sx2.6R90H15I001-G1T3dCH1dC | 18054 |
| IL6RaG4Sx3.6R90H15I001-G1T3dCH1dC | 18055 |
| IL6RaG4Sx4.6R90H15I001-G1T3dCH1dC | 18056 |
| IL6RaG4Sx5.6R90H15I001-G1T3dCH1dC | 18057 |
| IL6RaG4S.6R90H16IG001-G1T3dCH1dC | 18058 |
| IL6RaG4Sx2.6R90H16IG001-G1T3dCH1dC | 18059 |
| IL6RaG4Sx3.6R90H16IG001-G1T3dCH1dC | 18060 |
| IL6RaG4Sx4.6R90H16IG001-G1T3dCH1dC | 18061 |
| IL6RaG4Sx5.6R90H16IG001-G1T3dCH1dC | 18062 |

As control molecules not containing protease cleavage sequence, molecules were prepared in which the N-terminus of IL6R90-G1T3dCHdC (SEQ ID NO: 18030) was fused with the C-terminus of IL-6R via a linker (Table 5), and expression and purification were conducted. The control molecules thus prepared are also dimeric proteins each of which has two peptide chains having the sequences shown in Table 5.

TABLE 5

| Control molecules not containing a protease cleavage sequence | |
| --- | --- |
| Name | SEQ ID NO: |
| IL6RaG4S.IL6R90-G1T3dCH1dC | 18063 |
| IL6RaG4Sx2.IL6R90-G1T3dCH1dC | 18064 |
| IL6RaG4Sx3.IL6R90-G1T3dCH1dC | 18065 |
| IL6RaG4Sx4.IL6R90-G1T3dCH1dC | 18066 |
| IL6RaG4Sx5.IL6R90-G1T3dCH1dC | 18067 |

5-2. Evaluation of Protease Cleavage of Ligand-Binding Molecule-IL-6R Fusion Protein 5-2-1. Protease Treatment To 0.1 mg/mL of the ligand-binding molecule-IL-6R fusion protein prepared in Example 5-1, Recombinant Human Matriptase/ST14 Catalytic Domain (hMT-SP1, R&D systemsm 3946-SE-010) was added at a final concentration of 25 nM and incubated overnight at 37° C., thereby preparing a solution containing the protease-treated fusion protein. The conditions for preparing a solution containing a protease-untreated fusion protein were that the same volume of PBS was added in place of protease and stored under the same conditions.

5-2-2. Confirmation of Protease Cleavage of Anti-IL-6R Single-Domain Antibody-IL-6R Fusion Protein (SDS-PAGE)

SDS-PAGE was performed to confirm whether the ligand-binding molecule-IL-6R fusion proteins were cleaved by the protease treatment performed in Example 5-2-1. Nine μL of a solution containing the protease-treated fusion protein/ protease-untreated fusion protein prepared in Example 5-2-1 was mixed with 3 μL of sample buffer and incubated at 95° C. for 1 minute. Subsequently, electrophoresis was performed using Mini-PROTEAN TGX gel (4-20% 15 well) (Bio-Rad #456-1096), and the protein was stained with Sample Blue Safe Stain (novex, LC6065). The results are shown in FIGS. 13-16. As shown in FIGS. 13-16, while the control molecule containing no protease cleavage sequence shows a band at the same position regardless of whether it is treated or untreated with protease, the fusion proteins comprising a ligand-binding molecule containing a single-domain antibody introduced with a protease cleavage sequence show new bands only after they are treated with protease, indicating that the fusion proteins comprising a ligand-binding molecule containing a single-domain antibody introduced with a protease cleavage sequence are cleaved by the protease treatment.

5-2-3. Preparation of Biotinylated Anti-IL-6R Single-Domain Antibody-Containing Molecule As a method for detecting the release of IL-6R fused to a ligand-binding molecule, the following method was used: biotin was added to a single-domain antibody-containing molecule that recognizes IL-6R; and the binding of free IL-6R to the biotinylated anti-IL-6R single-domain antibody-containing molecule was detected. A biotinylated anti-IL-6R single-domain antibody-containing molecule was prepared as follows: an anti-IL-6R single-domain antibody-containing molecule was prepared which has a partial sequence of a single-domain antibody that is the same as the sequence of IL6R90-G1T3dCH1dC (SEQ ID NO: 18030), and IL6R90-FcBAPdC (SEQ ID NO: 18069) was prepared, which has addition of the biotin additional sequence (AviTag sequence, SEQ ID NO: 18068) at its C-terminus. A gene fragment encoding IL6R90-FcBAPdC was prepared and then introduced into a vector for expression in animal cells by a method known to those skilled in the art. At the same time, the genes for expression of EBNA1 and biotin ligase were simultaneously introduced into the vector, and biotin was added for biotin labeling. Cells introduced with the genes were cultured at 37° C., 8% $CO_2$, and the biotinylated anti-IL-6R single-domain antibody-containing molecule of interest (IL6R90-bio) was secreted into the culture supernatant. From the culture supernatant, IL6R90-bio was purified using a method known to those skilled in the art.

5-2-4. Evaluation of IL-6R Release from Fusion Protein by Protease Treatment

The release of IL-6R by treating the fusion protein with protease was evaluated using the biotinylated anti-IL-6R single-domain antibody-containing molecule (IL6R90-bio) prepared in Example 5-2-3 by biolayer interferometry (BLI method).

Figure 17:
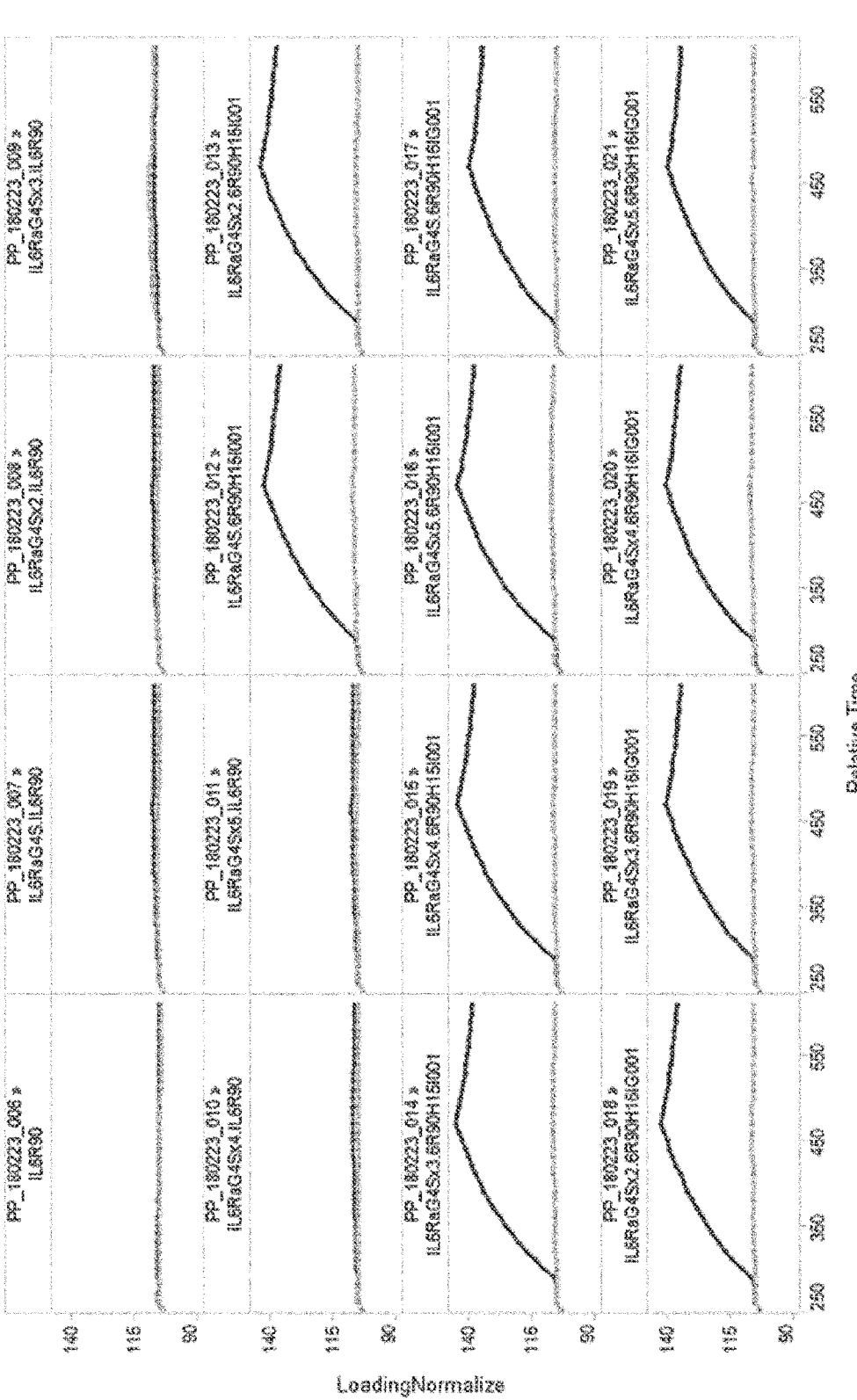
FIG. 17 shows real-time graphs evaluating the binding of free IL-6R to the IL6R90-bio present in solutions containing protease-treated or protease-untreated fusion proteins. The title of each graph is the name of the measured sample. The vertical axis indicates the relative binding of IL-6R and the biotinylated anti-IL-6R single-domain antibody-containing molecule (IL6R90-bio), and the horizontal axis shows the time (s). The gray line shows the data from the protease-untreated samples, and the black line shows the data from the protease-treated samples.
Figure 18:
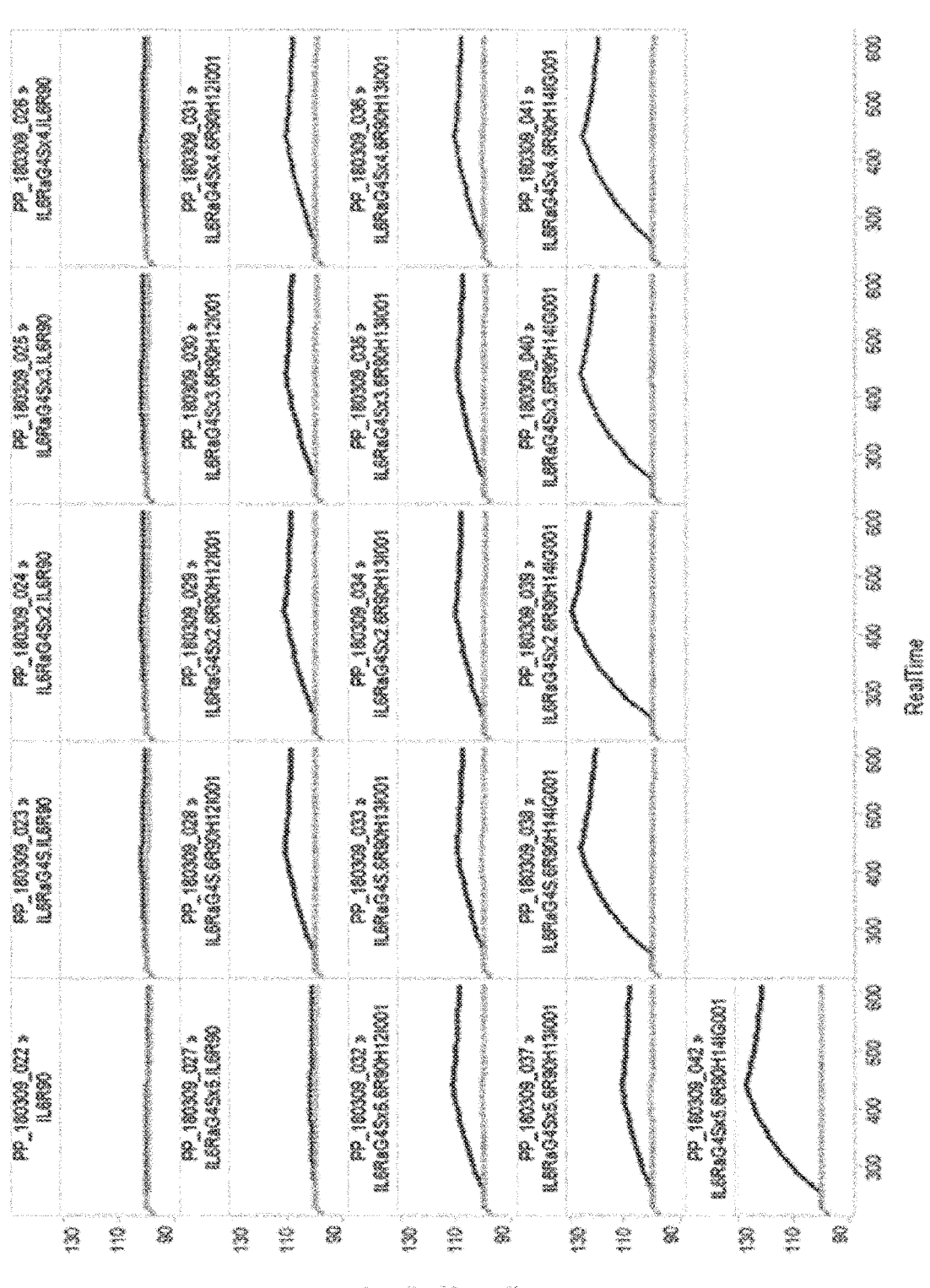
FIG. 18 shows the continuation of FIG. 17.

Each of the protease-treated fusion proteins prepared in Example 5-2-1, protease-untreated fusion proteins, and IL6R90-bio was dispensed into different wells of Tilted bottom (TW384) Micro plates (ForteBio, 18-5076). A Streptavidin biosensor (ForteBio, 18-5021) was hydrated with PBS, and the measurement was performed using Octet RED 384 at a setting of 27° C. Baseline measurements were performed in the wells containing PBS for 30 seconds, after which IL6R90-bio was allowed to bind to the Streptavidin sensor for 200 seconds. Again, the baseline measurements were performed in the wells containing PBS for 30 seconds, then the binding was measured for 180 seconds in the wells containing protease-treated fusion protein or protease-untreated fusion protein, and the dissociation was measured for 180 seconds in the wells containing PBS. FIGS. 17 and 18 show the graphs of real-time binding which show the binding. As shown in FIGS. 17 and 18, in the case of fusion proteins of IL-6R and a ligand-binding molecule containing a single-domain antibody introduced with a protease cleavage sequence, there was an increase in the amount of human IL-6R that binds to IL6R90-bio when treated with protease, as compared to when they were not treated with protease. Thus, the binding activity of the single-domain antibody in the fusion protein to IL-6R was attenuated by the protease treatment, and IL-6R was released from the fusion protein.

Example 6

Production and Evaluation of Fusion Proteins of Human PD-1 and a Ligand-Binding Molecule Containing an Anti-Human PD-1 Single-Domain Antibody Introduced with a Protease Cleavage Sequence (Ligand-Binding Molecule-PD-1 Fusion Protein)

6-1. Preparation of Fusion Proteins of Human PD-1 and a Ligand-Binding Molecule Containing an Anti-Human PD-1 Single-Domain Antibody Introduced with a Protease Cleavage Sequence PD102C3-G1T3noCyshinge (SEQ ID NO: 18070) and PD102C12-G1T3noCyshinge (SEQ ID NO: 18071), in which a human antibody constant region is fused to a single-domain antibody that binds human PD-1, were prepared using methods known to those skilled in the art. Then, after introducing a protease cleavage sequence, each of PD102C3-G1T3noCyshinge and PD102C12-G1T3noCyshinge is fused, at its N-terminus, to the C-terminus of the extracellular domain of human PD-1 (SEQ ID NO: 18072) via various linkers consisting of glycine and serine, thereby preparing ligand-binding molecule-PD-1 fusion proteins (Table 6). These fusion proteins were expressed by transient expression using Expi293 (Life Technologies) by a method known to those skilled in the art, and purification was performed using a protein A-based method known to those skilled in the art. The fusion proteins thus prepared are dimeric proteins each of which has two peptide chains having the sequences shown in Table 6.

TABLE 6

| Ligand-binding molecule-human PD1 fusion proteins | |
| --- | --- |
| Name | SEQ ID NO: |
| hPD1PD102C3H12-G1T3noCyshinge | 18073 |
| hPD1PD102C3H13-G1T3noCyshinge | 18074 |
| hPD1PD102C12H12-G1T3noCyshinge | 18075 |
| hPD1PD102C12H14-G1T3noCyshinge | 18076 |

6-2. Evaluation of Cleavage by Protease of Ligand-Binding Molecule-PD-1 Fusion Proteins 6-2-1. Protease Treatment To 0.1 mg/mL of the ligand-binding molecule-PD-1 fusion protein prepared in Example 6-1, Recombinant Human Matriptase/ST14 Catalytic Domain (hMT-SP1, R&D systemsm 3946-SE-010) was added at a final concentration of 25 nM and incubated overnight at 37° C., thereby preparing a solution containing the protease-treated fusion protein. The conditions for preparing a solution containing a protease-untreated fusion protein were that the same volume of PBS was added in place of protease and stored under the same conditions.

6-2-2. Confirmation of Protease Cleavage of Anti-PD-1 Single-Domain Antibody-PD-1 Fusion Protein (SDS-PAGE)

Figure 19:
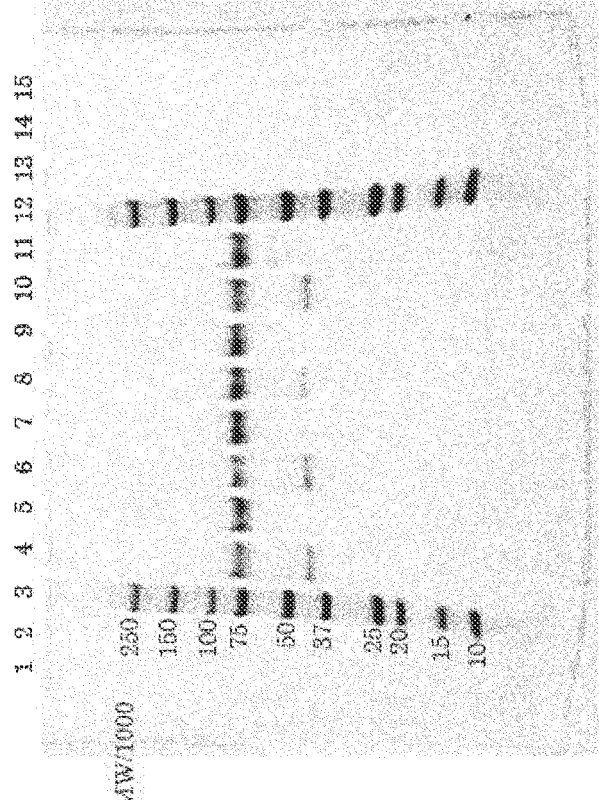
FIG. 19 shows the results of SDS-PAGE of protease-treated and protease-untreated fusion proteins.

SDS-PAGE was performed to confirm whether the ligand-binding molecule-PD-1 fusion proteins were cleaved by the protease treatment performed in Example 6-2-1. Nine μL of a solution containing the protease-treated fusion protein/protease-untreated fusion protein prepared in Example 6-2-1 was mixed with 3 μL of sample buffer and incubated at 95° C. for 1 minute. Subsequently, electrophoresis was performed using Mini-PROTEAN TGX gel (4-20% 15 well) (Bio-Rad #456-1096), and the protein was stained with Sample Blue Safe Stain (novex, LC6065). The results are shown in FIG. 19. As shown in FIG. 19, the fusion proteins containing a ligand-binding molecule containing a single-domain antibody introduced with a protease cleavage sequence show new bands only after protease treatment, indicating that the fusion proteins containing a ligand-binding molecule containing a single-domain antibody introduced with a protease cleavage sequence are cleaved by the protease treatment.

6-2-3. Preparation of Biotinylated Anti-PD-1 Single-Domain Antibody-Containing Molecule As a method for detecting the release of PD-1 fused to a ligand-binding molecule, the following method was used: biotin was added to a single-domain antibody-containing molecule that recognizes PD-1; and the binding of free PD-1 to the biotinylated anti-PD-1 single-domain antibody-containing molecule was detected. A biotinylated anti-PD-1 single-domain antibody-containing molecule was prepared as follows: a single-domain antibody-containing molecule was prepared which has a partial sequence of a single-domain antibody that is the same as the sequence of PD102C3-G1T3noCyshinge, and PD102C3-FcBAPdC (SEQ ID NO: 18077) was prepared by adding, at its C-terminus, the biotin additional sequence (AviTag sequence, SEQ ID NO: 18068). Also, an anti-PD-1 single-domain antibody-containing molecule was prepared which has a partial sequence of a single-domain antibody that is the same as the sequence of PD102C12-G1T3noCyshinge, and PD102C12-FcBAPdC (SEQ ID NO: 18078) was prepared by adding, at its C-terminus, the biotin additional sequence (AviTag sequence, SEQ ID NO: 18068). Gene fragments encoding PD102C3-FcBAPdC and PD102C12-FcBAPdC, respectively, were prepared and then introduced into a vector for expression in animal cells by a method known to those skilled in the art. At the same time, the genes for expression of EBNA1 and biotin ligase were simultaneously introduced into the vector, and biotin was added for biotin labeling. Cells introduced with the genes were cultured at 37° C., 8% $CO_2$, and the biotinylated anti-PD-1 single-domain antibody-containing molecule of interest (PD1-bio) was secreted into the culture supernatant. From the culture supernatant, PD1-bio was purified using a method known to those skilled in the art.

6-2-4. Evaluation of PD-1 Release from Fusion Protein by Protease Treatment

The release of PD-1 by treatment of the fusion protein with protease was evaluated using the biotinylated anti-PD-1 single-domain antibody-containing molecule (PD1-bio) prepared in Example 6-2-3 by biolayer interferometry (BLI method).

Figure 20:
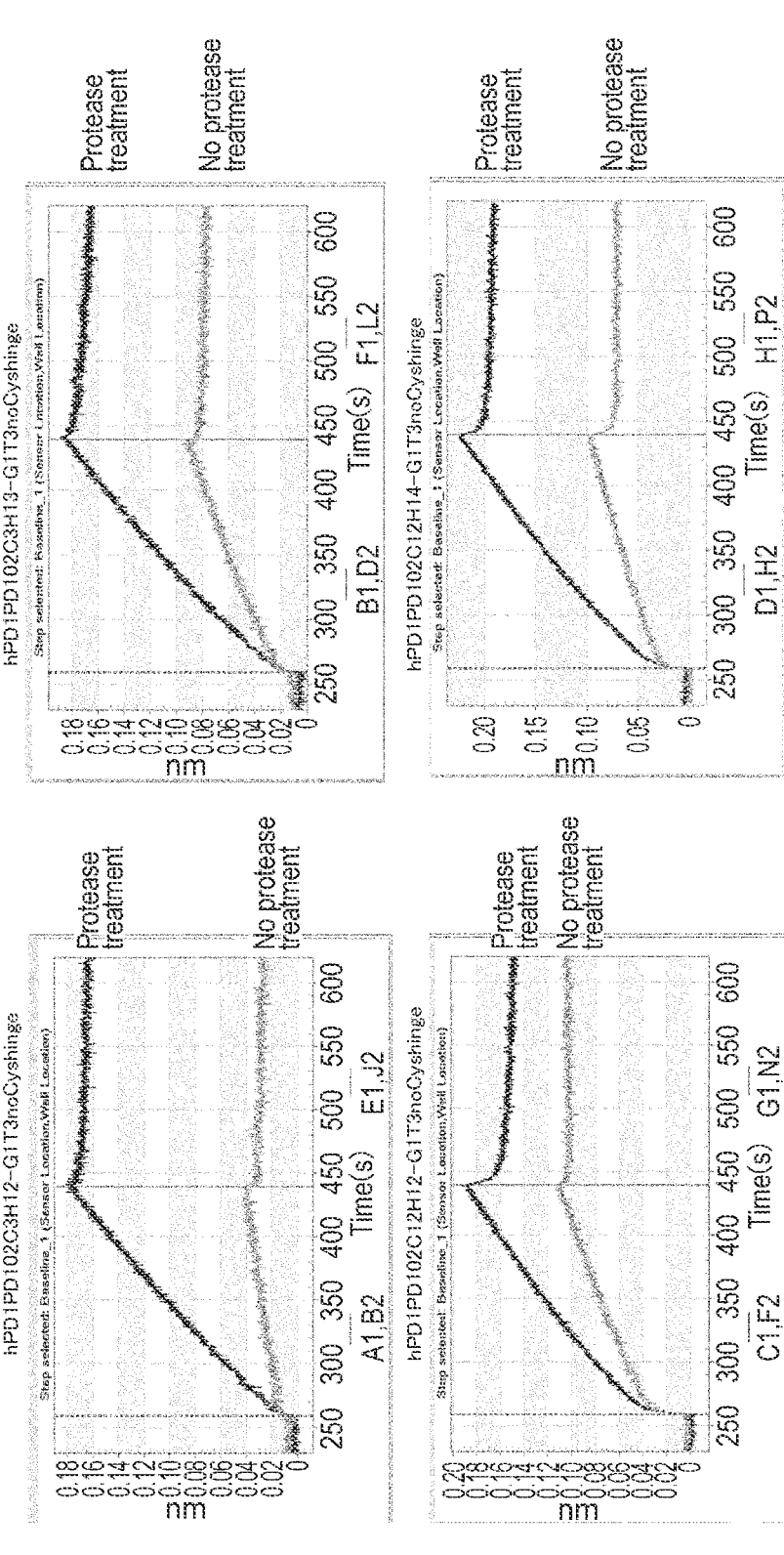
FIG. 20 shows real-time graphs showing the binding of free human PD-1 to the biotinylated anti-PD-1 single-domain antibody-containing molecule (PD1-bio) present in solutions containing protease-treated or protease-untreated fusion proteins. The title of each graph is the name of the measured sample. The vertical axis indicates the relative binding of PD1 and PD1-bio, and the horizontal axis shows the time (s). The gray line shows the data from the protease-untreated samples, and the black line shows the data from the protease-treated samples.

Each of the protease-treated fusion proteins prepared in Example 6-2-1, protease-untreated fusion proteins, and PD1-bio was dispensed into different wells of Tilted bottom (TW384) Micro plates (ForteBio, 18-5076). PD102C3-FcBAPdC or PD102C12-FcBAPdC is selected appropriately so that PD1-bio may bind to the same epitope to which the single domain antibody in the measured sample binds. A Streptavidin biosensor (ForteBio, 18-5021) was hydrated with PBS, and the measurement was performed using Octet RED 384 at a setting of 27° C. Baseline measurements were performed in the wells containing PBS for 30 seconds, after which PD1-bio was allowed to bind to the Streptavidin sensor for 200 seconds. Again, the baseline measurements were performed in the wells containing PBS for 30 seconds, then the binding was measured for 180 seconds in the wells containing protease-treated fusion protein or protease-untreated fusion protein, and the dissociation was measured for 180 seconds in the wells containing PBS. FIG. 20 shows the graphs of real-time binding, which graphs show the binding. As shown in FIG. 20, in the case of fusion proteins of PD-1 and a ligand-binding molecule containing a single-domain antibody introduced with a protease cleavage sequence, there was an increase in the amount of human PD-1 that binds to PD1-bio when they were treated with protease, as compared to when they were not treated with protease. Thus, the binding activity of the single-domain antibody in the fusion protein to PD-1 was attenuated by the protease treatment, and PD-1 was released from the fusion protein.

The above invention is described in detail with reference to actual instances and illustrations for the purpose of helping clear understanding. However, the description and illustrations provided in the present specification should not be interpreted as limiting the scope of the present disclosure. The disclosure of all patent literatures and scientific literatures cited herein is explicitly incorporated herein by reference in its entirety.

Example 7

Evaluation of Antibodies into which Various Protease Cleavage Sequences are Inserted 7-1. Preparation of Antibody Variants into which Protease Cleavage Sequences are Inserted The protease cleavage sequences listed in Table 7 were inserted into G7 (Heavy chain: G7H-G1T4 (SEQ ID NO: 18079); Light chain: G7L-LTO (SEQ ID NO:18080)), an antibody that neutralizes human CXCL10, between position 106a of the light-chain variable region (according to Kabat numbering) and position 107a of the light-chain constant region (according to Kabat numbering).

The antibody variants shown in Table 7, in which the antibody light-chain variants prepared above are combined with heavy chains, were expressed by transient expression using Expi293 cells (Life Technologies) by a method known to those skilled in the art, and purified using a protein A-based method known to those skilled in the art.

TABLE 7

| Antibody variants | Inserted sequences | Remarks on inserted sequence |
|---|---|---|
| G7L.106a.12aa | TSTSGRSANPRG | SEQ ID NO: 1 |
| G7L.N0001 | AFMTARSANPRG | Sequence consisting of the N-terminal 4th to 15th amino acids of SEQ ID NO: 8 |
| G7L.N0002 | AGYTSRSANPRG | Sequence consisting of the N-terminal 4th to 15th amino acids of SEQ ID NO: 9 |
| G7L.N0003 | AGYTTRSANPRG | Sequence consisting of the N-terminal 4th to 15th amino acids of SEQ ID NO: 10 |
| G7L.N0004 | ASFYGRSANPRG | Sequence consisting of the N-terminal 4th to 15th amino acids of SEQ ID NO: 11 |
| G7L.N0005 | ASSWGRSANPRG | Sequence consisting of the N-terminal 4th to 15th amino acids of SEQ ID NO: 12 |
| G7L.N0006 | ASWSGRSANPRG | Sequence consisting of the N-terminal 4th to 15th amino acids of SEQ ID NO: 17 |
| G7L.N0007 | ASYAGRSANPRG | Sequence consisting of the N-terminal 4th to 15th amino acids of SEQ ID NO: 18 |
| G7L.N0008 | ASYWGRSANPRG | Sequence consisting of the N-terminal 4th to 15th amino acids of SEQ ID NO: 19 |
| G7L.N0009 | ATASARSANPRG | Sequence consisting of the N-terminal 4th to 15th amino acids of SEQ ID NO: 20 |
| G7L.N0010 | ATAYGRSANPRG | Sequence consisting of the N-terminal 4th to 15th amino acids of SEQ ID NO: 21 |
| G7L.N0011 | ATWTGRSANPRG | Sequence consisting of the N-terminal 4th to 15th amino acids of SEQ ID NO: 26 |
| G7L.N0012 | ATWYARSANPRG | Sequence consisting of the N-terminal 4th to 15th amino acids of SEQ ID NO: 27 |
| G7L.N0013 | ATYGARSANPRG | Sequence consisting of the N-terminal 4th to 15th amino acids of SEQ ID NO: 28 |
| G7L.N0014 | ATYSARSANPRG | Sequence consisting of the N-terminal 4th to 15th amino acids of SEQ ID NO: 29 |
| G7L.N0015 | ATYWTRSANPRG | Sequence consisting of the N-terminal 4th to 15th amino acids of SEQ ID NO: 30 |
| G7L.N0016 | AWATARSANPRG | Sequence consisting of the N-terminal 4th to 15th amino acids of SEQ ID NO: 34 |
| G7L.N0017 | AWAYGRSANPRG | Sequence consisting of the N-terminal 4th to 15th amino acids of SEQ ID NO: 35 |
| G7L.N0018 | AWFGGRSANPRG | Sequence consisting of the N-terminal 4th to 15th amino acids of SEQ ID NO: 36 |
| G7L.N0019 | AWTAGRSANPRG | Sequence consisting of the N-terminal 4th to 15th amino acids of SEQ ID NO: 38 |
| G7L.N0020 | AWTTMRSANPRG | Sequence consisting of the N-terminal 4th to 15th amino acids of SEQ ID NO: 41 |
| G7L.N0021 | AYASGRSANPRG | Sequence consisting of the N-terminal 4th to 15th amino acids of SEQ ID NO: 42 |
| G7L.N0022 | AYSAGRSANPRG | Sequence consisting of the N-terminal 4th to 15th amino acids of SEQ ID NO: 46 |
| G7L.N0023 | AYSWGRSANPRG | Sequence consisting of the N-terminal 4th to 15th amino acids of SEQ ID NO: 48 |
| G7L.N0024 | AYWTSRSANPRG | Sequence consisting of the N-terminal 4th to 15th amino acids of SEQ ID NO: 49 |
| G7L.N0025 | FAGWGRSANPRG | Sequence consisting of the N-terminal 4th to 15th amino acids of SEQ ID NO: 50 |
| G7L.N0026 | FAMTGRSANPRG | Sequence consisting of the N-terminal 4th to 15th amino acids of SEQ ID NO: 51 |
| G7L.N0027 | FAQTARSANPRG | Sequence consisting of the N-terminal 4th to 15th amino acids of SEQ ID NO: 52 |
| G7L.N0028 | FITTTRSANPRG | Sequence consisting of the N-terminal 4th to 15th amino acids of SEQ ID NO: 56 |
| G7L.N0029 | FMATGRSANPRG | Sequence consisting of the N-terminal 4th to 15th amino acids of SEQ ID NO: 57 |
| G7L.N0030 | FMYGGRSANPRG | Sequence consisting of the N-terminal 4th to 15th amino acids of SEQ ID NO: 59 |
| G7L.N0031 | FSATGRSANPRG | Sequence consisting of the N-terminal 4th to 15th amino acids of SEQ ID NO: 61 |
| G7L.N0032 | FTASARSANPRG | Sequence consisting of the N-terminal 4th to 15th amino acids of SEQ ID NO: 64 |
| G7L.N0033 | FTATGRSANPRG | Sequence consisting of the N-terminal 4th to 15th amino acids of SEQ ID NO: 65 |

TABLE 7-continued

Inserted sequences and antibody variants

| Antibody variants | Inserted sequences | Remarks on inserted sequence |
| --- | --- | --- |
| G7L.N0034 | FTMTGRSANPRG | Sequence consisting of the N-terminal 4th to 15th amino acids of SEQ ID NO: 66 |
| G7L.N0035 | FTYGGRSANPRG | Sequence consisting of the N-terminal 4th to 15th amino acids of SEQ ID NO: 68 |
| G7L.N0036 | FYQTARSANPRG | Sequence consisting of the N-terminal 4th to 15th amino acids of SEQ ID NO: 71 |
| G7L.N0037 | FYTAARSANPRG | Sequence consisting of the N-terminal 4th to 15th amino acids of SEQ ID NO: 72 |
| G7L.N0038 | FYTAGRSANPRG | Sequence consisting of the N-terminal 4th to 15th amino acids of SEQ ID NO: 73 |
| G7L.N0039 | GAWTSRSANPRG | Sequence consisting of the N-terminal 4th to 15th amino acids of SEQ ID NO: 75 |
| G7L.N0040 | GAYTARSANPRG | Sequence consisting of the N-terminal 4th to 15th amino acids of SEQ ID NO: 76 |
| G7L.N0041 | GFYTSRSANPRG | Sequence consisting of the N-terminal 4th to 15th amino acids of SEQ ID NO: 78 |
| G7L.N0042 | GIYGGRSANPRG | Sequence consisting of the N-terminal 4th to 15th amino acids of SEQ ID NO: 81 |
| G7L.N0043 | GMYTGRSANPRG | Sequence consisting of the N-terminal 4th to 15th amino acids of SEQ ID NO: 83 |
| G7L.N0044 | GQYWGRSANPRG | Sequence consisting of the N-terminal 4th to 15th amino acids of SEQ ID NO: 84 |
| G7L.N0045 | GSWTARSANPRG | Sequence consisting of the N-terminal 4th to 15th amino acids of SEQ ID NO: 87 |
| G7L.N0046 | GSWTGRSANPRG | Sequence consisting of the N-terminal 4th to 15th amino acids of SEQ ID NO: 88 |
| G7L.N0047 | GSYSGRSANPRG | Sequence consisting of the N-terminal 4th to 15th amino acids of SEQ ID NO: 89 |
| G7L.N0048 | GTWWYRSANPRG | Sequence consisting of the N-terminal 4th to 15th amino acids of SEQ ID NO: 92 |
| G7L.N0049 | GTYYARSANPRG | Sequence consisting of the N-terminal 4th to 15th amino acids of SEQ ID NO: 93 |
| G7L.N0050 | GVATARSANPRG | Sequence consisting of the N-terminal 4th to 15th amino acids of SEQ ID NO: 94 |
| G7L.N0051 | GVWYGRSANPRG | Sequence consisting of the N-terminal 4th to 15th amino acids of SEQ ID NO: 95 |
| G7L.N0052 | GWAWGRSANPRG | Sequence consisting of the N-terminal 4th to 15th amino acids of SEQ ID NO: 96 |
| G7L.N0053 | GWGAGRSANPRG | Sequence consisting of the N-terminal 4th to 15th amino acids of SEQ ID NO: 97 |
| G7L.N0054 | GWGAYRSANPRG | Sequence consisting of the N-terminal 4th to 15th amino acids of SEQ ID NO: 98 |
| G7L.N0055 | GWSWGRSANPRG | Sequence consisting of the N-terminal 4th to 15th amino acids of SEQ ID NO: 100 |
| G7L.N0056 | GWYTARSANPRG | Sequence consisting of the N-terminal 4th to 15th amino acids of SEQ ID NO: 104 |
| G7L.N0057 | GWYYGRSANPRG | Sequence consisting of the N-terminal 4th to 15th amino acids of SEQ ID NO: 105 |
| G7L.N0058 | GYASARSANPRG | Sequence consisting of the N-terminal 4th to 15th amino acids of SEQ ID NO: 106 |
| G7L.N0059 | GYATGRSANPRG | Sequence consisting of the N-terminal 4th to 15th amino acids of SEQ ID NO: 107 |
| G7L.N0060 | GYSTTRSANPRG | Sequence consisting of the N-terminal 4th to 15th amino acids of SEQ ID NO: 108 |
| G7L.N0061 | GYVAGRSANPRG | Sequence consisting of the N-terminal 4th to 15th amino acids of SEQ ID NO: 111 |
| G7L.N0062 | GYWTGRSANPRG | Sequence consisting of the N-terminal 4th to 15th amino acids of SEQ ID NO: 114 |
| G7L.N0063 | HAYTARSANPRG | Sequence consisting of the N-terminal 4th to 15th amino acids of SEQ ID NO: 115 |
| G7L.N0064 | HTATGRSANPRG | Sequence consisting of the N-terminal 4th to 15th amino acids of SEQ ID NO: 117 |
| G7L.N0065 | HTNTGRSANPRG | Sequence consisting of the N-terminal 4th to 15th amino acids of SEQ ID NO: 118 |
| G7L.N0066 | HTTWGRSANPRG | Sequence consisting of the N-terminal 4th to 15th amino acids of SEQ ID NO: 120 |
| G7L.N0067 | HTWATRSANPRG | Sequence consisting of the N-terminal 4th to 15th amino acids of SEQ ID NO: 121 |
| G7L.N0068 | HYYTTRSANPRG | Sequence consisting of the N-terminal 4th to 15th amino acids of SEQ ID NO: 124 |
| G7L.N0069 | IAYSGRSANPRG | Sequence consisting of the N-terminal 4th to 15th amino acids of SEQ ID NO: 127 |
| G7L.N0070 | IGYTARSANPRG | Sequence consisting of the N-terminal 4th to 15th amino acids of SEQ ID NO: 130 |
| G7L.N0071 | IIMTGRSANPRG | Sequence consisting of the N-terminal 4th to 15th amino acids of SEQ ID NO: 132 |

TABLE 7-continued

Inserted sequences and antibody variants

| Antibody variants | Inserted sequences | Remarks on inserted sequence |
|---|---|---|
| G7L.N0072 | ISASGRSANPRG | Sequence consisting of the N-terminal 4th to 15th amino acids of SEQ ID NO: 133 |
| G7L.N0073 | ISQWGRSANPRG | Sequence consisting of the N-terminal 4th to 15th amino acids of SEQ ID NO: 134 |
| G7L.N0074 | ITATARSANPRG | Sequence consisting of the N-terminal 4th to 15th amino acids of SEQ ID NO: 135 |
| G7L.N0075 | ITGWGRSANPRG | Sequence consisting of the N-terminal 4th to 15th amino acids of SEQ ID NO: 137 |
| G7L.N0076 | ITTYYRSANPRG | Sequence consisting of the N-terminal 4th to 15th amino acids of SEQ ID NO: 139 |
| G7L.N0077 | ITYGGRSANPRG | Sequence consisting of the N-terminal 4th to 15th amino acids of SEQ ID NO: 140 |
| G7L.N0078 | IYATGRSANPRG | Sequence consisting of the N-terminal 4th to 15th amino acids of SEQ ID NO: 143 |
| G7L.N0079 | IYSTQRSANPRG | Sequence consisting of the N-terminal 4th to 15th amino acids of SEQ ID NO: 145 |
| G7L.N0080 | IYTTQRSANPRG | Sequence consisting of the N-terminal 4th to 15th amino acids of SEQ ID NO: 148 |
| G7L.N0081 | LAYTGRSANPRG | Sequence consisting of the N-terminal 4th to 15th amino acids of SEQ ID NO: 149 |
| G7L.N0082 | LTATARSANPRG | Sequence consisting of the N-terminal 4th to 15th amino acids of SEQ ID NO: 155 |
| G7L.N0083 | LTATGRSANPRG | Sequence consisting of the N-terminal 4th to 15th amino acids of SEQ ID NO: 156 |
| G7L.N0084 | LWSTQRSANPRG | Sequence consisting of the N-terminal 4th to 15th amino acids of SEQ ID NO: 161 |
| G7L.N0085 | MAWTARSANPRG | Sequence consisting of the N-terminal 4th to 15th amino acids of SEQ ID NO: 165 |
| G7L.N0086 | MIHTTRSANPRG | Sequence consisting of the N-terminal 4th to 15th amino acids of SEQ ID NO: 166 |
| G7L.N0087 | MSWTGRSANPRG | Sequence consisting of the N-terminal 4th to 15th amino acids of SEQ ID NO: 170 |
| G7L.N0088 | MWATARSANPRG | Sequence consisting of the N-terminal 4th to 15th amino acids of SEQ ID NO: 172 |
| G7L.N0089 | NVYTGRSANPRG | Sequence consisting of the N-terminal 4th to 15th amino acids of SEQ ID NO: 179 |
| G7L.N0090 | NWYYTRSANPRG | Sequence consisting of the N-terminal 4th to 15th amino acids of SEQ ID NO: 181 |
| G7L.N0091 | PVYTGRSANPRG | Sequence consisting of the N-terminal 4th to 15th amino acids of SEQ ID NO: 184 |
| G7L.N0092 | QSYTARSANPRG | Sequence consisting of the N-terminal 4th to 15th amino acids of SEQ ID NO: 187 |
| G7L.N0093 | QTTWGRSANPRG | Sequence consisting of the N-terminal 4th to 15th amino acids of SEQ ID NO: 189 |
| G7L.N0094 | QVWTGRSANPRG | Sequence consisting of the N-terminal 4th to 15th amino acids of SEQ ID NO: 191 |
| G7L.N0095 | QVWTYRSANPRG | Sequence consisting of the N-terminal 4th to 15th amino acids of SEQ ID NO: 192 |
| G7L.N0096 | QWITTRSANPRG | Sequence consisting of the N-terminal 4th to 15th amino acids of SEQ ID NO: 195 |
| G7L.N0097 | QWTWYRSANPRG | Sequence consisting of the N-terminal 4th to 15th amino acids of SEQ ID NO: 196 |
| G7L.N0098 | SGFTGRSANPRG | Sequence consisting of the N-terminal 4th to 15th amino acids of SEQ ID NO: 203 |
| G7L.N0099 | SGWYYRSANPRG | Sequence consisting of the N-terminal 4th to 15th amino acids of SEQ ID NO: 204 |
| G7L.N0100 | SGYGGRSANPRG | Sequence consisting of the N-terminal 4th to 15th amino acids of SEQ ID NO: 205 |
| G7L.N0101 | SGYWGRSANPRG | Sequence consisting of the N-terminal 4th to 15th amino acids of SEQ ID NO: 206 |
| G7L.N0102 | SHYTARSANPRG | Sequence consisting of the N-terminal 4th to 15th amino acids of SEQ ID NO: 208 |
| G7L.N0103 | SITFGRSANPRG | Sequence consisting of the N-terminal 4th to 15th amino acids of SEQ ID NO: 210 |
| G7L.N0104 | SIWGGRSANPRG | Sequence consisting of the N-terminal 4th to 15th amino acids of SEQ ID NO: 213 |
| G7L.N0105 | SIYSARSANPRG | Sequence consisting of the N-terminal 4th to 15th amino acids of SEQ ID NO: 214 |
| G7L.N0106 | SQWFTRSANPRG | Sequence consisting of the N-terminal 4th to 15th amino acids of SEQ ID NO: 218 |
| G7L.N0107 | SSAWARSANPRG | Sequence consisting of the N-terminal 4th to 15th amino acids of SEQ ID NO: 219 |
| G7L.N0108 | SSYTSRSANPRG | Sequence consisting of the N-terminal 4th to 15th amino acids of SEQ ID NO: 222 |

TABLE 7-continued

Inserted sequences and antibody variants

| Antibody variants | Inserted sequences | Remarks on inserted sequence |
|---|---|---|
| G7L.N0109 | STAWGRSANPRG | Sequence consisting of the N-terminal 4th to 15th amino acids of SEQ ID NO: 223 |
| G7L.N0110 | STFSARSANPRG | Sequence consisting of the N-terminal 4th to 15th amino acids of SEQ ID NO: 224 |
| G7L.N0111 | STFTGRSANPRG | Sequence consisting of the N-terminal 4th to 15th amino acids of SEQ ID NO: 225 |
| G7L.N0112 | STWSGRSANPRG | Sequence consisting of the N-terminal 4th to 15th amino acids of SEQ ID NO: 231 |
| G7L.N0113 | STYGARSANPRG | Sequence consisting of the N-terminal 4th to 15th amino acids of SEQ ID NO: 232 |
| G7L.N0114 | STYYTRSANPRG | Sequence consisting of the N-terminal 4th to 15th amino acids of SEQ ID NO: 233 |
| G7L.N0115 | SVYGGRSANPRG | Sequence consisting of the N-terminal 4th to 15th amino acids of SEQ ID NO: 235 |
| G7L.N0116 | SVYGSRSANPRG | Sequence consisting of the N-terminal 4th to 15th amino acids of SEQ ID NO: 236 |
| G7L.N0117 | SWAGGRSANPRG | Sequence consisting of the N-terminal 4th to 15th amino acids of SEQ ID NO: 237 |
| G7L.N0118 | SWSAGRSANPRG | Sequence consisting of the N-terminal 4th to 15th amino acids of SEQ ID NO: 240 |
| G7L.N0119 | SWTAARSANPRG | Sequence consisting of the N-terminal 4th to 15th amino acids of SEQ ID NO: 242 |
| G7L.N0120 | SYAVGRSANPRG | Sequence consisting of the N-terminal 4th to 15th amino acids of SEQ ID NO: 246 |
| G7L.N0121 | SYMWYRSANPRG | Sequence consisting of the N-terminal 4th to 15th amino acids of SEQ ID NO: 250 |
| G7L.N0122 | SYTWGRSANPRG | Sequence consisting of the N-terminal 4th to 15th amino acids of SEQ ID NO: 251 |
| G7L.N0123 | SYYAGRSANPRG | Sequence consisting of the N-terminal 4th to 15th amino acids of SEQ ID NO: 253 |
| G7L.N0124 | TAGWSRSANPRG | Sequence consisting of the N-terminal 4th to 15th amino acids of SEQ ID NO: 254 |
| G7L.N0125 | TAWTARSANPRG | Sequence consisting of the N-terminal 4th to 15th amino acids of SEQ ID NO: 257 |
| G7L.N0126 | TAWWYRSANPRG | Sequence consisting of the N-terminal 4th to 15th amino acids of SEQ ID NO: 258 |
| G7L.N0127 | TAYWGRSANPRG | Sequence consisting of the N-terminal 4th to 15th amino acids of SEQ ID NO: 259 |
| G7L.N0128 | TFATGRSANPRG | Sequence consisting of the N-terminal 4th to 15th amino acids of SEQ ID NO: 260 |
| G7L.N0129 | TFMTGRSANPRG | Sequence consisting of the N-terminal 4th to 15th amino acids of SEQ ID NO: 262 |
| G7L.N0130 | TFYTGRSANPRG | Sequence consisting of the N-terminal 4th to 15th amino acids of SEQ ID NO: 265 |
| G7L.N0131 | TFYTTRSANPRG | Sequence consisting of the N-terminal 4th to 15th amino acids of SEQ ID NO: 266 |
| G7L.N0132 | TGATARSANPRG | Sequence consisting of the N-terminal 4th to 15th amino acids of SEQ ID NO: 267 |
| G7L.N0133 | TGWTGRSANPRG | Sequence consisting of the N-terminal 4th to 15th amino acids of SEQ ID NO: 268 |
| G7L.N0134 | TGWWARSANPRG | Sequence consisting of the N-terminal 4th to 15th amino acids of SEQ ID NO: 269 |
| G7L.N0135 | TGYTARSANPRG | Sequence consisting of the N-terminal 4th to 15th amino acids of SEQ ID NO: 270 |
| G7L.N0136 | TGYTGRSANPRG | Sequence consisting of the N-terminal 4th to 15th amino acids of SEQ ID NO: 271 |
| G7L.N0137 | THWTSRSANPRG | Sequence consisting of the N-terminal 4th to 15th amino acids of SEQ ID NO: 272 |
| G7L.N0138 | TIWYTRSANPRG | Sequence consisting of the N-terminal 4th to 15th amino acids of SEQ ID NO: 275 |
| G7L.N0139 | TIWYYRSANPRG | Sequence consisting of the N-terminal 4th to 15th amino acids of SEQ ID NO: 276 |
| G7L.N0140 | TLYSGRSANPRG | Sequence consisting of the N-terminal 4th to 15th amino acids of SEQ ID NO: 278 |
| G7L.N0141 | TMFTARSANPRG | Sequence consisting of the N-terminal 4th to 15th amino acids of SEQ ID NO: 279 |
| G7L.N0142 | TSATARSANPRG | Sequence consisting of the N-terminal 4th to 15th amino acids of SEQ ID NO: 281 |
| G7L.N0143 | TSSWSRSANPRG | Sequence consisting of the N-terminal 4th to 15th amino acids of SEQ ID NO: 283 |
| G7L.N0144 | TSWAARSANPRG | Sequence consisting of the N-terminal 4th to 15th amino acids of SEQ ID NO: 285 |
| G7L.N0145 | TSWAGRSANPRG | Sequence consisting of the N-terminal 4th to 15th amino acids of SEQ ID NO: 286 |
| G7L.N0146 | TTFTARSANPRG | Sequence consisting of the N-terminal 4th to 15th amino acids of SEQ ID NO: 287 |

TABLE 7-continued

Inserted sequences and antibody variants

| Antibody variants | Inserted sequences | Remarks on inserted sequence |
|---|---|---|
| G7L.N0147 | TTGWGRSANPRG | Sequence consisting of the N-terminal 4th to 15th amino acids of SEQ ID NO: 288 |
| G7L.N0148 | TTTWARSANPRG | Sequence consisting of the N-terminal 4th to 15th amino acids of SEQ ID NO: 291 |
| G7L.N0149 | TTVWYRSANPRG | Sequence consisting of the N-terminal 4th to 15th amino acids of SEQ ID NO: 292 |
| G7L.N0150 | TTWAGRSANPRG | Sequence consisting of the N-terminal 4th to 15th amino acids of SEQ ID NO: 293 |
| G7L.N0151 | TTWTARSANPRG | Sequence consisting of the N-terminal 4th to 15th amino acids of SEQ ID NO: 294 |
| G7L.N0152 | TTWTHRSANPRG | Sequence consisting of the N-terminal 4th to 15th amino acids of SEQ ID NO: 295 |
| G7L.N0153 | TTWYTRSANPRG | Sequence consisting of the N-terminal 4th to 15th amino acids of SEQ ID NO: 296 |
| G7L.N0154 | TTYITRSANPRG | Sequence consisting of the N-terminal 4th to 15th amino acids of SEQ ID NO: 297 |
| G7L.N0155 | TTYTARSANPRG | Sequence consisting of the N-terminal 4th to 15th amino acids of SEQ ID NO: 298 |
| G7L.N0156 | TTYYVRSANPRG | Sequence consisting of the N-terminal 4th to 15th amino acids of SEQ ID NO: 299 |
| G7L.N0157 | TVASGRSANPRG | Sequence consisting of the N-terminal 4th to 15th amino acids of SEQ ID NO: 300 |
| G7L.N0158 | TVFTGRSANPRG | Sequence consisting of the N-terminal 4th to 15th amino acids of SEQ ID NO: 301 |
| G7L.N0159 | TWGTTRSANPRG | Sequence consisting of the N-terminal 4th to 15th amino acids of SEQ ID NO: 305 |
| G7L.N0160 | TWMTGRSANPRG | Sequence consisting of the N-terminal 4th to 15th amino acids of SEQ ID NO: 306 |
| G7L.N0161 | TWQTGRSANPRG | Sequence consisting of the N-terminal 4th to 15th amino acids of SEQ ID NO: 307 |
| G7L.N0162 | TWSWGRSANPRG | Sequence consisting of the N-terminal 4th to 15th amino acids of SEQ ID NO: 309 |
| G7L.N0163 | TWTWYRSANPRG | Sequence consisting of the N-terminal 4th to 15th amino acids of SEQ ID NO: 310 |
| G7L.N0164 | TWWGTRSANPRG | Sequence consisting of the N-terminal 4th to 15th amino acids of SEQ ID NO: 312 |
| G7L.N0165 | TWYWQRSANPRG | Sequence consisting of the N-terminal 4th to 15th amino acids of SEQ ID NO: 313 |
| G7L.N0166 | TYATARSANPRG | Sequence consisting of the N-terminal 4th to 15th amino acids of SEQ ID NO: 314 |
| G7L.N0167 | TYFTGRSANPRG | Sequence consisting of the N-terminal 4th to 15th amino acids of SEQ ID NO: 315 |
| G7L.N0168 | TYGAGRSANPRG | Sequence consisting of the N-terminal 4th to 15th amino acids of SEQ ID NO: 316 |
| G7L.N0169 | TYGWGRSANPRG | Sequence consisting of the N-terminal 4th to 15th amino acids of SEQ ID NO: 321 |
| G7L.N0170 | TYHTTRSANPRG | Sequence consisting of the N-terminal 4th to 15th amino acids of SEQ ID NO: 322 |
| G7L.N0171 | TYMSGRSANPRG | Sequence consisting of the N-terminal 4th to 15th amino acids of SEQ ID NO: 323 |
| G7L.N0172 | TYTFTRSANPRG | Sequence consisting of the N-terminal 4th to 15th amino acids of SEQ ID NO: 326 |
| G7L.N0173 | TYYTARSANPRG | Sequence consisting of the N-terminal 4th to 15th amino acids of SEQ ID NO: 328 |
| G7L.N0174 | VAYSGRSANPRG | Sequence consisting of the N-terminal 4th to 15th amino acids of SEQ ID NO: 330 |
| G7L.N0175 | VGYYGRSANPRG | Sequence consisting of the N-terminal 4th to 15th amino acids of SEQ ID NO: 332 |
| G7L.N0176 | VQATARSANPRG | Sequence consisting of the N-terminal 4th to 15th amino acids of SEQ ID NO: 336 |
| G7L.N0177 | VSASGRSANPRG | Sequence consisting of the N-terminal 4th to 15th amino acids of SEQ ID NO: 338 |
| G7L.N0178 | VSWTGRSANPRG | Sequence consisting of the N-terminal 4th to 15th amino acids of SEQ ID NO: 339 |
| G7L.N0179 | VSYTTRSANPRG | Sequence consisting of the N-terminal 4th to 15th amino acids of SEQ ID NO: 340 |
| G7L.N0180 | VTVWGRSANPRG | Sequence consisting of the N-terminal 4th to 15th amino acids of SEQ ID NO: 342 |
| G7L.N0181 | VTWATRSANPRG | Sequence consisting of the N-terminal 4th to 15th amino acids of SEQ ID NO: 343 |
| G7L.N0182 | VVSTQRSANPRG | Sequence consisting of the N-terminal 4th to 15th amino acids of SEQ ID NO: 345 |
| G7L.N0183 | VYATSRSANPRG | Sequence consisting of the N-terminal 4th to 15th amino acids of SEQ ID NO: 346 |

TABLE 7-continued

Inserted sequences and antibody variants

| Antibody variants | Inserted sequences | Remarks on inserted sequence |
| --- | --- | --- |
| G7L.N0184 | VYQTARSANPRG | Sequence consisting of the N-terminal 4th to 15th amino acids of SEQ ID NO: 348 |
| G7L.N0185 | WAGIYRSANPRG | Sequence consisting of the N-terminal 4th to 15th amino acids of SEQ ID NO: 352 |
| G7L.N0186 | WFTTHRSANPRG | Sequence consisting of the N-terminal 4th to 15th amino acids of SEQ ID NO: 356 |
| G7L.N0187 | WGMTGRSANPRG | Sequence consisting of the N-terminal 4th to 15th amino acids of SEQ ID NO: 359 |
| G7L.N0188 | WGSTTRSANPRG | Sequence consisting of the N-terminal 4th to 15th amino acids of SEQ ID NO: 362 |
| G7L.N0189 | WGTAGRSANPRG | Sequence consisting of the N-terminal 4th to 15th amino acids of SEQ ID NO: 363 |
| G7L.N0190 | WGWAGRSANPRG | Sequence consisting of the N-terminal 4th to 15th amino acids of SEQ ID NO: 366 |
| G7L.N0191 | WGYHTRSANPRG | Sequence consisting of the N-terminal 4th to 15th amino acids of SEQ ID NO: 367 |
| G7L.N0192 | WLTAGRSANPRG | Sequence consisting of the N-terminal 4th to 15th amino acids of SEQ ID NO: 370 |
| G7L.N0193 | WNYTGRSANPRG | Sequence consisting of the N-terminal 4th to 15th amino acids of SEQ ID NO: 373 |
| G7L.N0194 | WQATGRSANPRG | Sequence consisting of the N-terminal 4th to 15th amino acids of SEQ ID NO: 374 |
| G7L.N0195 | WSWYTRSANPRG | Sequence consisting of the N-terminal 4th to 15th amino acids of SEQ ID NO: 379 |
| G7L.N0196 | WTAAGRSANPRG | Sequence consisting of the N-terminal 4th to 15th amino acids of SEQ ID NO: 380 |
| G7L.N0197 | WTGWARSANPRG | Sequence consisting of the N-terminal 4th to 15th amino acids of SEQ ID NO: 383 |
| G7L.N0198 | WTSTTRSANPRG | Sequence consisting of the N-terminal 4th to 15th amino acids of SEQ ID NO: 384 |
| G7L.N0199 | WTTAGRSANPRG | Sequence consisting of the N-terminal 4th to 15th amino acids of SEQ ID NO: 385 |
| G7L.N0200 | WWWMTRSANPRG | Sequence consisting of the N-terminal 4th to 15th amino acids of SEQ ID NO: 388 |
| G7L.N0201 | WWWWPRSANPRG | Sequence consisting of the N-terminal 4th to 15th amino acids of SEQ ID NO: 389 |
| G7L.N0202 | WYGSQRSANPRG | Sequence consisting of the N-terminal 4th to 15th amino acids of SEQ ID NO: 390 |
| G7L.N0203 | WYTTMRSANPRG | Sequence consisting of the N-terminal 4th to 15th amino acids of SEQ ID NO: 393 |
| G7L.N0204 | YASYTRSANPRG | Sequence consisting of the N-terminal 4th to 15th amino acids of SEQ ID NO: 398 |
| G7L.N0205 | YAWGGRSANPRG | Sequence consisting of the N-terminal 4th to 15th amino acids of SEQ ID NO: 399 |
| G7L.N0206 | YAYTGRSANPRG | Sequence consisting of the N-terminal 4th to 15th amino acids of SEQ ID NO: 400 |
| G7L.N0207 | YAYTSRSANPRG | Sequence consisting of the N-terminal 4th to 15th amino acids of SEQ ID NO: 401 |
| G7L.N0208 | YAYTTRSANPRG | Sequence consisting of the N-terminal 4th to 15th amino acids of SEQ ID NO: 402 |
| G7L.N0209 | YFAGGRSANPRG | Sequence consisting of the N-terminal 4th to 15th amino acids of SEQ ID NO: 403 |
| G7L.N0210 | YFSSYRSANPRG | Sequence consisting of the N-terminal 4th to 15th amino acids of SEQ ID NO: 405 |
| G7L.N0211 | YGATSRSANPRG | Sequence consisting of the N-terminal 4th to 15th amino acids of SEQ ID NO: 406 |
| G7L.N0212 | YGGWGRSANPRG | Sequence consisting of the N-terminal 4th to 15th amino acids of SEQ ID NO: 408 |
| G7L.N0213 | YGSAGRSANPRG | Sequence consisting of the N-terminal 4th to 15th amino acids of SEQ ID NO: 411 |
| G7L.N0214 | YGTTQRSANPRG | Sequence consisting of the N-terminal 4th to 15th amino acids of SEQ ID NO: 413 |
| G7L.N0215 | YGTWGRSANPRG | Sequence consisting of the N-terminal 4th to 15th amino acids of SEQ ID NO: 414 |
| G7L.N0216 | YGVAGRSANPRG | Sequence consisting of the N-terminal 4th to 15th amino acids of SEQ ID NO: 415 |
| G7L.N0217 | YGVTHRSANPRG | Sequence consisting of the N-terminal 4th to 15th amino acids of SEQ ID NO: 416 |
| G7L.N0218 | YGWTGRSANPRG | Sequence consisting of the N-terminal 4th to 15th amino acids of SEQ ID NO: 417 |
| G7L.N0219 | YITTHRSANPRG | Sequence consisting of the N-terminal 4th to 15th amino acids of SEQ ID NO: 421 |
| G7L.N0220 | YMWTGRSANPRG | Sequence consisting of the N-terminal 4th to 15th amino acids of SEQ ID NO: 425 |
| G7L.N0221 | YQWTTRSANPRG | Sequence consisting of the N-terminal 4th to 15th amino acids of SEQ ID NO: 429 |

TABLE 7-continued

Inserted sequences and antibody variants

| Antibody variants | Inserted sequences | Remarks on inserted sequence |
|---|---|---|
| G7L.N0222 | YSATGRSANPRG | Sequence consisting of the N-terminal 4th to 15th amino acids of SEQ ID NO: 430 |
| G7L.N0223 | YSSSTRSANPRG | Sequence consisting of the N-terminal 4th to 15th amino acids of SEQ ID NO: 432 |
| G7L.N0224 | YSTWGRSANPRG | Sequence consisting of the N-terminal 4th to 15th amino acids of SEQ ID NO: 434 |
| G7L.N0225 | YSVVTRSANPRG | Sequence consisting of the N-terminal 4th to 15th amino acids of SEQ ID NO: 436 |
| G7L.N0226 | YSYGSRSANPRG | Sequence consisting of the N-terminal 4th to 15th amino acids of SEQ ID NO: 437 |
| G7L.N0227 | YTAIGRSANPRG | Sequence consisting of the N-terminal 4th to 15th amino acids of SEQ ID NO: 438 |
| G7L.N0228 | YTATARSANPRG | Sequence consisting of the N-terminal 4th to 15th amino acids of SEQ ID NO: 439 |
| G7L.N0229 | YTAYARSANPRG | Sequence consisting of the N-terminal 4th to 15th amino acids of SEQ ID NO: 440 |
| G7L.N0230 | YTGITRSANPRG | Sequence consisting of the N-terminal 4th to 15th amino acids of SEQ ID NO: 441 |
| G7L.N0231 | YTNWGRSANPRG | Sequence consisting of the N-terminal 4th to 15th amino acids of SEQ ID NO: 443 |
| G7L.N0232 | YTTTWRSANPRG | Sequence consisting of the N-terminal 4th to 15th amino acids of SEQ ID NO: 446 |
| G7L.N0233 | YTVTTRSANPRG | Sequence consisting of the N-terminal 4th to 15th amino acids of SEQ ID NO: 448 |
| G7L.N0234 | YTWTQRSANPRG | Sequence consisting of the N-terminal 4th to 15th amino acids of SEQ ID NO: 449 |
| G7L.N0235 | YWTSYRSANPRG | Sequence consisting of the N-terminal 4th to 15th amino acids of SEQ ID NO: 452 |
| G7L.N0236 | YYATWRSANPRG | Sequence consisting of the N-terminal 4th to 15th amino acids of SEQ ID NO: 453 |
| G7L.N0237 | YYQSGRSANPRG | Sequence consisting of the N-terminal 4th to 15th amino acids of SEQ ID NO: 455 |
| G7L.N0238 | YYTTQRSANPRG | Sequence consisting of the N-terminal 4th to 15th amino acids of SEQ ID NO: 456 |
| G7L.N0239 | TSTSGRAAIYYG | Sequence consisting of the N-terminal 1st to 12th amino acids of SEQ ID NO: 17202 |
| G7L.N0240 | TSTSGRAAYYYG | Sequence consisting of the N-terminal 1st to 12th amino acids of SEQ ID NO: 17203 |
| G7L.N0241 | TSTSGRAAAHNG | Sequence consisting of the N-terminal 1st to 12th amino acids of SEQ ID NO: 17204 |
| G7L.N0242 | TSTSGRAAAHYG | Sequence consisting of the N-terminal 1st to 12th amino acids of SEQ ID NO: 17205 |
| G7L.N0243 | TSTSGRAAGHMG | Sequence consisting of the N-terminal 1st to 12th amino acids of SEQ ID NO: 17206 |
| G7L.N0244 | TSTSGRAAGHQG | Sequence consisting of the N-terminal 1st to 12th amino acids of SEQ ID NO: 17207 |
| G7L.N0245 | TSTSGRAAHGGG | Sequence consisting of the N-terminal 1st to 12th amino acids of SEQ ID NO: 17208 |
| G7L.N0246 | TSTSGRAAHGSG | Sequence consisting of the N-terminal 1st to 12th amino acids of SEQ ID NO: 17209 |
| G7L.N0247 | TSTSGRAAHHFG | Sequence consisting of the N-terminal 1st to 12th amino acids of SEQ ID NO: 17210 |
| G7L.N0248 | TSTSGRAAHHMG | Sequence consisting of the N-terminal 1st to 12th amino acids of SEQ ID NO: 17211 |
| G7L.N0249 | TSTSGRAAHIAG | Sequence consisting of the N-terminal 1st to 12th amino acids of SEQ ID NO: 17212 |
| G7L.N0250 | TSTSGRAAHIHG | Sequence consisting of the N-terminal 1st to 12th amino acids of SEQ ID NO: 17213 |
| G7L.N0251 | TSTSGRAAHMHG | Sequence consisting of the N-terminal 1st to 12th amino acids of SEQ ID NO: 17214 |

TABLE 7-continued

Inserted sequences and antibody variants

| Antibody variants | Inserted sequences | Remarks on inserted sequence |
|---|---|---|
| G7L.N0252 | TSTSGRAAHQHG | Sequence consisting of the N-terminal 1st to 12th amino acids of SEQ ID NO: 17215 |
| G7L.N0253 | TSTSGRAAHTYG | Sequence consisting of the N-terminal 1st to 12th amino acids of SEQ ID NO: 17216 |
| G7L.N0254 | TSTSGRAAHVGG | Sequence consisting of the N-terminal 1st to 12th amino acids of SEQ ID NO: 17217 |
| G7L.N0255 | TSTSGRAAHVTG | Sequence consisting of the N-terminal 1st to 12th amino acids of SEQ ID NO: 17218 |
| G7L.N0256 | TSTSGRAAHYGG | Sequence consisting of the N-terminal 1st to 12th amino acids of SEQ ID NO: 17219 |
| G7L.N0257 | TSTSGRAAINYG | Sequence consisting of the N-terminal 1st to 12th amino acids of SEQ ID NO: 17220 |
| G7L.N0258 | TSTSGRAAMHIG | Sequence consisting of the N-terminal 1st to 12th amino acids of SEQ ID NO: 17221 |
| G7L.N0259 | TSTSGRAANHIG | Sequence consisting of the N-terminal 1st to 12th amino acids of SEQ ID NO: 17222 |
| G7L.N0260 | TSTSGRAAQHHG | Sequence consisting of the N-terminal 1st to 12th amino acids of SEQ ID NO: 17223 |
| G7L.N0261 | TSTSGRAASHHG | Sequence consisting of the N-terminal 1st to 12th amino acids of SEQ ID NO: 17224 |
| G7L.N0262 | TSTSGRAATYHG | Sequence consisting of the N-terminal 1st to 12th amino acids of SEQ ID NO: 17225 |
| G7L.N0263 | TSTSGRAGGHHG | Sequence consisting of the N-terminal 1st to 12th amino acids of SEQ ID NO: 17226 |
| G7L.N0264 | TSTSGRAGHAYG | Sequence consisting of the N-terminal 1st to 12th amino acids of SEQ ID NO: 17227 |
| G7L.N0265 | TSTSGRAGHHGG | Sequence consisting of the N-terminal 1st to 12th amino acids of SEQ ID NO: 17228 |
| G7L.N0266 | TSTSGRAGHHMG | Sequence consisting of the N-terminal 1st to 12th amino acids of SEQ ID NO: 17229 |
| G7L.N0267 | TSTSGRAGHHSG | Sequence consisting of the N-terminal 1st to 12th amino acids of SEQ ID NO: 17230 |
| G7L.N0268 | TSTSGRAGHHYG | Sequence consisting of the N-terminal 1st to 12th amino acids of SEQ ID NO: 17231 |
| G7L.N0269 | TSTSGRAGHIYG | Sequence consisting of the N-terminal 1st to 12th amino acids of SEQ ID NO: 17232 |
| G7L.N0270 | TSTSGRAGHSHG | Sequence consisting of the N-terminal 1st to 12th amino acids of SEQ ID NO: 17233 |
| G7L.N0271 | TSTSGRAGHTHG | Sequence consisting of the N-terminal 1st to 12th amino acids of SEQ ID NO: 17234 |
| G7L.N0272 | TSTSGRAGHTYG | Sequence consisting of the N-terminal 1st to 12th amino acids of SEQ ID NO: 17235 |
| G7L.N0273 | TSTSGRAGHYVG | Sequence consisting of the N-terminal 1st to 12th amino acids of SEQ ID NO: 17236 |
| G7L.N0274 | TSTSGRAGIYHG | Sequence consisting of the N-terminal 1st to 12th amino acids of SEQ ID NO: 17237 |
| G7L.N0275 | TSTSGRAGLHHG | Sequence consisting of the N-terminal 1st to 12th amino acids of SEQ ID NO: 17238 |
| G7L.N0276 | TSTSGRAGNYHG | Sequence consisting of the N-terminal 1st to 12th amino acids of SEQ ID NO: 17239 |

TABLE 7-continued

Inserted sequences and antibody variants

| Antibody variants | Inserted sequences | Remarks on inserted sequence |
|---|---|---|
| G7L.N0277 | TSTSGRAGQHHG | Sequence consisting of the N-terminal 1st to 12th amino acids of SEQ ID NO: 17240 |
| G7L.N0278 | TSTSGRAGSHHG | Sequence consisting of the N-terminal 1st to 12th amino acids of SEQ ID NO: 17241 |
| G7L.N0279 | TSTSGRAHAHVG | Sequence consisting of the N-terminal 1st to 12th amino acids of SEQ ID NO: 17242 |
| G7L.N0280 | TSTSGRAHHAVG | Sequence consisting of the N-terminal 1st to 12th amino acids of SEQ ID NO: 17243 |
| G7L.N0281 | TSTSGRAHHGFG | Sequence consisting of the N-terminal 1st to 12th amino acids of SEQ ID NO: 17244 |
| G7L.N0282 | TSTSGRAHHGIG | Sequence consisting of the N-terminal 1st to 12th amino acids of SEQ ID NO: 17245 |
| G7L.N0283 | TSTSGRAHHGTG | Sequence consisting of the N-terminal 1st to 12th amino acids of SEQ ID NO: 17246 |
| G7L.N0284 | TSTSGRAHHITG | Sequence consisting of the N-terminal 1st to 12th amino acids of SEQ ID NO: 17247 |
| G7L.N0285 | TSTSGRAHHMSG | Sequence consisting of the N-terminal 1st to 12th amino acids of SEQ ID NO: 17248 |
| G7L.N0286 | TSTSGRAHHMVG | Sequence consisting of the N-terminal 1st to 12th amino acids of SEQ ID NO: 17249 |
| G7L.N0287 | TSTSGRAHHSIG | Sequence consisting of the N-terminal 1st to 12th amino acids of SEQ ID NO: 17250 |
| G7L.N0288 | TSTSGRAHHTIG | Sequence consisting of the N-terminal 1st to 12th amino acids of SEQ ID NO: 17251 |
| G7L.N0289 | TSTSGRAHHTSG | Sequence consisting of the N-terminal 1st to 12th amino acids of SEQ ID NO: 17252 |
| G7L.N0290 | TSTSGRAHHVAG | Sequence consisting of the N-terminal 1st to 12th amino acids of SEQ ID NO: 17253 |
| G7L.N0291 | TSTSGRAHHVNG | Sequence consisting of the N-terminal 1st to 12th amino acids of SEQ ID NO: 17254 |
| G7L.N0292 | TSTSGRAHTHAG | Sequence consisting of the N-terminal 1st to 12th amino acids of SEQ ID NO: 17255 |
| G7L.N0293 | TSTSGRAHVAHG | Sequence consisting of the N-terminal 1st to 12th amino acids of SEQ ID NO: 17256 |
| G7L.N0294 | TSTSGRALAHHG | Sequence consisting of the N-terminal 1st to 12th amino acids of SEQ ID NO: 17257 |
| G7L.N0295 | TSTSGRAMHHSG | Sequence consisting of the N-terminal 1st to 12th amino acids of SEQ ID NO: 17258 |
| G7L.N0296 | TSTSGRAQGHHG | Sequence consisting of the N-terminal 1st to 12th amino acids of SEQ ID NO: 17259 |
| G7L.N0297 | TSTSGRAQTHHG | Sequence consisting of the N-terminal 1st to 12th amino acids of SEQ ID NO: 17260 |
| G7L.N0298 | TSTSGRASAHHG | Sequence consisting of the N-terminal 1st to 12th amino acids of SEQ ID NO: 17261 |
| G7L.N0299 | TSTSGRASHHGG | Sequence consisting of the N-terminal 1st to 12th amino acids of SEQ ID NO: 17262 |
| G7L.N0300 | TSTSGRATGHHG | Sequence consisting of the N-terminal 1st to 12th amino acids of SEQ ID NO: 17263 |
| G7L.N0301 | TSTSGRATHGHG | Sequence consisting of the N-terminal 1st to 12th amino acids of SEQ ID NO: 17264 |

TABLE 7-continued

Inserted sequences and antibody variants

| Antibody variants | Inserted sequences | Remarks on inserted sequence |
|---|---|---|
| G7L.N0302 | TSTSGRAVHHNG | Sequence consisting of the N-terminal 1st to 12th amino acids of SEQ ID NO: 17265 |
| G7L.N0303 | TSTSGRAVHYQG | Sequence consisting of the N-terminal 1st to 12th amino acids of SEQ ID NO: 17266 |
| G7L.N0304 | TSTSGRAYHAGG | Sequence consisting of the N-terminal 1st to 12th amino acids of SEQ ID NO: 17267 |
| G7L.N0305 | TSTSGRAYHHAG | Sequence consisting of the N-terminal 1st to 12th amino acids of SEQ ID NO: 17268 |
| G7L.N0306 | TSTSGRGAHHIG | Sequence consisting of the N-terminal 1st to 12th amino acids of SEQ ID NO: 17269 |
| G7L.N0307 | TSTSGRGAHHSG | Sequence consisting of the N-terminal 1st to 12th amino acids of SEQ ID NO: 17270 |
| G7L.N0308 | TSTSGRGAMHHG | Sequence consisting of the N-terminal 1st to 12th amino acids of SEQ ID NO: 17271 |
| G7L.N0309 | TSTSGRGGAHHG | Sequence consisting of the N-terminal 1st to 12th amino acids of SEQ ID NO: 17272 |
| G7L.N0310 | TSTSGRGGGGHG | Sequence consisting of the N-terminal 1st to 12th amino acids of SEQ ID NO: 17273 |
| G7L.N0311 | TSTSGRGGVHHG | Sequence consisting of the N-terminal 1st to 12th amino acids of SEQ ID NO: 17274 |
| G7L.N0312 | TSTSGRGHGGGG | Sequence consisting of the N-terminal 1st to 12th amino acids of SEQ ID NO: 17275 |
| G7L.N0313 | TSTSGRGTHHAG | Sequence consisting of the N-terminal 1st to 12th amino acids of SEQ ID NO: 17276 |
| G7L.N0314 | TSTSGRGVSHHG | Sequence consisting of the N-terminal 1st to 12th amino acids of SEQ ID NO: 17277 |
| G7L.N0315 | TSTSGRHAAHGG | Sequence consisting of the N-terminal 1st to 12th amino acids of SEQ ID NO: 17278 |
| G7L.N0316 | TSTSGRHAHQSG | Sequence consisting of the N-terminal 1st to 12th amino acids of SEQ ID NO: 17279 |
| G7L.N0317 | TSTSGRHGGHVG | Sequence consisting of the N-terminal 1st to 12th amino acids of SEQ ID NO: 17280 |
| G7L.N0318 | TSTSGRHGHTYG | Sequence consisting of the N-terminal 1st to 12th amino acids of SEQ ID NO: 17281 |
| G7L.N0319 | TSTSGRMAAHHG | Sequence consisting of the N-terminal 1st to 12th amino acids of SEQ ID NO: 17282 |
| G7L.N0320 | TSTSGRMAHHAG | Sequence consisting of the N-terminal 1st to 12th amino acids of SEQ ID NO: 17283 |
| G7L.N0321 | TSTSGRMAHHMG | Sequence consisting of the N-terminal 1st to 12th amino acids of SEQ ID NO: 17284 |
| G7L.N0322 | TSTSGRMAHHTG | Sequence consisting of the N-terminal 1st to 12th amino acids of SEQ ID NO: 17285 |
| G7L.N0323 | TSTSGRMAHVLG | Sequence consisting of the N-terminal 1st to 12th amino acids of SEQ ID NO: 17286 |
| G7L.N0324 | TSTSGRMAHYMG | Sequence consisting of the N-terminal 1st to 12th amino acids of SEQ ID NO: 17287 |
| G7L.N0325 | TSTSGRMATHHG | Sequence consisting of the N-terminal 1st to 12th amino acids of SEQ ID NO: 17288 |
| G7L.N0326 | TSTSGRMAVHHG | Sequence consisting of the N-terminal 1st to 12th amino acids of SEQ ID NO: 17289 |

TABLE 7-continued

Inserted sequences and antibody variants

| Antibody variants | Inserted sequences | Remarks on inserted sequence |
|---|---|---|
| G7L.N0327 | TSTSGRMGHHIG | Sequence consisting of the N-terminal 1st to 12th amino acids of SEQ ID NO: 17290 |
| G7L.N0328 | TSTSGRMGHHLG | Sequence consisting of the N-terminal 1st to 12th amino acids of SEQ ID NO: 17291 |
| G7L.N0329 | TSTSGRMGHHVG | Sequence consisting of the N-terminal 1st to 12th amino acids of SEQ ID NO: 17292 |
| G7L.N0330 | TSTSGRMGHHYG | Sequence consisting of the N-terminal 1st to 12th amino acids of SEQ ID NO: 17293 |
| G7L.N0331 | TSTSGRMGSHHG | Sequence consisting of the N-terminal 1st to 12th amino acids of SEQ ID NO: 17294 |
| G7L.N0332 | TSTSGRMGVGGG | Sequence consisting of the N-terminal 1st to 12th amino acids of SEQ ID NO: 17295 |
| G7L.N0333 | TSTSGRMVHHTG | Sequence consisting of the N-terminal 1st to 12th amino acids of SEQ ID NO: 17296 |
| G7L.N0334 | TSTSGRNAGHYG | Sequence consisting of the N-terminal 1st to 12th amino acids of SEQ ID NO: 17297 |
| G7L.N0335 | TSTSGRNAIHSG | Sequence consisting of the N-terminal 1st to 12th amino acids of SEQ ID NO: 17298 |
| G7L.N0336 | TSTSGRNAVHVG | Sequence consisting of the N-terminal 1st to 12th amino acids of SEQ ID NO: 17299 |
| G7L.N0337 | TSTSGRNGAHHG | Sequence consisting of the N-terminal 1st to 12th amino acids of SEQ ID NO: 17300 |
| G7L.N0338 | TSTSGRNGGHHG | Sequence consisting of the N-terminal 1st to 12th amino acids of SEQ ID NO: 17301 |
| G7L.N0339 | TSTSGRNGHTLG | Sequence consisting of the N-terminal 1st to 12th amino acids of SEQ ID NO: 17302 |
| G7L.N0340 | TSTSGRNGHYAG | Sequence consisting of the N-terminal 1st to 12th amino acids of SEQ ID NO: 17303 |
| G7L.N0341 | TSTSGRQAHHGG | Sequence consisting of the N-terminal 1st to 12th amino acids of SEQ ID NO: 17304 |
| G7L.N0342 | TSTSGRSAAHQG | Sequence consisting of the N-terminal 1st to 12th amino acids of SEQ ID NO: 17305 |
| G7L.N0343 | TSTSGRSAAHTG | Sequence consisting of the N-terminal 1st to 12th amino acids of SEQ ID NO: 17306 |
| G7L.N0344 | TSTSGRSAAHVG | Sequence consisting of the N-terminal 1st to 12th amino acids of SEQ ID NO: 17307 |
| G7L.N0345 | TSTSGRSAALHG | Sequence consisting of the N-terminal 1st to 12th amino acids of SEQ ID NO: 17308 |
| G7L.N0346 | TSTSGRSAGHHG | Sequence consisting of the N-terminal 1st to 12th amino acids of SEQ ID NO: 17310 |
| G7L.N0347 | TSTSGRSAGHLG | Sequence consisting of the N-terminal 1st to 12th amino acids of SEQ ID NO: 17311 |
| G7L.N0348 | TSTSGRSAGHYG | Sequence consisting of the N-terminal 1st to 12th amino acids of SEQ ID NO: 17312 |
| G7L.N0349 | TSTSGRSAGLGG | Sequence consisting of the N-terminal 1st to 12th amino acids of SEQ ID NO: 17313 |
| G7L.N0350 | TSTSGRSAGYYG | Sequence consisting of the N-terminal 1st to 12th amino acids of SEQ ID NO: 17314 |
| G7L.N0351 | TSTSGRSAHAHG | Sequence consisting of the N-terminal 1st to 12th amino acids of SEQ ID NO: 17315 |

TABLE 7-continued

Inserted sequences and antibody variants

| Antibody variants | Inserted sequences | Remarks on inserted sequence |
|---|---|---|
| G7L.N0352 | TSTSGRSAHFHG | Sequence consisting of the N-terminal 1st to 12th amino acids of SEQ ID NO: 17316 |
| G7L.N0353 | TSTSGRSAHGGG | Sequence consisting of the N-terminal 1st to 12th amino acids of SEQ ID NO: 17317 |
| G7L.N0354 | TSTSGRSAHIAG | Sequence consisting of the N-terminal 1st to 12th amino acids of SEQ ID NO: 17322 |
| G7L.N0355 | TSTSGRSAHIMG | Sequence consisting of the N-terminal 1st to 12th amino acids of SEQ ID NO: 17323 |
| G7L.N0356 | TSTSGRSAHTTG | Sequence consisting of the N-terminal 1st to 12th amino acids of SEQ ID NO: 17331 |
| G7L.N0357 | TSTSGRSAIGHG | Sequence consisting of the N-terminal 1st to 12th amino acids of SEQ ID NO: 17334 |
| G7L.N0358 | TSTSGRSAMHIG | Sequence consisting of the N-terminal 1st to 12th amino acids of SEQ ID NO: 17336 |
| G7L.N0359 | TSTSGRSAVHNG | Sequence consisting of the N-terminal 1st to 12th amino acids of SEQ ID NO: 17339 |
| G7L.N0360 | TSTSGRSGFHHG | Sequence consisting of the N-terminal 1st to 12th amino acids of SEQ ID NO: 17340 |
| G7L.N0361 | TSTSGRSGGHHG | Sequence consisting of the N-terminal 1st to 12th amino acids of SEQ ID NO: 17341 |
| G7L.N0362 | TSTSGRSGGMGG | Sequence consisting of the N-terminal 1st to 12th amino acids of SEQ ID NO: 17342 |
| G7L.N0363 | TSTSGRSGHAHG | Sequence consisting of the N-terminal 1st to 12th amino acids of SEQ ID NO: 17343 |
| G7L.N0364 | TSTSGRSGHGHG | Sequence consisting of the N-terminal 1st to 12th amino acids of SEQ ID NO: 17344 |
| G7L.N0365 | TSTSGRSGHWHG | Sequence consisting of the N-terminal 1st to 12th amino acids of SEQ ID NO: 17350 |
| G7L.N0366 | TSTSGRSHGGHG | Sequence consisting of the N-terminal 1st to 12th amino acids of SEQ ID NO: 17354 |
| G7L.N0367 | TSTSGRSHGHGG | Sequence consisting of the N-terminal 1st to 12th amino acids of SEQ ID NO: 17355 |
| G7L.N0368 | TSTSGRSHHGYG | Sequence consisting of the N-terminal 1st to 12th amino acids of SEQ ID NO: 17356 |
| G7L.N0369 | TSTSGRSHTGHG | Sequence consisting of the N-terminal 1st to 12th amino acids of SEQ ID NO: 17358 |
| G7L.N0370 | TSTSGRSQHHGG | Sequence consisting of the N-terminal 1st to 12th amino acids of SEQ ID NO: 17359 |
| G7L.N0371 | TSTSGRSSGHHG | Sequence consisting of the N-terminal 1st to 12th amino acids of SEQ ID NO: 17360 |
| G7L.N0372 | TSTSGRSSHHYG | Sequence consisting of the N-terminal 1st to 12th amino acids of SEQ ID NO: 17361 |
| G7L.N0373 | TSTSGRSSVHHG | Sequence consisting of the N-terminal 1st to 12th amino acids of SEQ ID NO: 17362 |
| G7L.N0374 | TSTSGRSTAHHG | Sequence consisting of the N-terminal 1st to 12th amino acids of SEQ ID NO: 17363 |
| G7L.N0375 | TSTSGRSTGHHG | Sequence consisting of the N-terminal 1st to 12th amino acids of SEQ ID NO: 17364 |
| G7L.N0376 | TSTSGRSYGHYG | Sequence consisting of the N-terminal 1st to 12th amino acids of SEQ ID NO: 17367 |

TABLE 7-continued

| Inserted sequences and antibody variants | | |
| --- | --- | --- |
| Antibody variants | Inserted sequences | Remarks on inserted sequence |
| G7L.N0377 | TSTSGRTAAHHG | Sequence consisting of the N-terminal 1st to 12th amino acids of SEQ ID NO: 17369 |
| G7L.N0378 | TSTSGRTGGHHG | Sequence consisting of the N-terminal 1st to 12th amino acids of SEQ ID NO: 17372 |
| G7L.N0379 | TSTSGRTGVHHG | Sequence consisting of the N-terminal 1st to 12th amino acids of SEQ ID NO: 17375 |
| G7L.N0380 | TSTSGRTSGHHG | Sequence consisting of the N-terminal 1st to 12th amino acids of SEQ ID NO: 17376 |
| G7L.N0381 | TSTSGRTTAHHG | Sequence consisting of the N-terminal 1st to 12th amino acids of SEQ ID NO: 17377 |
| G7L.N0382 | GSHHARGGGGGS | Sequence consisting of the N-terminal 3rd to 14th amino acids of SEQ ID NO: 17994 |
| G7L.N0383 | GSHHARHAGGGS | Sequence consisting of the N-terminal 3rd to 14th amino acids of SEQ ID NO: 17997 |
| G7L.N0384 | GSHHGRAGGGGS | Sequence consisting of the N-terminal 3rd to 14th amino acids of SEQ ID NO: 17995 |
| G7L.N0385 | GSHSGRHHGGGS | Sequence consisting of the N-terminal 3rd to 14th amino acids of SEQ ID NO: 17998 |
| G7L.N0386 | GSLWWRWWGGGS | Sequence consisting of the N-terminal 3rd to 14th amino acids of SEQ ID NO: 17999 |
| G7L.N0387 | GSYAARHHGGGS | Sequence consisting of the N-terminal 3rd to 14th amino acids of SEQ ID NO: 17996 |
| G7L.N0388 | GSHHARGGGGGS | Sequence consisting of the N-terminal 3rd to 14th amino acids of SEQ ID NO: 17994 |
| G7L.N0389 | GSHHGRAGGGGS | Sequence consisting of the N-terminal 3rd to 14th amino acids of SEQ ID NO: 17995 |
| G7L.N0390 | GSHHGRGGGGGS | Sequence consisting of the N-terminal 3rd to 14th amino acids of SEQ ID NO: 18000 |
| G7L.N0391 | GSHHGRGLGGGS | Sequence consisting of the N-terminal 3rd to 14th amino acids of SEQ ID NO: 18001 |
| G7L.N0392 | GSHTGRGGGGGS | Sequence consisting of the N-terminal 3rd to 14th amino acids of SEQ ID NO: 18003 |
| G7L.N0393 | GSYAARHHGGGS | Sequence consisting of the N-terminal 3rd to 14th amino acids of SEQ ID NO: 17996 |

7-2. Evaluation of Protease Cleavage of Antibody Variants into which Protease Cleavage Sequences are Inserted To evaluate whether the antibody variants prepared in Example 7-1 are cleaved by protease treatment, each antibody variant was treated by each of Recombinant Human u-Plasminogen Activator/Urokinase (human uPA, huPA) (R&D Systems; 1310-SE-010), Recombinant Human Matriptase/ST14 Catalytic Domain (human MT-SP1, hMT-SP1) (R&D Systems; 3946-SEB-010), and Recombinant Mouse u-Plasminogen Activator/Urokinase (mouse uPA, muPA) (abcam; ab92641). After 100 pg/mL of an antibody variant was allowed to react with huPA, hMT-SP1, or muPA in PBS at 37° C. for 1 hour, the antibody variant was evaluated by reduced capillary electrophoresis. Wes (Protein Simple) was used for the capillary electrophoresis, and anti-human lambda-chain HRP-labeled antibody (abcam; ab9007) was used for the detection. As a result, the peak near 36 kDa disappeared and a new peak was observed near 20 kDa in the protease-treated antibody variants. Thus, the peaks near 36 kDa and 20 kDa are considered to correspond to the uncleaved light-chain and cleaved light-chain, respectively. The area of each peak obtained after the protease treatment was output from the Wes's proprietary software (Compass for SW; Protein Simple), and the cleavage ratio (%) of an antibody variant was calculated according to the formula: (peak area of cleaved light chain)*100/(peak area of cleaved light chain+peak area of uncleaved light chain). The protease concentrations used in the huPA treatment, hMT-SP1 treatment, and muPA treatment, and the cleavage ratio (%) of the antibody variants are summarized in Tables 8, 9, 10, 11, 12, 13, 14, and 15. Among the antibody variants whose cleavage ratio was evaluated, 71 antibodies comprising G7L.106a.12aa were subjected to similar protease treatments again. The results are shown in Table 16. Among those, the antibody variants that showed equal or higher cleavage ratios in the huPA, hMT-SP1, and muPA treatments as compared to G7L.106a.12aa are shown in Table 17.

TABLE 8

| | Cleavage ratio of antibody variants by protease (%) | | |
| | Protease concentration and cleavage ratio (%) | | |
| Antibody variants | huPA 30 nM | hMT-SP1 3 nM | muPA 100 nM |
|---|---|---|---|
| G7L.106a.12aa | 20.5 | 34.8 | 22.2 |
| G7L.N0001 | 30.3 | 63.4 | 15.8 |
| G7L.N0002 | 6.0 | 35.2 | 9.4 |
| G7L.N0003 | 0.2 | 11.4 | 0.4 |
| G7L.N0004 | 1.5 | 84.8 | 12.9 |
| G7L.N0005 | 1.7 | 62.2 | 27.5 |
| G7L.N0007 | 2.2 | 75.2 | 11.8 |
| G7L.N0008 | 3.6 | 75.8 | 21.0 |
| G7L.N0009 | 11.8 | 65.3 | 7.3 |
| G7L.N0010 | 0.9 | 92.1 | 13.2 |
| G7L.N0011 | 43.8 | 23.6 | 21.3 |
| G7L.N0012 | 5.8 | 75.0 | 12.0 |
| G7L.N0013 | 1.4 | 55.6 | 2.3 |
| G7L.N0014 | 13.4 | 44.7 | 7.4 |
| G7L.N0015 | 0.0 | 4.0 | 0.4 |
| G7L.N0016 | 4.2 | 21.9 | 23.3 |
| G7L.N0017 | 0.1 | 71.5 | 12.0 |
| G7L.N0018 | 0.1 | 40.1 | 1.4 |
| G7L.N0019 | 0.0 | 62.9 | 7.7 |
| G7L.N0020 | 1.2 | 17.6 | 9.7 |
| G7L.N0021 | 4.3 | 86.1 | 17.1 |
| G7L.N0022 | 0.5 | 89.9 | 24.2 |
| G7L.N0023 | 0.4 | 73.2 | 23.2 |
| G7L.N0024 | 1.8 | 47.6 | 9.4 |
| G7L.N0025 | 0.5 | 80.8 | 18.2 |
| G7L.N0026 | 8.8 | 94.8 | 20.9 |
| G7L.N0027 | 5.1 | 62.8 | 21.3 |
| G7L.N0028 | 0.3 | 12.6 | 0.4 |
| G7L.N0029 | 11.0 | 93.9 | 18.6 |
| G7L.N0030 | 0.7 | 75.1 | 3.0 |
| G7L.N0031 | 16.5 | 82.3 | 28.2 |
| G7L.N0032 | 4.7 | 62.2 | 6.8 |
| G7L.N0033 | 11.1 | 87.7 | 23.2 |
| G7L.N0034 | 10.6 | 89.3 | 21.1 |
| G7L.N0035 | 0.6 | 72.4 | 3.9 |
| G7L.N0036 | 11.3 | 55.9 | 29.3 |
| G7L.N0037 | 0.8 | 60.9 | 18.6 |
| G7L.N0038 | 0.3 | 62.7 | 2.9 |
| G7L.N0039 | 0.9 | 24.7 | 27.3 |
| G7L.N0040 | 6.4 | 34.2 | 11.2 |
| G7L.N0041 | 2.4 | 42.1 | 4.8 |
| G7L.N0042 | 0.7 | 50.6 | 2.1 |
| G7L.N0043 | 14.1 | 63.9 | 17.4 |
| G7L.N0044 | 1.2 | 59.2 | 10.5 |
| G7L.N0045 | 8.2 | 35.9 | 11.8 |
| G7L.N0046 | 10.1 | 55.8 | 10.9 |
| G7L.N0047 | 6.9 | 63.8 | 8.6 |
| G7L.N0048 | 0.0 | 24.6 | 1.0 |

TABLE 9

| | Cleavage ratio of antibody variants by protease (%) | | |
| | Protease concentration and cleavage ratio (%) | | |
| Antibody variants | huPA 40 nM | hMT-SP1 3 nM | muPA 150 nM |
|---|---|---|---|
| G7L.106a.12aa | 35.9 | 22.3 | 31.9 |
| G7L.N0006 | 48.6 | 32.2 | 23.5 |
| G7L.N0049 | 10.3 | 27.5 | 22.7 |
| G7L.N0050 | 42.0 | 20.1 | 26.4 |
| G7L.N0051 | 12.2 | 42.1 | 24.9 |
| G7L.N0052 | 2.0 | 22.8 | 19.3 |
| G7L.N0053 | 4.1 | 23.0 | 22.6 |
| G7L.N0054 | 0.3 | 9.9 | 0.8 |
| G7L.N0055 | 6.7 | 28.1 | 27.6 |

TABLE 9-continued

| | Cleavage ratio of antibody variants by protease (%) | | |
| | Protease concentration and cleavage ratio (%) | | |
| Antibody variants | huPA 40 nM | hMT-SP1 3 nM | muPA 150 nM |
|---|---|---|---|
| G7L.N0056 | 59.4 | 21.9 | 38.6 |
| G7L.N0057 | 7.8 | 38.6 | 30.4 |
| G7L.N0058 | 34.3 | 29.4 | 24.3 |
| G7L.N0059 | 51.5 | 49.1 | 42.8 |
| G7L.N0060 | 2.4 | 20.2 | 1.2 |
| G7L.N0061 | 2.4 | 40.3 | 44.7 |
| G7L.N0062 | 61.2 | 25.8 | 38.9 |
| G7L.N0063 | 63.0 | 16.0 | 33.7 |
| G7L.N0064 | 68.5 | 43.6 | 38.6 |
| G7L.N0065 | 70.1 | 22.5 | 35.9 |
| G7L.N0066 | 5.8 | 41.5 | 30.4 |
| G7L.N0067 | 1.1 | 13.2 | 1.4 |
| G7L.N0068 | 3.0 | 14.0 | 1.3 |
| G7L.N0069 | 64.1 | 44.4 | 26.2 |
| G7L.N0070 | 63.1 | 23.6 | 42.2 |
| G7L.N0071 | 17.8 | 43.5 | 33.2 |
| G7L.N0072 | 61.1 | 30.8 | 39.9 |
| G7L.N0073 | 9.6 | 21.7 | 35.5 |
| G7L.N0074 | 49.0 | 10.9 | 32.0 |
| G7L.N0075 | 5.9 | 21.2 | 28.8 |
| G7L.N0076 | 0.3 | 14.8 | 3.2 |
| G7L.N0077 | 12.3 | 48.6 | 8.7 |
| G7L.N0078 | 44.5 | 31.9 | 37.9 |
| G7L.N0079 | 21.7 | 6.7 | 29.8 |
| G7L.N0080 | 16.9 | 3.2 | 24.3 |
| G7L.N0081 | 84.7 | 29.7 | 46.4 |
| G7L.N0082 | 52.9 | 19.9 | 36.9 |
| G7L.N0083 | 60.7 | 24.9 | 41.9 |
| G7L.N0084 | 23.4 | 15.0 | 24.8 |
| G7L.N0085 | 70.1 | 15.9 | 41.1 |
| G7L.N0086 | 3.3 | 4.4 | 0.6 |
| G7L.N0087 | 91.0 | 24.7 | 49.6 |
| G7L.N0088 | 59.6 | 19.5 | 38.0 |
| G7L.N0089 | 74.9 | 18.7 | 31.5 |
| G7L.N0090 | 0.6 | 3.2 | 0.6 |
| G7L.N0091 | 90.2 | 31.7 | 37.5 |
| G7L.N0092 | 56.9 | 13.7 | 41.1 |
| G7L.N0093 | 4.0 | 14.5 | 29.7 |
| G7L.N0094 | 83.6 | 19.2 | 29.9 |

TABLE 10

| | Cleavage ratio of antibody variants by protease (%) | | |
| | Protease concentration and cleavage ratio (%) | | |
| Antibody variants | huPA 40 nM | hMT-SP1 3 nM | muPA 150 nM |
|---|---|---|---|
| G7L.106a.12aa | 56.1 | 73.1 | 41.5 |
| G7L.N0095 | 10.0 | 37.4 | 5.6 |
| G7L.N0096 | 3.8 | 30.0 | 2.3 |
| G7L.N0097 | 0.5 | 43.0 | 5.3 |
| G7L.N0099 | 1.5 | 49.3 | 9.7 |
| G7L.N0100 | 13.5 | 75.5 | 21.3 |
| G7L.N0101 | 11.8 | 85.4 | 40.1 |
| G7L.N0103 | 6.5 | 93.9 | 31.2 |
| G7L.N0104 | 24.9 | 86.2 | 10.4 |
| G7L.N0105 | 40.0 | 58.5 | 19.3 |
| G7L.N0106 | 1.4 | 32.9 | 1.2 |
| G7L.N0107 | 1.6 | 47.9 | 16.6 |
| G7L.N0108 | 34.0 | 59.2 | 23.7 |
| G7L.N0109 | 4.9 | 80.5 | 32.3 |
| G7L.N0110 | 37.6 | 71.9 | 18.6 |
| G7L.N0111 | 79.4 | 89.8 | 40.4 |
| G7L.N0112 | 78.8 | 92.6 | 29.7 |
| G7L.N0113 | 10.8 | 62.4 | 11.1 |
| G7L.N0114 | 1.8 | 40.3 | 2.1 |
| G7L.N0115 | 22.7 | 83.6 | 12.9 |
| G7L.N0116 | 3.4 | 39.6 | 2.6 |

TABLE 10-continued

| Cleavage ratio of antibody variants by protease (%) | | |
| --- | --- | --- |
| Protease concentration and cleavage ratio (%) | | |
| | huPA | hMT-SP1 | muPA |
| Antibody variants | 40 nM | 3 nM | 150 nM |
| G7L.N0117 | 9.1 | 62.9 | 13.8 |
| G7L.N0118 | 11.3 | 91.2 | 32.0 |
| G7L.N0119 | 18.9 | 72.1 | 27.1 |
| G7L.N0120 | 10.6 | 94.3 | 29.9 |
| G7L.N0121 | 0.4 | 39.5 | 3.1 |
| G7L.N0122 | 7.9 | 81.6 | 43.2 |
| G7L.N0123 | 38.2 | 92.9 | 92.3 |
| G7L.N0124 | 2.5 | 37.9 | 12.3 |
| G7L.N0126 | 1.5 | 38.4 | 7.7 |
| G7L.N0127 | 22.1 | 88.8 | 46.3 |
| G7L.N0128 | 63.0 | 93.5 | 51.8 |
| G7L.N0129 | 76.0 | 94.9 | 42.5 |
| G7L.N0130 | 87.0 | 87.0 | 58.6 |
| G7L.N0131 | 3.4 | 26.0 | 0.9 |
| G7L.N0132 | 62.3 | 88.0 | 62.0 |
| G7L.N0133 | 90.6 | 84.0 | 63.1 |
| G7L.N0134 | 15.8 | 43.9 | 21.3 |
| G7L.N0136 | 85.4 | 87.2 | 75.5 |
| G7L.N0137 | 71.8 | 39.1 | 21.0 |
| G7L.N0138 | 1.8 | 34.8 | 1.8 |
| G7L.N0139 | 1.7 | 63.7 | 11.8 |
| G7L.N0140 | 78.0 | 88.9 | 30.5 |
| G7L.N0141 | 82.3 | 69.3 | 40.6 |
| G7L.N0098 | 76.8 | 91.1 | 57.0 |
| G7L.N0102 | 90.2 | 61.1 | 50.9 |
| G7L.N0125 | 79.2 | 58.5 | 53.7 |
| G7L.N0135 | 61.3 | 57.5 | 61.8 |
| G7L.N0142 | 65.9 | 65.0 | 52.8 |
| G7L.N0143 | 7.6 | 42.2 | 17.9 |
| G7L.N0144 | 24.4 | 61.6 | 23.5 |
| G7L.N0145 | 19.4 | 82.0 | 29.1 |
| G7L.N0146 | 56.3 | 61.0 | 34.9 |
| G7L.N0147 | 9.8 | 72.1 | 36.5 |
| G7L.N0148 | 6.8 | 58.2 | 24.6 |
| G7L.N0149 | 2.8 | 47.8 | 4.1 |
| G7L.N0150 | 17.1 | 91.3 | 21.7 |
| G7L.N0151 | 66.5 | 58.1 | 46.4 |
| G7L.N0152 | 25.0 | 23.6 | 17.7 |
| G7L.N0153 | 9.5 | 36.8 | 9.2 |
| G7L.N0154 | 4.1 | 34.8 | 3.4 |
| G7L.N0155 | 66.7 | 57.9 | 48.3 |
| G7L.N0156 | 1.7 | 30.4 | 2.1 |
| G7L.N0157 | 49.8 | 74.2 | 24.0 |
| G7L.N0158 | 74.6 | 80.7 | 34.0 |
| G7L.N0159 | 4.8 | 45.1 | 4.1 |
| G7L.N0160 | 54.5 | 84.4 | 38.8 |
| G7L.N0161 | 55.6 | 74.0 | 42.1 |
| G7L.N0162 | 17.2 | 77.8 | 40.9 |
| G7L.N0163 | 0.5 | 38.2 | 3.2 |
| G7L.N0164 | 0.5 | 12.0 | 1.0 |
| G7L.N0165 | 2.9 | 23.2 | 4.6 |
| G7L.N0166 | 53.1 | 68.1 | 46.7 |
| G7L.N0167 | 63.9 | 76.7 | 51.7 |
| G7L.N0168 | 12.4 | 67.2 | 32.4 |
| G7L.N0169 | 11.4 | 69.9 | 41.3 |
| G7L.N0170 | 6.7 | 31.4 | 5.1 |
| G7L.N0171 | 43.8 | 84.3 | 37.3 |
| G7L.N0172 | 0.9 | 41.5 | 1.9 |
| G7L.N0173 | 72.6 | 49.8 | 56.3 |
| G7L.N0174 | 83.0 | 89.0 | 28.9 |
| G7L.N0175 | 14.2 | 90.1 | 49.1 |
| G7L.N0176 | 69.4 | 69.1 | 41.8 |
| G7L.N0177 | 69.6 | 87.6 | 43.6 |
| G7L.N0178 | 88.4 | 90.1 | 51.3 |
| G7L.N0179 | 4.1 | 30.8 | 1.2 |
| G7L.N0180 | 2.0 | 89.7 | 28.1 |
| G7L.N0181 | 0.4 | 30.9 | 1.0 |
| G7L.N0182 | 34.0 | 22.0 | 21.9 |
| G7L.N0183 | 18.6 | 61.4 | 20.3 |
| G7L.N0184 | 54.7 | 60.6 | 42.9 |
| G7L.N0185 | 0.2 | 47.6 | 2.2 |
| G7L.N0186 | 13.3 | 16.0 | 13.3 |

TABLE 10-continued

| Cleavage ratio of antibody variants by protease (%) | | |
| --- | --- | --- |
| Protease concentration and cleavage ratio (%) | | |
| | huPA | hMT-SP1 | muPA |
| Antibody variants | 40 nM | 3 nM | 150 nM |
| G7L.N0187 | 57.5 | 90.9 | 49.0 |
| G7L.N0188 | 3.8 | 32.3 | 1.9 |

TABLE 11

| Cleavage ratio of antibody variants by protease (%) | | |
| --- | --- | --- |
| Protease concentration and cleavage ratio (%) | | |
| | huPA | hMT-SP1 | muPA |
| Antibody variants | 30 nM | 3 nM | 100 nM |
| G7L.106a.12aa | 49.3 | 59.7 | 22.2 |
| G7L.N0189 | 14.2 | 67.3 | 23.3 |
| G7L.N0190 | 19.6 | 83.0 | 16.6 |
| G7L.N0191 | 1.6 | 34.2 | 0.9 |
| G7L.N0192 | 15.6 | 64.4 | 18.0 |
| G7L.N0193 | 86.1 | 71.8 | 63.0 |
| G7L.N0194 | 89.3 | 83.4 | 43.8 |
| G7L.N0195 | 1.2 | 27.4 | 1.1 |
| G7L.N0196 | 9.4 | 38.7 | 19.1 |
| G7L.N0197 | 5.2 | 66.3 | 12.6 |
| G7L.N0198 | 13.5 | 80.5 | 1.8 |
| G7L.N0199 | 16.9 | 54.4 | 29.0 |
| G7L.N0200 | 0.6 | 31.9 | 0.8 |
| G7L.N0201 | 0.8 | 52.2 | 0.8 |
| G7L.N0202 | 19.1 | 52.1 | 6.9 |
| G7L.N0203 | 26.5 | 71.7 | 28.0 |
| G7L.N0204 | 0.4 | 72.4 | 1.4 |
| G7L.N0205 | 17.4 | 70.2 | 10.8 |
| G7L.N0206 | 85.6 | 25.6 | 38.8 |
| G7L.N0207 | 32.5 | 68.0 | 20.0 |
| G7L.N0208 | 6.3 | 95.9 | 1.9 |
| G7L.N0209 | 7.2 | 28.8 | 14.4 |
| G7L.N0210 | 0.8 | 75.0 | 1.2 |
| G7L.N0211 | 16.1 | 14.5 | 18.5 |
| G7L.N0212 | 5.4 | 69.4 | 28.8 |
| G7L.N0213 | 8.1 | 71.8 | 38.4 |
| G7L.N0214 | 31.9 | 24.5 | 30.8 |
| G7L.N0215 | 6.8 | 66.8 | 44.1 |
| G7L.N0216 | 5.2 | 92.3 | 29.5 |
| G7L.N0217 | 14.2 | 27.5 | 8.8 |
| G7L.N0218 | 76.2 | 74.8 | 58.7 |
| G7L.N0219 | 13.8 | 12.4 | 4.5 |
| G7L.N0220 | 75.7 | no data | 32.8 |
| G7L.N0221 | 5.2 | 23.3 | 1.1 |
| G7L.N0222 | 84.3 | 54.6 | 48.4 |
| G7L.N0223 | 3.2 | 35.3 | 1.9 |
| G7L.N0224 | 11.5 | 60.0 | 44.0 |
| G7L.N0225 | 4.1 | 40.2 | 1.1 |
| G7L.N0226 | 5.2 | 36.8 | 1.5 |
| G7L.N0227 | 4.1 | 81.6 | 18.5 |
| G7L.N0228 | 54.3 | 48.3 | 22.8 |
| G7L.N0229 | 8.1 | 59.6 | 19.7 |
| G7L.N0230 | 0.7 | 34.0 | 0.6 |
| G7L.N0231 | 15.6 | 61.1 | 30.2 |
| G7L.N0232 | 3.1 | 37.1 | 4.1 |
| G7L.N0233 | 5.9 | 42.2 | 0.9 |
| G7L.N0234 | 43.0 | 25.9 | 8.3 |
| G7L.N0235 | 0.9 | 34.6 | 0.8 |

TABLE 12

Cleavage ratio of antibody variants by protease (%)

| Antibody variants | Protease concentration and cleavage ratio (%) | | |
|---|---|---|---|
| | huPA 30 nM | hMT-SP1 3 nM | muPA 1000 nM |
| G7L.106a.12aa | 38.7 | 53.4 | 36.6 |
| G7L.N0236 | 1.9 | 52.9 | 14.3 |
| G7L.N0237 | 48.8 | 71.3 | 54.3 |
| G7L.N0238 | 23.7 | 22.3 | 34.2 |
| G7L.N0239 | 50.2 | 19.8 | 73.0 |
| G7L.N0240 | 34.2 | 19.0 | 58.4 |
| G7L.N0241 | 16.8 | 7.8 | 33.0 |
| G7L.N0242 | 23.3 | 7.8 | 41.8 |
| G7L.N0243 | 17.2 | 15.0 | 45.0 |
| G7L.N0244 | 17.5 | 16.6 | 45.8 |
| G7L.N0245 | 23.5 | 31.5 | 32.4 |
| G7L.N0246 | 20.6 | 29.0 | 30.8 |
| G7L.N0247 | 32.1 | 31.4 | 46.4 |
| G7L.N0248 | 26.6 | 28.9 | 38.5 |
| G7L.N0249 | 20.1 | 26.1 | 34.4 |
| G7L.N0250 | 20.3 | 26.7 | 36.2 |
| G7L.N0251 | 27.8 | 27.1 | 47.6 |
| G7L.N0252 | 26.0 | 23.1 | 39.5 |
| G7L.N0253 | 24.8 | 26.7 | 47.5 |
| G7L.N0254 | 26.5 | 29.3 | 43.0 |
| G7L.N0255 | 17.4 | 25.5 | 37.4 |
| G7L.N0256 | 34.3 | 30.9 | 53.2 |
| G7L.N0257 | 33.0 | 19.1 | 50.6 |
| G7L.N0258 | 14.5 | 13.4 | 42.0 |
| G7L.N0259 | 26.3 | 18.6 | 50.4 |
| G7L.N0260 | 29.2 | 15.9 | 46.2 |
| G7L.N0261 | 28.6 | 21.4 | 45.3 |
| G7L.N0262 | 43.1 | 22.8 | 69.9 |
| G7L.N0263 | 8.9 | 21.5 | 18.9 |
| G7L.N0264 | 7.6 | 26.9 | 8.9 |
| G7L.N0265 | 7.0 | 26.5 | 6.8 |
| G7L.N0266 | 5.7 | 21.3 | 8.0 |
| G7L.N0267 | 5.8 | 20.6 | 7.0 |
| G7L.N0268 | 10.3 | 21.7 | 10.8 |
| G7L.N0269 | 4.5 | 21.4 | 9.2 |
| G7L.N0270 | 7.0 | 25.3 | 8.9 |
| G7L.N0271 | 5.6 | 20.5 | 9.4 |
| G7L.N0272 | 6.4 | 19.2 | 11.5 |
| G7L.N0273 | 5.4 | 18.5 | 8.0 |
| G7L.N0274 | 7.1 | 13.1 | 9.6 |
| G7L.N0275 | 4.6 | 10.8 | 8.0 |
| G7L.N0276 | 4.3 | 14.5 | 14.6 |
| G7L.N0277 | 1.9 | 3.6 | 5.7 |
| G7L.N0278 | 2.8 | 9.6 | 6.6 |
| G7L.N0279 | 1.7 | 2.7 | 3.1 |
| G7L.N0280 | 7.0 | 8.4 | 3.5 |
| G7L.N0281 | 2.0 | 7.7 | 4.6 |
| G7L.N0282 | 3.3 | 7.4 | 3.0 |

TABLE 13

Cleavage ratio of antibody variants by protease (%)

| Antibody variants | Protease concentration and cleavage ratio (%) | | |
|---|---|---|---|
| | huPA 30 nM | hMT-SP1 3 nM | muPA 1000 nM |
| G7L.106a.12aa | 34.5 | 59.1 | 36.9 |
| G7L.N0283 | 3.2 | 9.0 | 2.8 |
| G7L.N0284 | 4.1 | 8.9 | 3.4 |
| G7L.N0285 | 7.6 | 13.5 | 2.9 |
| G7L.N0286 | 12.1 | 11.2 | 2.9 |
| G7L.N0287 | 12.0 | 11.1 | 2.5 |
| G7L.N0288 | 9.7 | 7.5 | 2.2 |
| G7L.N0289 | 4.5 | 7.8 | 2.6 |
| G7L.N0290 | 3.7 | 8.4 | 2.6 |
| G7L.N0291 | 2.2 | 6.0 | 2.7 |
| G7L.N0292 | 3.4 | 5.0 | 3.5 |
| G7L.N0293 | 5.9 | 7.0 | 4.4 |

TABLE 13-continued

Cleavage ratio of antibody variants by protease (%)

| Antibody variants | Protease concentration and cleavage ratio (%) | | |
|---|---|---|---|
| | huPA 30 nM | hMT-SP1 3 nM | muPA 1000 nM |
| G7L.N0294 | 2.6 | 13.3 | 4.0 |
| G7L.N0295 | 5.2 | 36.3 | 6.3 |
| G7L.N0296 | 0.7 | 6.3 | 1.1 |
| G7L.N0297 | 1.3 | 7.9 | 1.6 |
| G7L.N0298 | 4.2 | 5.9 | 6.7 |
| G7L.N0299 | 6.4 | 18.4 | 8.1 |
| G7L.N0300 | 4.0 | 4.6 | 12.2 |
| G7L.N0301 | 4.5 | 14.3 | 5.8 |
| G7L.N0302 | 9.3 | 15.9 | 22.6 |
| G7L.N0303 | 10.7 | 16.9 | 19.3 |
| G7L.N0304 | 11.4 | 14.9 | 7.2 |
| G7L.N0305 | 9.9 | 14.9 | 3.7 |
| G7L.N0306 | 4.8 | 9.5 | 6.4 |
| G7L.N0307 | 5.1 | 12.2 | 5.6 |
| G7L.N0309 | 2.4 | 4.5 | 0.7 |
| G7L.N0310 | 1.7 | 3.5 | 1.4 |
| G7L.N0311 | 1.5 | 2.1 | 0.5 |
| G7L.N0312 | 0.3 | 0.8 | 0.2 |
| G7L.N0313 | 2.1 | 3.5 | 1.0 |
| G7L.N0314 | 3.3 | 0.9 | 4.9 |
| G7L.N0315 | 4.0 | 4.4 | 10.5 |
| G7L.N0316 | 3.6 | 3.2 | 8.1 |
| G7L.N0317 | 1.2 | 7.4 | 4.2 |
| G7L.N0318 | 1.2 | 5.5 | 1.9 |
| G7L.N0319 | 24.7 | 12.9 | 31.7 |
| G7L.N0320 | 28.1 | 13.1 | 30.9 |
| G7L.N0321 | 26.5 | 12.5 | 29.0 |
| G7L.N0322 | 24.7 | 10.6 | 30.9 |
| G7L.N0323 | 14.0 | 9.2 | 19.1 |
| G7L.N0324 | 26.6 | 10.8 | 29.0 |
| G7L.N0325 | 30.4 | 12.3 | 35.8 |
| G7L.N0326 | 35.3 | 14.8 | 35.4 |
| G7L.N0327 | 4.3 | 8.3 | 4.7 |
| G7L.N0328 | 4.6 | 11.3 | 4.5 |
| G7L.N0329 | 4.5 | 10.0 | 5.1 |

TABLE 14

Cleavage ratio of antibody variants by protease (%)

| Antibody variants | Protease concentration and cleavage ratio (%) | | |
|---|---|---|---|
| | huPA 30 nM | hMT-SP1 3 nM | muPA 1000 nM |
| G7L.106a.12aa | 46.0 | 55.0 | 35.1 |
| G7L.N0308 | 10.1 | 5.6 | 6.9 |
| G7L.N0330 | 13.2 | 11.7 | 10.6 |
| G7L.N0331 | 9.5 | 11.5 | 7.8 |
| G7L.N0332 | 5.0 | 11.5 | 4.6 |
| G7L.N0333 | 15.4 | 10.0 | 24.4 |
| G7L.N0334 | 24.3 | 8.8 | 20.2 |
| G7L.N0335 | 26.5 | 10.8 | 14.3 |
| G7L.N0336 | 28.7 | 7.8 | 17.0 |
| G7L.N0337 | 3.2 | 4.2 | 1.4 |
| G7L.N0338 | 4.9 | 5.9 | 2.4 |
| G7L.N0339 | 2.0 | 2.4 | 1.0 |
| G7L.N0340 | 3.4 | 2.2 | 1.0 |
| G7L.N0341 | 10.7 | 2.9 | 14.9 |
| G7L.N0342 | 28.0 | 28.0 | 28.7 |
| G7L.N0343 | 29.4 | 30.3 | 33.1 |
| G7L.N0344 | 35.6 | 28.5 | 35.0 |
| G7L.N0345 | 40.1 | 26.5 | 32.4 |
| G7L.N0346 | 36.1 | 24.5 | 51.9 |
| G7L.N0347 | 29.0 | 20.8 | 41.5 |
| G7L.N0348 | 39.0 | 23.0 | 54.4 |
| G7L.N0349 | 26.6 | 25.7 | 41.5 |
| G7L.N0350 | 39.7 | 21.1 | 60.8 |
| G7L.N0351 | 39.5 | 31.9 | 32.7 |
| G7L.N0352 | 42.1 | 30.8 | 38.8 |

TABLE 14-continued

Cleavage ratio of antibody variants by protease (%)

| | Protease concentration and cleavage ratio (%) | | |
|---|---|---|---|
| Antibody variants | huPA 30 nM | hMT-SP1 3 nM | muPA 1000 nM |
| G7L.N0353 | 36.0 | 32.4 | 32.8 |
| G7L.N0354 | 37.7 | 26.5 | 36.2 |
| G7L.N0355 | 30.3 | 26.6 | 38.3 |
| G7L.N0356 | 22.1 | 19.0 | 31.8 |
| G7L.N0357 | 46.5 | 30.9 | 37.6 |
| G7L.N0358 | 34.8 | 24.5 | 45.1 |
| G7L.N0359 | 43.2 | 25.1 | 47.5 |
| G7L.N0360 | 16.2 | 24.6 | 15.2 |
| G7L.N0361 | 16.4 | 23.3 | 15.2 |
| G7L.N0362 | 13.6 | 25.3 | 15.1 |
| G7L.N0363 | 16.8 | 25.9 | 9.1 |
| G7L.N0364 | 14.1 | 23.2 | 8.9 |
| G7L.N0365 | 23.0 | 29.0 | 12.1 |
| G7L.N0366 | 4.9 | 6.6 | 4.8 |
| G7L.N0367 | 4.1 | 9.4 | 3.8 |
| G7L.N0368 | 5.1 | 11.8 | 3.9 |
| G7L.N0369 | 5.9 | 6.7 | 6.8 |
| G7L.N0370 | 3.2 | 13.0 | 2.2 |
| G7L.N0371 | 10.0 | 12.1 | 13.5 |
| G7L.N0372 | 12.0 | 16.1 | 13.0 |
| G7L.N0373 | 11.1 | 19.4 | 11.1 |
| G7L.N0374 | 15.2 | 12.9 | 25.0 |
| G7L.N0375 | 22.4 | 6.8 | 26.7 |

TABLE 15

Cleavage ratio of antibody variants by protease (%)

| | Protease concentration and cleavage ratio (%) | | |
|---|---|---|---|
| Antibody variants | huPA 30 nM | hMT-SP1 3 nM | muPA 1000 nM |
| G7L.106a.12aa | 41.4 | 56.8 | 33.2 |
| G7L.N0376 | 12.3 | 8.6 | 5.1 |
| G7L.N0377 | 23.6 | 21.7 | 9.3 |
| G7L.N0378 | 7.6 | 17.1 | 4.8 |
| G7L.N0379 | 14.3 | 14.2 | 2.4 |
| G7L.N0380 | 6.6 | 7.0 | 3.3 |
| G7L.N0381 | 6.8 | 5.2 | 5.4 |
| G7L.N0382 | 0.0 | 5.0 | 0.1 |
| G7L.N0383 | 0.2 | 10.9 | 2.4 |
| G7L.N0384 | 0.1 | 14.1 | 2.9 |
| G7L.N0385 | 0.4 | 1.0 | 0.2 |
| G7L.N0386 | 0.1 | 0.6 | 0.0 |
| G7L.N0387 | 0.1 | 1.3 | 0.2 |
| G7L.N0388 | 0.0 | 5.1 | 0.1 |
| G7L.N0389 | 0.0 | 14.9 | 2.6 |
| G7L.N0390 | 0.1 | 3.8 | 0.3 |
| G7L.N0391 | 0.0 | 5.3 | 0.1 |
| G7L.N0392 | 1.1 | 2.5 | 0.8 |
| G7L.N0393 | 0.1 | 1.6 | 0.2 |

TABLE 16

Cleavage ratio of antibody variants by protease (%)

| | Protease concentration and cleavage ratio (%) | | |
|---|---|---|---|
| Antibody variants | huPA 30 nM | hMT-SP1 3 nM | muPA 1000 nM |
| G7L.106a.12aa | 37.6 | 63.2 | 39.0 |
| G7L.N0001 | 55.2 | 76.9 | 41.4 |
| G7L.N0006 | 46.6 | 88.5 | 30.7 |
| G7L.N0011 | 72.7 | 84.4 | 47.2 |
| G7L.N0050 | 40.2 | 54.4 | 35.6 |
| G7L.N0056 | 50.2 | 48.1 | 54.1 |

TABLE 16-continued

Cleavage ratio of antibody variants by protease (%)

| | Protease concentration and cleavage ratio (%) | | |
|---|---|---|---|
| Antibody variants | huPA 30 nM | hMT-SP1 3 nM | muPA 1000 nM |
| G7L.N0058 | 24.0 | 77.6 | 31.9 |
| G7L.N0059 | 38.7 | 86.0 | 56.0 |
| G7L.N0062 | 43.5 | 64.8 | 54.2 |
| G7L.N0063 | 45.8 | 52.3 | 43.1 |
| G7L.N0064 | 43.8 | 79.7 | 51.1 |
| G7L.N0065 | 51.8 | 48.6 | 49.8 |
| G7L.N0069 | 49.0 | 92.9 | 33.0 |
| G7L.N0070 | 55.0 | 70.8 | 61.5 |
| G7L.N0072 | 61.4 | 90.9 | 50.0 |
| G7L.N0074 | 41.8 | 73.2 | 39.0 |
| G7L.N0078 | 45.3 | 91.5 | 55.1 |
| G7L.N0081 | 85.5 | 89.8 | 62.5 |
| G7L.N0082 | 45.6 | 64.7 | 44.6 |
| G7L.N0083 | 55.8 | 83.1 | 54.2 |
| G7L.N0085 | 63.0 | 61.1 | 56.3 |
| G7L.N0087 | 79.4 | 83.9 | 64.4 |
| G7L.N0088 | 57.5 | 66.2 | 49.4 |
| G7L.N0089 | 65.0 | 72.7 | 39.9 |
| G7L.N0091 | 73.7 | 88.1 | 51.0 |
| G7L.N0092 | 54.5 | 47.6 | 50.3 |
| G7L.N0094 | 68.4 | 71.7 | 43.1 |
| G7L.N0098 | 37.0 | 73.5 | 49.0 |
| G7L.N0102 | 70.8 | 45.8 | 45.3 |
| G7L.N0111 | 41.6 | 80.7 | 41.9 |
| G7L.N0112 | 40.3 | 87.1 | 24.9 |
| G7L.N0125 | 44.8 | 47.7 | 52.5 |
| G7L.N0128 | 34.3 | 90.0 | 54.5 |
| G7L.N0129 | 35.8 | 91.7 | 38.2 |
| G7L.N0130 | 54.1 | 71.6 | 51.4 |
| G7L.N0132 | 32.5 | 77.2 | 50.2 |
| G7L.N0133 | 42.6 | 68.8 | 51.9 |
| G7L.N0135 | 35.0 | 54.4 | 52.5 |
| G7L.N0136 | 42.3 | 70.8 | 64.1 |
| G7L.N0137 | 37.9 | 36.4 | 17.4 |
| G7L.N0140 | 36.6 | 69.3 | 22.1 |
| G7L.N0141 | 42.9 | 51.1 | 34.9 |
| G7L.N0142 | 42.6 | 44.8 | 44.3 |
| G7L.N0146 | 35.7 | 44.3 | 38.5 |
| G7L.N0151 | 42.6 | 43.4 | 42.0 |
| G7L.N0155 | 42.2 | 44.4 | 43.6 |
| G7L.N0157 | 31.3 | 63.0 | 25.7 |
| G7L.N0158 | 41.5 | 68.8 | 29.5 |
| G7L.N0160 | 27.3 | 71.4 | 34.8 |
| G7L.N0161 | 29.2 | 60.6 | 36.6 |
| G7L.N0166 | 29.0 | 66.0 | 46.6 |
| G7L.N0167 | 33.8 | 57.6 | 50.3 |
| G7L.N0173 | 37.7 | 45.5 | 56.5 |
| G7L.N0174 | 33.5 | 83.6 | 31.9 |
| G7L.N0176 | 37.7 | 58.3 | 41.4 |
| G7L.N0177 | 28.7 | 75.8 | 39.4 |
| G7L.N0178 | 81.4 | 66.8 | 46.6 |
| G7L.N0184 | 51.2 | 47.6 | 45.0 |
| G7L.N0187 | 65.8 | 82.5 | 50.6 |
| G7L.N0193 | 83.1 | 52.8 | 66.3 |
| G7L.N0194 | 83.3 | 63.1 | 53.2 |
| G7L.N0206 | 88.4 | 67.8 | 43.5 |
| G7L.N0218 | 82.7 | 60.5 | 64.2 |
| G7L.N0220 | 76.0 | 64.6 | 43.2 |
| G7L.N0222 | 83.7 | 65.1 | 63.4 |
| G7L.N0228 | 61.8 | 46.6 | 35.6 |
| G7L.N0237 | 52.7 | 56.1 | 44.8 |
| G7L.N0239 | 66.9 | 13.5 | 58.9 |
| G7L.N0262 | 51.4 | 15.5 | 50.9 |
| G7L.N0326 | 52.8 | 11.0 | 37.6 |
| G7L.N0357 | 43.7 | 22.2 | 31.0 |

TABLE 17

| Antibody variants | Inserted sequences | Remarks on inserted sequence |
|---|---|---|
| G7LN0001 | AFMTARSANPRG | Sequence consisting of the N-terminal 4th to 15th amino acids of SEQ ID NO: 8 |
| G7LN0011 | AFMTARSANPRG | Sequence consisting of the N-terminal 4th to 15th amino acids of SEQ ID NO: 26 |
| G7LN0059 | GYATGRSANPRG | Sequence consisting of the N-terminal 4th to 15th amino acids of SEQ ID NO: 107 |
| G7LN0062 | GYWTGRSANPRG | Sequence consisting of the N-terminal 4th to 15th amino acids of SEQ ID NO: 114 |
| G7LN0064 | HTATGRSANPRG | Sequence consisting of the N-terminal 4th to 15th amino acids of SEQ ID NO: 117 |
| G7LN0070 | IGYTARSANPRG | Sequence consisting of the N-terminal 4th to 15th amino acids of SEQ ID NO: 130 |
| G7LN0072 | ISASGRSANPRG | Sequence consisting of the N-terminal 4th to 15th amino acids of SEQ ID NO: 133 |
| G7LN0074 | ITATARSANPRG | Sequence consisting of the N-terminal 4th to 15th amino acids of SEQ ID NO: 135 |
| G7LN0078 | IYATGRSANPRG | Sequence consisting of the N-terminal 4th to 15th amino acids of SEQ ID NO: 143 |
| G7LN0081 | LAYTGRSANPRG | Sequence consisting of the N-terminal 4th to 15th amino acids of SEQ ID NO: 149 |
| G7LN0082 | LTATGRSANPRG | Sequence consisting of the N-terminal 4th to 15th amino acids of SEQ ID NO: 155 |
| G7LN0083 | LTATGRSANPRG | Sequence consisting of the N-terminal 4th to 15th amino acids of SEQ ID NO: 156 |
| G7LN0087 | MSWTGRSANPRG | Sequence consisting of the N-terminal 4th to 15th amino acids of SEQ ID NO: 170 |
| G7LN0088 | MVATGRSANPRG | Sequence consisting of the N-terminal 4th to 15th amino acids of SEQ ID NO: 172 |
| G7LN0089 | NVYTGRSANPRG | Sequence consisting of the N-terminal 4th to 15th amino acids of SEQ ID NO: 179 |
| G7LN0091 | PVYTGRSANPRG | Sequence consisting of the N-terminal 4th to 15th amino acids of SEQ ID NO: 184 |
| G7LN0094 | QWVTGRSANPRG | Sequence consisting of the N-terminal 4th to 15th amino acids of SEQ ID NO: 191 |
| G7LN0098 | SGFTGRSANPRG | Sequence consisting of the N-terminal 4th to 15th amino acids of SEQ ID NO: 203 |
| G7LN0111 | STFTGRSANPRG | Sequence consisting of the N-terminal 4th to 15th amino acids of SEQ ID NO: 225 |
| G7LN0130 | TFYTGRSANPRG | Sequence consisting of the N-terminal 4th to 15th amino acids of SEQ ID NO: 265 |
| G7LN0133 | TGWTGRSANPRG | Sequence consisting of the N-terminal 4th to 15th amino acids of SEQ ID NO: 268 |
| G7LN0136 | TGYTGRSANPRG | Sequence consisting of the N-terminal 4th to 15th amino acids of SEQ ID NO: 271 |
| G7LN0178 | VSWTGRSANPRG | Sequence consisting of the N-terminal 4th to 15th amino acids of SEQ ID NO: 339 |
| G7LN0187 | WGMTGRSANPRG | Sequence consisting of the N-terminal 4th to 15th amino acids of SEQ ID NO: 359 |
| G7LN0206 | YAYTGRSANPRG | Sequence consisting of the N-terminal 4th to 15th amino acids of SEQ ID NO: 400 |
| G7LN0220 | YMWTGRSANPRG | Sequence consisting of the N-terminal 4th to 15th amino acids of SEQ ID NO: 425 |
| G7LN0222 | YSATGRSANPRG | Sequence consisting of the N-terminal 4th to 15th amino acids of SEQ ID NO: 430 |

INDUSTRIAL APPLICABILITY

The peptide sequences of the present disclosure are useful as protease substrates, and these substrates are useful in various therapeutic, diagnostic, and prophylactic applications. Also, polypeptides comprising the peptide sequences of the present disclosure as a protease cleavage sequence are useful in various therapeutic, diagnostic, and prophylactic applications.

When the polypeptides of the present disclosure are polypeptides comprising an antigen-binding domain and a carrying moiety having an inhibiting domain, the polypeptides and pharmaceutical compositions comprising them allow the delivery of the antigen-binding domain in blood while inhibiting the antigen-binding activity of the antigen-binding domain. Also, use of the polypeptides allows the antigen-binding domain to exert the antigen-binding activity specifically at the diseased sites. Furthermore, the polypeptides have a shorter half-life when they are exerting their antigen-binding activity compared to when they are being delivered, which reduces the concern of acting systemically; thus, they are extremely useful for the treatment of diseases.

When the polypeptides of the present disclosure are ligand-binding molecules, the ligand-binding molecules are delivered in vivo while being bound to the ligand and cleaved in the diseased tissue, which weakens the binding to the ligand and allows for diseased tissue-specific release of the ligand, and thus, the diseased tissue can be exposed to the ligand in a specific manner. In addition, since the biological activity of the ligand is suppressed during the delivery of the ligand-binding molecule, the concern that the ligand may act systemically can be reduced; thus, they are extremely useful for the treatment of diseases.

SEQUENCE LISTING

The patent contains a lengthy sequence listing. A copy of the sequence listing is available in electronic form from the USPTO web site (https://seqdata.uspto.gov/docdetail?docId=US12680093B2). An electronic copy of the sequence listing will also be available from the USPTO upon request and payment of the fee set forth in 37 CFR 1.19(b)(3).

The invention claimed is:

1. A protease substrate comprising a sequence selected from the following:

the sequence spanning from the N-terminal fourth to fifteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425;

the sequence spanning from the N-terminal fourth to thirteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425; or the sequence spanning from the N-terminal sixth to thirteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425.

2. A method for releasing a ligand bound to a ligand-binding molecule, wherein the method comprises cleaving, by protease, a portion contained in the ligand-binding molecule capable of binding to the ligand, wherein the portion has at least one sequence selected from the following:

the sequence spanning from the N-terminal fourth to fifteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425;

the sequence spanning from the N-terminal fourth to thirteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425;

the sequence spanning from the N-terminal sixth to thirteenth amino acids of a sequence selected from SEQ ID NOs: 430, 400, 8, 26, 107, 114, 117, 130, 133, 135, 143, 149, 155, 156, 170, 172, 179, 184, 191, 203, 225, 265, 268, 271, 339, 359, and 425.

3. A polypeptide comprising the protease substrate of claim 1, wherein the polypeptide comprises an antigen-binding domain and a carrying moiety, and wherein the carrying moiety has an inhibiting domain for inhibiting the antigen-binding activity of the antigen-binding domain.

4. A polypeptide comprising the protease substrate of claim 1, wherein the polypeptide comprising the protease cleavage sequence is a ligand-binding molecule capable of binding to a ligand, and wherein the binding of the ligand-binding molecule to the ligand in a state where the protease cleavage sequence is cleaved is attenuated compared to the binding of the ligand-binding molecule to the ligand in a state where the protease cleavage sequence is not cleaved.

5. A polypeptide comprising the protease substrate of claim 1, wherein the polypeptide is a ligand-binding molecule capable of binding to a ligand, wherein the ligand-binding molecule comprises a single-domain antibody, wherein the single-domain antibody is capable of binding to a ligand and is introduced with at least one of the protease cleavage sequences, wherein the binding of the ligand-binding molecule to the ligand in a state where the protease cleavage sequence is cleaved is attenuated compared to the binding of the ligand-binding molecule to the ligand in a state where the protease cleavage sequence is not cleaved.

6. The polypeptide of claim 4 which is a fusion protein, wherein the polypeptide is fused to the ligand.

7. A pharmaceutical composition comprising the polypeptide of claim 3.

8. A pharmaceutical composition comprising the polypeptide of claim 4 and the ligand.

9. A polynucleotide encoding the polypeptide of claim 3.

10. A vector comprising the polynucleotide according to claim 9.

11. A host cell comprising the polynucleotide according to claim 9.

12. A method for producing a polypeptide comprising culturing the host cell according to claim 11.

13. A polynucleotide encoding the protease substrate of claim 1.

14. A vector comprising the polynucleotide according to claim 13.

15. A host cell comprising the polynucleotide according to claim 13.

16. A method for producing a protease substrate comprising culturing the host cell according to claim 15.

* * * * *